United States Patent
Manoharan et al.

(10) Patent No.: US 9,682,922 B2
(45) Date of Patent: *Jun. 20, 2017

(54) BIODEGRADABLE LIPIDS FOR THE DELIVERY OF ACTIVE AGENTS

(71) Applicant: ALNYLAM PHARMACEUTICALS, INC., Cambridge, MA (US)

(72) Inventors: Muthiah Manoharan, Cambridge, MA (US); Martin Maier, Cambridge, MA (US); Muthusamy Jayaraman, Cambridge, MA (US); Shigeo Matsuda, Cambridge, MA (US); Jayaprakash K. Nair, Cambridge, MA (US); Kallanthottathil G. Rajeev, Cambridge, MA (US); Akin Akinc, Cambridge, MA (US); Thomas A. Baillie, Seattle, WA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,945

(22) Filed: Mar. 18, 2015

(65) Prior Publication Data

US 2016/0009637 A1 Jan. 14, 2016

Related U.S. Application Data

(63) Continuation of application No. 13/153,200, filed on Jun. 3, 2011, now Pat. No. 9,012,498.

(60) Provisional application No. 61/351,146, filed on Jun. 3, 2010, provisional application No. 61/489,197, filed on May 23, 2011.

(51) Int. Cl.
```
C07C 229/12    (2006.01)
C12N 15/88     (2006.01)
A61K 31/713    (2006.01)
A61K 39/00     (2006.01)
A61K 47/44     (2017.01)
C12N 15/113    (2010.01)
```

(52) U.S. Cl.
CPC .......... *C07C 229/12* (2013.01); *A61K 31/713* (2013.01); *A61K 39/0005* (2013.01); *A61K 47/44* (2013.01); *C12N 15/113* (2013.01); *C12N 15/88* (2013.01); *C12N 2310/14* (2013.01); *C12N 2320/30* (2013.01)

(58) Field of Classification Search
CPC ..................................................... C07C 229/12
See application file for complete search history.

(56) References Cited

FOREIGN PATENT DOCUMENTS

WO    WO-2010054401 A1    5/2010

OTHER PUBLICATIONS

Chesnoy, et al., Structure and Function of Lipid-DNA Complexes for Gene Delivery, Annu. Rev. Biophys. Biomol. Struct., 2000, 29:27-47.
Lv, et al., Toxicity of Cationic Lipids and Cationic Polymers in Gene Delivery, Journal of Controlled Release, 2006, 114:100-109.
International Search Report issued in PCT/US2011/039164, issued on Dec. 8, 2011.
Aberle, et al., A Novel Tetraester Construct That Reduces Cationic Lipid-Associated Cytotoxicity Implications for the Onset of Cytotoxicity, Biochemistry, 1998, 6533-6540.
Farhood, et al., Effect of Cationic Cholesterol. Derivatives on Gene Transer and Protein Kinase C Activity, Biochimica et Biophysica Acta 1992, 111:239-246.
Leventis, et al., Interactions of Mammalian Cells with Lipid Dispersions Containing Novel Metabolizable Cationic Amphiphiles, Biochimica et Biophysica Acta (1990) 1023:124-132.
Tang, et al., Synthesis of a Single-tailed Cationic Lipid and Investigation of its Transfection, J Control Release, Dec. 6, 1999, 62:3:345-58.

*Primary Examiner* — Rei-Tsang Shiao
(74) *Attorney, Agent, or Firm* — Blank Rome LLP

(57) ABSTRACT

The present invention relates to a cationic lipid having one or more biodegradable groups located in the mid- or distal section of a lipidic moiety (e.g., a hydrophobic chain) of the cationic lipid. These cationic lipids may be incorporated into a lipid particle for delivering an active agent, such as a nucleic acid. The invention also relates to lipid particles comprising a neutral lipid, a lipid capable of reducing aggregation, a cationic lipid of the present invention, and optionally, a sterol. The lipid particle may further include a therapeutic agent such as a nucleic acid.

18 Claims, 4 Drawing Sheets

BIODEGRADABLE LIPIDS FOR THE DELIVERY OF ACTIVE AGENTS

CLAIM OF PRIORITY

This application is a continuation of U.S. patent application Ser. No. 13/153,200, filed Jun. 3, 2011, which claims the benefit of U.S. Patent Application No. 61/351,146, filed Jun. 3, 2010, and U.S. Patent Application No. 61/489,197, filed May 23, 2011, each of which is incorporated by reference in its entirety.

TECHNICAL FIELD

The present invention relates to biodegradable lipids and to their use for the delivery of active agents such as nucleic acids.

BACKGROUND

Therapeutic nucleic acids include, e.g., small interfering RNA (siRNA), micro RNA (miRNA), antisense oligonucleotides, ribozymes, plasmids, immune stimulating nucleic acids, antisense, antimir, microRNA mimic, supermir, U1 adaptor, and aptamer. These nucleic acids act via a variety of mechanisms. In the case of siRNA or miRNA, these nucleic acids can down-regulate intracellular levels of specific proteins through a process termed RNA interference (RNAi). Following introduction of siRNA or miRNA into the cell cytoplasm, these double-stranded RNA constructs can bind to a protein termed RISC. The sense strand of the siRNA or miRNA is displaced from the RISC complex providing a template within RISC that can recognize and bind mRNA with a complementary sequence to that of the bound siRNA or miRNA. Having bound the complementary mRNA the RISC complex cleaves the mRNA and releases the cleaved strands. RNAi can provide down-regulation of specific proteins by targeting specific destruction of the corresponding mRNA that encodes for protein synthesis.

The therapeutic applications of RNAi are extremely broad, since siRNA and miRNA constructs can be synthesized with any nucleotide sequence directed against a target protein. To date, siRNA constructs have shown the ability to specifically down-regulate target proteins in both in vitro and in vivo models. In addition, siRNA constructs are currently being evaluated in clinical studies.

However, two problems currently faced by siRNA or miRNA constructs are, first, their susceptibility to nuclease digestion in plasma and, second, their limited ability to gain access to the intracellular compartment where they can bind RISC when administered systemically as the free siRNA or miRNA. These double-stranded constructs can be stabilized by incorporation of chemically modified nucleotide linkers within the molecule, for example, phosphothioate groups. However, these chemical modifications provide only limited protection from nuclease digestion and may decrease the activity of the construct. Intracellular delivery of siRNA or miRNA can be facilitated by use of carrier systems such as polymers, cationic liposomes or by chemical modification of the construct, for example by the covalent attachment of cholesterol molecules. However, improved delivery systems are required to increase the potency of siRNA and miRNA molecules and reduce or eliminate the requirement for chemical modification.

Antisense oligonucleotides and ribozymes can also inhibit mRNA translation into protein. In the case of antisense constructs, these single stranded deoxynucleic acids have a complementary sequence to that of the target protein mRNA and can bind to the mRNA by Watson-Crick base pairing. This binding either prevents translation of the target mRNA and/or triggers RNase H degradation of the mRNA transcripts. Consequently, antisense oligonucleotides have tremendous potential for specificity of action (i.e., down-regulation of a specific disease-related protein). To date, these compounds have shown promise in several in vitro and in vivo models, including models of inflammatory disease, cancer, and HIV (reviewed in Agrawal, Trends in Biotech. 14:376-387 (1996)). Antisense can also affect cellular activity by hybridizing specifically with chromosomal DNA. Advanced human clinical assessments of several antisense drugs are currently underway. Targets for these drugs include the bcl2 and apolipoprotein B genes and mRNA products.

Immune-stimulating nucleic acids include deoxyribonucleic acids and ribonucleic acids. In the case of deoxyribonucleic acids, certain sequences or motifs have been shown to illicit immune stimulation in mammals. These sequences or motifs include the CpG motif, pyrimidine-rich sequences and palindromic sequences. It is believed that the CpG motif in deoxyribonucleic acids is specifically recognized by an endosomal receptor, toll-like receptor 9 (TLR-9), which then triggers both the innate and acquired immune stimulation pathway. Certain immune stimulating ribonucleic acid sequences have also been reported. It is believed that these RNA sequences trigger immune activation by binding to toll-like receptors 6 and 7 (TLR-6 and TLR-7). In addition, double-stranded RNA is also reported to be immune stimulating and is believe to activate via binding to TLR-3.

One well known problem with the use of therapeutic nucleic acids relates to the stability of the phosphodiester internucleotide linkage and the susceptibility of this linker to nucleases. The presence of exonucleases and endonucleases in serum results in the rapid digestion of nucleic acids possessing phosphodiester linkers and, hence, therapeutic nucleic acids can have very short half-lives in the presence of serum or within cells. (Zelphati, O., et al., Antisense. Res. Dev. 3:323-338 (1993); and Thierry, A. R., et al., pp 147-161 in Gene Regulation: Biology of Antisense RNA and DNA (Eds. Erickson, R P and Izant, J G; Raven Press, NY (1992)). Therapeutic nucleic acid being currently being developed do not employ the basic phosphodiester chemistry found in natural nucleic acids, because of these and other known problems.

This problem has been partially overcome by chemical modifications that reduce serum or intracellular degradation. Modifications have been tested at the internucleotide phosphodiester bridge (e.g., using phosphorothioate, methylphosphonate or phosphoramidate linkages), at the nucleotide base (e.g., 5-propynyl-pyrimidines), or at the sugar (e.g., 2'-modified sugars) (Uhlmann E., et al. Antisense: Chemical Modifications. Encyclopedia of Cancer, Vol. X., pp 64-81 Academic Press Inc. (1997)). Others have attempted to improve stability using 2'-5' sugar linkages (see, e.g., U.S. Pat. No. 5,532,130). Other changes have been attempted. However, none of these solutions have proven entirely satisfactory, and in vivo free therapeutic nucleic acids still have only limited efficacy.

In addition, as noted above relating to siRNA and miRNA, problems remain with the limited ability of therapeutic nucleic acids to cross cellular membranes (see, Vlassov, et al., Biochim. Biophys. Acta 1197:95-1082 (1994)) and in the problems associated with systemic toxicity, such as complement-mediated anaphylaxis, altered coagulatory properties, and cytopenia (Galbraith, et al., *Antisense Nucl. Acid Drug Des.* 4:201-206 (1994)).

To attempt to improve efficacy, investigators have also employed lipid-based carrier systems to deliver chemically modified or unmodified therapeutic nucleic acids. In Zelphati, O and Szoka, F. C., *J. Contr. Rel.* 41:99-119 (1996), the authors refer to the use of anionic (conventional) liposomes, pH sensitive liposomes, immunoliposomes, fusogenic liposomes, and cationic lipid/antisense aggregates. Similarly siRNA has been administered systemically in cationic liposomes, and these nucleic acid-lipid particles have been reported to provide improved down-regulation of target proteins in mammals including non-human primates (Zimmermann et al., *Nature* 441: 111-114 (2006)).

In spite of this progress, there remains a need in the art for improved lipid-therapeutic nucleic acid compositions that are suitable for general therapeutic use. Preferably, these compositions would encapsulate nucleic acids with high-efficiency, have high drug:lipid ratios, protect the encapsulated nucleic acid from degradation and clearance in serum, be suitable for systemic delivery, and provide intracellular delivery of the encapsulated nucleic acid. In addition, these lipid-nucleic acid particles should be well-tolerated and provide an adequate therapeutic index, such that patient treatment at an effective dose of the nucleic acid is not associated with significant toxicity and/or risk to the patient. Compositions, methods of making the compositions, and methods of using the compositions to introduce nucleic acids into cells, including for the treatment of diseases are provided.

SUMMARY

The present invention relates to a cationic lipid having one or more biodegradable groups located in the mid- or distal section of a lipidic moiety (e.g., a hydrophobic chain) of the cationic lipid. These cationic lipids may be incorporated into a lipid particle for delivering an active agent, such as a nucleic acid (e.g., an siRNA). The incorporation of the biodegradable group(s) into the cationic lipid results in faster metabolism and removal of the cationic lipid from the body following delivery of the active agent to a target area. As a result, these cationic lipids have substantially lower toxicity than similar cationic lipids without the biodegradable groups.

In one embodiment, the cationic lipid is a compound of the formula:

(ii) $R^1$ and $R^2$, together with the nitrogen atom to which they are attached, form an optionally substituted heterocyclic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl (e.g., a 6-member ring) with (a) the adjacent nitrogen atom and (b) the $(R)_a$ group adjacent to the nitrogen atom;

each occurrence of R is, independently, —$(CR^3R^4)$—;

each occurrence of $R^3$ and $R^4$ are, independently H, OH, alkyl, alkoxy, —$NH_2$, alkylamino, or dialkylamino (in one preferred embodiment, each occurrence of $R^3$ and $R^4$ are, independently H or $C_1$-$C_4$ alkyl);

or $R^3$ and $R^4$, together with the carbon atom to which they are directly attached, form a cycloalkyl group, wherein no more than three R groups in each chain attached to the carbon C* are cycloalkyl (e.g., cyclopropyl);

the dashed line to Q is absent or a bond;

when the dashed line to Q is absent then Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N(R)—, —N($R^5$)C(O)O—, —C(O)S—, —C(S)O— or —C($R^5$)=N—O—C(O)—; or when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

$Q^1$ and $Q^2$ are each, independently, absent, —O—, —S—, —OC(O)—, —C(O)O—, —SC(O)—, —C(O)S—, —OC(S)—, —C(S)O—, —S—S—, —C(O)(N$R^5$)—, —N($R^5$)C(O)—, —C(S)(N$R^5$)—, —N($R^5$)C(O)—, —N($R^5$)C(O)N($R^5$)—, or —OC(O)O—;

$Q^3$ and $Q^4$ are each, independently, H, —$(CR^3R^4)$—, aryl, or a cholesterol moiety;

each occurrence of $A^1$, $A^2$, $A^3$ and $A^4$ is, independently, —$(CR^5R^5$—$CR^5$=$CR^5)$—;

each occurrence of $R^5$ is, independently, H or alkyl;

$M^1$ and $M^2$ are each, independently, a biodegradable group (e.g., —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)($CR^3R^4$)C(O)O—, or —OC(O)($CR^3R^4$)C(O)—);

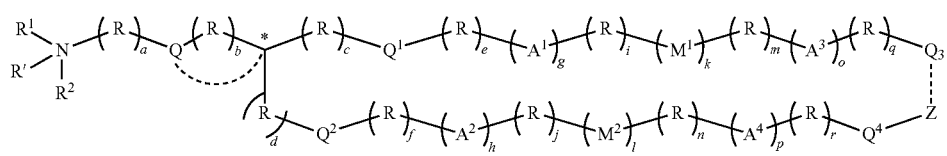

Formula (I)

or a salt thereof (e.g., a pharmaceutically acceptable salt thereof), wherein

R' is absent, hydrogen, or alkyl (e.g., $C_1$-$C_4$ alkyl);

with respect to $R^1$ and $R^2$, (i) $R^1$ and $R^2$ are each, independently, optionally substituted alkyl, alkenyl, alkynyl, cycloalkyl, cycloalkylalkyl, or heterocycle;

Z is absent, alkylene or —O—P(O)(OH)—O—;

each ------ attached to Z is an optional bond, such that when Z is absent, $Q^3$ and $Q^4$ are not directly covalently bound together;

a is 1, 2, 3, 4, 5 or 6;

b is 0, 1, 2, or 3;

c, d, e, f, i, j, m, n, q and r are each, independently, 0, 1, 2, 3, 4, 5, 6, 7, 8, 9, or 10;

g and h are each, independently, 0, 1 or 2;

k and l are each, independently, 0 or 1, where at least one of k and l is 1; and o and p are each, independently, 0, 1 or 2, wherein (i) the compound does not contain the following moiety:

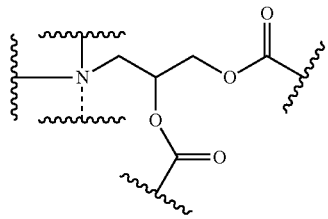

wherein ---- is an optional bond; and (ii) $Q^3$ and $Q^4$ are each, independently, separated from the tertiary carbon atom marked with an asterisk (*) by a chain of 8 or more atoms (e.g., 12 or 14 or more atoms).

In one embodiment, (i) $R^1$ and $R^2$ are each, independently, optionally substituted alkyl, alkenyl, alkynyl, cycloalkyl, cycloalkylalkyl, or heterocycle; or (ii) $R^1$ and $R^2$, together with the nitrogen atom to which they are attached, form an optionally substituted heterocylic ring.

In a preferred embodiment of the compound of formula (I),
(a) when $Q^1$ is a biodegradable group (e.g., —C(O)O—), then c is at least 4;
(b) when $Q^2$ is a biodegradable group, then d is at least 4; and
(c) $Q^3$ and $Q^4$ are each, independently, separated from the tertiary carbon atom marked with an asterisk (*) by a chain of 10 or more atoms (e.g., 12 or 14 or more atoms).

In another preferred embodiment, a carbon atom alpha or beta to a biodegradable group (e.g., —C(O)O—) in formula (I) may be substituted with one or two alkyl groups (e.g., one $C_1$-$C_4$ alkyl group, such as a —CH$_3$ substituent, or two $C_1$-$C_4$ alkyl groups, such as two —CH$_3$ substituents) or have a spirocyclic group (e.g., a $C_3$-$C_5$ cycloalkyl such as a $C_3$ cycloalkyl). For example, a carbon atom alpha or beta to a biodegradable group can be independently selected from

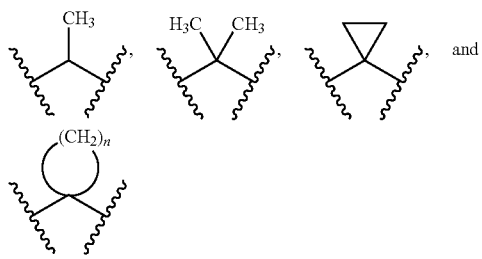

(where n is 4-6).

In one embodiment, the $M^1$ or $M^2$ group and neighboring variable(s) form the group:

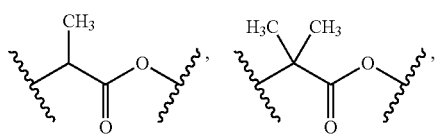

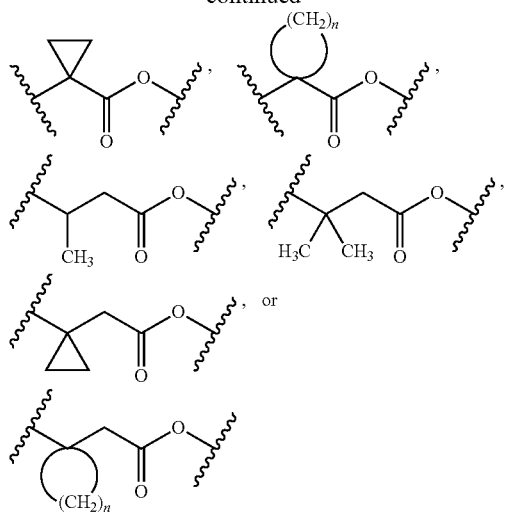

(where n is 4-6).

Yet another embodiment is a cationic lipid of the formula

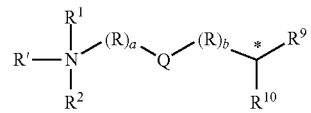

Formula (IA-1)

or a salt thereof (e.g., a pharmaceutically acceptable salt thereof), wherein $R^1$, $R^2$, R, a, and b are as defined with respect to formula (I);

Q is absent or is —O—, —NH—, —S—, —C(O)O—, —OC(O)—, —C(O)N(R$^4$)—, —N(R$^5$)C(O)—, —S—S—, —OC(O)O—, —O—N=C(R$^5$)—, —C(R$^5$)=N—O—, —OC(O)N(R$^5$)—, —N(R$^5$)C(O)N(R$^5$)—, —N(R$^5$)C(O)O—, —C(O)S—, —C(S)O— or —C(R$^5$)=N—O—C(O)—;

R' is absent, hydrogen, or alkyl (e.g., $C_1$-$C_4$ alkyl); and
each of $R^9$ and $R^{10}$ are independently $C_{12}$-$C_{24}$ alkyl (e.g., $C_{12}$-$C_{20}$ alkyl), $C_{12}$-$C_{24}$ alkenyl (e.g., $C_{12}$-$C_{20}$ alkenyl), or $C_{12}$-$C_{24}$ alkoxy (e.g., $C_{12}$-$C_{20}$ alkoxy) having one or more biodegradable groups; each biodegradable group independently interrupts the $C_{12}$-$C_{24}$ alkyl, alkenyl, or alkoxy group or is substituted at the terminus of the $C_{12}$-$C_{24}$ alkyl, alkenyl, or alkoxy group,
wherein
(i) the compound does not contain the following moiety:

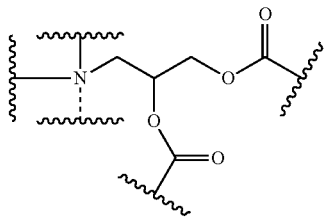

wherein ---- is an optional bond; and (ii) the terminus of $R^9$ and $R^{10}$ is separated from the tertiary carbon atom marked with an asterisk (*) by a chain of 8 or more atoms (e.g., 12 or 14 or more atoms).

In another embodiment, the cationic lipid is a compound of the formula:

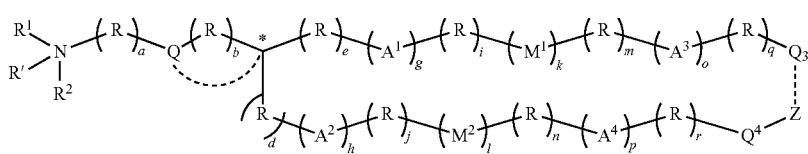

Formula (IA-2)

or a salt thereof (e.g., a pharmaceutically acceptable salt thereof), wherein

R' is absent, hydrogen, or alkyl (e.g., $C_1$-$C_4$ alkyl);

$R^1$ and $R^2$ are each, independently, optionally substituted $C_1$-$C_4$ alkyl, $C_2$-$C_4$ alkenyl, $C_2$-$C_4$ alkynyl, $C_3$-$C_6$ cycloalkyl, ($C_3$-$C_6$ cycloalkyl)$C_1$-$C_4$ alkyl, or a monocyclic heterocycle; or $R^1$ and $R^2$, together with the nitrogen atom to which they are attached, form an optionally substituted 5- or 6-membered heterocyclic ring (e.g., a $C_5$ or $C_6$ heterocyclic ring);

each occurrence of R is, independently, —($CR^3R^4$)—;

each occurrence of $R^3$ and $R^4$ are, independently H, OH, alkyl, alkoxy, —$NH_2$, alkylamino, or dialkylamino (in one preferred embodiment, each occurrence of $R^3$ and $R^4$ are, independently H or $C_1$-$C_4$ alkyl);

or $R^3$ and $R^4$, together with the carbon atom to which they are directly attached, form a $C_3$-$C_6$ cycloalkyl group, wherein no more than three R groups in each chain attached to the carbon C* are cycloalkyl (e.g., cyclopropyl);

the dashed line to Q is absent or a bond;

when the dashed line to Q is absent, Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; or when the dashed line to Q is a bond, b is 0 and Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

$Q^3$ and $Q^4$ are each, independently, H, —($CR^3R^4$)—, aryl, or a cholesterol moiety;

each occurrence of $A^1$, $A^2$, $A^3$ and $A^4$ is, independently, —($CR^5R^5$—$CR^5$=$CR^5$)—;

each occurrence of $R^5$ is, independently, H or alkyl;

$M^1$ and $M^2$ are each, independently, —C(O)—O—, —OC(O)—, —C($R^5$)=N—, —C($R^5$)=N—O—, —O—C(O)O—, —C(O)N($R^5$)—, —C(O)S—, —C(S)O—, —OSi($R^5$)$_2$O—, —C(O)(CR³R⁴)C(O)O—, or —OC(O)(CR³R⁴)C(O)—;

Z is absent, alkylene or —O—P(O)(OH)—O—;

each ------ attached to Z is an optional bond, such that when Z is absent, $Q^3$ and $Q^4$ are not directly covalently bound together;

a is 1, 2, 3, 4, 5 or 6;

b is 0, 1, 2, or 3;

d, e, i, j, m, n, q and r are each, independently, 0, 1, 2, 3, 4, 5, 6, 7, 8, 9, or 10;

g and h are each, independently, 0, 1 or 2;

the sum of d+3h is at least 4, and the sum of e+3 g is at least 4;

k and l are each, independently, 0 or 1, where at least one of k and l is 1; and o and p are each, independently, 0, 1 or 2, wherein $Q^3$ and $Q^4$ are each, independently, separated from the tertiary carbon atom marked with an asterisk (*) by a chain of 8 or more atoms (e.g., 12 or 14 or more atoms).

In one embodiment, R' in formula (IA-2) is absent or hydrogen. In one embodiment, R' in formula (IA-2) is absent or alkyl (e.g., methyl).

In one embodiment, $R^1$ and $R^2$ in formula (IA-2) are each, independently, $C_1$-$C_4$ alkyl (e.g., methyl or ethyl).

In one embodiment, each occurrence of R in formula (IA-2) is, independently, —$CH_2$— or —$CH(CH_3)$—.

In one embodiment, $Q^3$ and $Q^4$ in formula (IA-2) are each, independently, H, aryl, or a cholesterol moiety.

In one embodiment, each occurrence of $A^1$, $A^2$, $A^3$ and $A^4$ in formula (IA-2) is, independently, —($CH_2$—CH=CH)—;

In one embodiment, $M^1$ and $M^2$ in formula (IA-2) are each —C(O)—O—.

In one embodiment of the compound of formula (IA-2), Z is absent and each ------ is absent (i.e., $Q^3$ and $Q^4$ are not directly covalently bound together).

In one embodiment, the sum of e+3 g+i+m+3o+q in formula (IA-2) is from about 8 to about 20. In another embodiment, the sum of e+3 g+i+m+3o+q in formula (IA-2) is from about 12 to about 20.

In one embodiment, the sum of d+3h+j+n+3p+r in formula (IA-2) is from about 8 to about 20. In another embodiment, the sum of d+3h+j+n+3p+r in formula (IA-2) is from about 12 to about 20.

In another embodiment, the cationic lipid is a compound of the formula

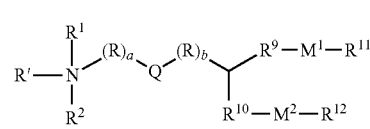

Formula (IB)

wherein $R^1$, $R^2$, R, a, b, $M^1$, and $M^2$ are as defined with respect to formula (I);

Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—;

R' is absent, hydrogen, or alkyl (e.g., $C_1$-$C_4$ alkyl);

each of $R^9$ and $R^{10}$ are independently alkylene, or alkenylene; and each of $R^{11}$ and $R^{12}$ are independently alkyl or alkenyl, optionally terminated by $COOR^{13}$ where each $R^{13}$ is independently alkyl (e.g., $C_1$-$C_4$ alkyl such as methyl or ethyl);

$R^9$, $M^1$, and $R^{11}$ are together at least 8 carbons atoms in length (e.g., 12 or 14 carbon atoms or longer); and $R^{10}$, $M^2$, and $R^{12}$ are together at least 8 carbons atoms in length (e.g., 12 or 14 carbon atoms or longer).

In a preferred embodiment of the compound of formula (IB), $R^9$ and $R^{10}$ are each independently $C_4$-$C_{12}$ alkylene or $C_4$-$C_{12}$ alkenylene, $M^1$ and $M^2$ are —C(O)O—, and $R^{11}$ and $R^{12}$ are $C_4$-$C_{12}$ alkylene or $C_4$-$C_{12}$ alkenylene. In one embodiment, $R^9$, $M^1$, and $R^{11}$ are together at 12 to 24 carbons atoms in length. In another embodiment, $R^9$, $M^1$, and $R^{11}$ are together at 14 to 18 carbons atoms in length. In one embodiment, $R^{10}$, $M^2$, and $R^{12}$ are together at 12 to 24 carbons atoms in length. In another embodiment, $R^{10}$, $M^2$, and $R^{12}$ are together at 14 to 18 carbons atoms in length.

The R'$R^1R^2$N—$(R)_a$-Q-$(R)_b$— group can be any of the head groups described herein, including those shown in Table 1 below, and salts thereof. In one preferred embodiment, R'$R^1R^2$N—$(R)_a$-Q-$(R)_b$— is $(CH_3)_2$N—$(CH_2)_3$—C(O)O—, $(CH_3)_2$N—$(CH_2)_2$—NH—C(O)O—, $(CH_3)_2$N—$(CH_2)_2$—OC(O)—NH—, or $(CH_3)_2$N—$(CH_2)_3$—C$(CH_3)$=N—O—.

In yet another embodiment, the cationic lipid is a compound of the formula

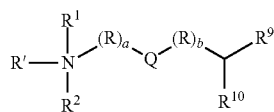

Formula (IC)

wherein $R^1$, $R^2$, R, a, and b are as defined with respect to formula (I);

Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; R' is absent, hydrogen, or alkyl (e.g., $C_1$-$C_4$ alkyl);

each of $R^9$ and $R^{10}$ are independently $C_{12}$-$C_{24}$ alkyl or alkenyl substituted at its terminus with a biodegradable group, such as —COO$R^{13}$ where each $R^{13}$ is independently alkyl (preferably $C_1$-$C_4$ alkyl such as methyl or ethyl).

In a preferred embodiment of the compound of formula (IC), $R^9$ and $R^{10}$ are each independently $C_{14}$-$C_{18}$ alkylene or $C_{14}$-$C_{18}$ alkenylene. In another preferred embodiment, the biodegradable group is —COO$R^{13}$ where $R^{13}$ is $C_1$-$C_4$ alkyl (such as methyl or ethyl).

The R'$R^1R^2$N—$(R)_a$-Q-$(R)_b$— group can be any of the head groups described herein, including those shown in Table 1 below. In one preferred embodiment, R'$R^1R^2$N—$(R)_a$-Q-$(R)_b$— is $(CH_3)_2$N—$(CH_2)_3$—C(O)O—, $(CH_3)_2$N—$(CH_2)_2$—NH—C(O)O—, $(CH_3)_2$N—$(CH_2)_2$—OC(O)—NH—, or $(CH_3)_2$N—$(CH_2)_3$—C$(CH_3)$=N—O—.

Yet another embodiment are intermediates of the formula:

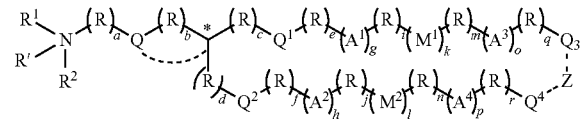

Formula (ID)

or a salt thereof (e.g., a pharmaceutically acceptable salt thereof), wherein

R' is absent, hydrogen, or alkyl (e.g., $C_1$-$C_4$ alkyl);

$R^1$ and $R^2$ are each, independently, optionally substituted alkyl, alkenyl, alkynyl, cycloalkyl, cycloalkylalkyl, or heterocycle; or $R^1$ and $R^2$, together with the nitrogen atom to which they are attached, form an optionally substituted heterocylic ring;

each occurrence of R is, independently, —($CR^3R^4$)—;

each occurrence of $R^3$ and $R^4$ are, independently H, OH, alkyl, alkoxy, —$NH_2$, alkylamino, or dialkylamino (in one preferred embodiment, each occurrence of $R^3$ and $R^4$ are, independently H or alkyl);

or $R^3$ and $R^4$, together with the carbon atom to which they are directly attached, form a cycloalkyl group, wherein no more than three R groups in each chain attached to the carbon C* are cycloalkyl (e.g., cyclopropyl);

the dashed line to Q is absent or a bond;

when the dashed line to Q is absent, Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; or when the dashed line to Q is a bond, b is 0 and Q and the tertiary carbon adjacent to it (C*) form a substituted or unsubstituted, mono- or bi-cyclic heterocyclic group having from 5 to 10 ring atoms (e.g., the heteroatoms in the heterocyclic group are selected from O and S, preferably O);

$Q^1$ and $Q^2$ are each, independently, absent, —O—, —S—, —OC(O)—, —C(O)O—, —SC(O)—, —C(O)S—, —OC(S)—, —C(S)O—, —S—S—, —C(O)(N$R^5$)—, —N($R^5$)C(O)—, —C(S)(N$R^5$)—, —N($R^5$)C(O)—, —N($R^5$)C(O)N($R^5$)—, or —OC(O)O—;

$Q^3$ and $Q^4$ are each, independently, H, —($CR^3R^4$)—, aryl, —OH, or a cholesterol moiety;

each occurrence of $A^1$, $A^2$, $A^3$ and $A^4$ is, independently, —($CR^5R^5$—$CR^5$=$CR^5$)—;

each occurrence of $R^5$ is, independently, H or alkyl;

$M^1$ and $M^2$ are each, independently, a biodegradable group (e.g., —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)($CR^3R^4$)C(O)O—, or —OC(O)($CR^3R^4$)C(O)—);

Z is absent, alkylene or —O—P(O)(OH)—O—;

each ------ attached to Z is an optional bond, such that when Z is absent, $Q^3$ and $Q^4$ are not directly covalently bound together;

a is 1, 2, 3, 4, 5 or 6;

b is 0, 1, 2, or 3;

c, d, e, f, i, j, m, n, q and r are each, independently, 0, 1, 2, 3, 4, 5, 6, 7, 8, 9, or 10; g and h are each, independently, 0, 1 or 2;

k and l are each, independently, 0 or 1;

and p are each, independently, 0, 1 or 2, wherein
(i) the compound does not contain the following moiety:

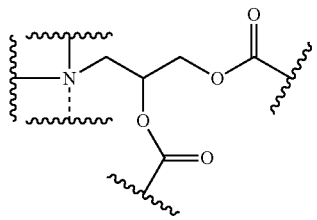

wherein ---- is an optional bond; and (ii) $Q^3$ and $Q^4$ are each, independently, separated from the tertiary carbon atom marked with an asterisk (*) by a chain of 8 or more atoms (e.g., 12 or 14 or more atoms).

In yet a further embodiment, the cationic lipid is a compound of formula IE:

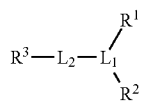

Formula (IE)

or a salt thereof (e.g., a pharmaceutically acceptable salt thereof),
wherein $R^1$ is a $C_{10}$ to $C_{30}$ group having the formula $-L^{1a}-(CR^{1a}R^{1b})_\alpha-[L^{1b}-(CR^{1a}R^{1b})_\beta]_\gamma-L^{1c}-R^{1c}$, where $L^{1a}$ is a bond, $-CR^{1a}R^{1b}-$, $-O-$, $-CO-$, $-NR^{1d}-$, $-S-$, or a combination thereof;

each $R^{1a}$ and each $R^{1b}$, independently, is H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; $-OR^{1c}$; $-NR^{1c}R^{1d}$; aryl; heteroaryl; or heterocyclyl;

each $L^{1b}$, independently, is a bond, $-(CR^{1a}R^{1b})_{1-2}-$, $-O-$, $-CO-$, $-NR^{1d}-$, $-S-$,

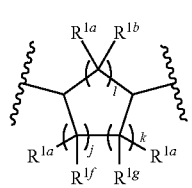

or a combination thereof; or can have the formula

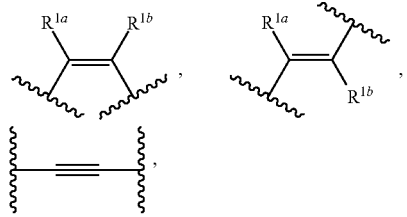

where j, k, and l are each independently 0, 1, 2, or 3, provided that the sum of j, k and l is at least 1 and no greater than 8; and $R^{1f}$ and $R^{1g}$ are each independently $R^{1b}$ or adjacent $R^{1f}$ and $R^{1g}$, taken together, are optionally a bond; or can have the formula

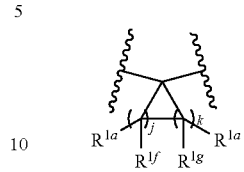

where j and k are each independently 0, 1, 2, 3, or 4 provided that the sum of j and k is at least 1; and $R^{1f}$ and $R^{1g}$ are each independently $R^{1b}$, or adjacent $R^{1f}$ and $R^{1g}$, taken together, are optionally a bond;

or can have the formula:

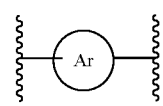

where —Ar— is a 6 to 14 membered arylene group optionally substituted by zero to six independent $R^{1a}$ groups;

or can have the formula:

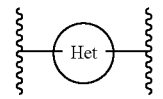

where -Het- is a 3 to 14 membered heterocyclylene or heteroarylene group optionally substituted by zero to six independent $R^{1a}$ groups;

$L^{1c}$ is $-(CR^{1a}R^{1b})_{1-2}-$, $-O-$, $-CO-$, $-NR^{1d}-$, $-S-$,

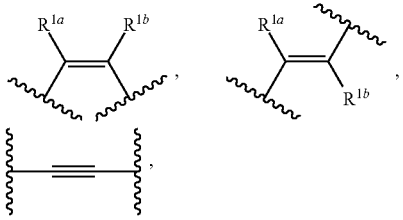

or a combination thereof;

$R^{1c}$ is H; halo; hydroxy; cyano; $C_1$-$C_6$ alkyl optionally substituted by halo, hydroxy, alkoxy, or aryl; $C_3$-$C_8$ cycloalkyl optionally substituted by halo, hydroxy, alkoxy, or aryl; aryl; heteroaryl; or heterocyclyl; or $R^{1c}$ has the formula:

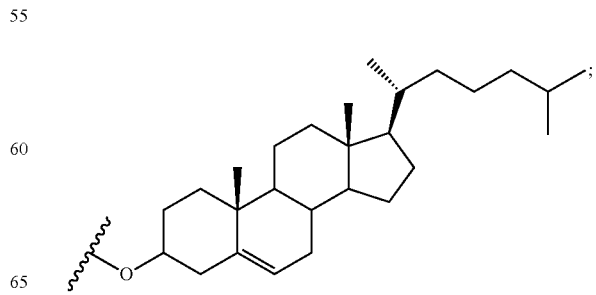

$R^{1d}$ is H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; aryl; heteroaryl; or heterocyclyl;

α is 0-6, inclusive;

each β, independently, is 0-6, inclusive;

γ is 0-6, inclusive;

$R^2$ is a $C_{10}$ to $C_{30}$ group having the formula -$L^{2a}$-$(CR^{2a}R^{2b})_\delta$-$[L^{2b}$-$(CR^{2a}R^{2b})_\epsilon]_\zeta$-$L^{2c}$-$R^{2c}$, where $L^{2a}$ is a bond, —$CR^{2a}R^{2b}$—, —O—, —CO—, —$NR^{2d}$—, —S—, or a combination thereof;

each $R^{2a}$ and each $R^{2b}$, independently, can be H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; —$OR^{2c}$; —$NR^{2c}R^{2d}$; aryl; heteroaryl; or heterocyclyl;

each $L^{2b}$, independently, can be a bond, —$(CR^{2a}R^{2b})_{1-2}$—, —O—, —CO—, —$NR^{2d}$—, —S—,

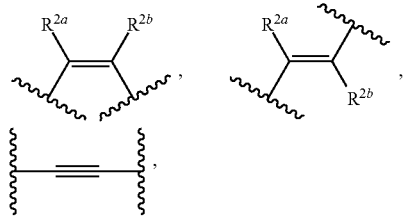

or a combination thereof;
or can have the formula

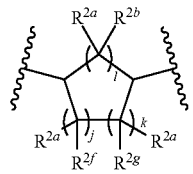

where j, k, and l are each independently 0, 1, 2, or 3, provided that the sum of j, k and l is at least 1 and no greater than 8; and $R^{2f}$ and $R^{2g}$ are each independently $R^{2b}$, or adjacent $R^{2f}$ and $R^{2g}$, taken together, are optionally a bond; or can have the formula

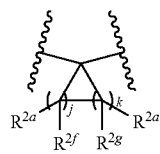

where j and k are each independently 0, 1, 2, 3, or 4 provided that the sum of j and k is at least 1; and $R^{2f}$ and $R^{2g}$ are each independently $R^{2b}$, or adjacent $R^{2f}$ and $R^{2g}$, taken together, are optionally a bond;
or can have the formula:

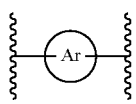

wherein —Ar— is a 6 to 14 membered arylene group optionally substituted by zero to six independent $R^{2a}$ groups;

or can have the formula:

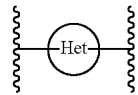

where -Het- is a 3 to 14 membered heterocyclylene or heteroarylene group optionally substituted by zero to six independent $R^{2a}$ groups;

$L^{2c}$ is —$(CR^{2a}R^{2b})_{1-2}$—, —O—, —CO—, —$NR^{2d}$—, —S—,

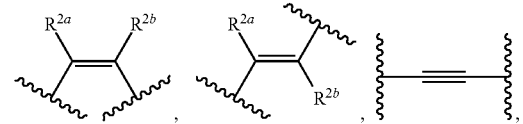

or a combination thereof;

$R^{2c}$ is H; halo; hydroxy; cyano; $C_1$-$C_6$ alkyl optionally substituted by halo, hydroxy, alkoxy or aryl; $C_3$-$C_8$ cycloalkyl optionally substituted by halo, hydroxy, alkoxy or aryl; aryl; heteroaryl; or heterocyclyl; or $R^{2c}$ has the formula:

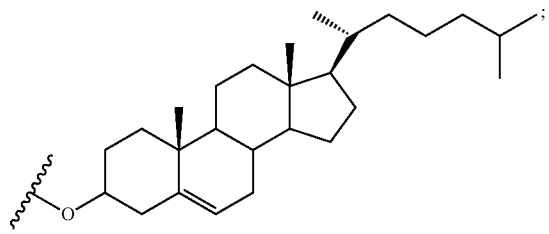 [SMILES: *OC1CC[C@@]2(C)C(=CCC3C2CC[C@@]2(C)C3CC[C@@H]2[C@H](C)CCCC(C)C)C1]

$R^{2d}$ is H; halo; hydroxy; cyano; $C_1$-$C_6$ alkyl optionally substituted by halo, hydroxy, or alkoxy; $C_3$-$C_8$ cycloalkyl optionally substituted by halo, hydroxy, or alkoxy; aryl; heteroaryl; or heterocyclyl;

δ is 0-6, inclusive;

each ε, independently, is 0-6, inclusive;

ζ is 0-6, inclusive;

$L_1$ is $C(R^a)$, —$(CR^5R^6)_xC(R^a)$—, or $P(Q_2)$;

$R^a$ is H, alkyl, alkoxy, —OH, —N(Q)Q, or —SQ;

$L_2$ is —$(CR^5R^6)_x$—, —C(O)—$(CR^5R^6)_x$—, —$(CR^5R^6)_x$C(O)—, —$(CR^5R^6)_x$—$CR^5$=$CR^5$—$(CR^5R^6)_y$—, —C(O)—$(CR^5R^6)_x$—$CR^5$=$CR^5$—$(CR^5R^6)_y$—, —$(CR^5R^6)_x$—$CR^5$=$CR^5$—$(CR^5R^6)_y$—C(O)—, —O—, —S—, —N(Q)-, —C(O)O—, —OC(O)—, —C(O)—, —N(Q)C(O)—, —C(O)N(Q)-, —N(Q)C(O)O—, —OC(O)N(Q)-, S(O), —N(Q)S(O)$_2$N(Q)-, —S(O)$_2$—, —N(Q)S(O)$_2$—, —SS—, —O—N=, =N—O—, —C(O)—N(Q)-N=, —N(Q)-N=, —N(Q)-O—, —C(O)S—, arylene, heteroarylene, cyclalkylene, or heterocyclylene;

each x, independently, can be 0-6, inclusive;

each y, independently, can be 0-6, inclusive'

$R^3$ is of the formula:

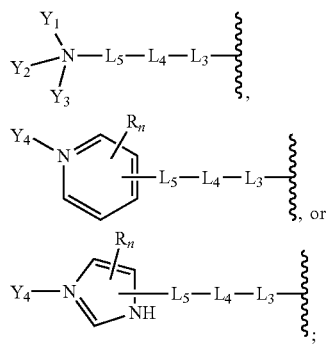

$Y_1$ is alkyl, cycloalkyl, aryl, aralkyl, or alkynyl, wherein $Y_1$ is optionally substituted by 0 to 6 independent $R_n$;

$Y_2$ is alkyl, cycloalkyl, aryl, aralkyl, or alkynyl, wherein $Y_2$ is optionally substituted by 0 to 6 independent $R_n$;

$Y_3$ is absent, or if present, is alkyl, cycloalkyl, aryl, aralkyl, or alkynyl, wherein $Y_3$ is optionally substituted by 0 to 6 independent $R_n$;

$Y_4$ is absent, or if present, is alkyl, cycloalkyl, aryl, aralkyl, or alkynyl, wherein $Y_4$ is optionally substituted by 0 to 6 independent $R_n$;

or any two of $Y_1$, $Y_2$, and $Y_3$ are taken together with the N atom to which they are attached to form a 3- to 8-member heterocycle optionally substituted by 0 to 6 independent $R_n$;

or $Y_1$, $Y_2$, and $Y_3$ are all be taken together with the N atom to which they are attached to form a bicyclic 5- to 12-member heterocycle optionally substituted by 0 to 6 independent $R_n$;

each $R_n$, independently, can be H, halo, cyano, hydroxy, amino, alkyl, alkoxy, cycloalkyl, aryl, heteroaryl, or heterocyclyl;

$L_3$ is a bond, —N(Q)-, —O—, —S—, —(CR$_7$R$_8$)$_a$—, —C(O)—, or a combination of any two of these;

$L_4$ cis a bond, —N(Q)-, —O—, —S—, —(CR$_7$R$_8$)$_a$—, —C(O)—, or a combination of any two of these;

$L_5$ is a bond, —N(Q)-, —O—, —S—, —(CR$_7$R$_8$)$_a$—, —C(O)—, or a combination of any two of these;

each occurrence of $R_7$ and $R_8$ is, independently, H, halo, cyano, hydroxy, amino, alkyl, alkoxy, cycloalkyl, aryl, heteroaryl, or heterocyclyl;

or two $R_7$ groups on adjacent carbon atoms can be taken together to form a double bond between their respective carbon atoms;

or two $R_7$ groups on adjacent carbon atoms and two $R_8$ groups on the same adjacent carbon atoms can be taken together to form a triple bond between their respective carbon atoms;

or, an $R_7$ or $R_8$ substituent from any of $L_3$, $L_4$, or $L_5$ can be optionally taken with an $R_7$ or $R_8$ substituent from any of $L_3$, $L_4$, or $L_5$ to form a 3- to 8-member cycloalkyl, heterocyclyl, aryl, or heteroaryl group;

or any one of $Y_1$, $Y_2$, or $Y_3$, can be optionally taken together with an $R_7$ or $R_8$ group from any of $L_3$, $L_4$, and $L_5$, and atoms to which they are attached, to form a 3- to 8-member heterocyclyl group;

each a, independently, can be 0, 1, 2, or 3;

each occurrence of $R_5$ and $R_6$ can be, independently, H, halo, cyano, hydroxy, amino, alkyl, alkoxy, cycloalkyl, aryl, heteroaryl, or heterocyclyl;

each Q, independently, is H, alkyl, acyl, cycloalkyl, alkenyl, alkynyl, aryl, heteroaryl or heterocyclyl; and Each $Q_2$, independently, is O, S, N(Q)Q, alkyl or alkoxy.

In some embodiments, $L_1$ can be —C(R$_5$R$_6$)$_x$C(R$_a$)—; or $L_1$ can be —CH$_2$—C(R$_a$)—. $L_2$ can be —C(O)O—, —OC(O)—, —N(Q)C(O)—, —C(O)N(Q)-, —N(Q)C(O)O—, —OC(O)N(Q)-, —SS—, —O—N=, or =N—O—. $L_2$ can be —C(O)O—, —OC(O)—, —SS—, or =N—O—.

In some embodiments, -L$^{1a}$-(CR$^{1a}$R$^{1b}$)$_\alpha$— can be —(CH$_2$)$_8$—. -L$^{2a}$-(CR$^{2a}$R$^{2b}$)$_\delta$— can be —(CH$_2$)$_8$—. L$^{1b}$-(CR$^{1a}$R$^{1b}$)$_\beta$ can be CH$_2$CH$_2$CH$_2$, CH=CH—CH$_2$, or

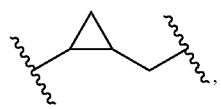 [SMILES: *CC1CC1*]

and β is 1, 2, or 3. L$^{2b}$-(CR$^{2a}$R$^{2b}$)$_\epsilon$ can be CH$_2$CH$_2$CH$_2$, CH=CH—CH$_2$, or

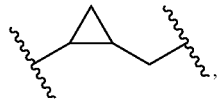 [SMILES: *CC1CC1*]

and ε is 1, 2, or 3.

In one embodiment of the compound of formula IE, at least one L$^{1a}$, L$^{1b}$, L$^{1c}$, L$^{2a}$, L$^{2b}$, or L$^{2c}$ present in the compound is a biodegradable group, such as ester —C(O)O—, —OC(O)—, disulfide (—S—S—), —C(R$^5$)=N—, —O—C(O)O—, —C(O)N(R$^5$)—, —N(R$^5$)C(O)—, —N(R$^5$)C(O)N(R$^5$)—, —C(O)S—, —SC(O)—, —C(O)(CR$^{1a}$R$^{1b}$)C(O)O—, or —OC(O)(CR$^{1a}$R$^{1b}$)C(O)—. In another embodiment of the compound of formula IE, at least one L$^{1a}$, L$^{1b}$, and L$^{1c}$ present in the compound is a biodegradable group and at one L$^{2a}$, L$^{2b}$, or L$^{2c}$ present in the compound is a biodegradable group (such as those mentioned above). In yet another embodiment of the compound of formula IE, a in R$^1$ is at least 4, δ in R$^2$ is at least 4, at least one L$^{1a}$, L$^{1b}$, and L$^{1c}$ present in the compound is a biodegradable group and at one L$^{2a}$, L$^{2b}$, or L$^{2c}$ present in the compound is a biodegradable group (such as those mentioned above). In another embodiment, the carbon chain in R$^1$ and/or R$^2$ is saturated. In yet another embodiment, the carbon chain in R$^1$ and/or R$^2$ contains one or two double bonds.

In yet another embodiment, the cationic lipid is a compound selected from compounds of formulas II-XXIII:

(II)

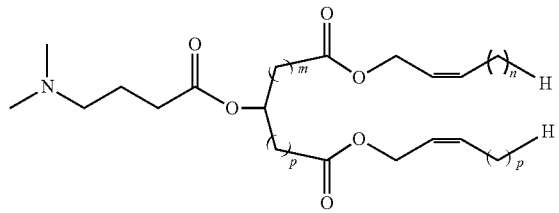

(III)

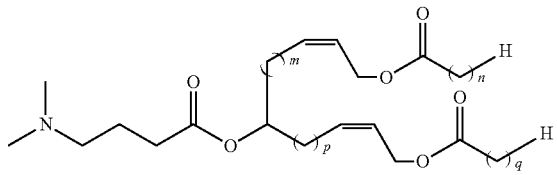

-continued
(IV)
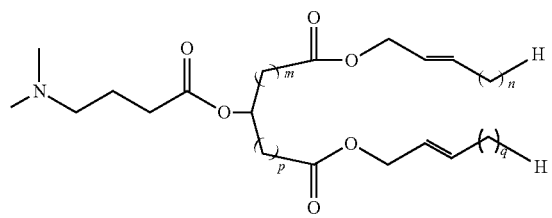
(V)
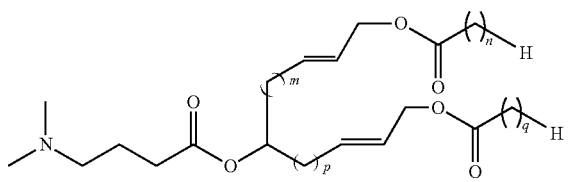
(VI)
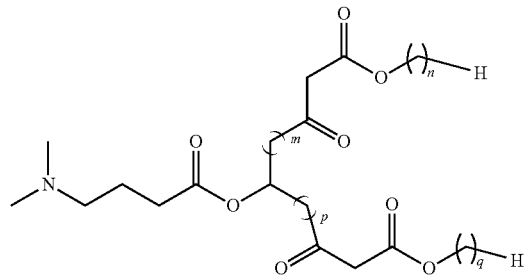
(VII)
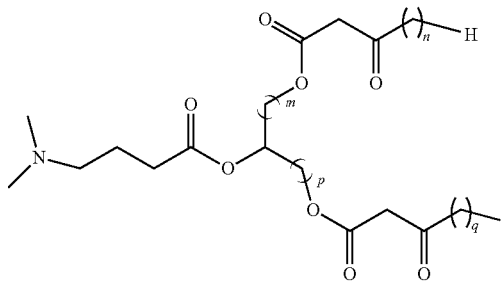
(VIII)
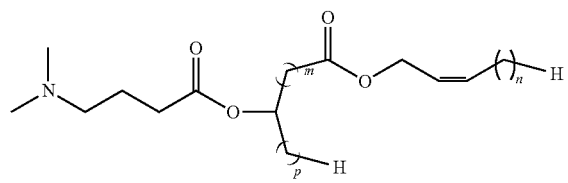
(IX)
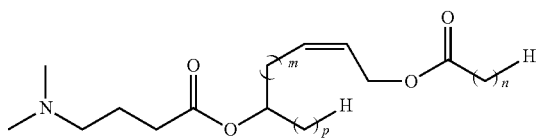
(X)
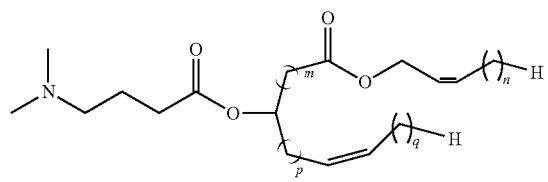
(XI)
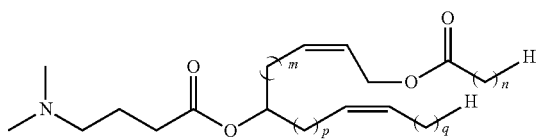
(XII)
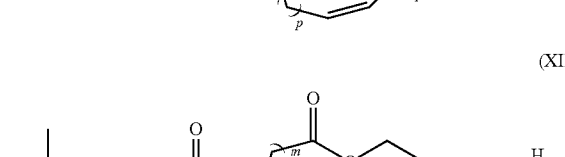
(XIII)
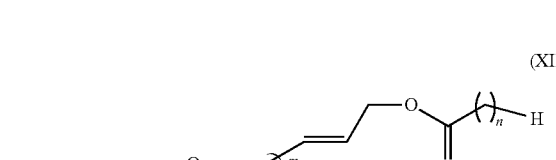
(XIV)
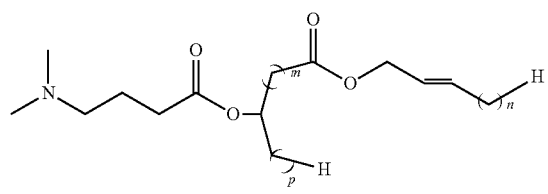
(XV)
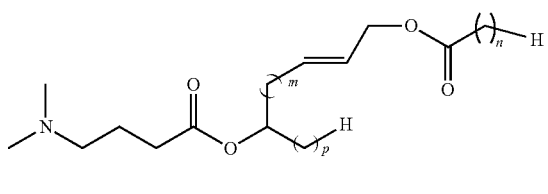
(XVI)
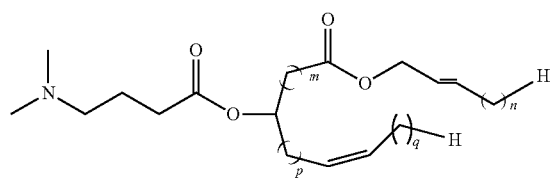
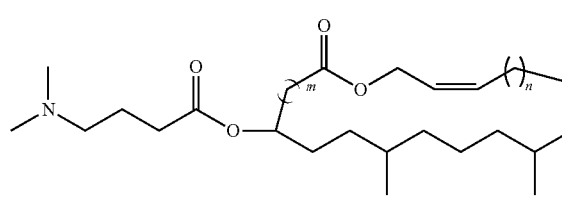

-continued
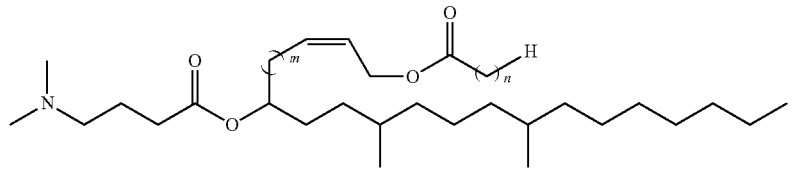
(XVII)
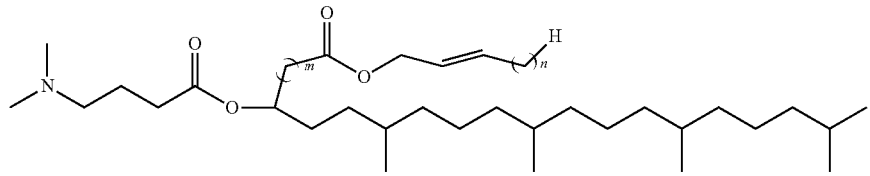
(XVIII)
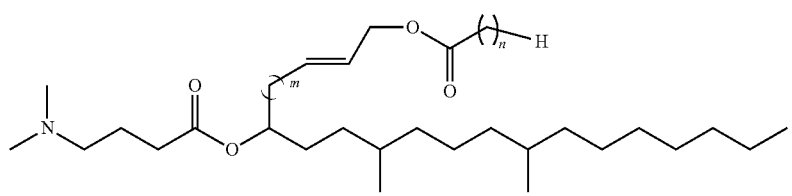
(XIX)
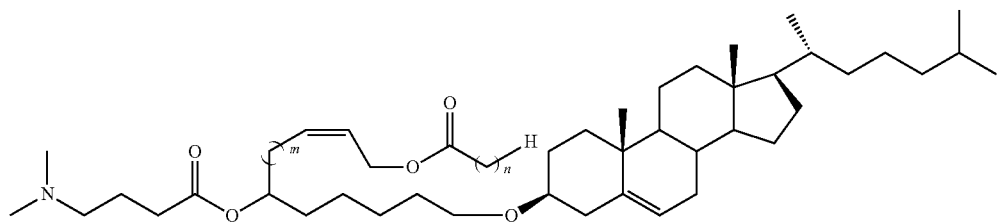
(XX)
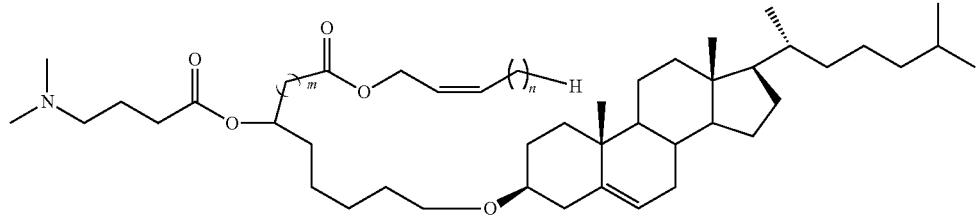
(XXI)
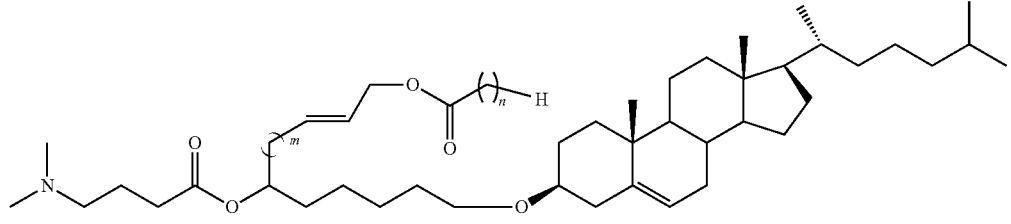
(XXII)
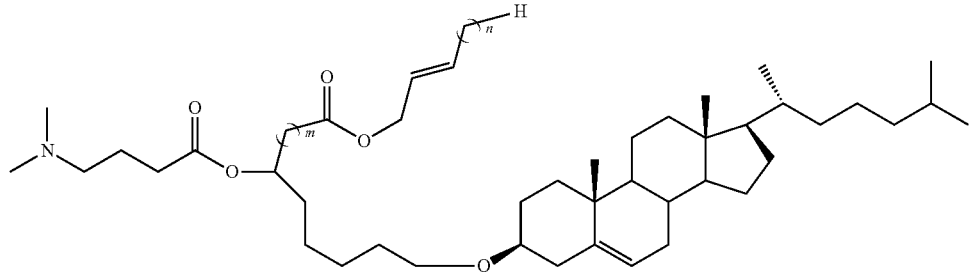
(XXIII)

and salts thereof (e.g., pharmaceutically acceptable salts thereof),
wherein
m, n, o and p are each, individually, 1-25, with the proviso that:
(i) in Formulas (II), (IV), (VI) and (VII), m and p are both 4 or greater;
(ii) in Formulas (VIII), (X), (XII), (XIV), (XVI), (XVIII), (XXI) and (XXIII), m is 4 or greater; and
(iii) in Formulas (VIII), (IX), (XII) and (XIII), p is 8 or greater (e.g., 12 or 14 or greater).

In another embodiment, the present invention relates to a cationic lipid or a salt thereof having:
(i) a central carbon atom,
(ii) a nitrogen containing head group directly bound to the central carbon atom, and
(iii) two hydrophobic tails directly bound to the central carbon atom, each hydrophobic tail comprising a $C_8$ or greater aliphatic group (preferably a $C_{14}$ or greater aliphatic group) attached to the central carbon atom, where one or both of the aliphatic group(s) (a) is interrupted by a biodegradable group such that there is a chain of at least four carbon atoms between the biodegradable group and the central carbon atom, or (b) includes a biodegradable group at the terminal end of the hydrophobic tail. For instance, the biodegradable group is selected from —OC(O)—, —C(O)O—, —SC(O)—, —C(O)S—, —OC(S)—, —C(S)O—, —S—S—, —C(O)(NR$^5$)—, —N(R$^5$)C(O)—, —C(S)(NR$^5$)—, —N(R$^5$)C(O)—, —N(R$^5$)C(O)N(R)—, and —OC(O)O—.

Yet another embodiment is a lipid particle that includes a cationic lipid of the present invention. In one embodiment, the lipid particle includes a compound of any of formulas II-XXIII as described herein. In another embodiment, the lipid particle includes a compound of formula I as described herein. In another embodiment, the lipid particle includes a compound of formula IA-1, IA-2, IB, IC, ID or IE as described herein.

In a preferred embodiment, the lipid particle includes a neutral lipid, a lipid capable of reducing aggregation, a cationic lipid, and optionally, a sterol (e.g., cholesterol). Suitable neutral lipids include, but are not limited to, distearoylphosphatidylcholine (DSPC), dipalmitoylphosphatidylcholine (DPPC), POPC, DOPE, and SM. Suitable lipids capable of reducing aggregation include, but are not limited to, a PEG lipid, such as PEG-DMA, PEG-DMG, or a combination thereof.

The lipid particle may further include an active agent (e.g., a therapeutic agent). The active agent can be a nucleic acid such as a plasmid, an immunostimulatory oligonucleotide, an siRNA, an antisense oligonucleotide, a microRNA, an antagomir, an aptamer, or a ribozyme.

In another embodiment, the lipid particle includes a cationic lipid of the present invention, a neutral lipid and a sterol. The lipid particle may further include an active agent, such as a nucleic acid.

Yet another embodiment of the invention is a pharmaceutical composition which includes a lipid particle of the present invention and a pharmaceutically acceptable carrier.

Yet another embodiment is a method of delivering a nucleic acid molecule in a subject comprising administering to the subject a lipid particle comprising the nucleic acid molecule and a cationic lipid (or a salt thereof), the cationic lipid having
(i) a central carbon atom,
(ii) an nitrogen containing head group directly bound to the central carbon atom, and
(iii) two hydrophobic tails directly bound to the central carbon atom, each hydrophobic tail comprising a $C_8$ or greater aliphatic group (preferably a $C_{14}$ or greater aliphatic group) attached to the central carbon atom, where one or both of the aliphatic group(s) (a) is interrupted by a biodegradable group such that there is a chain of at least four carbon atoms between the biodegradable group and the central carbon atom, or (b) includes a biodegradable group at the terminal end of the hydrophobic tail.

In one embodiment, the cationic lipid remains intact until delivery of the nucleic acid molecule after which cleavage of the hydrophobic tail occurs in vivo.

Yet another aspect is a method of modulating the expression of a target gene in a cell by providing to the cell a lipid particle of the present invention. The active agent can be a nucleic acid selected from a plasmid, an immunostimulatory oligonucleotide, an siRNA, an antisense oligonucleotide, a microRNA, an antagomir, an aptamer, and a ribozyme.

Yet another aspect is a method of treating a disease or disorder characterized by the overexpression of a polypeptide in a subject by providing to the subject a pharmaceutical composition of the present invention, wherein the active agent is a nucleic acid selected from an siRNA, a microRNA, and an antisense oligonucleotide, and wherein the siRNA, microRNA, or antisense oligonucleotide includes a polynucleotide that specifically binds to a polynucleotide that encodes the polypeptide, or a complement thereof.

Yet another aspect is a method of treating a disease or disorder characterized by underexpression of a polypeptide in a subject by providing to the subject a pharmaceutical composition of the present invention, wherein the active agent is a plasmid that encodes the polypeptide or a functional variant or fragment thereof.

Yet another aspect is a method of inducing an immune response in a subject by providing to the subject a pharmaceutical composition wherein the active agent is an immunostimulatory oligonucleotide.

Yet another aspect is a transfection agent that includes the composition or lipid particles described above, where the composition or lipid particles include a nucleic acid. The agent, when contacted with cells, can efficiently deliver nucleic acids to the cells. Yet another aspect is a method of delivering a nucleic acid to the interior of a cell, by obtaining or forming a composition or lipid particles described above, and contacting the composition or lipid particles with a cell.

Other features and aspects will be apparent from the description and the claims.

DETAILED DESCRIPTION

Figure 1:
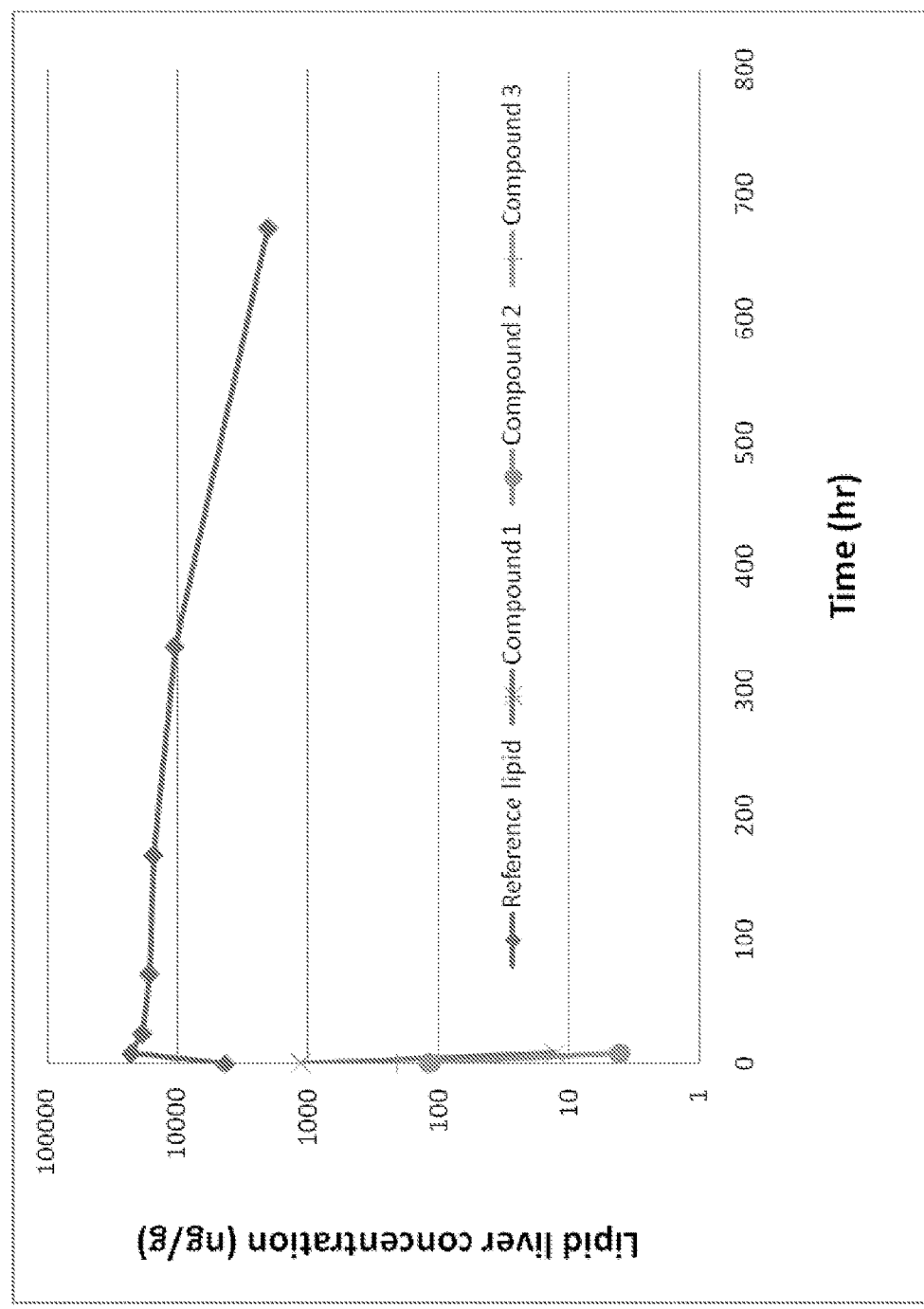
FIG. 1 is a graph of the concentration of a cationic lipid (Compounds 1-3 and reference lipid) in the liver of mice over time, after administration of the cationic lipid in a lipid particle as described in Example 14.

In one aspect, the present invention relates to a lipid particle that includes a neutral lipid, a lipid capable of reducing aggregation, a cationic lipid, and optionally a sterol. In certain embodiments, the lipid particle further includes an active agent (e.g., a therapeutic agent). Various exemplary embodiments of these lipids, lipid particles and compositions comprising the same, and their use to deliver therapeutic agents and modulate gene and protein expression are described in further detail below.

The Cationic Lipid

In one embodiment, the cationic lipid is a compound of formula I-XXIII. In another embodiment, the cationic lipid is a compound of one of formulas II-XXIII. In one embodiment, the cationic lipid is a compound of formula I. In another embodiment, the cationic lipid is a compound of formula IA-1, IA-2, IB, IC or ID. The following disclosure represents various embodiments of a compound of Formula I.

In one embodiment, $M^1$ and $M^2$ are each, independently: —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, or —OC(O)(C$R^3R^4$)C(O)—.

In another embodiment, $M^1$ and $M^2$ are each, independently: —OC(O)—, —C(O)—O—, —C($R^5$)=N—, —N=C($R^5$)—, —C($R^5$)=N—O—, —O—N=C($R^5$)—, —O—C(O)O—, —C(O)N($R^5$)—, —N($R^5$)C(O)—, —C(O)S—, —SC(O)—, —C(S)O—, —OC(S)—, —OSi($R^5$)$_2$O—, —C(O)(C$R^3R^4$)C(O)O—, or —OC(O)(C$R^3R^4$)C(O)—.

In yet another embodiment, $M^1$ and $M^2$ are each, independently: —C(O)—O—, —OC(O)—, —C($R^5$)=N—, —C($R^5$)=N—O—, —O—C(O)O—, —C(O)N($R^5$)—, —C(O)S—, —C(S)O—, —OSi($R^5$)$_2$O—, —C(O)(C$R^3R^4$)C(O)O—, or —OC(O)(C$R^3R^4$)C(O)—.

In another embodiment, $M^1$ and $M^2$ are each —C(O)O—.

In one embodiment, $R^1$ and $R^2$ are each, individually, optionally substituted alkyl, cycloalkyl, cycloalkylalkyl, or heterocycle. In one embodiment, $R^1$ is alkyl and $R^2$ is alkyl, cycloalkyl or cycloalkylalkyl. In one embodiment, $R^1$ and $R^2$ are each, individually, alkyl (e.g., $C_1$-$C_4$ alkyl, such as methyl, ethyl, or isopropyl). In one embodiment, $R^1$ and $R^2$ are both methyl. In another embodiment, $R^1$ and $R^2$, together with the nitrogen atom to which they are attached, form an optionally substituted heterocyclic ring (e.g., N-methylpiperazinyl). In another embodiment, one of $R^1$ and $R^2$ is

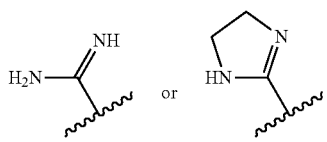

(e.g., $R^1$ is one of the two aforementioned groups and $R^2$ is hydrogen).

In one embodiment, R' is hydrogen or alkyl. In another embodiment, R' is hydrogen or methyl. In one embodiment, R' is absent. In one embodiment, R' is absent or methyl.

For compounds in which R' is not absent, the nitrogen atom to which R' is attached carries a positive charge, and the compound also contains a negatively charged counter ion. The counterion can be any anion, such as an organic or inorganic anion. Suitable examples of anions include, but are not limited to, tosylate, methanesulfonate, acetate, citrate, malonate, tartarate, succinate, benzoate, ascorbate, α-ketoglutarate, α-glycerophosphate, halide (e.g., chloride), sulfate, nitrate, bicarbonate, and carbonate. In one embodiment, the counterion is a halide (e.g., Cl).

In one embodiment each R is, independently, —(C$R^3R^4$)—, wherein $R^3$ and $R^4$ are each, independently, H or alkyl (e.g., $C_1$-$C_4$ alkyl). For example, in one embodiment each R is, independently, —(CH$R^4$)—, wherein each $R^4$ is, independently H or alkyl (e.g., $C_1$-$C_4$ alkyl). In another embodiment, each R is, independently, —CH$_2$—, —C(CH$_3$)$_2$— or —CH(iPr)- (where iPr is isopropyl). In another embodiment, each R is —CH$_2$—.

In another embodiment $R^5$ is, in each case, hydrogen or methyl. For example, $R^5$ can be, in each case, hydrogen.

In one embodiment, Q is absent, —C(O)O—, —OC(O)—, —C(O)N($R^4$)—, —N($R^5$)C(O)—, —S—S—, —OC(O)O—, —C($R^5$)=N—O—, —OC(O)N($R^5$)—, —N($R^5$)C(O)N(R)—, —N($R^5$)C(O)O—, —C(O)S—, —C(S)O— or —C($R^5$)=N—O—C(O)—. In one embodiment, Q is —C(O)O—.

In one embodiment, $Q^1$ and $Q^2$ are each, independently, absent or —O—. For example, in one embodiment, $Q^1$ and $Q^2$ are each absent. In another embodiment, $Q^1$ and $Q^2$ are each —O—.

In one embodiment, the dashed line to Q is absent, b is 0 and R'$R^1R^2$N—(R)$_a$-Q- and the tertiary carbon adjacent to it (C*) form the following group:

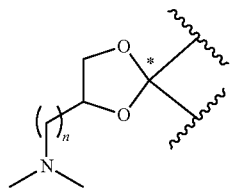

where n is 1 to 4 (e.g., n is 2).

In one embodiment, the dashed line to Q is absent, b is 0 and R'$R^1R^2$N—(R)$_a$-Q- and the tertiary carbon adjacent to it form the following group:

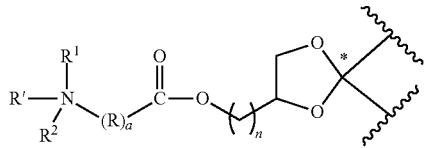

where n is 1 to 4 (e.g., n is 2), and $R^1$, $R^2$, R, a, and b are as defined with respect to formula (I). In one embodiment, a is 3.

In one embodiment, the dashed line to Q is absent, b is 0 and R'$R^1R^2$N—(R)$_a$-Q- and the tertiary carbon adjacent to it form the following group:

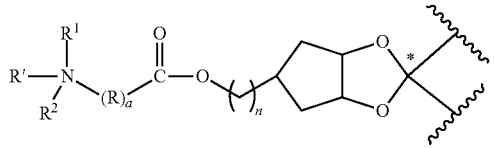

where n is 1 to 4 (e.g., n is 2), and $R^1$, $R^2$, R, a, and b are as defined with respect to formula (I). In one embodiment, a is 0. For example, the group can be:

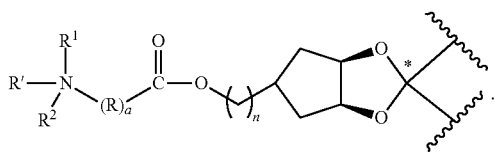

In one embodiment, b is 0. In another embodiment, a is 2, 3, or 4 and b is 0. For example, in one embodiment, a is 3 and b is 0. In another embodiment, a is 3, b is 0, and Q is —C(O)O—.

In one embodiment, the compound of formula (I) is of subformula:

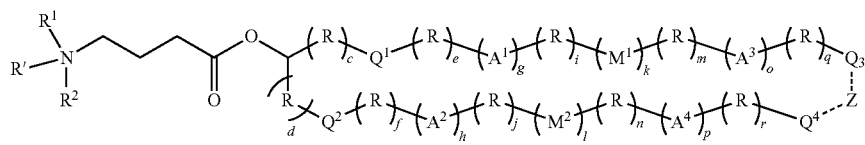

Formula (IF) wherein R, R', $R^1$, $R^2$, $A^1$, $A^2$, $A^3$, $A^4$, $Q^1$, $Q^2$, $Q^3$, $Q^4$, c, d, e, f, g, h, i, j, k, l, m, n, o, p, q and r are as defined in any of the embodiments disclosed herein.

In additional embodiments of the compound of formula (IF), one or more of the following applies:
(i) $Q^1$ and $Q^2$ are absent;
(ii) $M^1$ and $M^2$ are both —C(O)O—;
(iii) g and h are both 1;
(iv) g and h are both 0;
(v) c and e total 7;
(vi) d and f total 7;
(vii) c, e, and i total 7;
(viii) d, f and j total 7;
(ix) i and j are each 7;
(x) k and l are both 1;
(xi) m and n are both 0;
(xii) m and q total 1 or m and q total 2;
(xiii) m and l total 6;
(xiv) r and n total 6;
(xv) p and o are both 0;
(xvi) n and r total 2 or n and r total 1; and
(xvii) $Q^3$ is H.

In certain embodiments, the biodegradable group present in the cationic lipid is selected from an ester (e.g., —C(O)O— or —OC(O)—), disulfide (—S—S—), oxime (e.g., —C(H)=N—O— or —O—N=C(H)—), —C(O)—O—, —OC(O)—, —C($R^5$)=N—, —N=C($R^5$)—, —C($R^5$)=N—O—, —O—N=C($R^5$)—, —O—C(O)O—, —C(O)N($R^5$), —N($R^5$)C(O)—, —C(S)(N$R^5$)—, (N$R^5$)C(S)—, —N($R^5$)C(O)N(R)—, —C(O)S—, —SC(O)—, —C(S)O—, —OC(S)—, —OSi($R^5$)$_2$O—, —C(O)(C$R^3R^4$)C(O)O—, or —OC(O)(C$R^3R^4$)C(O)—.

In one embodiment, the aliphatic group in one or both of the hydrophobic tails of the cationic lipid includes at least one carbon-carbon double bond.

A suitable cholesterol moiety for the cationic lipids of the present invention (including compounds of formulas (I), IA-2, ID, IE and IF) has the formula:

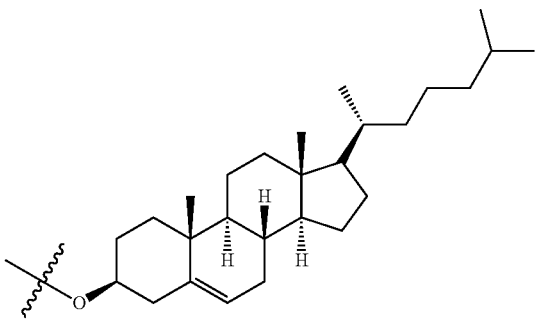

Additional embodiments include a cationic lipid having a head group, one or more hydrophobic tails, and a linker between the head group and the one or more tails. The head group can include an amine; for example an amine having a desired $pK_a$. The $pK_a$ can be influenced by the structure of the lipid, particularly the nature of head group; e.g., the presence, absence, and location of functional groups such as anionic functional groups, hydrogen bond donor functional groups, hydrogen bond acceptor groups, hydrophobic groups (e.g., aliphatic groups), hydrophilic groups (e.g., hydroxyl or methoxy), or aryl groups. The head group amine can be a cationic amine; a primary, secondary, or tertiary amine; the head group can include one amine group (monoamine), two amine groups (diamine), three amine groups (triamine), or a larger number of amine groups, as in an oligoamine or polyamine. The head group can include a functional group that is less strongly basic than an amine, such as, for example, an imidazole, a pyridine, or a guanidinium group. The head group can be zwitterionic. Other head groups are suitable as well.

The one or more hydrophobic tails can include two hydrophobic chains, which may be the same or different. The tails can be aliphatic, for example, they can be composed of carbon and hydrogen, either saturated or unsaturated but without aromatic rings. The tails can be fatty acid tails. Some such groups include octanyl, nonanyl, decyl, lauryl, myristyl, palmityl, stearyl, α-linoleyl, stearidonyl, linoleyl, γ-linolenyl, arachadonyl, and oleyl. Other hydrophobic tails are suitable as well.

The linker can include, for example, a glyceride linker, an acyclic glyceride analog linker, or a cyclic linker (including a spiro linker, a bicyclic linker, and a polycyclic linker). The linker can include functional groups such as an ether, an ester, a phosphate, a phosphonate, a phosphorothioate, a sulfonate, a disulfide, an acetal, a ketal, an imine, a hydrazone, or an oxime. Other linkers and functional groups are suitable as well.

In one embodiment, the cationic lipid is a racemic mixture. In another embodiment, the cationic lipid is enriched in one diastereomer, e.g. the cationic lipid has at least 95%, at least 90%, at least 80% or at least 70% diastereomeric excess. In yet another embodiment, the cationic lipid is enriched in one enantiomer, e.g. the lipid has at least 95%, at least 90%, at least 80% or at least 70% enantiomer excess. In yet another embodiment, the cationic lipid is chirally pure, e.g. is a single optical isomer. In yet another embodiment, the cationic lipid is enriched for one optical isomer.

Where a double bond is present (e.g., a carbon-carbon double bond or carbon-nitrogen double bond), there can be isomerism in the configuration about the double bond (i.e. cis/trans or E/Z isomerism). Where the configuration of a double bond is illustrated in a chemical structure, it is understood that the corresponding isomer can also be present. The amount of isomer present can vary, depending on the relative stabilities of the isomers and the energy required to convert between the isomers. Accordingly, some double bonds are, for practical purposes, present in only a single configuration, whereas others (e.g., where the relative stabilities are similar and the energy of conversion low) may be present as inseparable equilibrium mixture of configurations.

In some cases, a double-bonded unsaturation can be replaced by a cyclic unsaturation. The cyclic unsaturation can be a cycloaliphatic unsaturation, e.g., a cyclopropyl, cyclobutyl, cyclopentyl, cyclohexyl, cycloheptyl, or cyclooctyl group. In some cases, the cyclic group can be a polycyclic group, e.g., a bicyclic group or tricyclic group. A bicyclic group can be bridged, fused, or have a spiro structure.

In some cases, a double bond moiety can be replaced by a cyclopropyl moiety, e.g.,

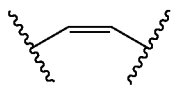 [SMILES: */C=C\*]

can be replaced by

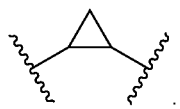 [SMILES: *C1CC1*]

For example, the moiety shown below has two carbon-carbon double bonds, each of which can independently be replaced by a cyclic moiety, e.g., a cyclopropyl moiety. Thus, substitutes for:

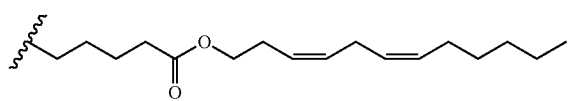 [SMILES: *CCCCC(=O)OCC/C=C\C/C=C\CCCCC]

can include:

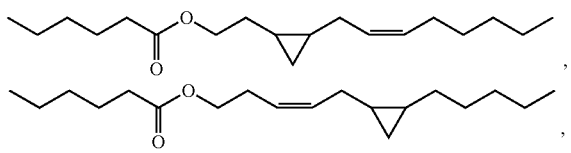

and

-continued

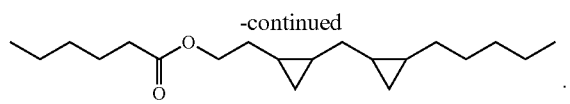

For further example, substitutes for

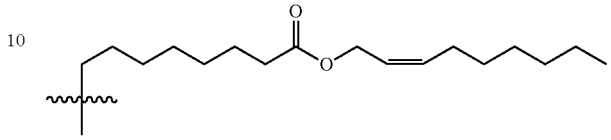

include:

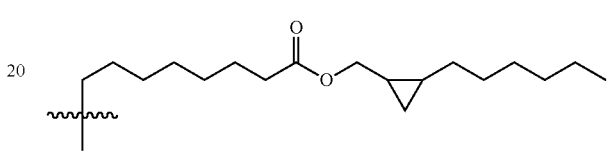

For further example, substitutes for

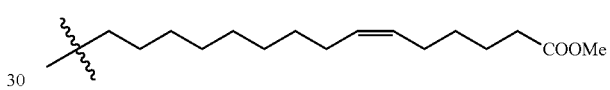

include:

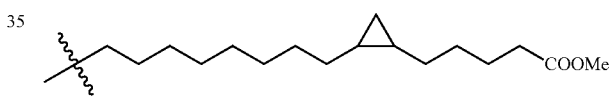

For further example, substitutes for

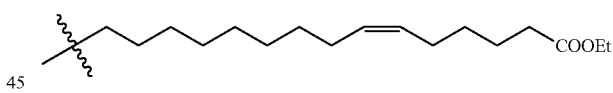

include:

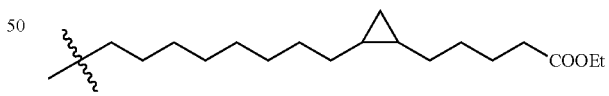

The cationic lipid includes one or more biodegradable groups. The biodegradable group(s) include one or more bonds that may undergo bond breaking reactions in a biological environment, e.g., in an organism, organ, tissue, cell, or organelle. Functional groups that contain a biodegradable bond include, for example, esters, dithiols, and oximes. Biodegradation can be a factor that influences the clearance of the compound from the body when administered to a subject. Biodegradation can be measured in a cell based assay, where a formulation including a cationic lipid is exposed to cells, and samples are taken at various time points. The lipid fractions can be extracted from the cells and separated and analyzed by LC-MS. From the LC-MS data, rates of biodegradation (e.g., as $t_{1/2}$ values) can be measured.

For example, the compound

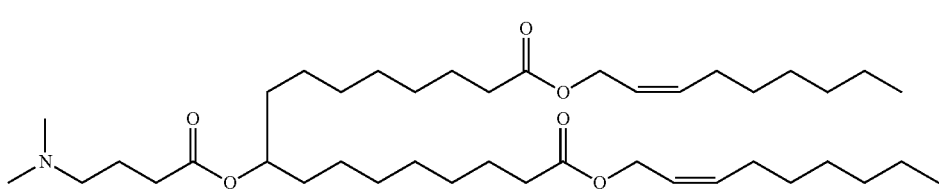
Compound 1 includes an ester linkage in each aliphatic chain, which can undergo hydrolysis in a biological environment, for example, when exposed to, e.g., a lipase or an esterase. The structure of the compound, of course, influences the rate at which the compound undergoes biodegradation. Thus, a related compound such as

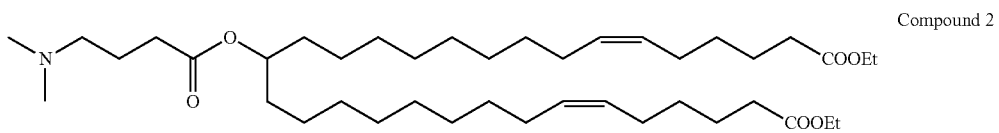 [SMILES: CCOC(=O)CCCC/C=C\CCCCCCCCC(CCCCCCCC/C=C\CCCCC(=O)OCC)OC(=O)CCCN(C)C]
Compound 2 would be expected to exhibit a different rate of biodegradation. Greater effects on that rate would be expected from changes in the structure of the compound at the site of hydrolysis. One modification that can influence the rate of hydrolysis, and thereby influence the rate of biodegradation and clearance from a subject's body, is to make the leaving group of the hydrolysis reaction have a primary, rather than secondary, alcohol.

For example, without wishing to be bound by theory, Compounds 1 and 2 shown above may be metabolized as shown in FIG. 2.

In one embodiment, a cationic lipid of any of the embodiments described herein has an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

In another embodiment, a cationic lipid of any of the embodiments described herein containing a biodegradable group or groups has an in vivo half life ($t_{1/2}$) (e.g., in the liver, spleen or plasma) of less than about 10% (e.g., less than about 7.5%, less than about 5%, less than about 2.5%) of that for the same cationic lipid without the biodegradable group or groups.

Some cationic lipids can be conveniently represented as a hydrophobic group combined with a headgroup. By way of example, the compound:

can be thought of as a combination of a headgroup and a hydrophobic group as follows:

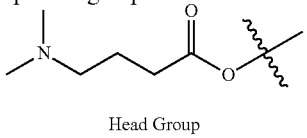
Head Group

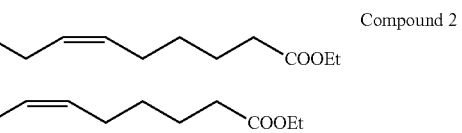

-continued

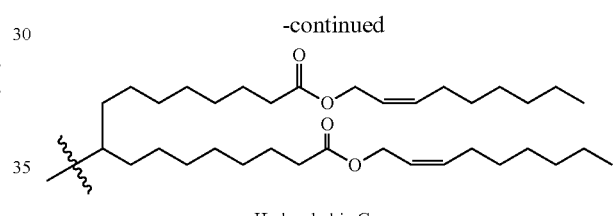
Hydrophobic Group

Thus, some suitable head groups include those depicted in Table 1:

TABLE 1

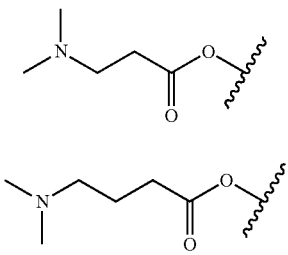

Compound 1

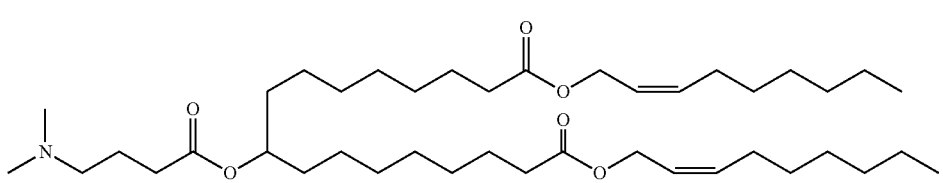

TABLE 1-continued
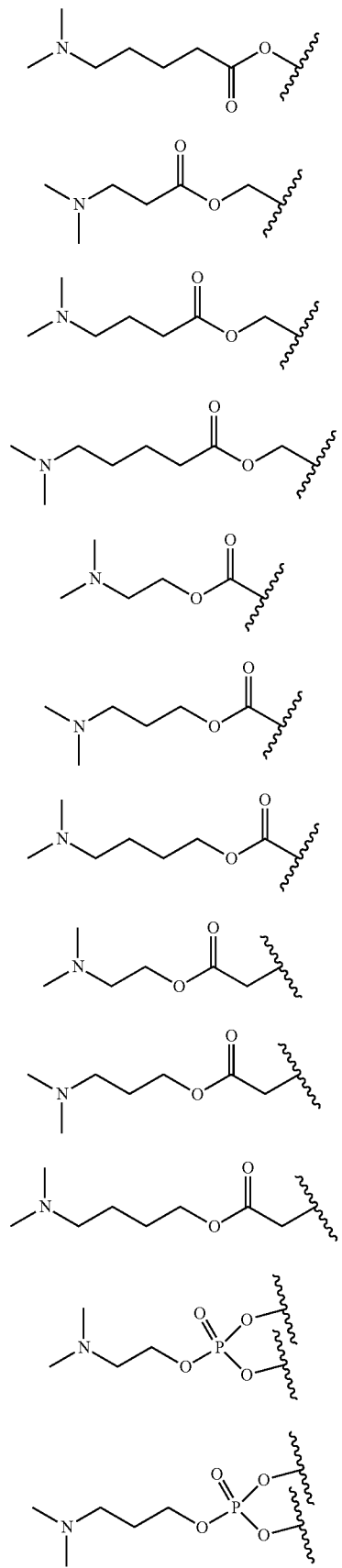
TABLE 1-continued
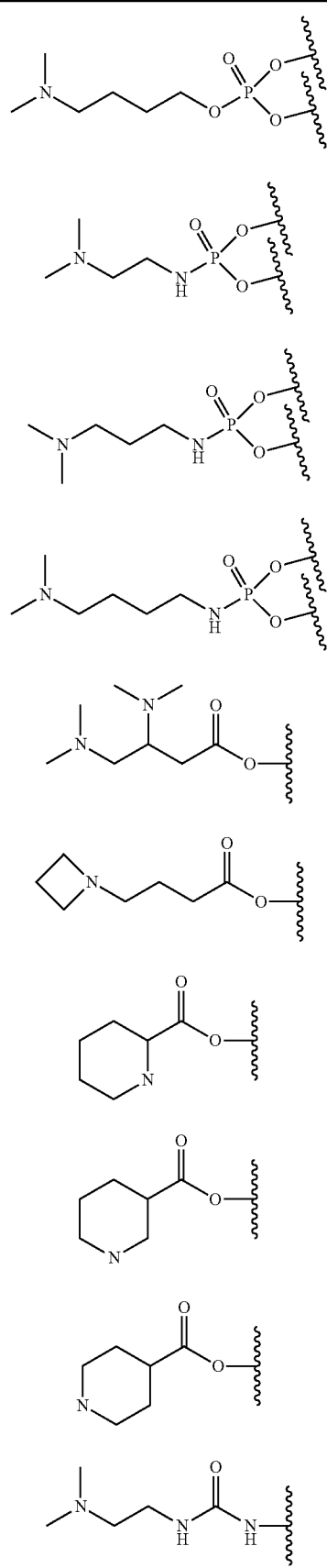

TABLE 1-continued

TABLE 1-continued

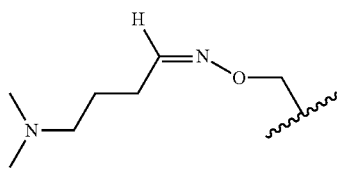 [SMILES: *CO/N=C\CCCN(C)C]

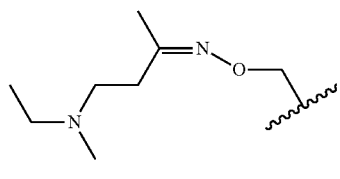 [SMILES: *CO/N=C(/C)CCN(C)CC]

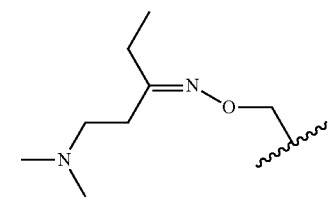 [SMILES: *CO/N=C(/CC)CCN(C)C]

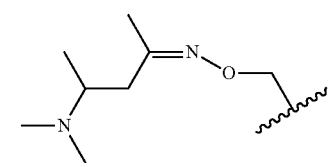 [SMILES: *CO/N=C(/C)CC(C)N(C)C]

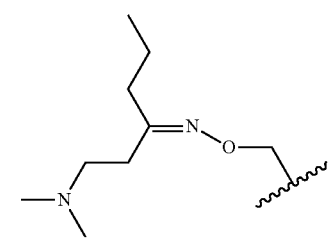 [SMILES: *CO/N=C(/CCC)CCN(C)C]

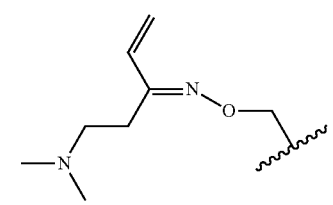 [SMILES: *CO/N=C(/C=C)CCN(C)C]

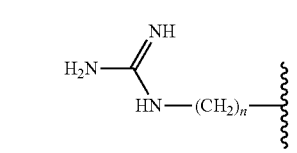

(where n is 0-5)

TABLE 1-continued

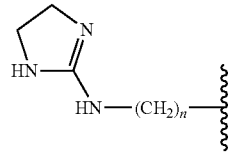

(where n is 0-5)

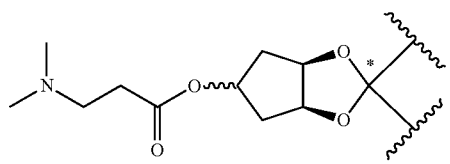

(the carbon with an asterisk is the tertiary carbon of the cation lipid and is not part of the head group)

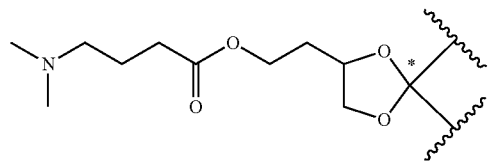

(the carbon with an asterisk is the tertiary carbon of the cation lipid and is not part of the head group)

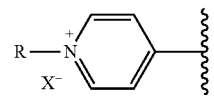

R = H, alkyl (e.g., methyl)
X = halogen (e.g., Cl)

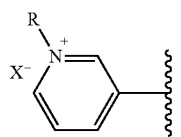

R = H, alkyl (e.g., methyl)
X = halogen (e.g., Cl)

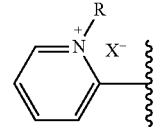

R = H, alkyl (e.g., methyl)
X = halogen (e.g., Cl)

Some suitable hydrophobic tail groups include those depicted in Table 2:

TABLE 2
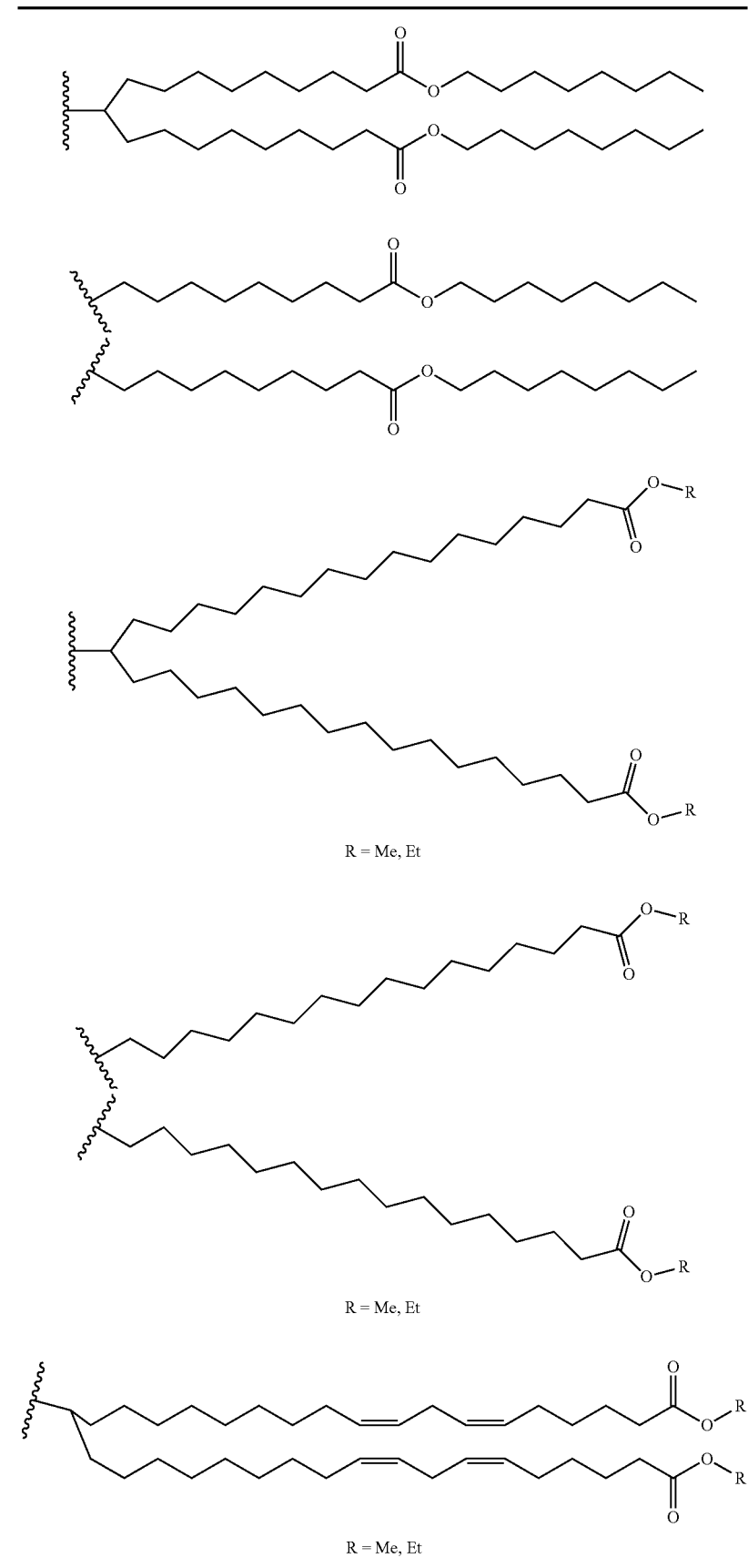

TABLE 2-continued
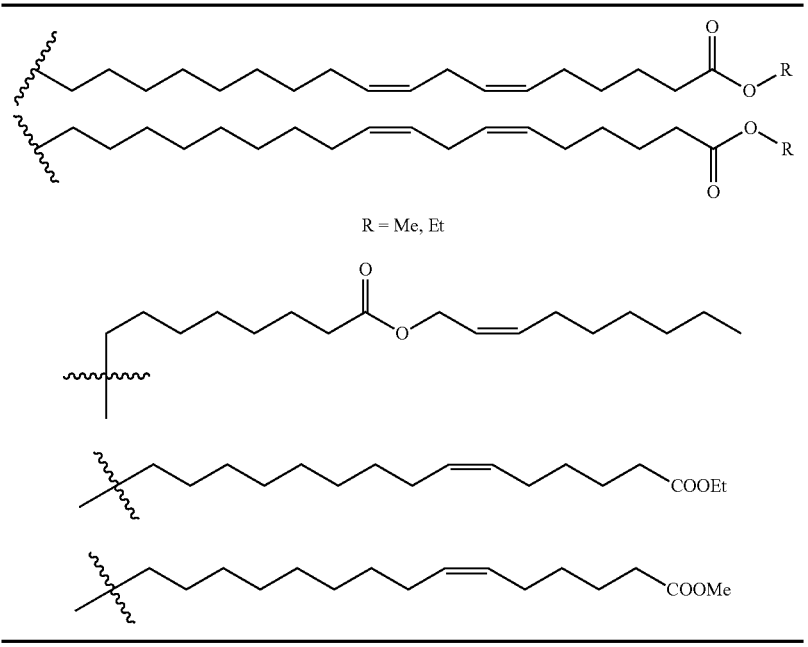
R = Me, Et
In another aspect, the present invention relates to a method of preparing a compound of any of formulas I-XXIII. Suitable exemplary synthetic methods are illustrated in Schemes A-G below. The variables in the schemes below are the same as those variables at the same position in formulas I-XXIII above.
Scheme A
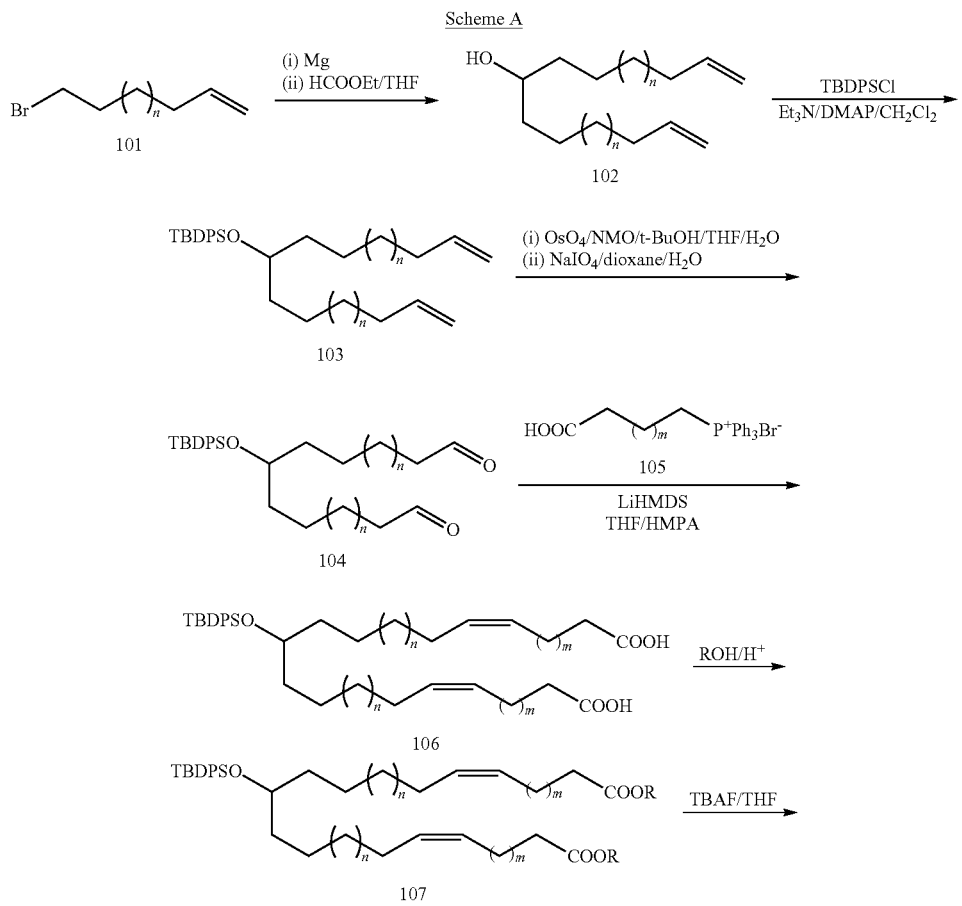

-continued
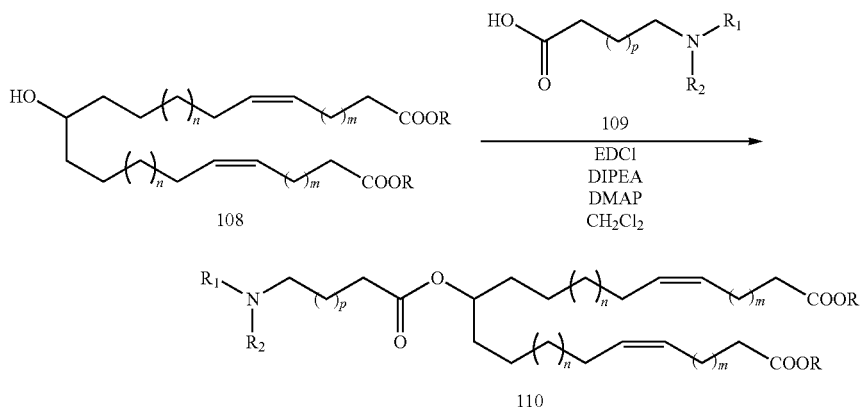
n = 0-8 m = 0-8 p = 0-3 R = R₁ = R₂ = Me, Et, Pr, Bn, t-Bu, Ph, alkyl, aryl, cycloalkyl, etc.
The lipid chain length and linker length in Scheme A can be varied. Additionally, the R group in the ester functionality and substituents on the nitrogen atom can be derivatized.
Scheme B
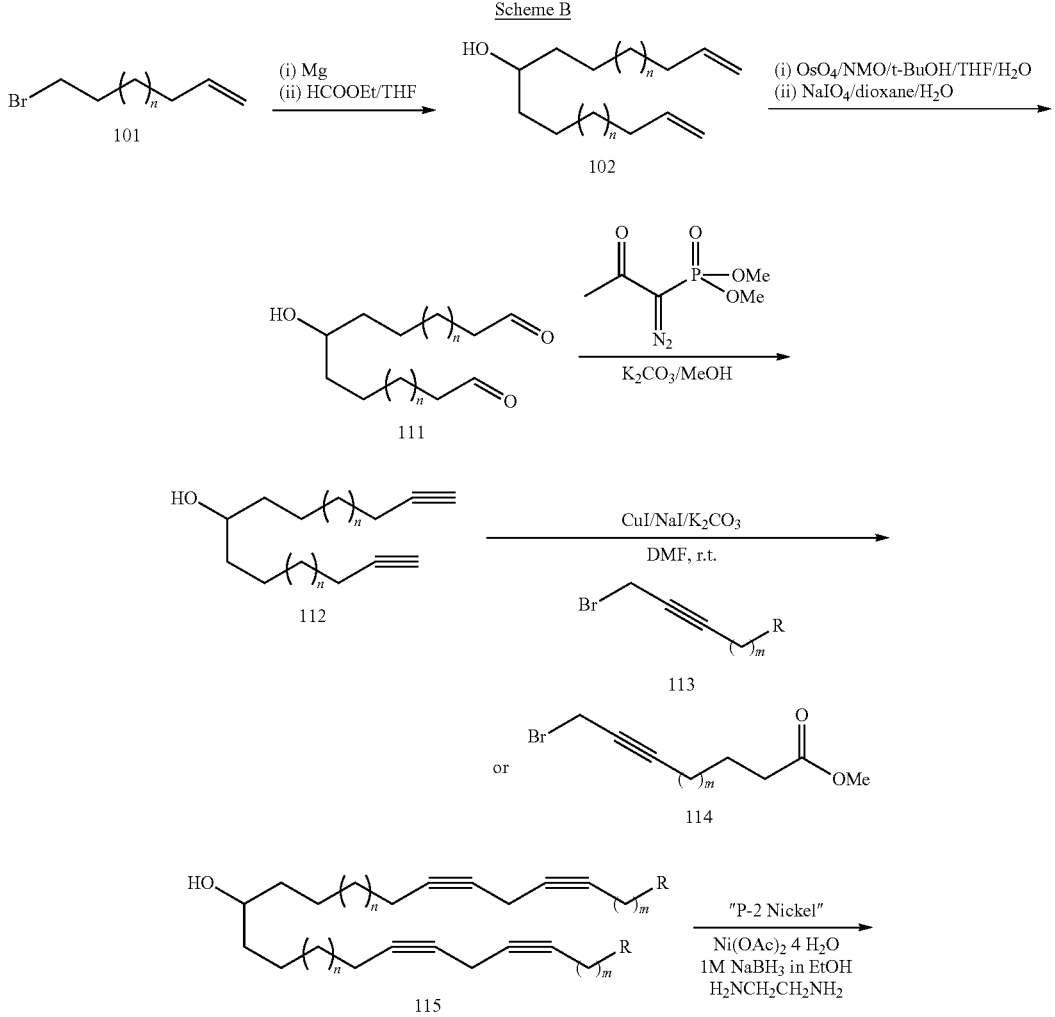

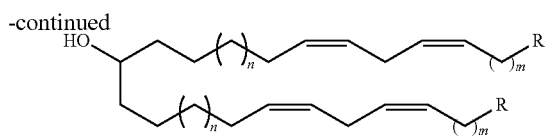

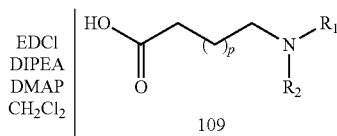

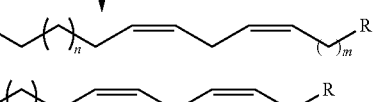

n = 0-8  m = 0-8  p = 0-3  R = Me, Et, Pr, Bn, t-Bu, Ph, alkyl, aryl, cycloalkyl, and alkyl esters, etc. $R_1 = R_2$ = Me, Et, Pr, Bn, t-Bu, Ph, alkyl, aryl, cycloalkyl As shown in Scheme B, copper-mediated coupling affords a di-yne containing lipid chain with terminal functional groups R, which can be reduced to generate di-ene containing lipid chains. The length of the linker and lipid chain can be varied, and the functional substituent groups (R, $R_1$, $R_2$) can be derivatized.

Scheme C

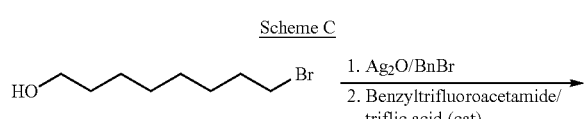
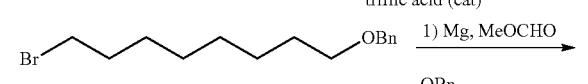
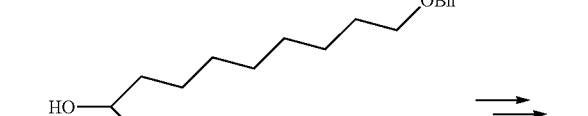
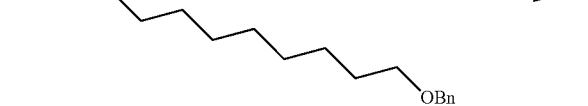
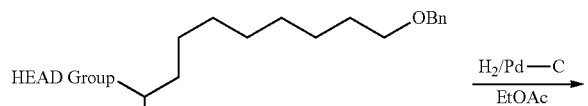
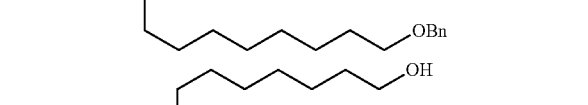

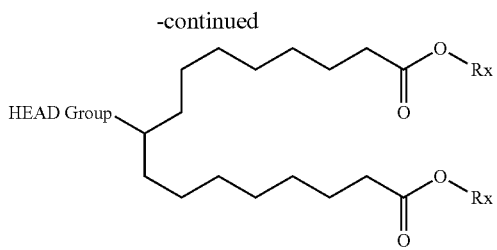

where Rx is alkyl, substituted alkyl, alkenyl, substituted alkenyl, alkynyl, substituted alkynyl, aryl, or substituted aryl, and HEAD Group is defined in Table 1.

The HEAD Group in Scheme C can be any head group disclosed herein (see, e.g., Table 1).

Scheme D

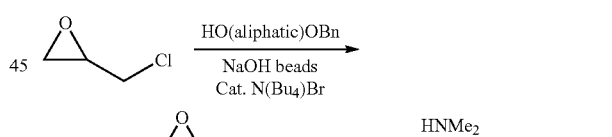
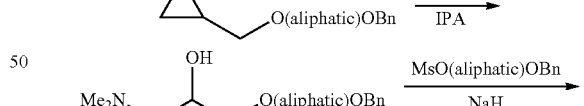
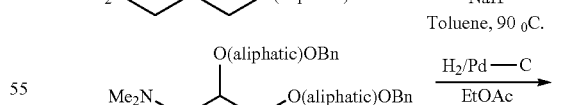
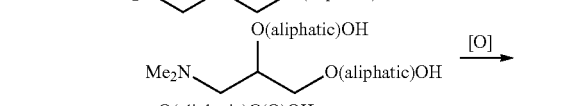
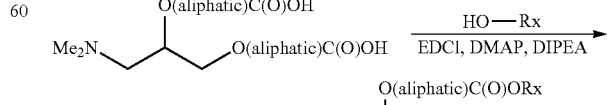

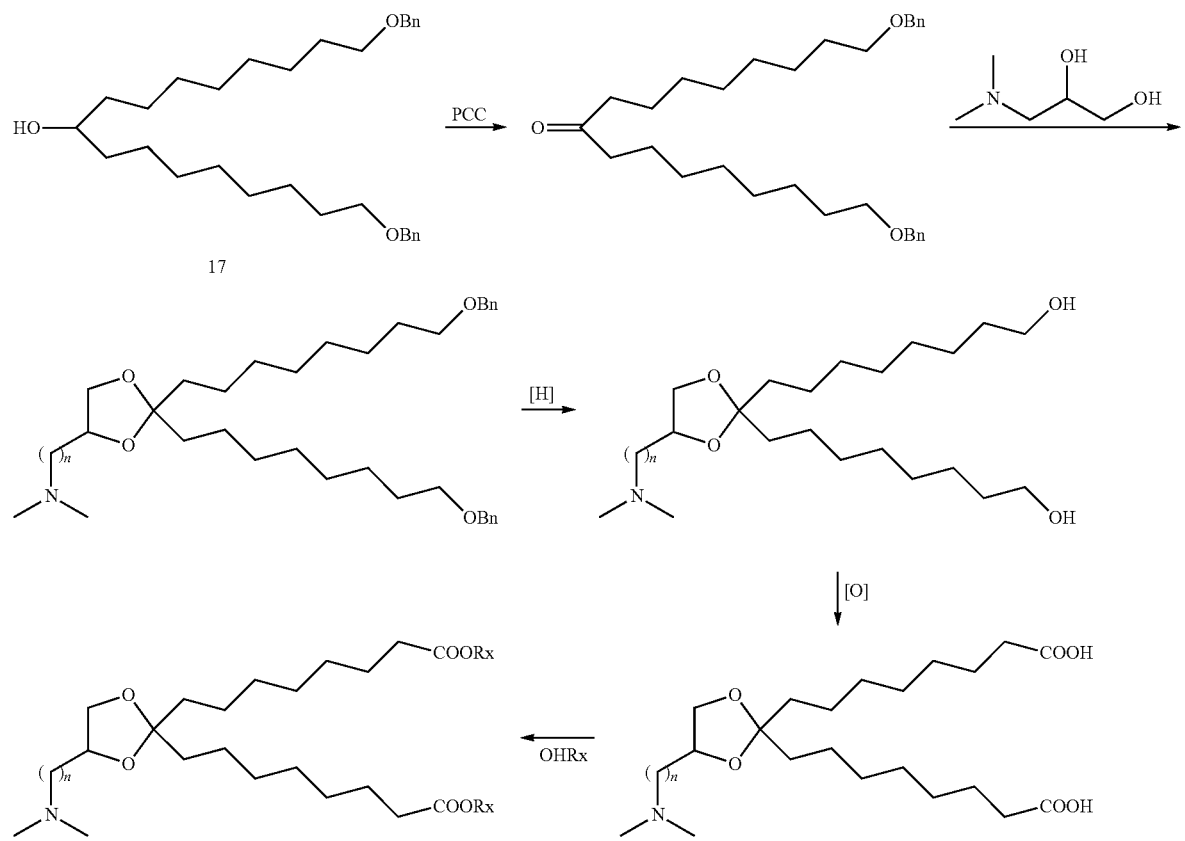
Scheme E
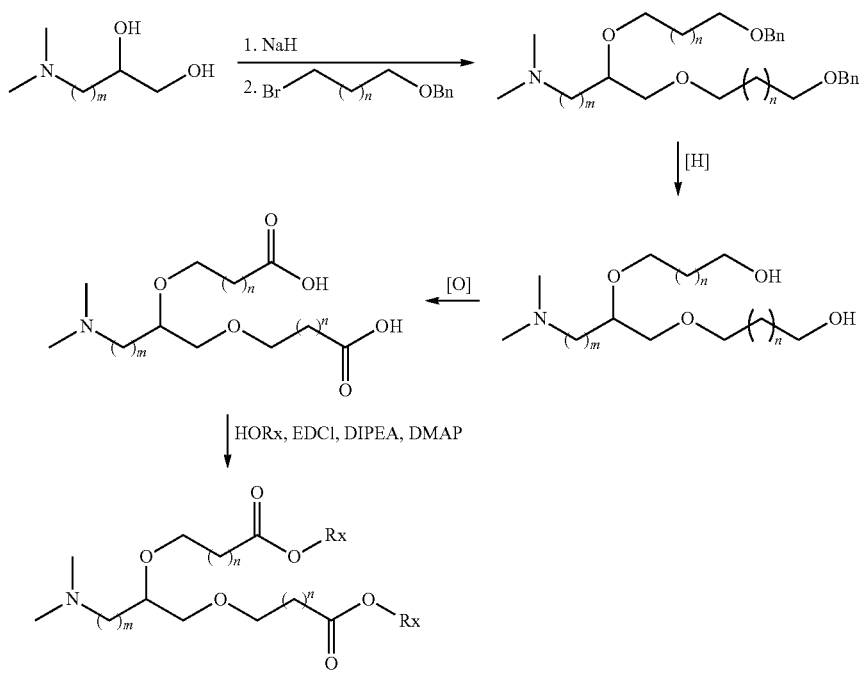
Scheme F

Scheme G
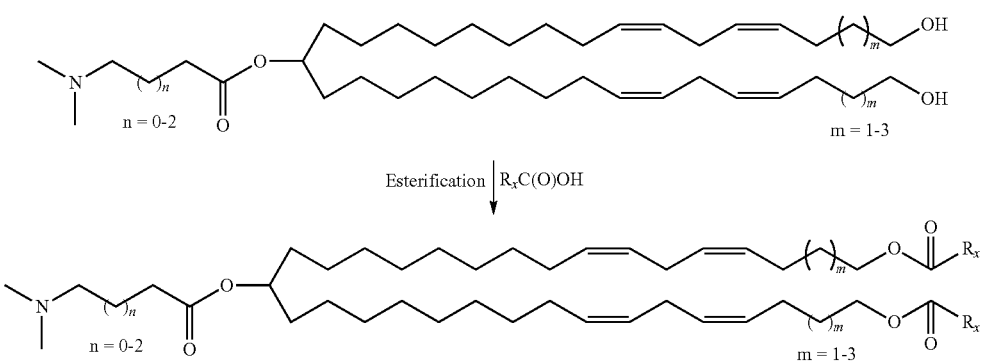
Examples of cationic lipids of the present invention include those shown in Tables 3-13 below, and salts thereof (including pharmaceutically acceptable salts thereof).
TABLE 3
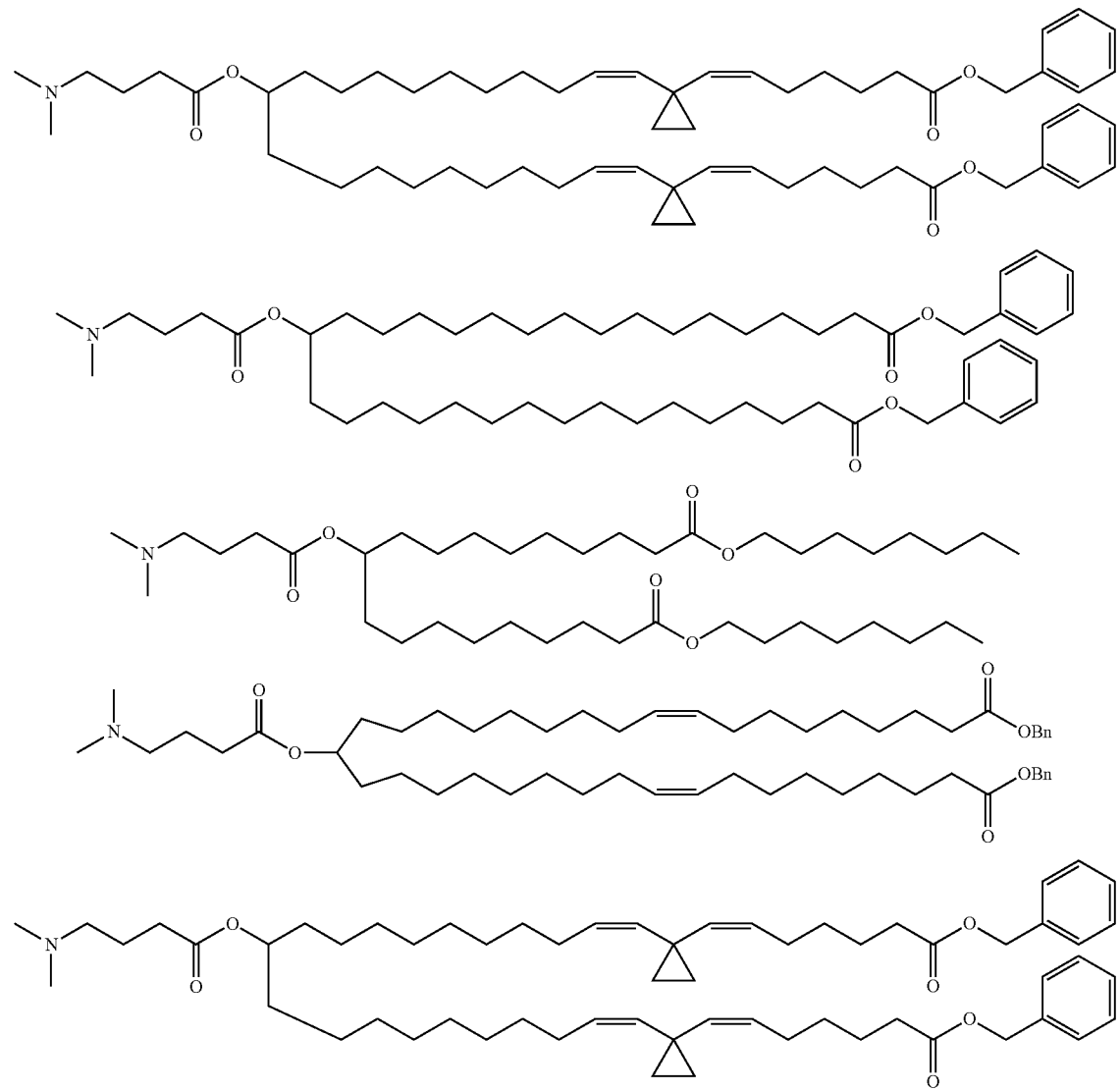

TABLE 4
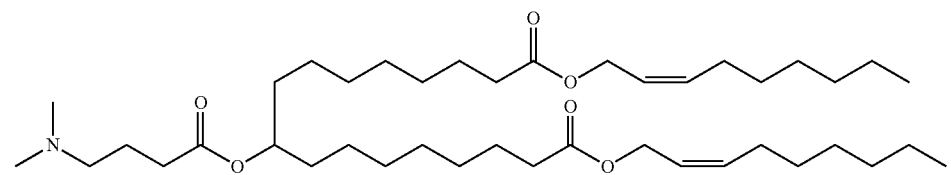 [SMILES: CCCCCC/C=C\COC(=O)CCCCCCCC(CCCCCCCC(=O)OC/C=C\CCCCCC)OC(=O)CCCN(C)C]
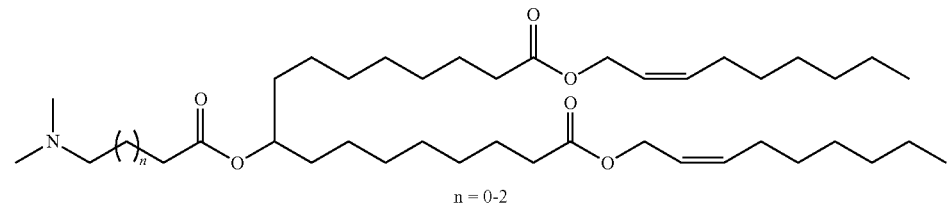
n = 0-2
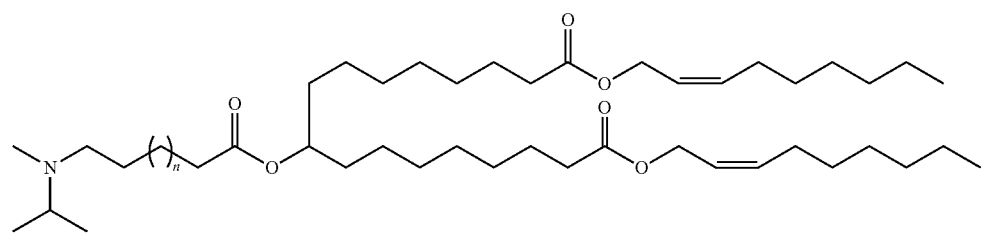
n = 0-2
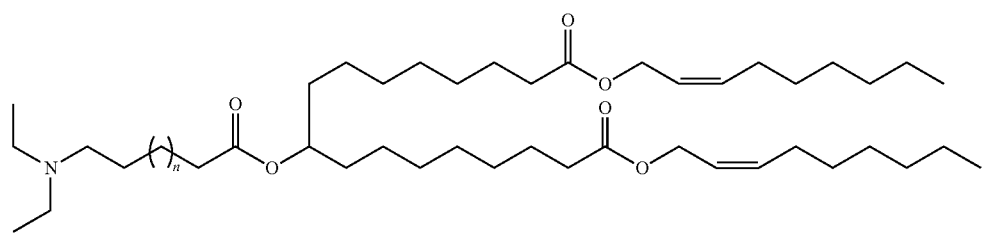
n = 0-2
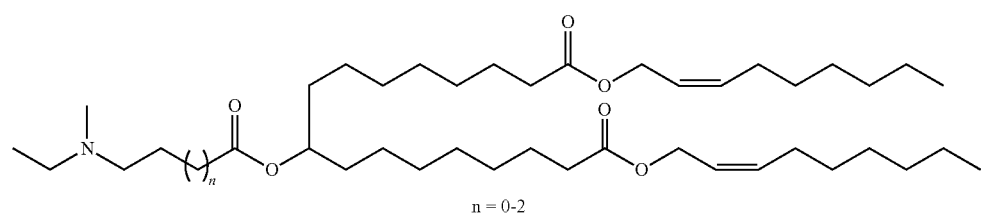
n = 0-2
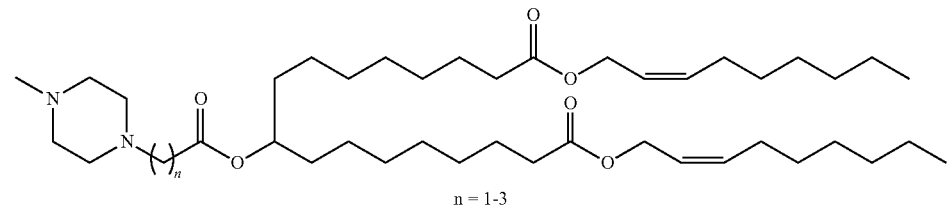
n = 1-3
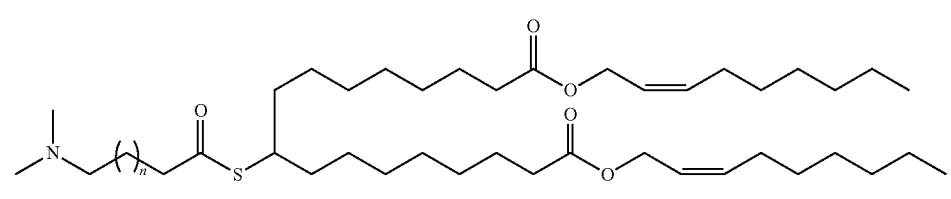
n = 0-2

TABLE 4-continued
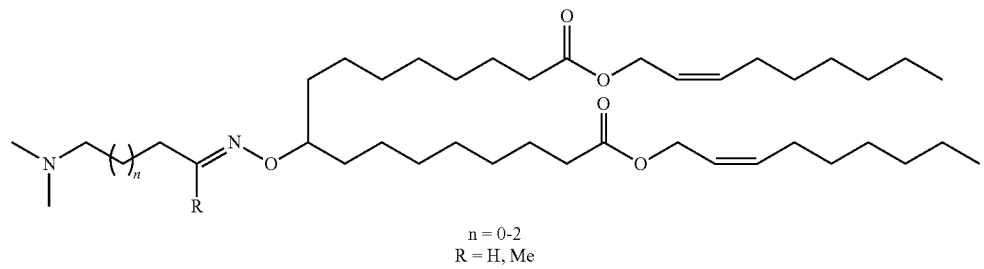
n = 0-2
R = H, Me
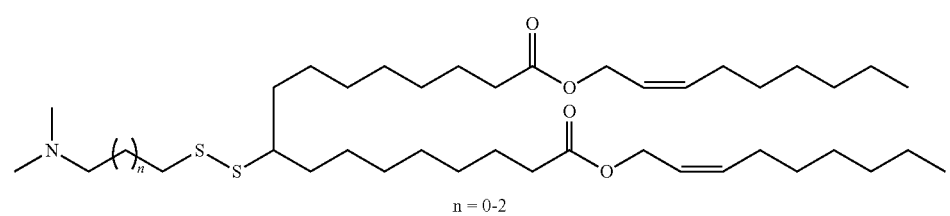
n = 0-2
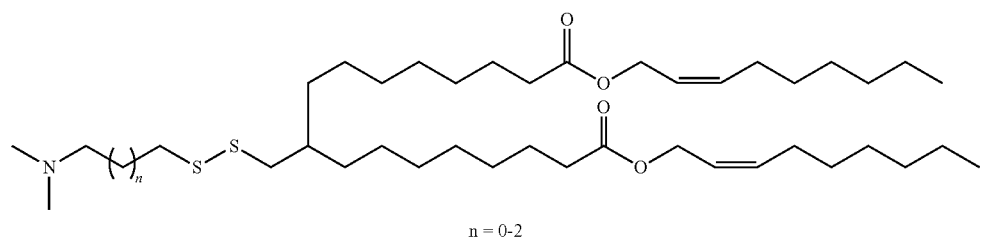
n = 0-2
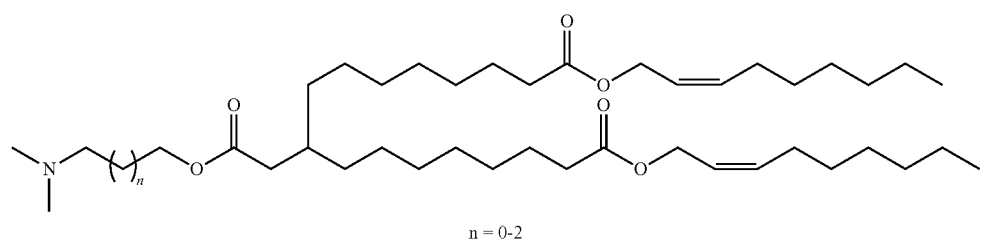
n = 0-2
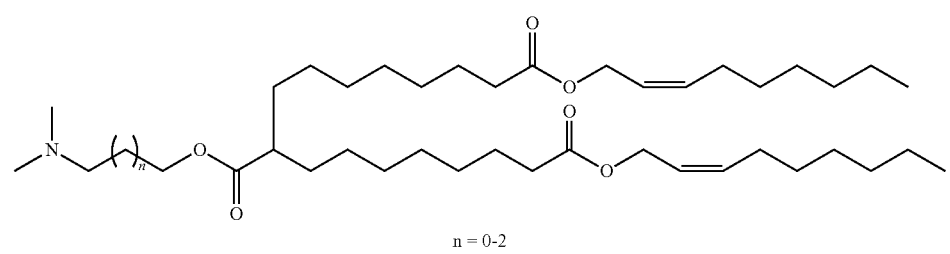
n = 0-2
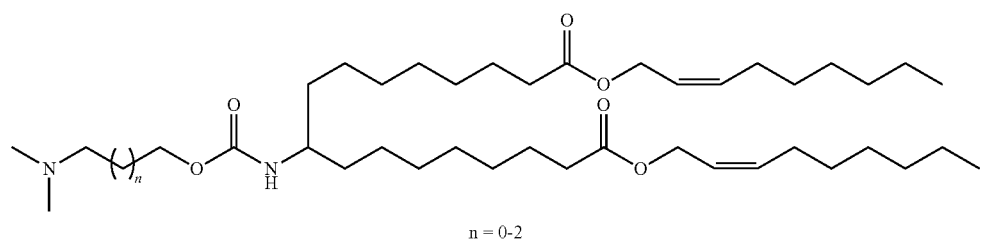
n = 0-2

TABLE 4-continued
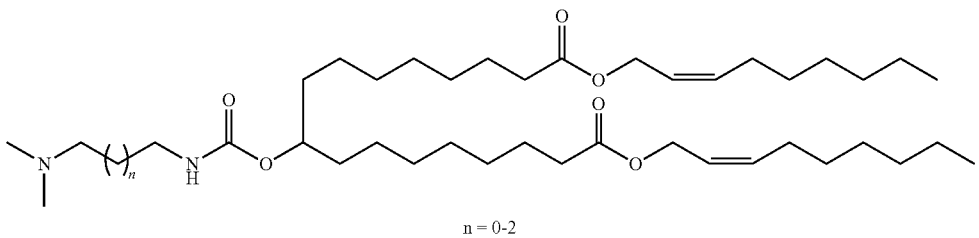
n = 0-2
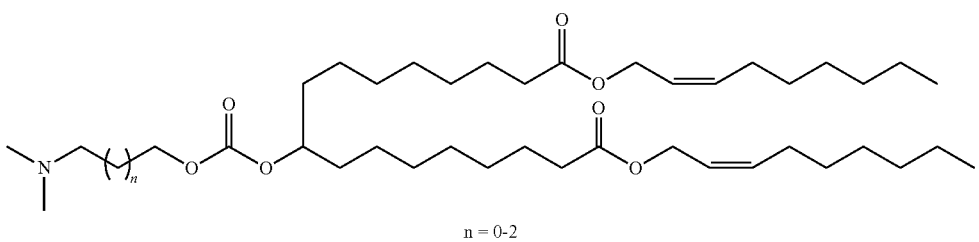
n = 0-2
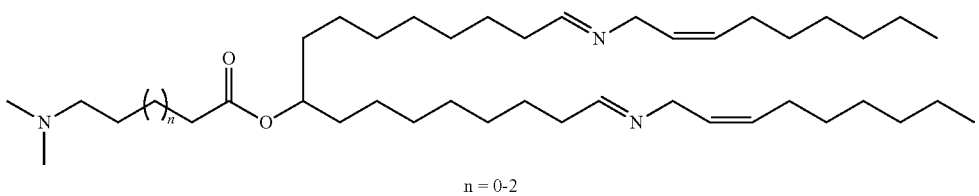
n = 0-2
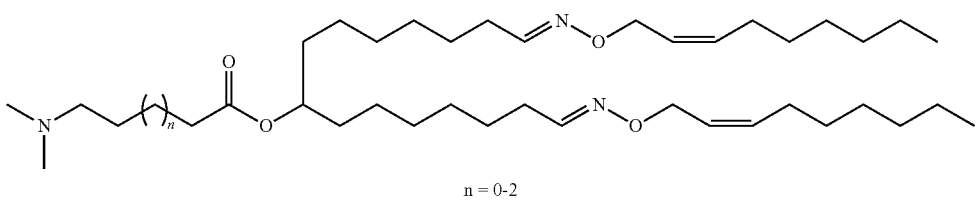
n = 0-2
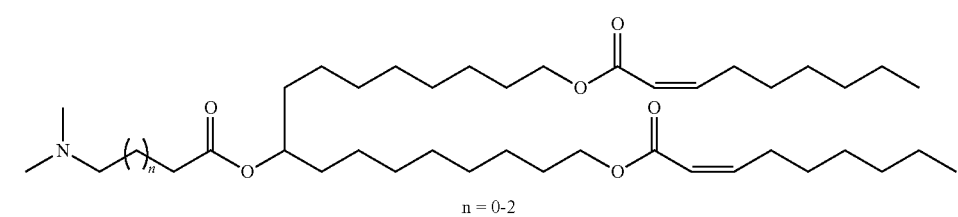
n = 0-2
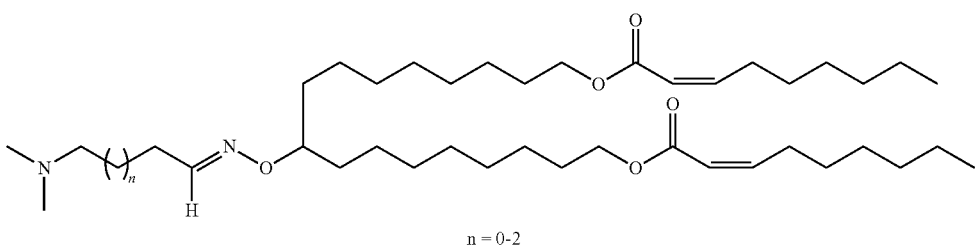
n = 0-2
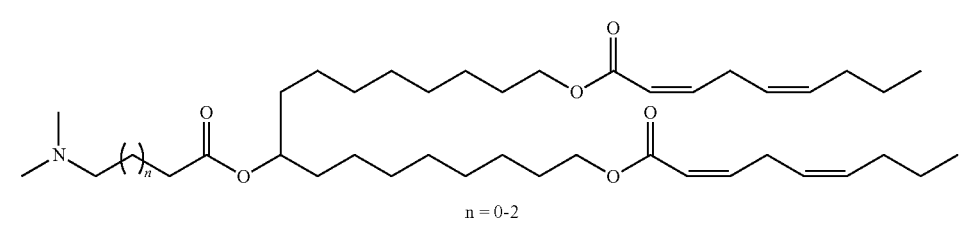
n = 0-2

TABLE 4-continued
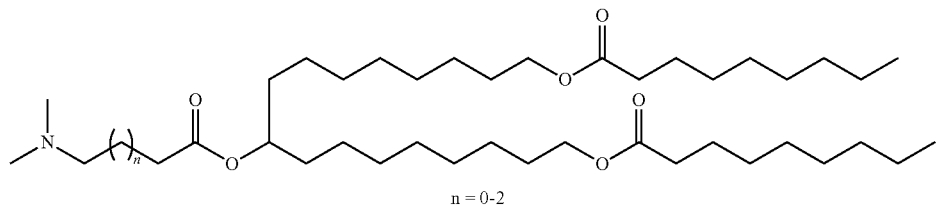
n = 0-2
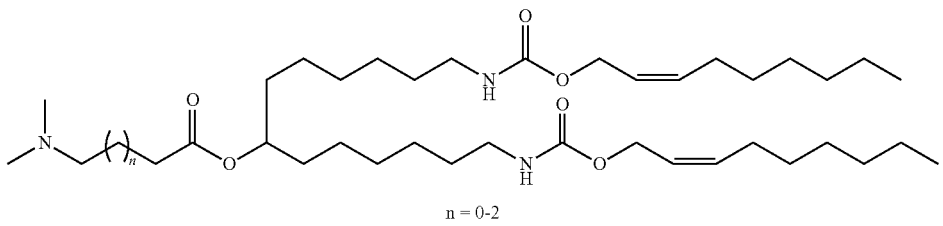
n = 0-2
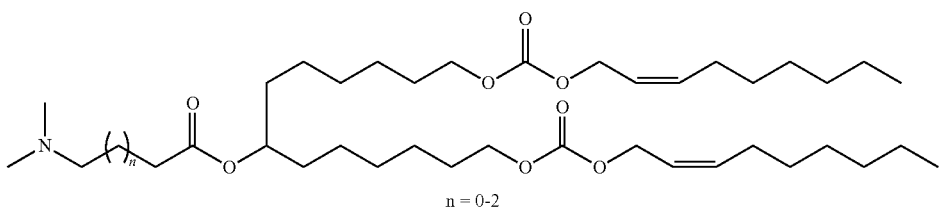
n = 0-2
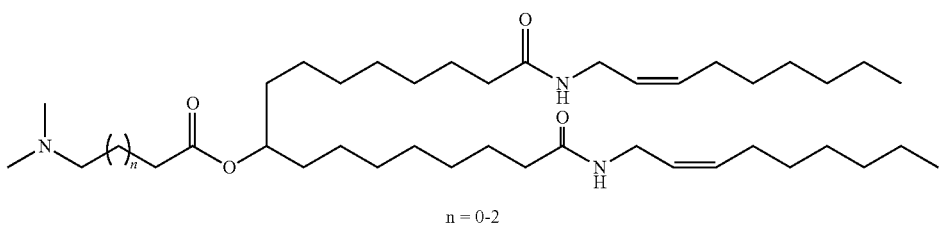
n = 0-2
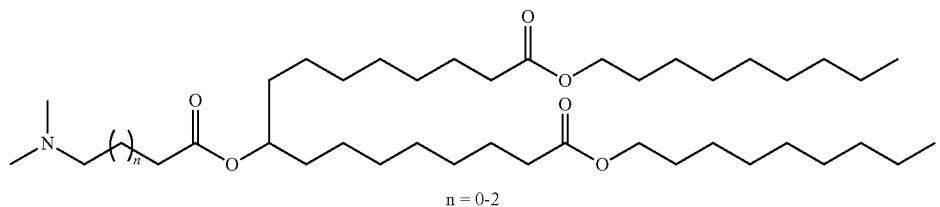
n = 0-2
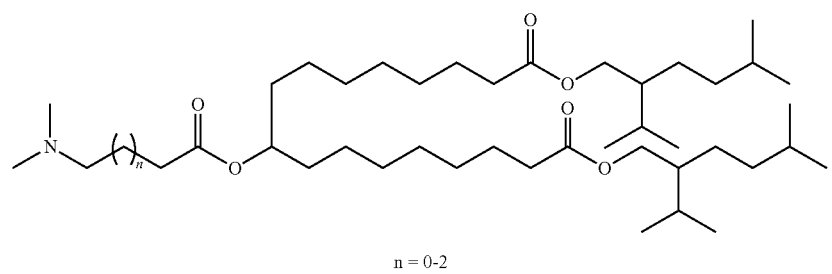
n = 0-2

TABLE 4-continued
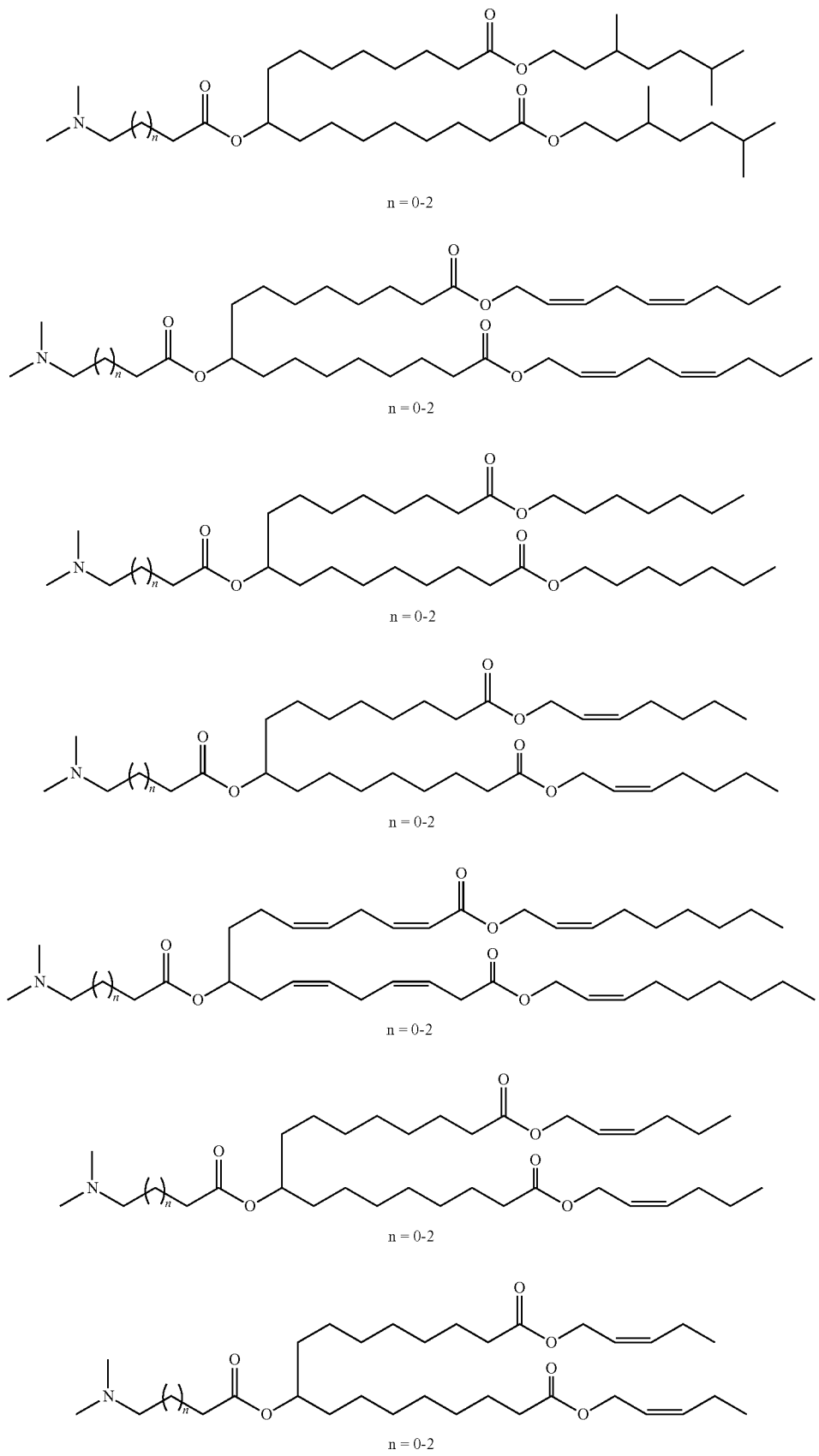

TABLE 4-continued
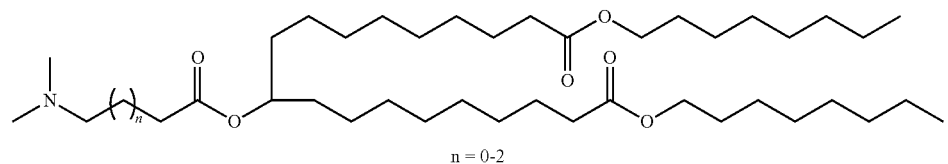
n = 0-2
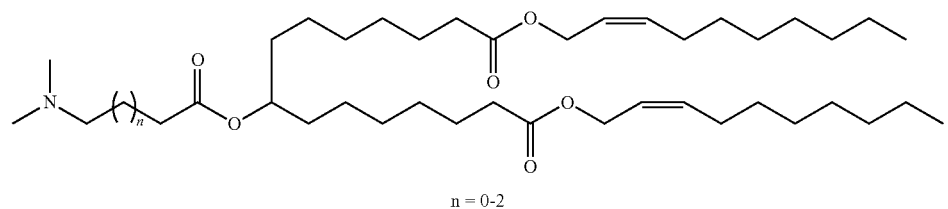
n = 0-2
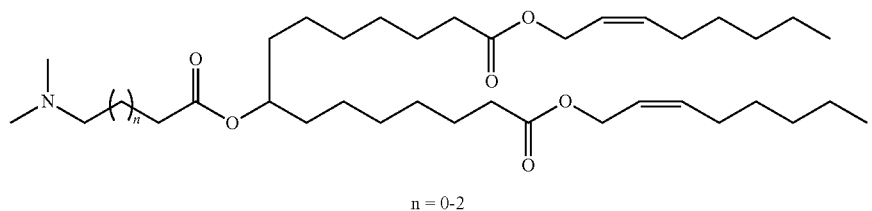
n = 0-2
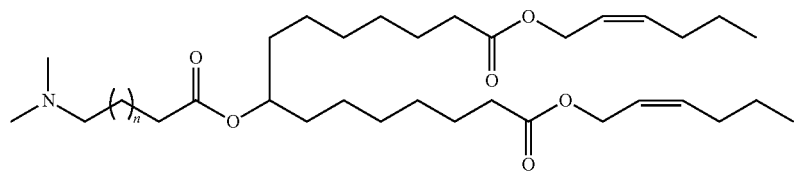
n = 0-2
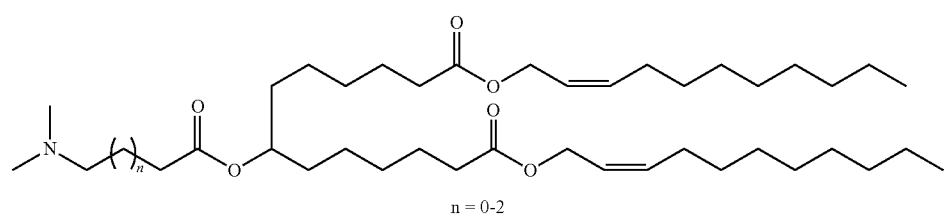
n = 0-2
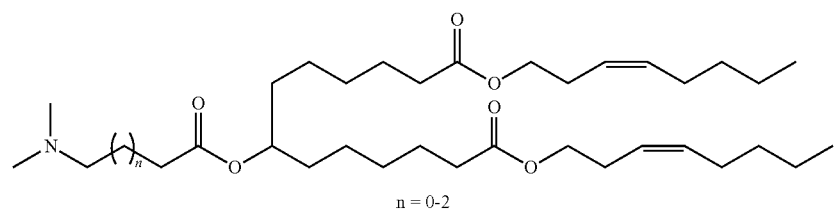
n = 0-2
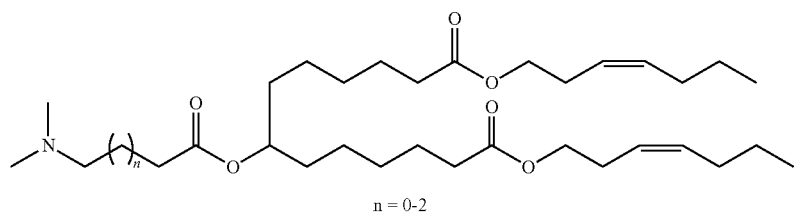
n = 0-2

TABLE 4-continued
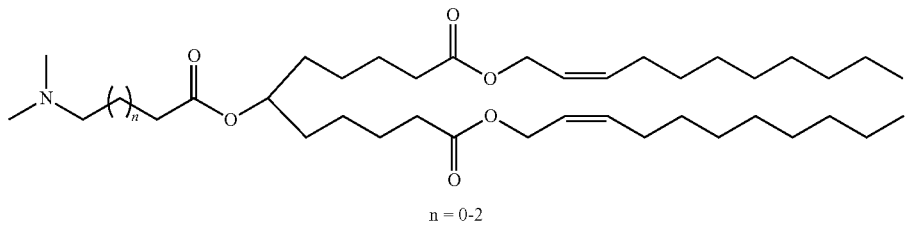
n = 0-2
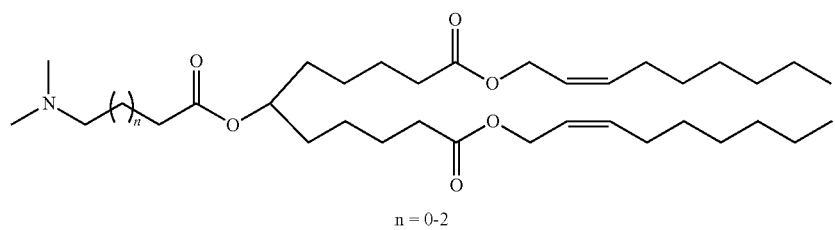
n = 0-2
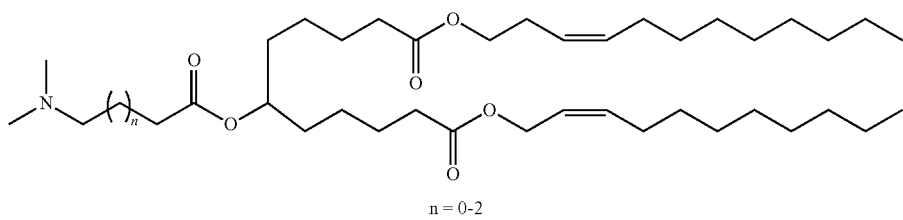
n = 0-2
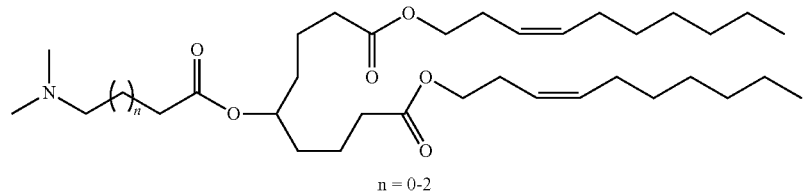
n = 0-2
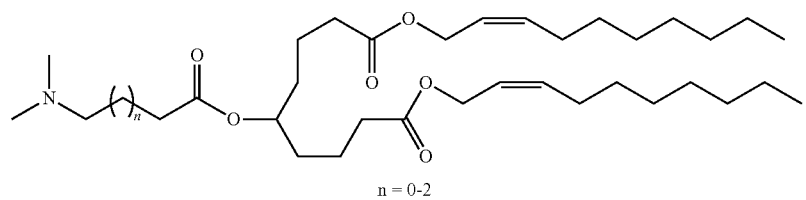
n = 0-2
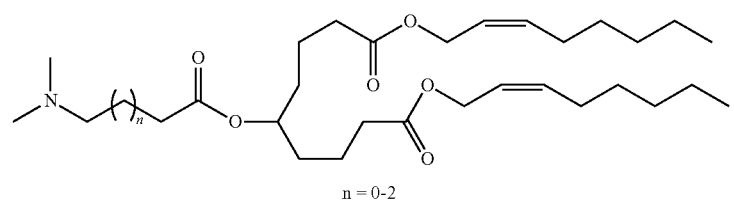
n = 0-2
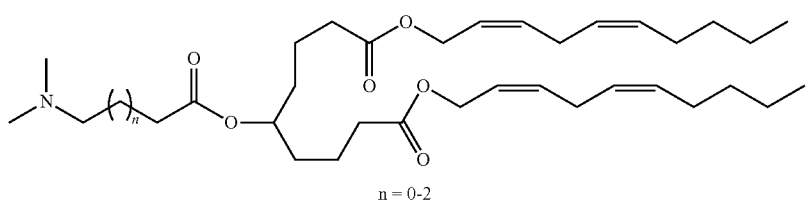
n = 0-2

TABLE 4-continued
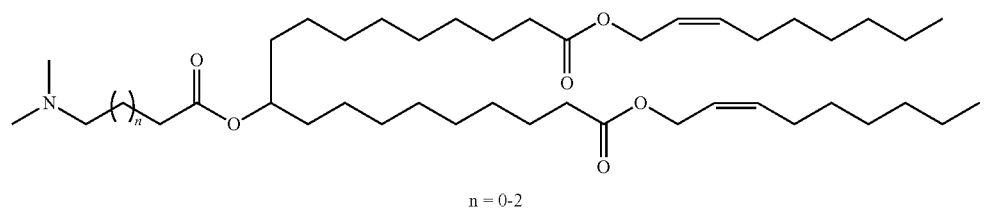
n = 0-2
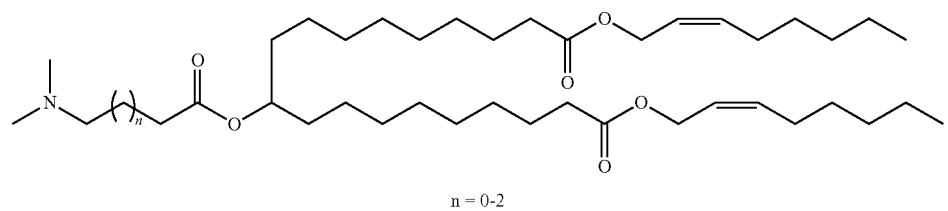
n = 0-2
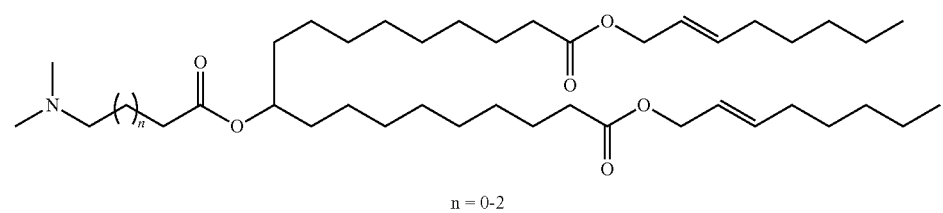
n = 0-2
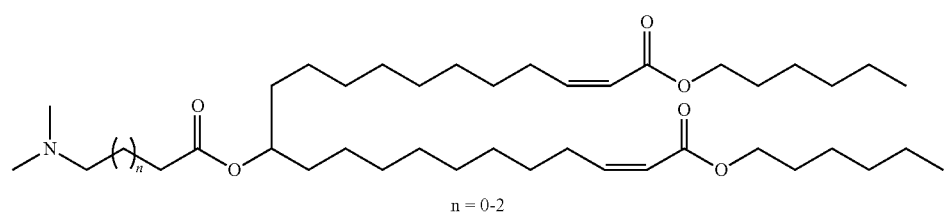
n = 0-2
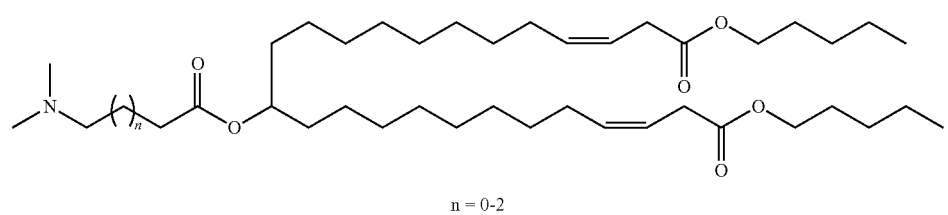
n = 0-2
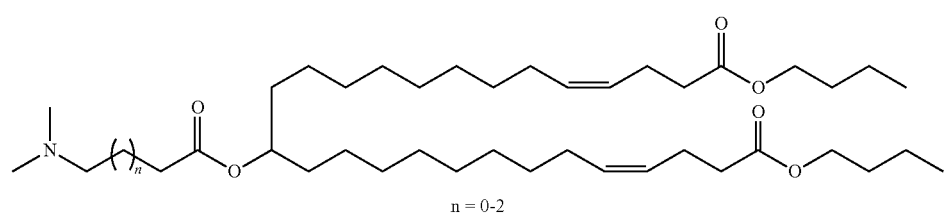
n = 0-2
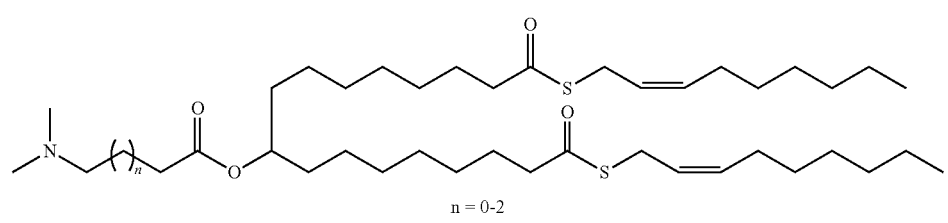
n = 0-2

TABLE 4-continued
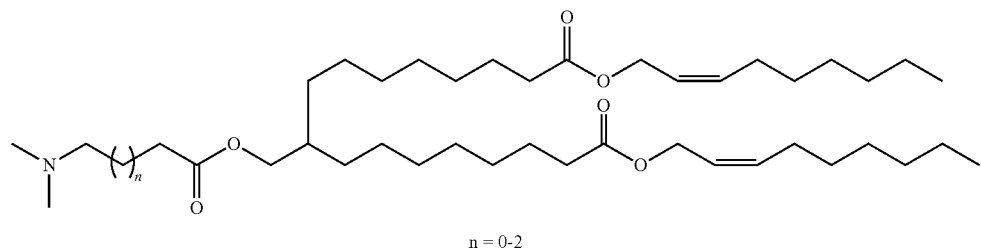
n = 0-2
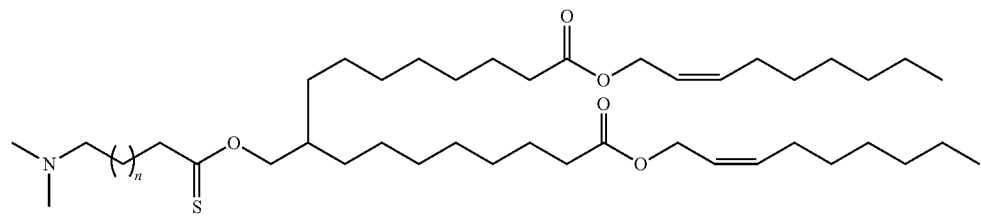
n = 0-2
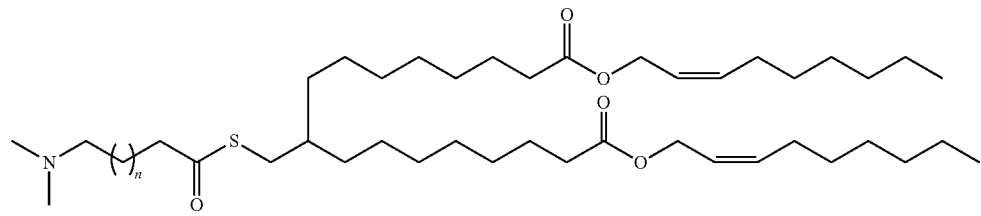
n = 0-2
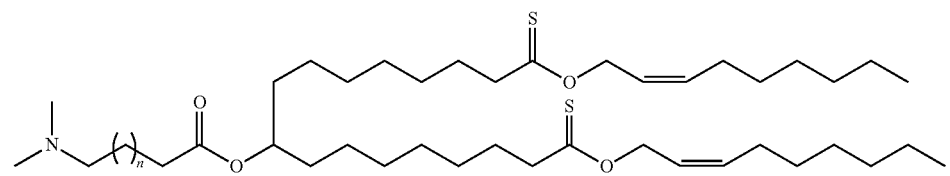
n = 0-2
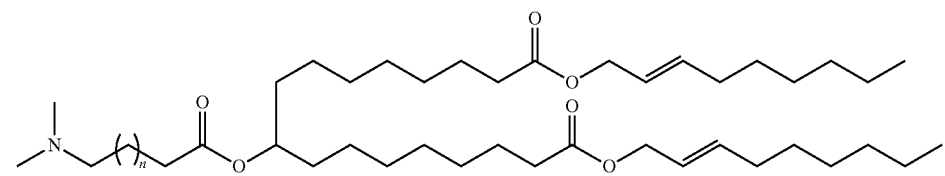
n = 0-2
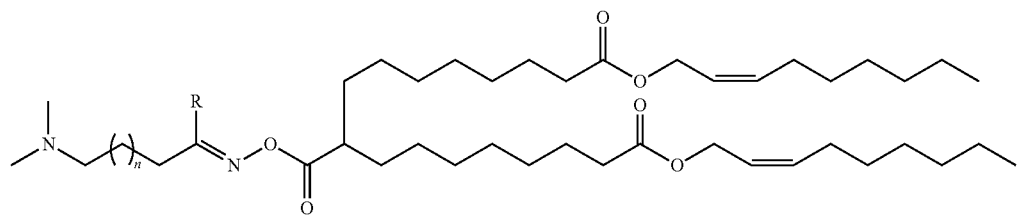
R = H, Me
n = 0-2

TABLE 4-continued
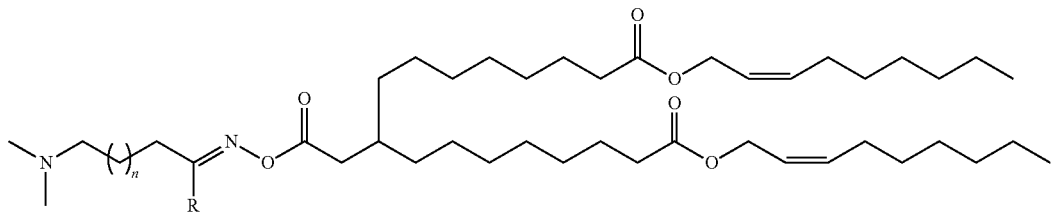
R = H, Me
n = 0-2
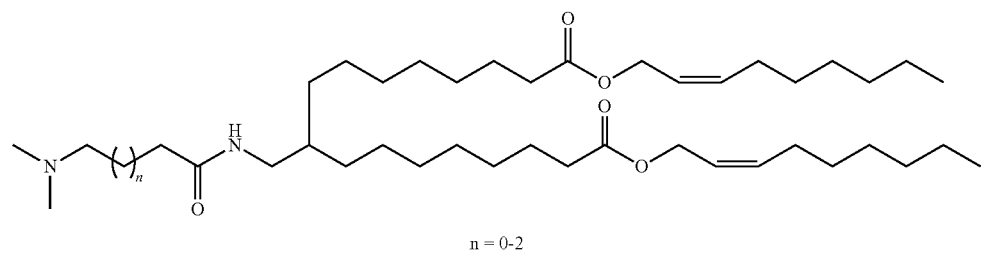
n = 0-2
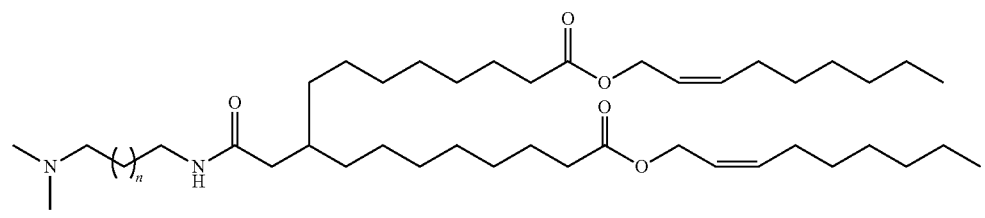
n = 0-2
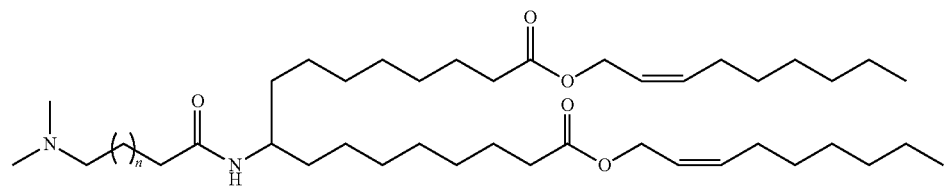
n = 0-2
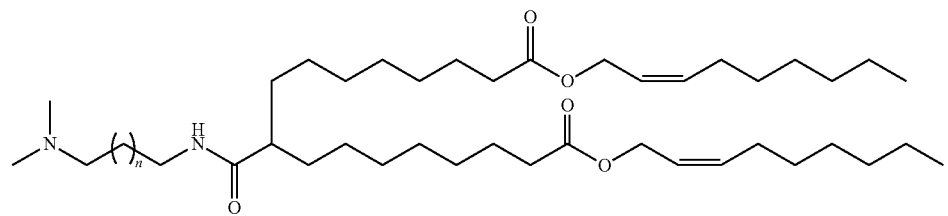
n = 0-2
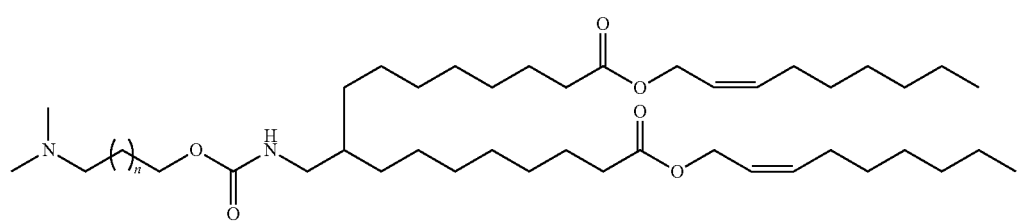
n = 0-2

TABLE 4-continued
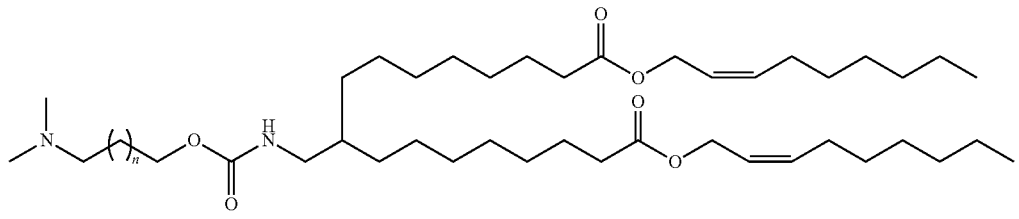
n = 0-2
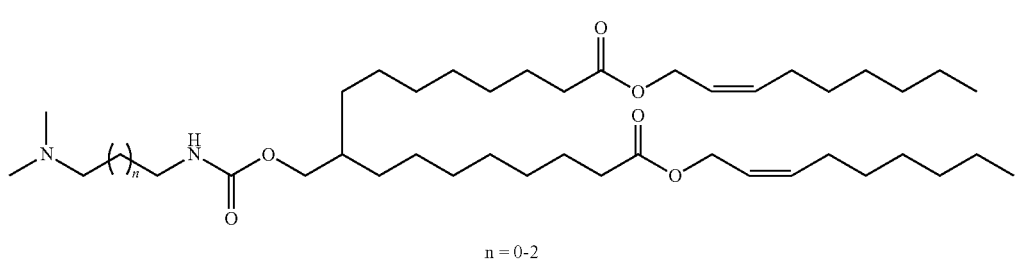
n = 0-2
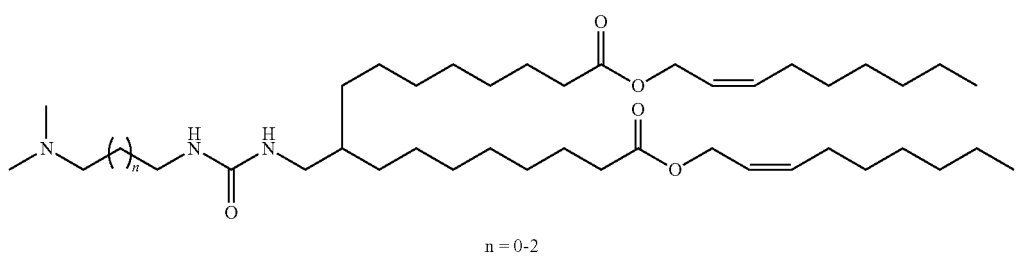
n = 0-2
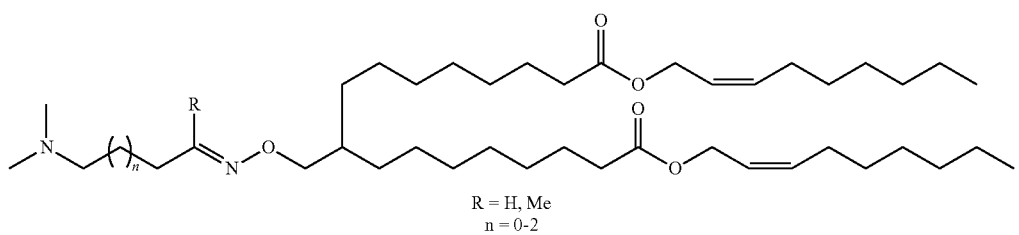
R = H, Me
n = 0-2
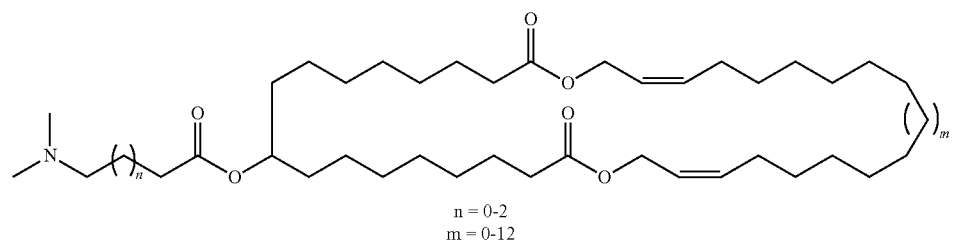
n = 0-2
m = 0-12
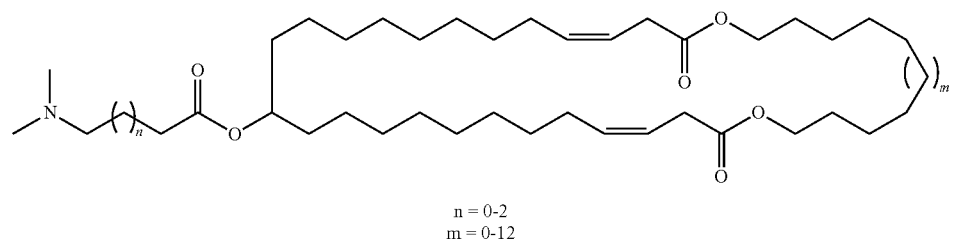
n = 0-2
m = 0-12

TABLE 4-continued
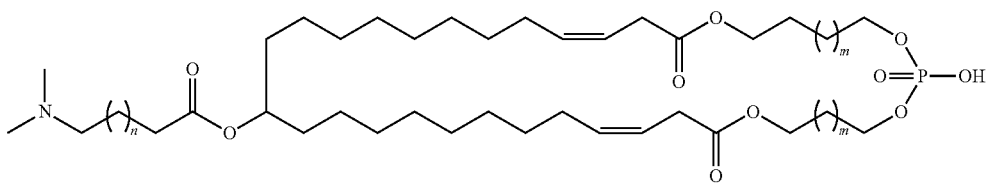
n = 0-2
m = 0-12
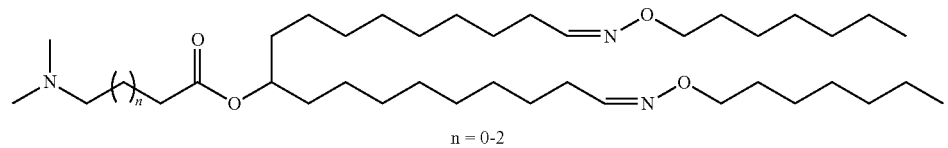
n = 0-2
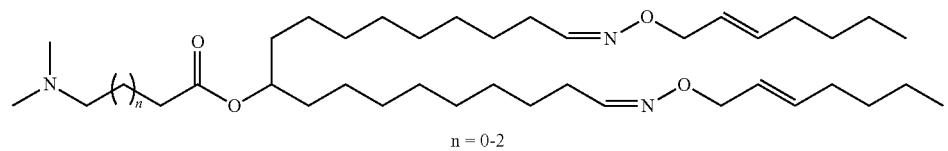
n = 0-2
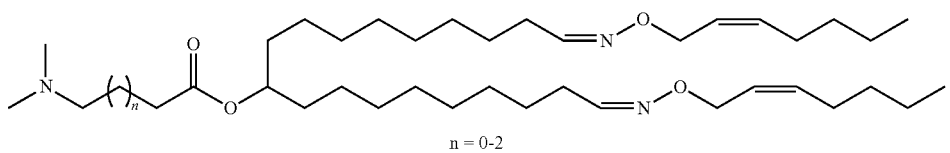
n = 0-2
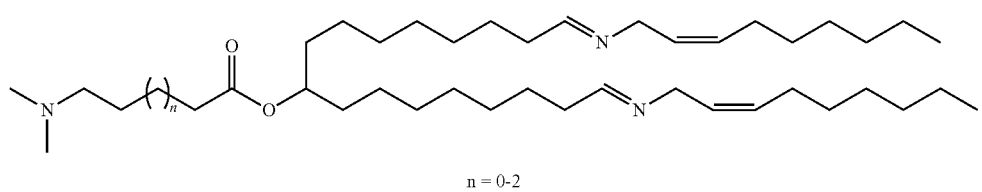
n = 0-2
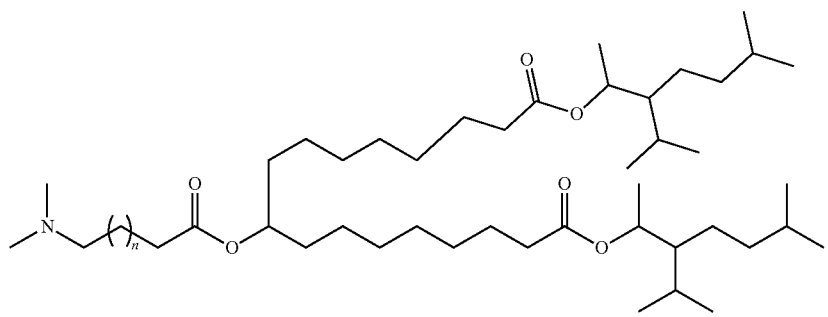
n = 0-2
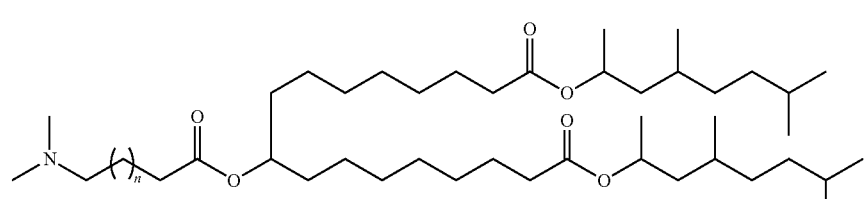
n = 0-2

TABLE 4-continued
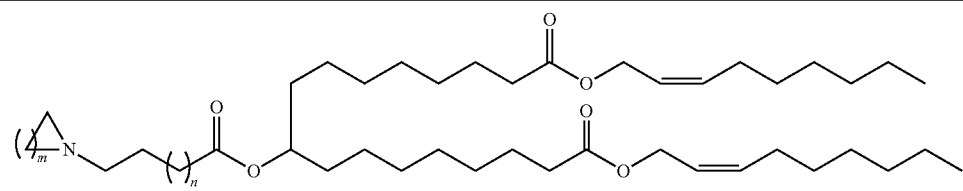
m = 1-6;
n = 0-3
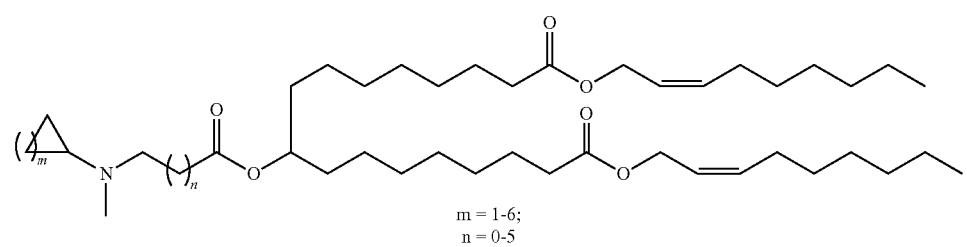
m = 1-6;
n = 0-5
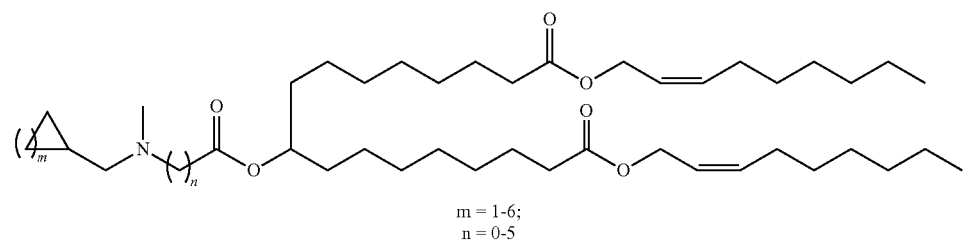
m = 1-6;
n = 0-5
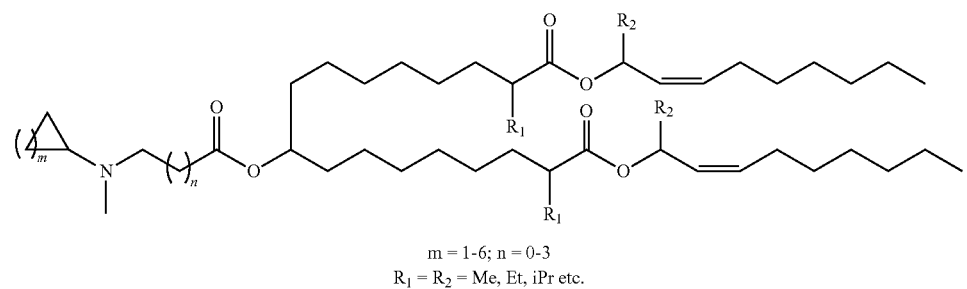
m = 1-6; n = 0-3
R₁ = R₂ = Me, Et, iPr etc.
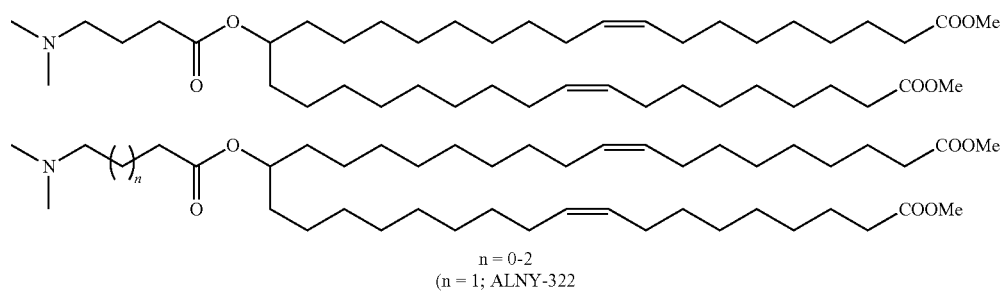
n = 0-2
(n = 1; ALNY-322
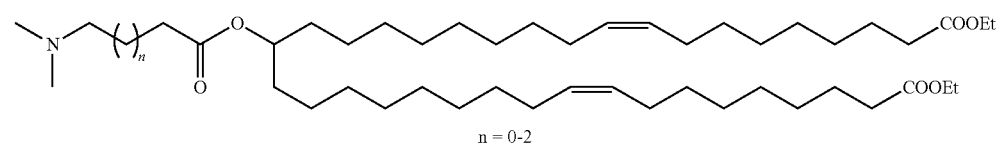
n = 0-2
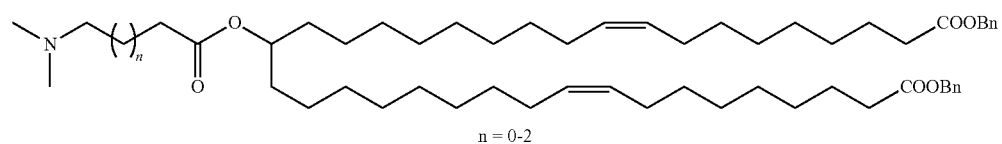
n = 0-2

TABLE 4-continued
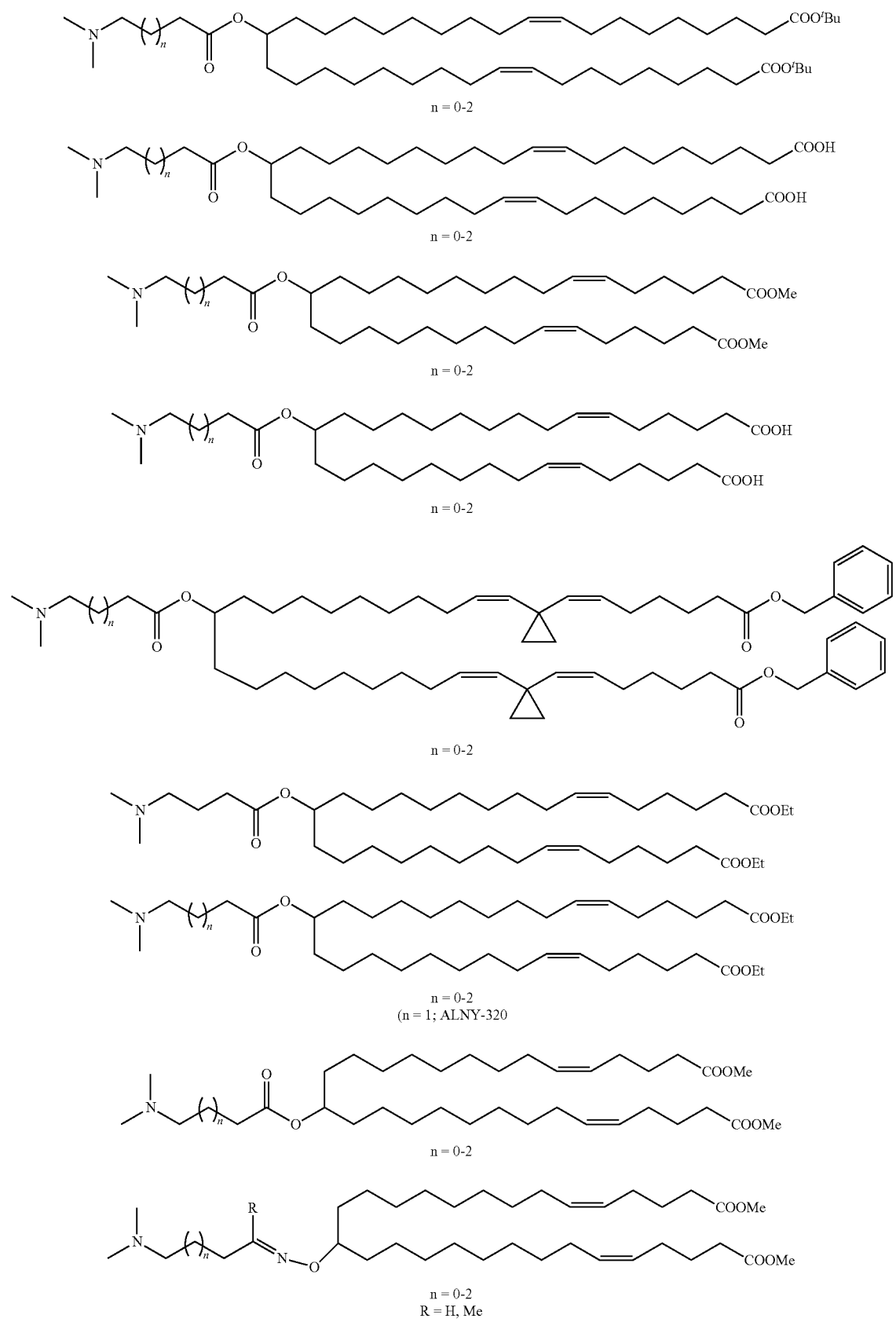

TABLE 4-continued
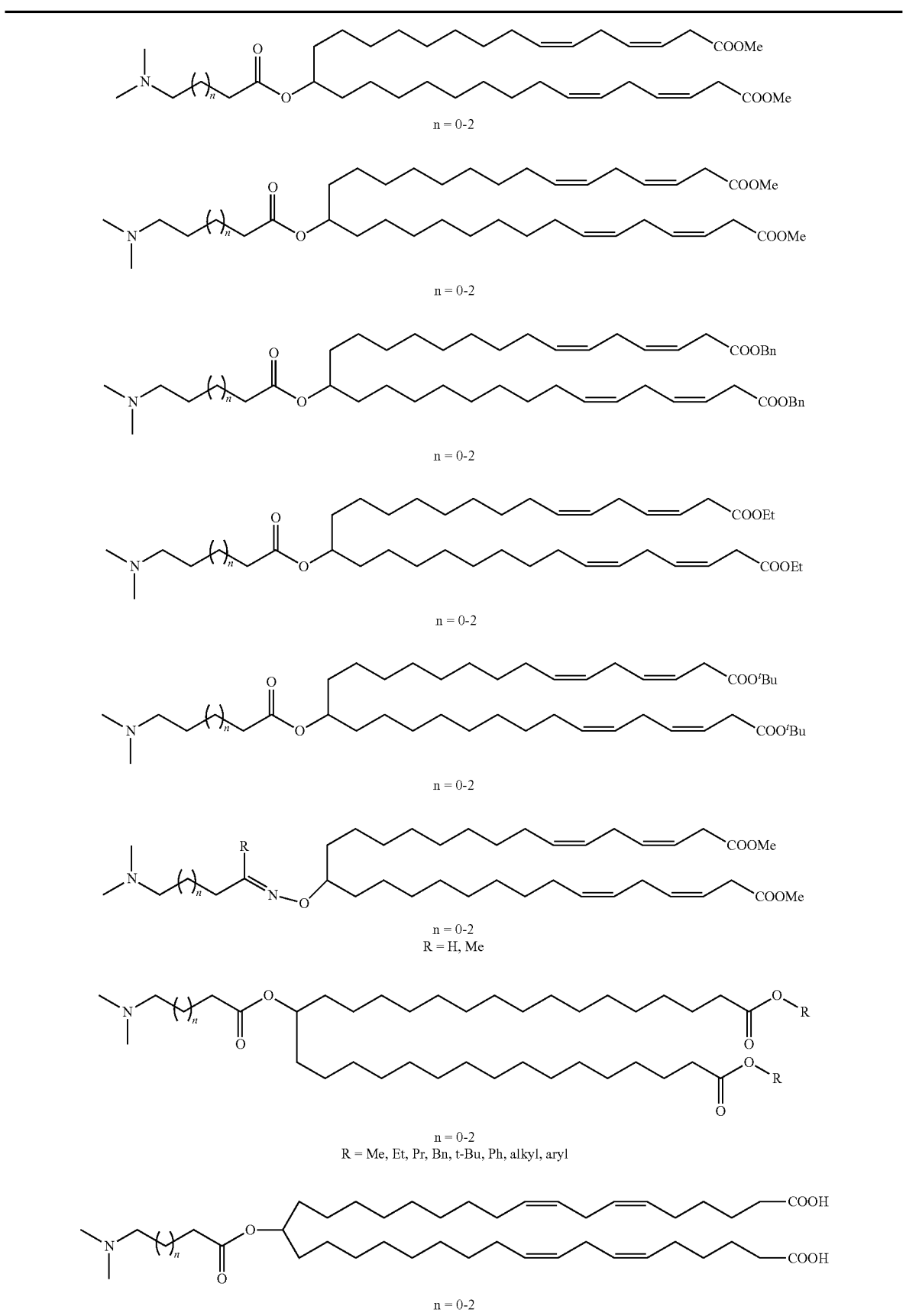

TABLE 4-continued
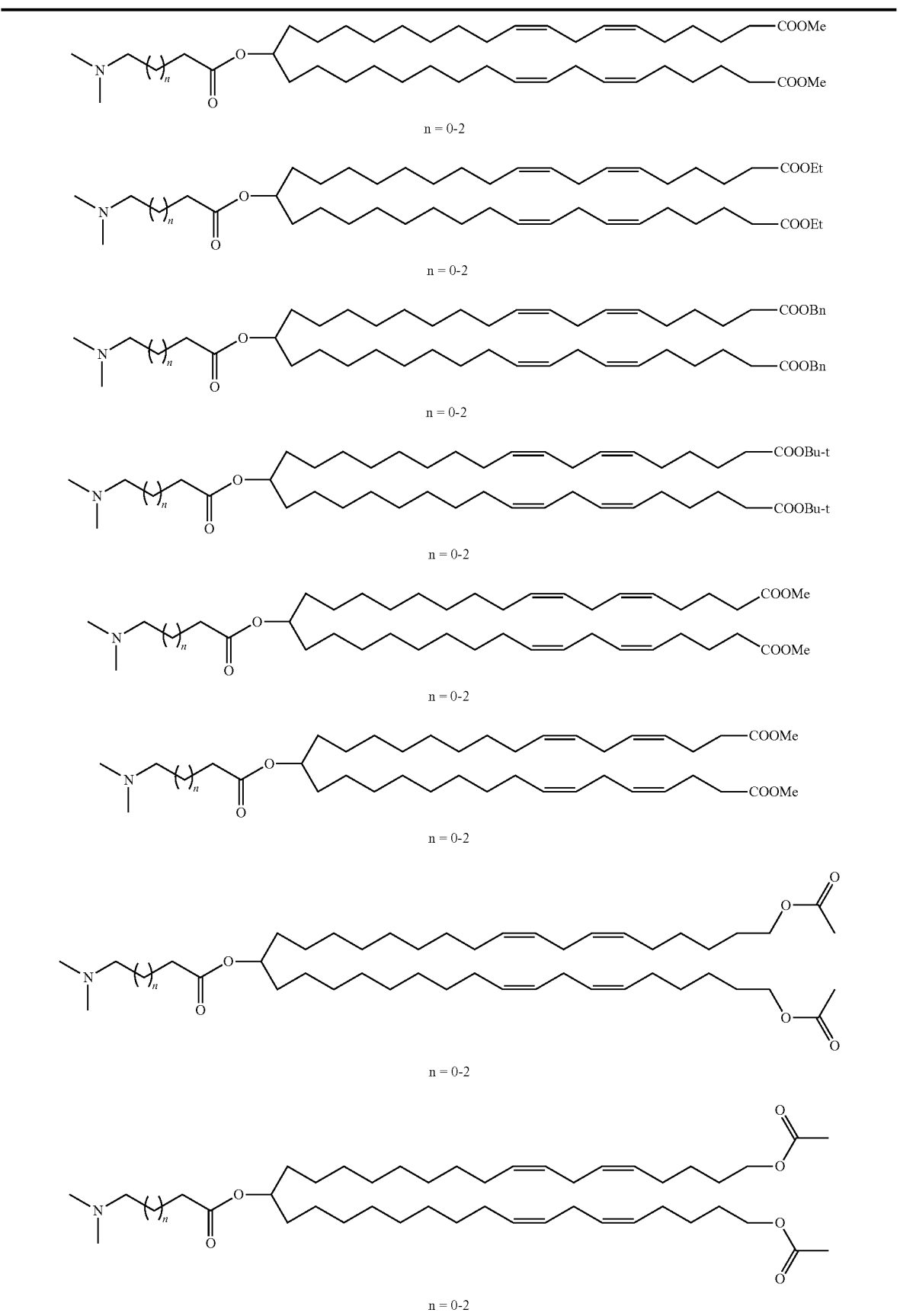

TABLE 4-continued
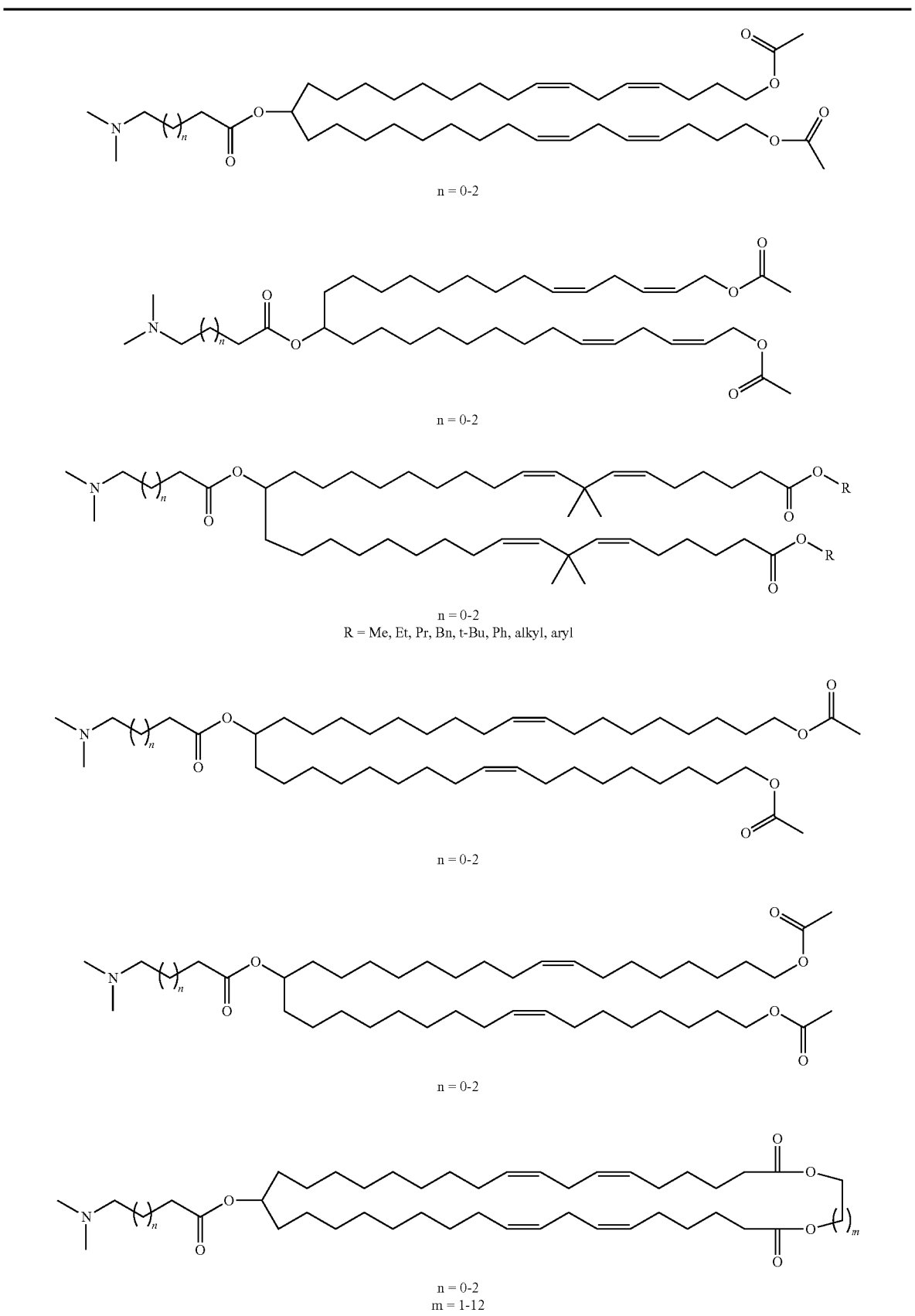

TABLE 4-continued
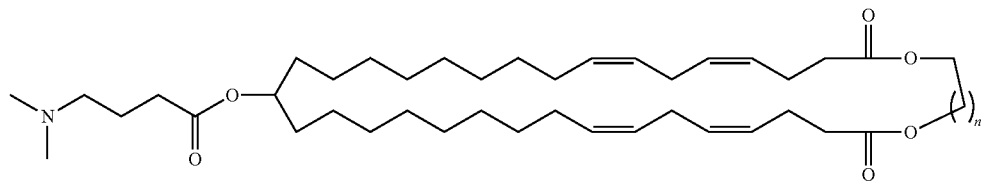
n = 1-12
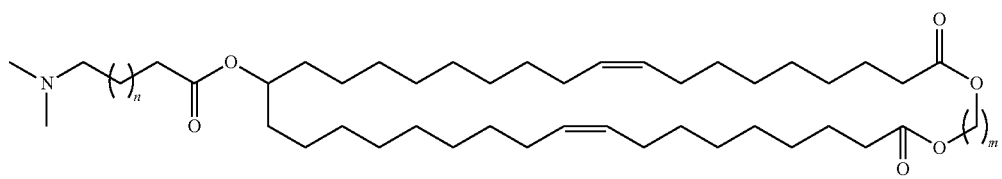
n = 0-2
m = 2-12
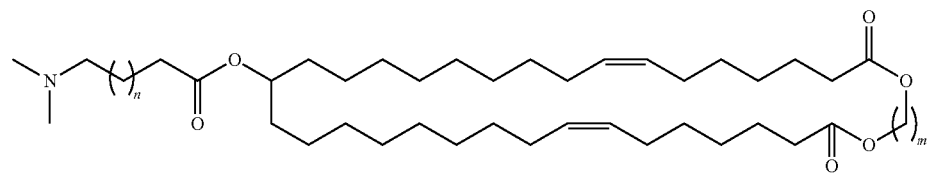
n = 0-2
m = 2-12
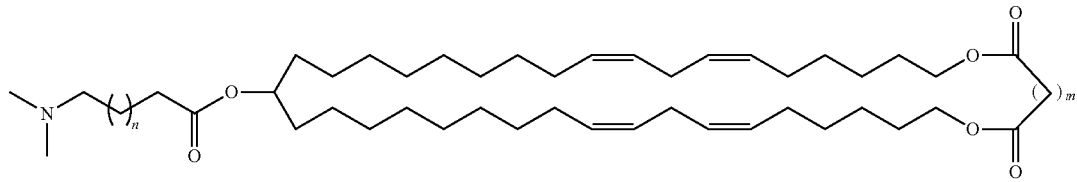
n = 0-2
m = 1-12
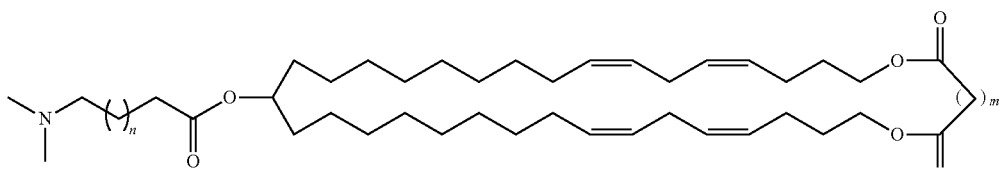
n = 0-2
m = 1-12
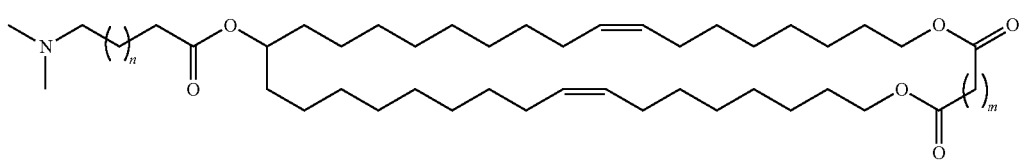
n = 0-2
m = 1-12

TABLE 4-continued
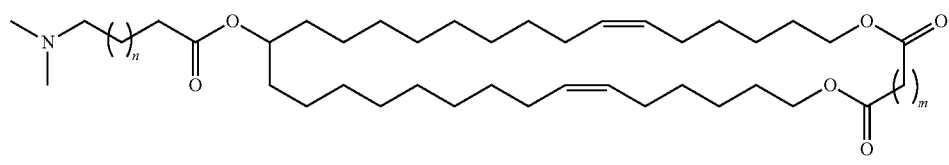
n = 0-2
m = 1-12
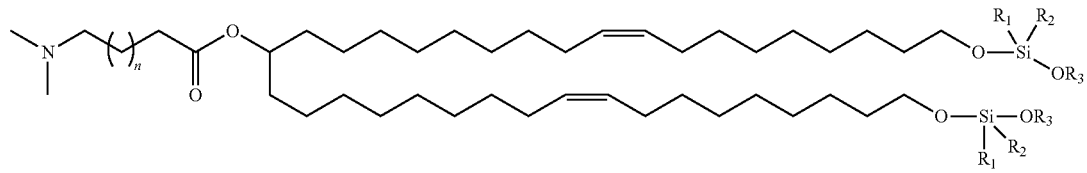
n = 0-2
R₁ = R₂ = R₃ = Me, Et, iPr
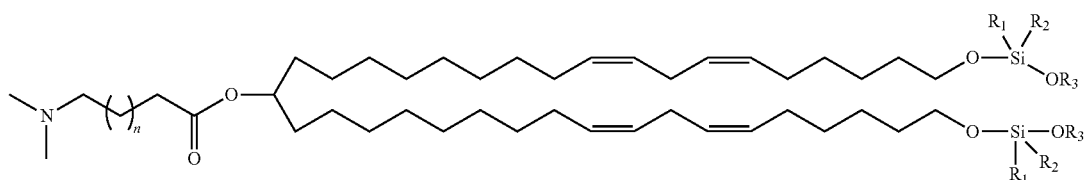
n = 0-2
R₁ = R₂ = R₃ = Me, Et, iPr
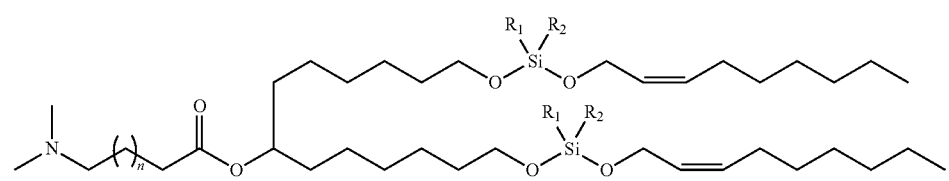
n = 0-2
R₁ = R₂ = Me, Et, iPr
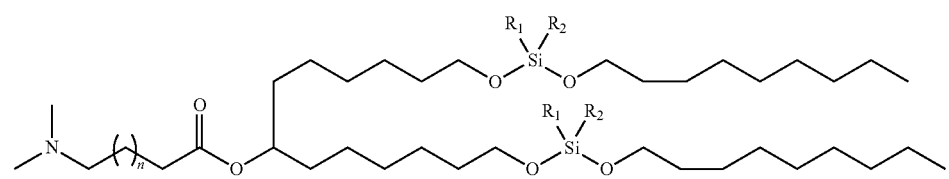
n = 0-2
R₁ = R₂ = Me, Et, iPr
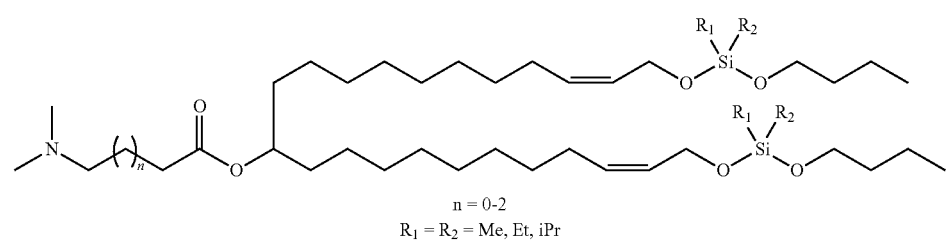
n = 0-2
R₁ = R₂ = Me, Et, iPr TABLE 4-continued
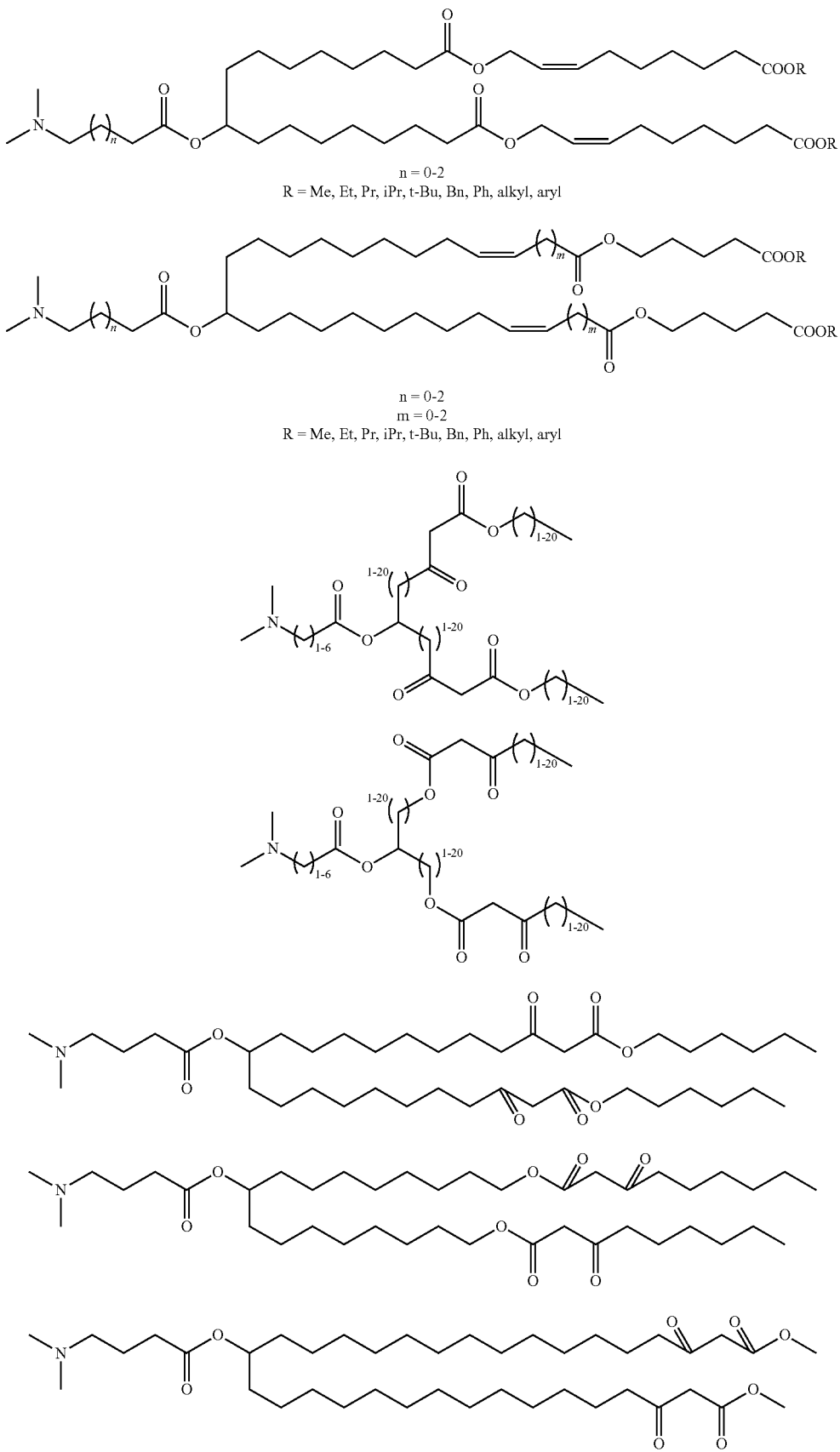

TABLE 4-continued
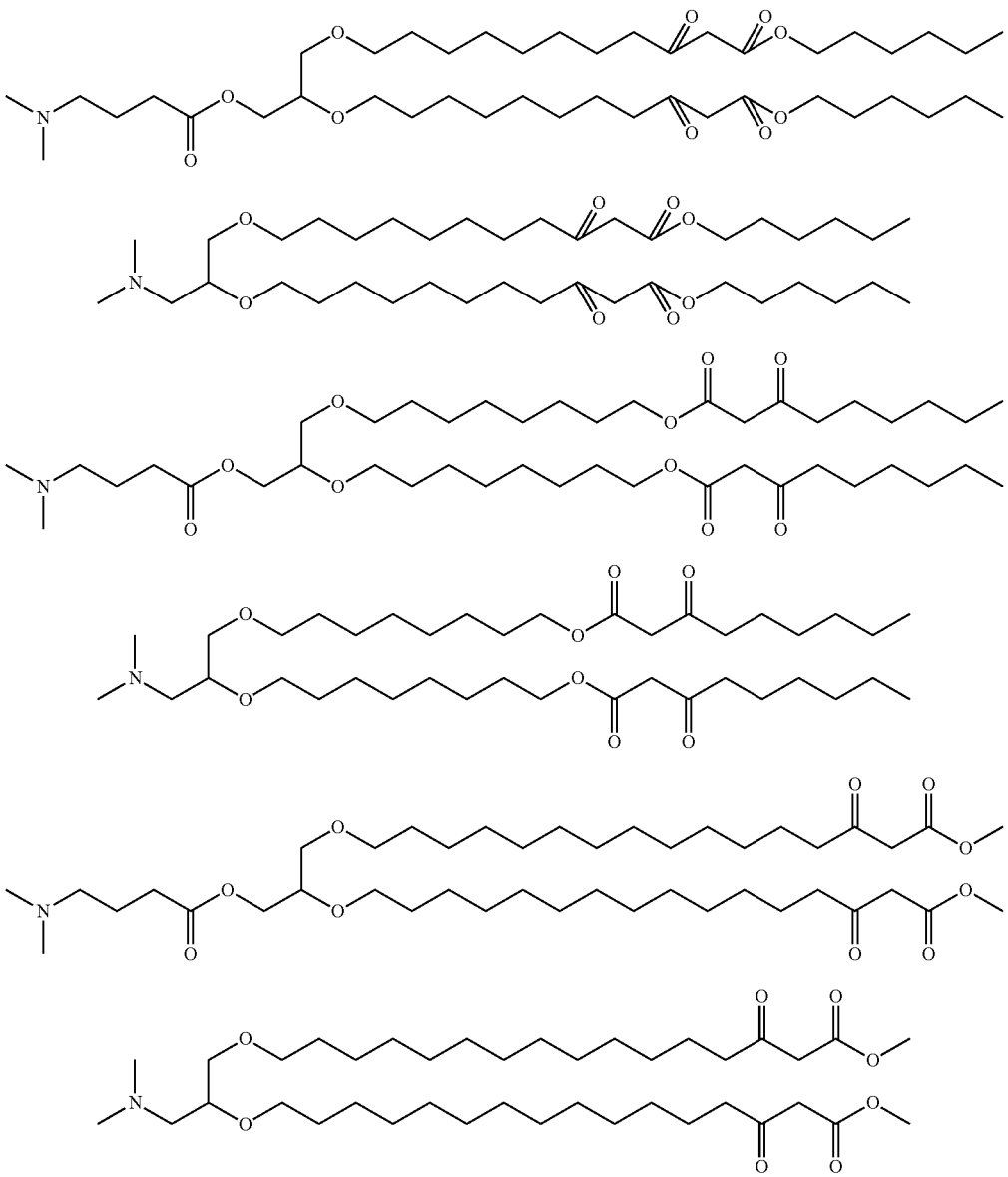
TABLE 5
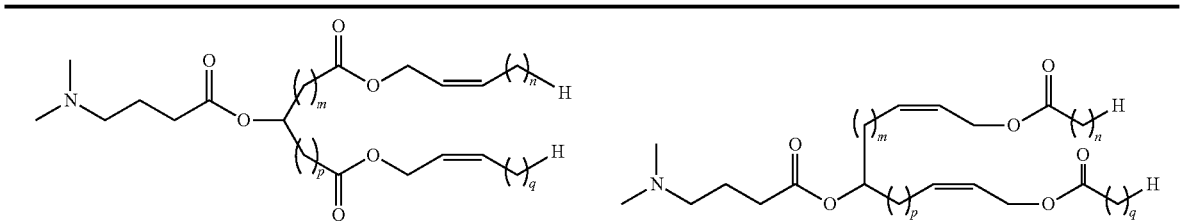
| m | n | p | q | m | n | p | q |
|---|---|---|---|---|---|---|---|
| 1 | 12 | 1 | 12 | 12 | 1 | 12 | 1 |
| 2 | 11 | 2 | 11 | 11 | 2 | 11 | 2 |
| 3 | 10 | 3 | 10 | 10 | 3 | 10 | 3 |
| 4 | 9 | 4 | 9 | 9 | 4 | 9 | 4 |
| 5 | 8 | 5 | 8 | 8 | 5 | 8 | 5 |
| 6 | 7 | 6 | 7 | 7 | 6 | 7 | 6 |
| 7 | 6 | 7 | 6 | 6 | 7 | 6 | 7 |

TABLE 5-continued
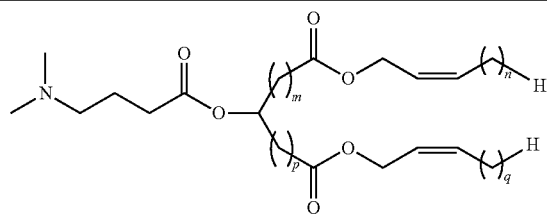 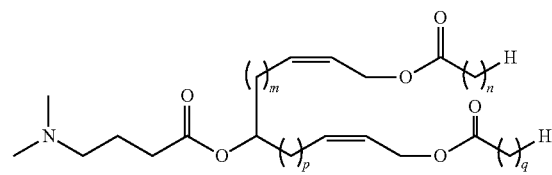
| m | n | p | q | m | n | p | q |
|---|---|---|---|---|---|---|---|
| 8 | 5 | 8 | 5 | 5 | 8 | 5 | 8 |
| 9 | 4 | 9 | 4 | 4 | 9 | 4 | 9 |
| 10 | 3 | 10 | 3 | 3 | 10 | 3 | 10 |
| 11 | 2 | 11 | 2 | 2 | 11 | 2 | 11 |
| 12 | 1 | 12 | 1 | 1 | 12 | 1 | 12 |
| 1 | 12 | 2 | 11 | 12 | 1 | 11 | 2 |
| 2 | 11 | 3 | 10 | 11 | 2 | 10 | 3 |
| 3 | 10 | 4 | 9 | 10 | 3 | 9 | 4 |
| 4 | 9 | 5 | 8 | 9 | 4 | 8 | 5 |
| 5 | 8 | 6 | 7 | 8 | 5 | 7 | 6 |
| 6 | 7 | 7 | 6 | 7 | 6 | 6 | 7 |
| 7 | 6 | 8 | 5 | 6 | 7 | 5 | 8 |
| 8 | 5 | 9 | 4 | 5 | 8 | 4 | 9 |
| 9 | 4 | 10 | 3 | 4 | 9 | 3 | 10 |
| 10 | 3 | 11 | 2 | 3 | 10 | 2 | 11 |
| 11 | 2 | 12 | 1 | 2 | 11 | 1 | 12 |
| 12 | 1 | 1 | 12 | 1 | 12 | 12 | 1 |
| 1 | 12 | 3 | 10 | 12 | 1 | 10 | 3 |
| 2 | 11 | 4 | 9 | 11 | 2 | 9 | 4 |
| 3 | 10 | 5 | 8 | 10 | 3 | 8 | 5 |
| 4 | 9 | 6 | 7 | 9 | 4 | 7 | 6 |
| 5 | 8 | 7 | 6 | 8 | 5 | 6 | 7 |
| 6 | 7 | 8 | 5 | 7 | 6 | 5 | 8 |
| 7 | 6 | 9 | 4 | 6 | 7 | 4 | 9 |
| 8 | 5 | 10 | 3 | 5 | 8 | 3 | 10 |
| 9 | 4 | 11 | 2 | 4 | 9 | 2 | 11 |
| 10 | 3 | 12 | 1 | 3 | 10 | 1 | 12 |
| 11 | 2 | 2 | 11 | 2 | 11 | 11 | 2 |
| 12 | 1 | 4 | 9 | 1 | 12 | 10 | 3 |
| 1 | 12 | 4 | 9 | 12 | 1 | 9 | 4 |
| 2 | 11 | 5 | 8 | 11 | 2 | 8 | 5 |
| 3 | 10 | 6 | 7 | 10 | 3 | 7 | 6 |
| 4 | 9 | 7 | 6 | 9 | 4 | 6 | 7 |
| 5 | 8 | 8 | 5 | 8 | 5 | 5 | 8 |
| 6 | 7 | 9 | 4 | 7 | 6 | 4 | 9 |
| 7 | 6 | 10 | 3 | 6 | 7 | 3 | 10 |
| 8 | 5 | 11 | 2 | 5 | 8 | 2 | 11 |
| 9 | 4 | 12 | 1 | 4 | 9 | 1 | 12 |
| 10 | 3 | 2 | 11 | 3 | 10 | 11 | 2 |
| 11 | 2 | 3 | 10 | 2 | 11 | 10 | 3 |
| 12 | 1 | 4 | 9 | 1 | 12 | 11 | 2 |
| 1 | 12 | 5 | 8 | 12 | 1 | 8 | 5 |
| 2 | 11 | 6 | 7 | 11 | 2 | 7 | 6 |
| 3 | 10 | 7 | 6 | 10 | 3 | 6 | 7 |
| 4 | 9 | 8 | 5 | 9 | 4 | 5 | 8 |
| 5 | 8 | 9 | 4 | 8 | 5 | 4 | 9 |
| 6 | 7 | 10 | 3 | 7 | 6 | 3 | 10 |
| 7 | 6 | 11 | 2 | 6 | 7 | 2 | 11 |
| 8 | 5 | 12 | 1 | 5 | 8 | 1 | 12 |
| 9 | 4 | 2 | 11 | 4 | 9 | 11 | 2 |
| 10 | 3 | 3 | 10 | 3 | 10 | 10 | 3 |
| 11 | 2 | 4 | 9 | 2 | 11 | 11 | 2 |
| 12 | 1 | 5 | 8 | 1 | 12 | 12 | 1 |
| 1 | 12 | 6 | 7 | 12 | 1 | 7 | 6 |
| 2 | 11 | 7 | 6 | 11 | 2 | 6 | 7 |
| 3 | 10 | 8 | 5 | 10 | 3 | 5 | 8 |
| 4 | 9 | 9 | 4 | 9 | 4 | 4 | 9 |
| 5 | 8 | 10 | 3 | 8 | 5 | 3 | 10 |
| 6 | 7 | 11 | 2 | 7 | 6 | 2 | 11 |
| 7 | 6 | 12 | 1 | 6 | 7 | 1 | 12 |
| 8 | 5 | 2 | 11 | 5 | 8 | 11 | 2 |
| 9 | 4 | 3 | 10 | 4 | 9 | 10 | 3 |
| 10 | 3 | 4 | 9 | 3 | 10 | 11 | 2 |
| 11 | 2 | 5 | 8 | 2 | 11 | 12 | 1 |
| 12 | 1 | 6 | 7 | 1 | 12 | 1 | 12 |
| 1 | 12 | 7 | 6 | 12 | 1 | 6 | 7 |
| 2 | 11 | 8 | 5 | 11 | 2 | 5 | 8 |

TABLE 5-continued
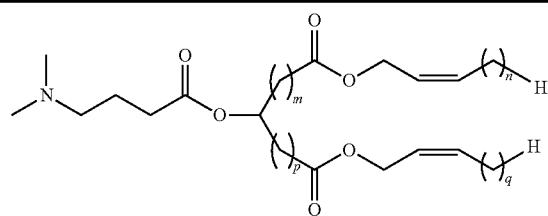 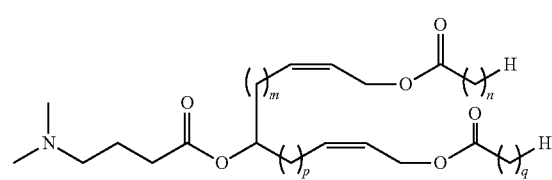
| m | n | p | q | m | n | p | q |
|---|---|---|---|---|---|---|---|
| 3 | 10 | 9 | 4 | 10 | 3 | 4 | 9 |
| 4 | 9 | 8 | 5 | 9 | 4 | 3 | 10 |
| 5 | 8 | 9 | 4 | 8 | 5 | 2 | 11 |
| 6 | 7 | 10 | 3 | 7 | 6 | 1 | 12 |
| 7 | 6 | 11 | 2 | 6 | 7 | 11 | 2 |
| 8 | 5 | 12 | 1 | 5 | 8 | 10 | 3 |
| 9 | 4 | 2 | 11 | 4 | 9 | 11 | 2 |
| 10 | 3 | 3 | 10 | 3 | 10 | 12 | 1 |
| 11 | 2 | 4 | 9 | 2 | 11 | 1 | 12 |
| 12 | 1 | 5 | 8 | 1 | 12 | 2 | 11 |
TABLE 6
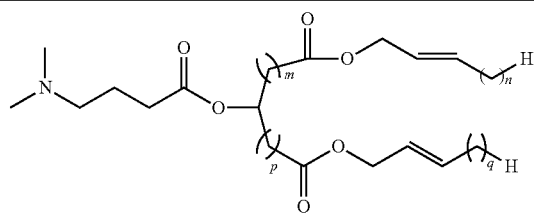 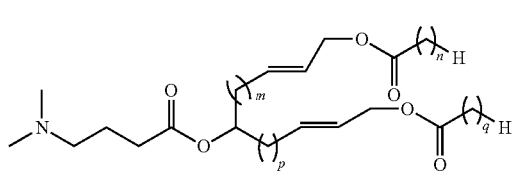
| m | n | p | q | m | n | p | q |
|---|---|---|---|---|---|---|---|
| 1 | 12 | 1 | 12 | 12 | 1 | 12 | 1 |
| 2 | 11 | 2 | 11 | 11 | 2 | 11 | 2 |
| 3 | 10 | 3 | 10 | 10 | 3 | 10 | 3 |
| 4 | 9 | 4 | 9 | 9 | 4 | 9 | 4 |
| 5 | 8 | 5 | 8 | 8 | 5 | 8 | 5 |
| 6 | 7 | 6 | 7 | 7 | 6 | 7 | 6 |
| 7 | 6 | 7 | 6 | 6 | 7 | 6 | 7 |
| 8 | 5 | 8 | 5 | 5 | 8 | 5 | 8 |
| 9 | 4 | 9 | 4 | 4 | 9 | 4 | 9 |
| 10 | 3 | 10 | 3 | 3 | 10 | 3 | 10 |
| 11 | 2 | 11 | 2 | 2 | 11 | 2 | 11 |
| 12 | 1 | 12 | 1 | 1 | 12 | 1 | 12 |
| 1 | 12 | 2 | 11 | 12 | 1 | 11 | 2 |
| 2 | 11 | 3 | 10 | 11 | 2 | 10 | 3 |
| 3 | 10 | 4 | 9 | 10 | 3 | 9 | 4 |
| 4 | 9 | 5 | 8 | 9 | 4 | 8 | 5 |
| 5 | 8 | 6 | 7 | 8 | 5 | 7 | 6 |
| 6 | 7 | 7 | 6 | 7 | 6 | 6 | 7 |
| 7 | 6 | 8 | 5 | 6 | 7 | 5 | 8 |
| 8 | 5 | 9 | 4 | 5 | 8 | 4 | 9 |
| 9 | 4 | 10 | 3 | 4 | 9 | 3 | 10 |
| 10 | 3 | 11 | 2 | 3 | 10 | 2 | 11 |
| 11 | 2 | 12 | 1 | 2 | 11 | 1 | 12 |
| 12 | 1 | 1 | 12 | 1 | 12 | 12 | 1 |
| 1 | 12 | 3 | 10 | 12 | 1 | 10 | 3 |
| 2 | 11 | 4 | 9 | 11 | 2 | 9 | 4 |
| 3 | 10 | 5 | 8 | 10 | 3 | 8 | 5 |
| 4 | 9 | 6 | 7 | 9 | 4 | 7 | 6 |
| 5 | 8 | 7 | 6 | 8 | 5 | 6 | 7 |
| 6 | 7 | 8 | 5 | 7 | 6 | 5 | 8 |
| 7 | 6 | 9 | 4 | 6 | 7 | 4 | 9 |
| 8 | 5 | 10 | 3 | 5 | 8 | 3 | 10 |
| 9 | 4 | 11 | 2 | 4 | 9 | 2 | 11 |
| 10 | 3 | 12 | 1 | 3 | 10 | 1 | 12 |
| 11 | 2 | 2 | 11 | 2 | 11 | 11 | 2 |
| 12 | 1 | 4 | 9 | 1 | 12 | 10 | 3 |
| 1 | 12 | 4 | 9 | 12 | 1 | 9 | 4 |
| 2 | 11 | 5 | 8 | 11 | 2 | 8 | 5 |
| 3 | 10 | 6 | 7 | 10 | 3 | 7 | 6 |
| 4 | 9 | 7 | 6 | 9 | 4 | 6 | 7 |

TABLE 6-continued

| m | n | p | q | m | n | p | q |
|---|---|---|---|---|---|---|---|
| 5 | 8 | 8 | 5 | 8 | 5 | 5 | 8 |
| 6 | 7 | 9 | 4 | 7 | 6 | 4 | 9 |
| 7 | 6 | 10 | 3 | 6 | 7 | 3 | 10 |
| 8 | 5 | 11 | 2 | 5 | 8 | 2 | 11 |
| 9 | 4 | 12 | 1 | 4 | 9 | 1 | 12 |
| 10 | 3 | 2 | 11 | 3 | 10 | 11 | 2 |
| 11 | 2 | 3 | 10 | 2 | 11 | 10 | 3 |
| 12 | 1 | 4 | 9 | 1 | 12 | 11 | 2 |
| 1 | 12 | 5 | 8 | 12 | 1 | 8 | 5 |
| 2 | 11 | 6 | 7 | 11 | 2 | 7 | 6 |
| 3 | 10 | 7 | 6 | 10 | 3 | 6 | 7 |
| 4 | 9 | 8 | 5 | 9 | 4 | 5 | 8 |
| 5 | 8 | 9 | 4 | 8 | 5 | 4 | 9 |
| 6 | 7 | 10 | 3 | 7 | 6 | 3 | 10 |
| 7 | 6 | 11 | 2 | 6 | 7 | 2 | 11 |
| 8 | 5 | 12 | 1 | 5 | 8 | 1 | 12 |
| 9 | 4 | 2 | 11 | 4 | 9 | 11 | 2 |
| 10 | 3 | 3 | 10 | 3 | 10 | 10 | 3 |
| 11 | 2 | 4 | 9 | 2 | 11 | 11 | 2 |
| 12 | 1 | 5 | 8 | 1 | 12 | 12 | 1 |
| 1 | 12 | 6 | 7 | 12 | 1 | 7 | 6 |
| 2 | 11 | 7 | 6 | 11 | 2 | 6 | 7 |
| 3 | 10 | 8 | 5 | 10 | 3 | 5 | 8 |
| 4 | 9 | 9 | 4 | 9 | 4 | 4 | 9 |
| 5 | 8 | 10 | 3 | 8 | 5 | 3 | 10 |
| 6 | 7 | 11 | 2 | 7 | 6 | 2 | 11 |
| 7 | 6 | 12 | 1 | 6 | 7 | 1 | 12 |
| 8 | 5 | 2 | 11 | 5 | 8 | 11 | 2 |
| 9 | 4 | 3 | 10 | 4 | 9 | 10 | 3 |
| 10 | 3 | 4 | 9 | 3 | 10 | 11 | 2 |
| 11 | 2 | 5 | 8 | 2 | 11 | 12 | 1 |
| 12 | 1 | 6 | 7 | 1 | 12 | 1 | 12 |
| 1 | 12 | 7 | 6 | 12 | 1 | 6 | 7 |
| 2 | 11 | 8 | 5 | 11 | 2 | 5 | 8 |
| 3 | 10 | 9 | 4 | 10 | 3 | 4 | 9 |
| 4 | 9 | 8 | 5 | 9 | 4 | 3 | 10 |
| 5 | 8 | 9 | 4 | 8 | 5 | 2 | 11 |
| 6 | 7 | 10 | 3 | 7 | 6 | 1 | 12 |
| 7 | 6 | 11 | 2 | 6 | 7 | 11 | 2 |
| 8 | 5 | 12 | 1 | 5 | 8 | 10 | 3 |
| 9 | 4 | 2 | 11 | 4 | 9 | 11 | 2 |
| 10 | 3 | 3 | 10 | 3 | 10 | 12 | 1 |
| 11 | 2 | 4 | 9 | 2 | 11 | 1 | 12 |
| 12 | 1 | 5 | 8 | 1 | 12 | 2 | 11 |

TABLE 7

| m | n | p | q | m | n | p | q |
|---|---|---|---|---|---|---|---|
| 1 | 13 | 1 | 13 | 1 | 13 | 1 | 13 |
| 2 | 12 | 2 | 12 | 2 | 12 | 2 | 12 |

TABLE 7-continued

| m | n | p | q | m | n | p | q |
|---|---|---|---|---|---|---|---|
| 3 | 11 | 3 | 11 | 3 | 11 | 3 | 11 |
| 4 | 10 | 4 | 10 | 4 | 10 | 4 | 10 |
| 5 | 9 | 5 | 9 | 5 | 9 | 5 | 9 |
| 6 | 8 | 6 | 8 | 6 | 8 | 6 | 8 |
| 7 | 7 | 7 | 7 | 7 | 7 | 7 | 7 |
| 8 | 6 | 8 | 6 | 8 | 6 | 8 | 6 |
| 9 | 5 | 9 | 5 | 9 | 5 | 9 | 5 |
| 10 | 4 | 10 | 4 | 10 | 4 | 10 | 4 |
| 11 | 3 | 11 | 3 | 11 | 3 | 11 | 3 |
| 12 | 2 | 12 | 2 | 12 | 2 | 12 | 2 |
| 13 | 1 | 13 | 1 | 13 | 1 | 13 | 1 |
| 1 | 13 | 2 | 12 | 1 | 13 | 2 | 12 |
| 2 | 12 | 3 | 11 | 2 | 12 | 3 | 11 |
| 3 | 11 | 4 | 10 | 3 | 11 | 4 | 10 |
| 4 | 10 | 5 | 9 | 4 | 10 | 5 | 9 |
| 5 | 9 | 6 | 8 | 5 | 9 | 6 | 8 |
| 6 | 8 | 7 | 7 | 6 | 8 | 7 | 7 |
| 7 | 7 | 8 | 6 | 7 | 7 | 8 | 6 |
| 8 | 6 | 9 | 5 | 8 | 6 | 9 | 5 |
| 9 | 5 | 10 | 4 | 9 | 5 | 10 | 4 |
| 10 | 4 | 11 | 3 | 10 | 4 | 11 | 3 |
| 11 | 3 | 12 | 2 | 11 | 3 | 12 | 2 |
| 12 | 2 | 13 | 1 | 12 | 2 | 13 | 1 |
| 13 | 1 | 1 | 13 | 13 | 1 | 1 | 13 |
| 1 | 13 | 3 | 11 | 1 | 13 | 3 | 11 |
| 2 | 12 | 4 | 10 | 2 | 12 | 4 | 10 |
| 3 | 11 | 5 | 9 | 3 | 11 | 5 | 9 |
| 4 | 10 | 6 | 8 | 4 | 10 | 6 | 8 |
| 5 | 9 | 7 | 7 | 5 | 9 | 7 | 7 |
| 6 | 8 | 8 | 6 | 6 | 8 | 8 | 6 |
| 7 | 7 | 9 | 5 | 7 | 7 | 9 | 5 |
| 8 | 6 | 10 | 4 | 8 | 6 | 10 | 4 |
| 9 | 5 | 11 | 3 | 9 | 5 | 11 | 3 |
| 10 | 4 | 12 | 2 | 10 | 4 | 12 | 2 |
| 11 | 3 | 13 | 1 | 11 | 3 | 13 | 1 |
| 12 | 2 | 1 | 13 | 12 | 2 | 1 | 13 |
| 13 | 1 | 2 | 12 | 13 | 1 | 2 | 14 |

TABLE 8

| m | n | p | m | n | p |
|---|---|---|---|---|---|
| 1 | 12 | 18 | 12 | 1 | 18 |
| 2 | 11 | 18 | 11 | 2 | 18 |
| 3 | 10 | 18 | 10 | 3 | 18 |
| 4 | 9 | 18 | 9 | 4 | 18 |
| 5 | 8 | 18 | 8 | 5 | 18 |
| 6 | 7 | 18 | 7 | 6 | 18 |
| 7 | 6 | 18 | 6 | 7 | 18 |
| 8 | 5 | 18 | 5 | 8 | 18 |
| 9 | 4 | 18 | 4 | 9 | 18 |
| 10 | 3 | 18 | 3 | 10 | 18 |
| 11 | 2 | 18 | 2 | 11 | 18 |

TABLE 8-continued
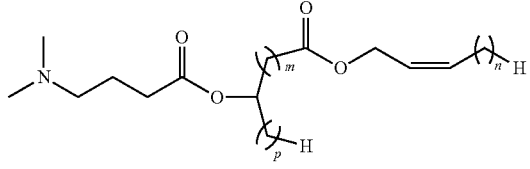
| m | n | p | m | n | p |
|---|---|---|---|---|---|
| 12 | 1 | 18 | 1 | 12 | 18 |
| 1 | 12 | 17 | 12 | 1 | 17 |
| 2 | 11 | 17 | 11 | 2 | 17 |
| 3 | 10 | 17 | 10 | 3 | 17 |
| 4 | 9 | 17 | 9 | 4 | 17 |
| 5 | 8 | 17 | 8 | 5 | 17 |
| 6 | 7 | 17 | 7 | 6 | 17 |
| 7 | 6 | 17 | 6 | 7 | 17 |
| 8 | 5 | 17 | 5 | 8 | 17 |
| 9 | 4 | 17 | 4 | 9 | 17 |
| 10 | 3 | 17 | 3 | 10 | 17 |
| 11 | 2 | 17 | 2 | 11 | 17 |
| 12 | 1 | 17 | 1 | 12 | 17 |
| 1 | 12 | 16 | 12 | 1 | 16 |
| 2 | 11 | 16 | 11 | 2 | 16 |
| 3 | 10 | 16 | 10 | 3 | 16 |
| 4 | 9 | 16 | 9 | 4 | 16 |
| 5 | 8 | 16 | 8 | 5 | 16 |
| 6 | 7 | 16 | 7 | 6 | 16 |
| 7 | 6 | 16 | 6 | 7 | 16 |
| 8 | 5 | 16 | 5 | 8 | 16 |
| 9 | 4 | 16 | 4 | 9 | 16 |
| 10 | 3 | 16 | 3 | 10 | 16 |
| 11 | 2 | 16 | 2 | 11 | 16 |
| 12 | 1 | 16 | 1 | 12 | 16 |
| 1 | 12 | 15 | 12 | 1 | 15 |
| 2 | 11 | 15 | 11 | 2 | 15 |
| 3 | 10 | 15 | 10 | 3 | 15 |
| 4 | 9 | 15 | 9 | 4 | 15 |
| 5 | 8 | 15 | 8 | 5 | 15 |
| 6 | 7 | 15 | 7 | 6 | 15 |
| 7 | 6 | 15 | 6 | 7 | 15 |
| 8 | 5 | 15 | 5 | 8 | 15 |
| 9 | 4 | 15 | 4 | 9 | 15 |
| 10 | 3 | 15 | 3 | 10 | 15 |
| 11 | 2 | 15 | 2 | 11 | 15 |
| 12 | 1 | 15 | 1 | 12 | 15 |
| 1 | 12 | 14 | 12 | 1 | 14 |
| 2 | 11 | 14 | 11 | 2 | 14 |
| 3 | 10 | 14 | 10 | 3 | 14 |
| 4 | 9 | 14 | 9 | 4 | 14 |
| 5 | 8 | 14 | 8 | 5 | 14 |
| 6 | 7 | 14 | 7 | 6 | 14 |
| 7 | 6 | 14 | 6 | 7 | 14 |
| 8 | 5 | 14 | 5 | 8 | 14 |
| 9 | 4 | 14 | 4 | 9 | 14 |
| 10 | 3 | 14 | 3 | 10 | 14 |
| 11 | 2 | 14 | 2 | 11 | 14 |
| 12 | 1 | 14 | 1 | 12 | 14 |
| 1 | 12 | 13 | 12 | 1 | 13 |
| 2 | 11 | 13 | 11 | 2 | 13 |
| 3 | 10 | 13 | 10 | 3 | 13 |
| 4 | 9 | 13 | 9 | 4 | 13 |
| 5 | 8 | 13 | 8 | 5 | 13 |
| 6 | 7 | 13 | 7 | 6 | 13 |
| 7 | 6 | 13 | 6 | 7 | 13 |
| 8 | 5 | 13 | 5 | 8 | 13 |
| 9 | 4 | 13 | 4 | 9 | 13 |
| 10 | 3 | 13 | 3 | 10 | 13 |
| 11 | 2 | 13 | 2 | 11 | 13 |
| 12 | 1 | 13 | 1 | 12 | 13 |
| 1 | 12 | 12 | 12 | 1 | 12 |
| 2 | 11 | 12 | 11 | 2 | 12 |
| 3 | 10 | 12 | 10 | 3 | 12 |
| 4 | 9 | 12 | 9 | 4 | 12 |
| 5 | 8 | 12 | 8 | 5 | 12 |
| 6 | 7 | 12 | 7 | 6 | 12 |
| 7 | 6 | 12 | 6 | 7 | 12 |
| 8 | 5 | 12 | 5 | 8 | 12 |

TABLE 8-continued
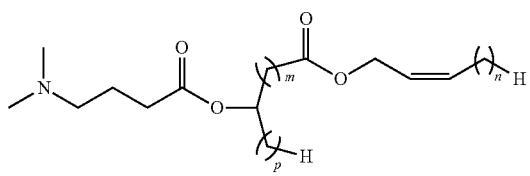 101
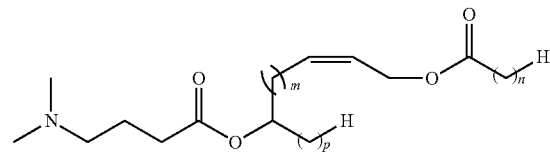 102
| m | n | p | m | n | p |
|---|---|---|---|---|---|
| 9 | 4 | 12 | 4 | 9 | 12 |
| 10 | 3 | 12 | 3 | 10 | 12 |
| 11 | 2 | 12 | 2 | 11 | 12 |
| 12 | 1 | 12 | 1 | 12 | 12 |
| 1 | 12 | 11 | 12 | 1 | 11 |
| 2 | 11 | 11 | 11 | 2 | 11 |
| 3 | 10 | 11 | 10 | 3 | 11 |
| 4 | 9 | 11 | 9 | 4 | 11 |
| 5 | 8 | 11 | 8 | 5 | 11 |
| 6 | 7 | 11 | 7 | 6 | 11 |
| 7 | 6 | 11 | 6 | 7 | 11 |
| 8 | 5 | 11 | 5 | 8 | 11 |
| 9 | 4 | 11 | 4 | 9 | 11 |
| 10 | 3 | 11 | 3 | 10 | 11 |
| 11 | 2 | 11 | 2 | 11 | 11 |
| 12 | 1 | 11 | 1 | 12 | 11 |
| 12 | 1 | 10 | 12 | 1 | 10 |
| 1 | 12 | 10 | 11 | 2 | 10 |
| 2 | 11 | 10 | 10 | 3 | 10 |
| 3 | 10 | 10 | 9 | 4 | 10 |
| 4 | 9 | 10 | 8 | 5 | 10 |
| 5 | 8 | 10 | 7 | 6 | 10 |
| 6 | 7 | 10 | 6 | 7 | 10 |
| 7 | 6 | 10 | 5 | 8 | 10 |
| 8 | 5 | 10 | 4 | 9 | 10 |
| 9 | 4 | 10 | 3 | 10 | 10 |
| 10 | 3 | 10 | 2 | 11 | 10 |
| 11 | 2 | 10 | 1 | 12 | 10 |
| 12 | 1 | 10 | 12 | 1 | 10 |
| 1 | 12 | 9 | 11 | 2 | 9 |
| 2 | 11 | 9 | 10 | 3 | 9 |
| 3 | 10 | 9 | 9 | 4 | 9 |
| 4 | 9 | 9 | 8 | 5 | 9 |
| 5 | 8 | 9 | 7 | 6 | 9 |
| 6 | 7 | 9 | 6 | 7 | 9 |
| 7 | 6 | 9 | 5 | 8 | 9 |
| 8 | 5 | 9 | 4 | 9 | 9 |
| 9 | 4 | 9 | 3 | 10 | 9 |
| 10 | 3 | 9 | 2 | 11 | 9 |
| 11 | 2 | 9 | 1 | 12 | 9 |
| 12 | 1 | 9 | 12 | 1 | 9 |
| 1 | 12 | 8 | 11 | 2 | 8 |
| 2 | 11 | 8 | 10 | 3 | 8 |
| 3 | 10 | 8 | 9 | 4 | 8 |
| 4 | 9 | 8 | 8 | 5 | 8 |
| 5 | 8 | 8 | 7 | 6 | 8 |
| 6 | 7 | 8 | 6 | 7 | 8 |
| 7 | 6 | 8 | 5 | 8 | 8 |
| 8 | 5 | 8 | 4 | 9 | 8 |
| 9 | 4 | 8 | 3 | 10 | 8 |
| 10 | 3 | 8 | 2 | 11 | 8 |
| 11 | 2 | 8 | 1 | 12 | 8 |
| 12 | 1 | 8 | 12 | 1 | 8 |

TABLE 9

| m | n | p | q | m | n | p | q |
|---|---|---|---|---|---|---|---|
| 1 | 12 | 8 | 8 | 12 | 1 | 8 | 8 |
| 2 | 11 | 8 | 8 | 11 | 2 | 8 | 8 |
| 3 | 10 | 8 | 8 | 10 | 3 | 8 | 8 |
| 4 | 9 | 8 | 8 | 9 | 4 | 8 | 8 |
| 5 | 8 | 8 | 8 | 8 | 5 | 8 | 8 |
| 6 | 7 | 8 | 8 | 7 | 6 | 8 | 8 |
| 7 | 6 | 8 | 8 | 6 | 7 | 8 | 8 |
| 8 | 5 | 8 | 8 | 5 | 8 | 8 | 8 |
| 9 | 4 | 8 | 8 | 4 | 9 | 8 | 8 |
| 10 | 3 | 8 | 8 | 3 | 10 | 8 | 8 |
| 11 | 2 | 8 | 8 | 2 | 11 | 8 | 8 |
| 12 | 1 | 8 | 8 | 1 | 12 | 8 | 8 |
| 1 | 12 | 9 | 7 | 12 | 1 | 9 | 7 |
| 2 | 11 | 9 | 7 | 11 | 2 | 9 | 7 |
| 3 | 10 | 9 | 7 | 10 | 3 | 9 | 7 |
| 4 | 9 | 9 | 7 | 9 | 4 | 9 | 7 |
| 5 | 8 | 9 | 7 | 8 | 5 | 9 | 7 |
| 6 | 7 | 9 | 7 | 7 | 6 | 9 | 7 |
| 7 | 6 | 9 | 7 | 6 | 7 | 9 | 7 |
| 8 | 5 | 9 | 7 | 5 | 8 | 9 | 7 |
| 9 | 4 | 9 | 7 | 4 | 9 | 9 | 7 |
| 10 | 3 | 9 | 7 | 3 | 10 | 9 | 7 |
| 11 | 2 | 9 | 7 | 2 | 11 | 9 | 7 |
| 12 | 1 | 9 | 7 | 1 | 12 | 9 | 7 |
| 1 | 12 | 10 | 6 | 12 | 1 | 10 | 6 |
| 2 | 11 | 10 | 6 | 11 | 2 | 10 | 6 |
| 3 | 10 | 10 | 6 | 10 | 3 | 10 | 6 |
| 4 | 9 | 10 | 6 | 9 | 4 | 10 | 6 |
| 5 | 8 | 10 | 6 | 8 | 5 | 10 | 6 |
| 6 | 7 | 10 | 6 | 7 | 6 | 10 | 6 |
| 7 | 6 | 10 | 6 | 6 | 7 | 10 | 6 |
| 8 | 5 | 10 | 6 | 5 | 8 | 10 | 6 |
| 9 | 4 | 10 | 6 | 4 | 9 | 10 | 6 |
| 10 | 3 | 10 | 6 | 3 | 10 | 10 | 6 |
| 11 | 2 | 10 | 6 | 2 | 11 | 10 | 6 |
| 12 | 1 | 10 | 6 | 1 | 12 | 10 | 6 |
| 1 | 12 | 11 | 5 | 12 | 1 | 11 | 5 |
| 2 | 11 | 11 | 5 | 11 | 2 | 11 | 5 |
| 3 | 10 | 11 | 5 | 10 | 3 | 11 | 5 |
| 4 | 9 | 11 | 5 | 9 | 4 | 11 | 5 |
| 5 | 8 | 11 | 5 | 8 | 5 | 11 | 5 |
| 6 | 7 | 11 | 5 | 7 | 6 | 11 | 5 |
| 7 | 6 | 11 | 5 | 6 | 7 | 11 | 5 |
| 8 | 5 | 11 | 5 | 5 | 8 | 11 | 5 |
| 9 | 4 | 11 | 5 | 4 | 9 | 11 | 5 |
| 10 | 3 | 11 | 5 | 3 | 10 | 11 | 5 |
| 11 | 2 | 11 | 5 | 2 | 11 | 11 | 5 |
| 12 | 1 | 11 | 5 | 1 | 12 | 11 | 5 |
| 1 | 12 | 12 | 4 | 12 | 1 | 12 | 4 |
| 2 | 11 | 12 | 4 | 11 | 2 | 12 | 4 |
| 3 | 10 | 12 | 4 | 10 | 3 | 12 | 4 |
| 4 | 9 | 12 | 4 | 9 | 4 | 12 | 4 |
| 5 | 8 | 12 | 4 | 8 | 5 | 12 | 4 |
| 6 | 7 | 12 | 4 | 7 | 6 | 12 | 4 |
| 7 | 6 | 12 | 4 | 6 | 7 | 12 | 4 |
| 8 | 5 | 12 | 4 | 5 | 8 | 12 | 4 |
| 9 | 4 | 12 | 4 | 4 | 9 | 12 | 4 |
| 10 | 3 | 12 | 4 | 3 | 10 | 12 | 4 |
| 11 | 2 | 12 | 4 | 2 | 11 | 12 | 4 |
| 12 | 1 | 12 | 4 | 1 | 12 | 12 | 4 |
| 1 | 12 | 13 | 3 | 12 | 1 | 13 | 3 |
| 2 | 11 | 13 | 3 | 11 | 2 | 13 | 3 |
| 3 | 10 | 13 | 3 | 10 | 3 | 13 | 3 |
| 4 | 9 | 13 | 3 | 9 | 4 | 13 | 3 |
| 5 | 8 | 13 | 3 | 8 | 5 | 13 | 3 |
| 6 | 7 | 13 | 3 | 7 | 6 | 13 | 3 |
| 7 | 6 | 13 | 3 | 6 | 7 | 13 | 3 |
| 8 | 5 | 13 | 3 | 5 | 8 | 13 | 3 |
| 9 | 4 | 13 | 3 | 4 | 9 | 13 | 3 |

TABLE 9-continued

| m | n | p | q | m | n | p | q |
|---|---|---|---|---|---|---|---|
| 10 | 3 | 13 | 3 | 3 | 10 | 13 | 3 |
| 11 | 2 | 13 | 3 | 2 | 11 | 13 | 3 |
| 12 | 1 | 13 | 3 | 1 | 12 | 13 | 3 |
| 1 | 12 | 14 | 2 | 12 | 1 | 14 | 2 |
| 2 | 11 | 14 | 2 | 11 | 2 | 14 | 2 |
| 3 | 10 | 14 | 2 | 10 | 3 | 14 | 2 |
| 4 | 9 | 14 | 2 | 9 | 4 | 14 | 2 |
| 5 | 8 | 14 | 2 | 8 | 5 | 14 | 2 |
| 6 | 7 | 14 | 2 | 7 | 6 | 14 | 2 |
| 7 | 6 | 14 | 2 | 6 | 7 | 14 | 2 |
| 8 | 5 | 14 | 2 | 5 | 8 | 14 | 2 |
| 9 | 4 | 14 | 2 | 4 | 9 | 14 | 2 |
| 10 | 3 | 14 | 2 | 3 | 10 | 14 | 2 |
| 11 | 2 | 14 | 2 | 2 | 11 | 14 | 2 |
| 12 | 1 | 14 | 2 | 1 | 12 | 14 | 2 |
| 1 | 12 | 7 | 9 | 12 | 1 | 7 | 9 |
| 2 | 11 | 7 | 9 | 11 | 2 | 7 | 9 |
| 3 | 10 | 7 | 9 | 10 | 3 | 7 | 9 |
| 4 | 9 | 7 | 9 | 9 | 4 | 7 | 9 |
| 5 | 8 | 7 | 9 | 8 | 5 | 7 | 9 |
| 6 | 7 | 7 | 9 | 7 | 6 | 7 | 9 |
| 7 | 6 | 7 | 9 | 6 | 7 | 7 | 9 |
| 8 | 5 | 7 | 9 | 5 | 8 | 7 | 9 |
| 9 | 4 | 7 | 9 | 4 | 9 | 7 | 9 |
| 10 | 3 | 7 | 9 | 3 | 10 | 7 | 9 |
| 11 | 2 | 7 | 9 | 2 | 11 | 7 | 9 |
| 12 | 1 | 7 | 9 | 1 | 12 | 7 | 9 |
| 12 | 1 | 6 | 10 | 12 | 1 | 6 | 10 |
| 1 | 12 | 6 | 10 | 11 | 2 | 6 | 10 |
| 2 | 11 | 6 | 10 | 10 | 3 | 6 | 10 |
| 3 | 10 | 6 | 10 | 9 | 4 | 6 | 10 |
| 4 | 9 | 6 | 10 | 8 | 5 | 6 | 10 |
| 5 | 8 | 6 | 10 | 7 | 6 | 6 | 10 |
| 6 | 7 | 6 | 10 | 6 | 7 | 6 | 10 |
| 7 | 6 | 6 | 10 | 5 | 8 | 6 | 10 |
| 8 | 5 | 6 | 10 | 4 | 9 | 6 | 10 |
| 9 | 4 | 6 | 10 | 3 | 10 | 6 | 10 |
| 10 | 3 | 6 | 10 | 2 | 11 | 6 | 10 |
| 11 | 2 | 6 | 10 | 1 | 12 | 6 | 10 |
| 12 | 1 | 6 | 10 | 12 | 1 | 6 | 10 |
| 1 | 12 | 5 | 11 | 11 | 2 | 5 | 11 |
| 2 | 11 | 5 | 11 | 10 | 3 | 5 | 11 |
| 3 | 10 | 5 | 11 | 9 | 4 | 5 | 11 |
| 4 | 9 | 5 | 11 | 8 | 5 | 5 | 11 |
| 5 | 8 | 5 | 11 | 7 | 6 | 5 | 11 |
| 6 | 7 | 5 | 11 | 6 | 7 | 5 | 11 |
| 7 | 6 | 5 | 11 | 5 | 8 | 5 | 11 |
| 8 | 5 | 5 | 11 | 4 | 9 | 5 | 11 |
| 9 | 4 | 5 | 11 | 3 | 10 | 5 | 11 |
| 10 | 3 | 5 | 11 | 2 | 11 | 5 | 11 |
| 11 | 2 | 5 | 11 | 1 | 12 | 5 | 11 |
| 12 | 1 | 5 | 11 | 12 | 1 | 5 | 11 |
| 1 | 12 | 4 | 12 | 11 | 2 | 4 | 12 |
| 2 | 11 | 4 | 12 | 10 | 3 | 4 | 12 |
| 3 | 10 | 4 | 12 | 9 | 4 | 4 | 12 |
| 4 | 9 | 4 | 12 | 8 | 5 | 4 | 12 |
| 5 | 8 | 4 | 12 | 7 | 6 | 4 | 12 |
| 6 | 7 | 4 | 12 | 6 | 7 | 4 | 12 |
| 7 | 6 | 4 | 12 | 5 | 8 | 4 | 12 |
| 8 | 5 | 4 | 12 | 4 | 9 | 4 | 12 |
| 9 | 4 | 4 | 12 | 3 | 10 | 4 | 12 |
| 10 | 3 | 4 | 12 | 2 | 11 | 4 | 12 |
| 11 | 2 | 4 | 12 | 1 | 12 | 4 | 12 |
| 12 | 1 | 4 | 12 | 12 | 1 | 4 | 12 |

TABLE 10

| m | n | p | m | n | p |
|---|---|---|---|---|---|
| 1 | 12 | 18 | 12 | 1 | 18 |
| 2 | 11 | 18 | 11 | 2 | 18 |
| 3 | 10 | 18 | 10 | 3 | 18 |
| 4 | 9 | 18 | 9 | 4 | 18 |
| 5 | 8 | 18 | 8 | 5 | 18 |
| 6 | 7 | 18 | 7 | 6 | 18 |
| 7 | 6 | 18 | 6 | 7 | 18 |
| 8 | 5 | 18 | 5 | 8 | 18 |
| 9 | 4 | 18 | 4 | 9 | 18 |
| 10 | 3 | 18 | 3 | 10 | 18 |
| 11 | 2 | 18 | 2 | 11 | 18 |
| 12 | 1 | 18 | 1 | 12 | 18 |
| 1 | 12 | 17 | 12 | 1 | 17 |
| 2 | 11 | 17 | 11 | 2 | 17 |
| 3 | 10 | 17 | 10 | 3 | 17 |
| 4 | 9 | 17 | 9 | 4 | 17 |
| 5 | 8 | 17 | 8 | 5 | 17 |
| 6 | 7 | 17 | 7 | 6 | 17 |
| 7 | 6 | 17 | 6 | 7 | 17 |
| 8 | 5 | 17 | 5 | 8 | 17 |
| 9 | 4 | 17 | 4 | 9 | 17 |
| 10 | 3 | 17 | 3 | 10 | 17 |
| 11 | 2 | 17 | 2 | 11 | 17 |
| 12 | 1 | 17 | 1 | 12 | 17 |
| 1 | 12 | 16 | 12 | 1 | 16 |
| 2 | 11 | 16 | 11 | 2 | 16 |
| 3 | 10 | 16 | 10 | 3 | 16 |
| 4 | 9 | 16 | 9 | 4 | 16 |
| 5 | 8 | 16 | 8 | 5 | 16 |
| 6 | 7 | 16 | 7 | 6 | 16 |
| 7 | 6 | 16 | 6 | 7 | 16 |
| 8 | 5 | 16 | 5 | 8 | 16 |
| 9 | 4 | 16 | 4 | 9 | 16 |
| 10 | 3 | 16 | 3 | 10 | 16 |
| 11 | 2 | 16 | 2 | 11 | 16 |
| 12 | 1 | 16 | 1 | 12 | 16 |
| 1 | 12 | 15 | 12 | 1 | 15 |
| 2 | 11 | 15 | 11 | 2 | 15 |
| 3 | 10 | 15 | 10 | 3 | 15 |
| 4 | 9 | 15 | 9 | 4 | 15 |
| 5 | 8 | 15 | 8 | 5 | 15 |
| 6 | 7 | 15 | 7 | 6 | 15 |
| 7 | 6 | 15 | 6 | 7 | 15 |
| 8 | 5 | 15 | 5 | 8 | 15 |
| 9 | 4 | 15 | 4 | 9 | 15 |
| 10 | 3 | 15 | 3 | 10 | 15 |
| 11 | 2 | 15 | 2 | 11 | 15 |
| 12 | 1 | 15 | 1 | 12 | 15 |
| 1 | 12 | 14 | 12 | 1 | 14 |
| 2 | 11 | 14 | 11 | 2 | 14 |
| 3 | 10 | 14 | 10 | 3 | 14 |
| 4 | 9 | 14 | 9 | 4 | 14 |
| 5 | 8 | 14 | 8 | 5 | 14 |
| 6 | 7 | 14 | 7 | 6 | 14 |
| 7 | 6 | 14 | 6 | 7 | 14 |
| 8 | 5 | 14 | 5 | 8 | 14 |
| 9 | 4 | 14 | 4 | 9 | 14 |
| 10 | 3 | 14 | 3 | 10 | 14 |
| 11 | 2 | 14 | 2 | 11 | 14 |
| 12 | 1 | 14 | 1 | 12 | 14 |
| 1 | 12 | 13 | 12 | 1 | 13 |
| 2 | 11 | 13 | 11 | 2 | 13 |
| 3 | 10 | 13 | 10 | 3 | 13 |
| 4 | 9 | 13 | 9 | 4 | 13 |
| 5 | 8 | 13 | 8 | 5 | 13 |
| 6 | 7 | 13 | 7 | 6 | 13 |
| 7 | 6 | 13 | 6 | 7 | 13 |
| 8 | 5 | 13 | 5 | 8 | 13 |
| 9 | 4 | 13 | 4 | 9 | 13 |
| 10 | 3 | 13 | 3 | 10 | 13 |

TABLE 10-continued
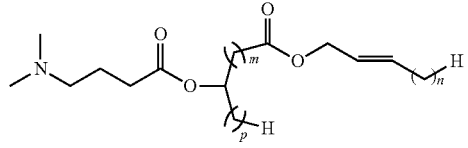
| m | n | p | m | n | p |
|---|---|---|---|---|---|
| 11 | 2 | 13 | 2 | 11 | 13 |
| 12 | 1 | 13 | 1 | 12 | 13 |
| 1 | 12 | 12 | 12 | 1 | 12 |
| 2 | 11 | 12 | 11 | 2 | 12 |
| 3 | 10 | 12 | 10 | 3 | 12 |
| 4 | 9 | 12 | 9 | 4 | 12 |
| 5 | 8 | 12 | 8 | 5 | 12 |
| 6 | 7 | 12 | 7 | 6 | 12 |
| 7 | 6 | 12 | 6 | 7 | 12 |
| 8 | 5 | 12 | 5 | 8 | 12 |
| 9 | 4 | 12 | 4 | 9 | 12 |
| 10 | 3 | 12 | 3 | 10 | 12 |
| 11 | 2 | 12 | 2 | 11 | 12 |
| 12 | 1 | 12 | 1 | 12 | 12 |
| 1 | 12 | 11 | 12 | 1 | 11 |
| 2 | 11 | 11 | 11 | 2 | 11 |
| 3 | 10 | 11 | 10 | 3 | 11 |
| 4 | 9 | 11 | 9 | 4 | 11 |
| 5 | 8 | 11 | 8 | 5 | 11 |
| 6 | 7 | 11 | 7 | 6 | 11 |
| 7 | 6 | 11 | 6 | 7 | 11 |
| 8 | 5 | 11 | 5 | 8 | 11 |
| 9 | 4 | 11 | 4 | 9 | 11 |
| 10 | 3 | 11 | 3 | 10 | 11 |
| 11 | 2 | 11 | 2 | 11 | 11 |
| 12 | 1 | 11 | 1 | 12 | 11 |
| 12 | 1 | 10 | 12 | 1 | 10 |
| 1 | 12 | 10 | 11 | 2 | 10 |
| 2 | 11 | 10 | 10 | 3 | 10 |
| 3 | 10 | 10 | 9 | 4 | 10 |
| 4 | 9 | 10 | 8 | 5 | 10 |
| 5 | 8 | 10 | 7 | 6 | 10 |
| 6 | 7 | 10 | 6 | 7 | 10 |
| 7 | 6 | 10 | 5 | 8 | 10 |
| 8 | 5 | 10 | 4 | 9 | 10 |
| 9 | 4 | 10 | 3 | 10 | 10 |
| 10 | 3 | 10 | 2 | 11 | 10 |
| 11 | 2 | 10 | 1 | 12 | 10 |
| 12 | 1 | 10 | 12 | 1 | 10 |
| 1 | 12 | 9 | 11 | 2 | 9 |
| 2 | 11 | 9 | 10 | 3 | 9 |
| 3 | 10 | 9 | 9 | 4 | 9 |
| 4 | 9 | 9 | 8 | 5 | 9 |
| 5 | 8 | 9 | 7 | 6 | 9 |
| 6 | 7 | 9 | 6 | 7 | 9 |
| 7 | 6 | 9 | 5 | 8 | 9 |
| 8 | 5 | 9 | 4 | 9 | 9 |
| 9 | 4 | 9 | 3 | 10 | 9 |
| 10 | 3 | 9 | 2 | 11 | 9 |
| 11 | 2 | 9 | 1 | 12 | 9 |
| 12 | 1 | 9 | 12 | 1 | 9 |
| 1 | 12 | 8 | 11 | 2 | 8 |
| 2 | 11 | 8 | 10 | 3 | 8 |
| 3 | 10 | 8 | 9 | 4 | 8 |
| 4 | 9 | 8 | 8 | 5 | 8 |
| 5 | 8 | 8 | 7 | 6 | 8 |
| 6 | 7 | 8 | 6 | 7 | 8 |
| 7 | 6 | 8 | 5 | 8 | 8 |
| 8 | 5 | 8 | 4 | 9 | 8 |
| 9 | 4 | 8 | 3 | 10 | 8 |
| 10 | 3 | 8 | 2 | 11 | 8 |
| 11 | 2 | 8 | 1 | 12 | 8 |
| 12 | 1 | 8 | 12 | 1 | 8 |

TABLE 11
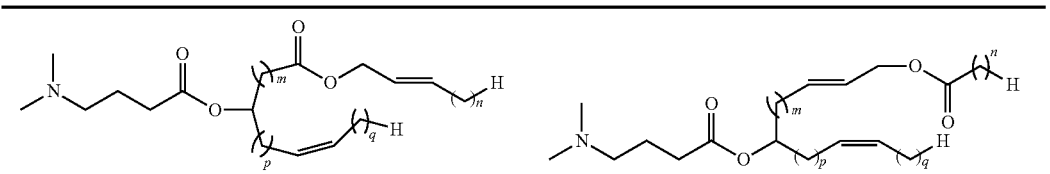
| m | n | p | q | m | n | p | q |
|---|---|---|---|---|---|---|---|
| 1 | 12 | 8 | 8 | 12 | 1 | 8 | 8 |
| 2 | 11 | 8 | 8 | 11 | 2 | 8 | 8 |
| 3 | 10 | 8 | 8 | 10 | 3 | 8 | 8 |
| 4 | 9 | 8 | 8 | 9 | 4 | 8 | 8 |
| 5 | 8 | 8 | 8 | 8 | 5 | 8 | 8 |
| 6 | 7 | 8 | 8 | 7 | 6 | 8 | 8 |
| 7 | 6 | 8 | 8 | 6 | 7 | 8 | 8 |
| 8 | 5 | 8 | 8 | 5 | 8 | 8 | 8 |
| 9 | 4 | 8 | 8 | 4 | 9 | 8 | 8 |
| 10 | 3 | 8 | 8 | 3 | 10 | 8 | 8 |
| 11 | 2 | 8 | 8 | 2 | 11 | 8 | 8 |
| 12 | 1 | 8 | 8 | 1 | 12 | 8 | 8 |
| 1 | 12 | 9 | 7 | 12 | 1 | 9 | 7 |
| 2 | 11 | 9 | 7 | 11 | 2 | 9 | 7 |
| 3 | 10 | 9 | 7 | 10 | 3 | 9 | 7 |
| 4 | 9 | 9 | 7 | 9 | 4 | 9 | 7 |
| 5 | 8 | 9 | 7 | 8 | 5 | 9 | 7 |
| 6 | 7 | 9 | 7 | 7 | 6 | 9 | 7 |
| 7 | 6 | 9 | 7 | 6 | 7 | 9 | 7 |
| 8 | 5 | 9 | 7 | 5 | 8 | 9 | 7 |
| 9 | 4 | 9 | 7 | 4 | 9 | 9 | 7 |
| 10 | 3 | 9 | 7 | 3 | 10 | 9 | 7 |
| 11 | 2 | 9 | 7 | 2 | 11 | 9 | 7 |
| 12 | 1 | 9 | 7 | 1 | 12 | 9 | 7 |
| 1 | 12 | 10 | 6 | 12 | 1 | 10 | 6 |
| 2 | 11 | 10 | 6 | 11 | 2 | 10 | 6 |
| 3 | 10 | 10 | 6 | 10 | 3 | 10 | 6 |
| 4 | 9 | 10 | 6 | 9 | 4 | 10 | 6 |
| 5 | 8 | 10 | 6 | 8 | 5 | 10 | 6 |
| 6 | 7 | 10 | 6 | 7 | 6 | 10 | 6 |
| 7 | 6 | 10 | 6 | 6 | 7 | 10 | 6 |
| 8 | 5 | 10 | 6 | 5 | 8 | 10 | 6 |
| 9 | 4 | 10 | 6 | 4 | 9 | 10 | 6 |
| 10 | 3 | 10 | 6 | 3 | 10 | 10 | 6 |
| 11 | 2 | 10 | 6 | 2 | 11 | 10 | 6 |
| 12 | 1 | 10 | 6 | 1 | 12 | 10 | 6 |
| 1 | 12 | 11 | 5 | 12 | 1 | 11 | 5 |
| 2 | 11 | 11 | 5 | 11 | 2 | 11 | 5 |
| 3 | 10 | 11 | 5 | 10 | 3 | 11 | 5 |
| 4 | 9 | 11 | 5 | 9 | 4 | 11 | 5 |
| 5 | 8 | 11 | 5 | 8 | 5 | 11 | 5 |
| 6 | 7 | 11 | 5 | 7 | 6 | 11 | 5 |
| 7 | 6 | 11 | 5 | 6 | 7 | 11 | 5 |
| 8 | 5 | 11 | 5 | 5 | 8 | 11 | 5 |
| 9 | 4 | 11 | 5 | 4 | 9 | 11 | 5 |
| 10 | 3 | 11 | 5 | 3 | 10 | 11 | 5 |
| 11 | 2 | 11 | 5 | 2 | 11 | 11 | 5 |
| 12 | 1 | 11 | 5 | 1 | 12 | 11 | 5 |
| 1 | 12 | 12 | 4 | 12 | 1 | 12 | 4 |
| 2 | 11 | 12 | 4 | 11 | 2 | 12 | 4 |
| 3 | 10 | 12 | 4 | 10 | 3 | 12 | 4 |
| 4 | 9 | 12 | 4 | 9 | 4 | 12 | 4 |
| 5 | 8 | 12 | 4 | 8 | 5 | 12 | 4 |
| 6 | 7 | 12 | 4 | 7 | 6 | 12 | 4 |
| 7 | 6 | 12 | 4 | 6 | 7 | 12 | 4 |
| 8 | 5 | 12 | 4 | 5 | 8 | 12 | 4 |
| 9 | 4 | 12 | 4 | 4 | 9 | 12 | 4 |
| 10 | 3 | 12 | 4 | 3 | 10 | 12 | 4 |
| 11 | 2 | 12 | 4 | 2 | 11 | 12 | 4 |
| 12 | 1 | 12 | 4 | 1 | 12 | 12 | 4 |
| 1 | 12 | 13 | 3 | 12 | 1 | 13 | 3 |
| 2 | 11 | 13 | 3 | 11 | 2 | 13 | 3 |
| 3 | 10 | 13 | 3 | 10 | 3 | 13 | 3 |
| 4 | 9 | 13 | 3 | 9 | 4 | 13 | 3 |
| 5 | 8 | 13 | 3 | 8 | 5 | 13 | 3 |
| 6 | 7 | 13 | 3 | 7 | 6 | 13 | 3 |
| 7 | 6 | 13 | 3 | 6 | 7 | 13 | 3 |
| 8 | 5 | 13 | 3 | 5 | 8 | 13 | 3 |
| 9 | 4 | 13 | 3 | 4 | 9 | 13 | 3 |

TABLE 11-continued

| m | n | p | q | m | n | p | q |
|---|---|---|---|---|---|---|---|
| 10 | 3 | 13 | 3 | 3 | 10 | 13 | 3 |
| 11 | 2 | 13 | 3 | 2 | 11 | 13 | 3 |
| 12 | 1 | 13 | 3 | 1 | 12 | 13 | 3 |
| 1 | 12 | 14 | 2 | 12 | 1 | 14 | 2 |
| 2 | 11 | 14 | 2 | 11 | 2 | 14 | 2 |
| 3 | 10 | 14 | 2 | 10 | 3 | 14 | 2 |
| 4 | 9 | 14 | 2 | 9 | 4 | 14 | 2 |
| 5 | 8 | 14 | 2 | 8 | 5 | 14 | 2 |
| 6 | 7 | 14 | 2 | 7 | 6 | 14 | 2 |
| 7 | 6 | 14 | 2 | 6 | 7 | 14 | 2 |
| 8 | 5 | 14 | 2 | 5 | 8 | 14 | 2 |
| 9 | 4 | 14 | 2 | 4 | 9 | 14 | 2 |
| 10 | 3 | 14 | 2 | 3 | 10 | 14 | 2 |
| 11 | 2 | 14 | 2 | 2 | 11 | 14 | 2 |
| 12 | 1 | 14 | 2 | 1 | 12 | 14 | 2 |
| 1 | 12 | 7 | 9 | 12 | 1 | 7 | 9 |
| 2 | 11 | 7 | 9 | 11 | 2 | 7 | 9 |
| 3 | 10 | 7 | 9 | 10 | 3 | 7 | 9 |
| 4 | 9 | 7 | 9 | 9 | 4 | 7 | 9 |
| 5 | 8 | 7 | 9 | 8 | 5 | 7 | 9 |
| 6 | 7 | 7 | 9 | 7 | 6 | 7 | 9 |
| 7 | 6 | 7 | 9 | 6 | 7 | 7 | 9 |
| 8 | 5 | 7 | 9 | 5 | 8 | 7 | 9 |
| 9 | 4 | 7 | 9 | 4 | 9 | 7 | 9 |
| 10 | 3 | 7 | 9 | 3 | 10 | 7 | 9 |
| 11 | 2 | 7 | 9 | 2 | 11 | 7 | 9 |
| 12 | 1 | 7 | 9 | 1 | 12 | 7 | 9 |
| 12 | 1 | 6 | 10 | 12 | 1 | 6 | 10 |
| 1 | 12 | 6 | 10 | 11 | 2 | 6 | 10 |
| 2 | 11 | 6 | 10 | 10 | 3 | 6 | 10 |
| 3 | 10 | 6 | 10 | 9 | 4 | 6 | 10 |
| 4 | 9 | 6 | 10 | 8 | 5 | 6 | 10 |
| 5 | 8 | 6 | 10 | 7 | 6 | 6 | 10 |
| 6 | 7 | 6 | 10 | 6 | 7 | 6 | 10 |
| 7 | 6 | 6 | 10 | 5 | 8 | 6 | 10 |
| 8 | 5 | 6 | 10 | 4 | 9 | 6 | 10 |
| 9 | 4 | 6 | 10 | 3 | 10 | 6 | 10 |
| 10 | 3 | 6 | 10 | 2 | 11 | 6 | 10 |
| 11 | 2 | 6 | 10 | 1 | 12 | 6 | 10 |
| 12 | 1 | 6 | 10 | 12 | 1 | 6 | 10 |
| 1 | 12 | 5 | 11 | 11 | 2 | 5 | 11 |
| 2 | 11 | 5 | 11 | 10 | 3 | 5 | 11 |
| 3 | 10 | 5 | 11 | 9 | 4 | 5 | 11 |
| 4 | 9 | 5 | 11 | 8 | 5 | 5 | 11 |
| 5 | 8 | 5 | 11 | 7 | 6 | 5 | 11 |
| 6 | 7 | 5 | 11 | 6 | 7 | 5 | 11 |
| 7 | 6 | 5 | 11 | 5 | 8 | 5 | 11 |
| 8 | 5 | 5 | 11 | 4 | 9 | 5 | 11 |
| 9 | 4 | 5 | 11 | 3 | 10 | 5 | 11 |
| 10 | 3 | 5 | 11 | 2 | 11 | 5 | 11 |
| 11 | 2 | 5 | 11 | 1 | 12 | 5 | 11 |
| 12 | 1 | 5 | 11 | 12 | 1 | 5 | 11 |
| 1 | 12 | 4 | 12 | 11 | 2 | 4 | 12 |
| 2 | 11 | 4 | 12 | 10 | 3 | 4 | 12 |
| 3 | 10 | 4 | 12 | 9 | 4 | 4 | 12 |
| 4 | 9 | 4 | 12 | 8 | 5 | 4 | 12 |
| 5 | 8 | 4 | 12 | 7 | 6 | 4 | 12 |
| 6 | 7 | 4 | 12 | 6 | 7 | 4 | 12 |
| 7 | 6 | 4 | 12 | 5 | 8 | 4 | 12 |
| 8 | 5 | 4 | 12 | 4 | 9 | 4 | 12 |
| 9 | 4 | 4 | 12 | 3 | 10 | 4 | 12 |
| 10 | 3 | 4 | 12 | 2 | 11 | 4 | 12 |
| 11 | 2 | 4 | 12 | 1 | 12 | 4 | 12 |
| 12 | 1 | 4 | 12 | 12 | 1 | 4 | 12 |

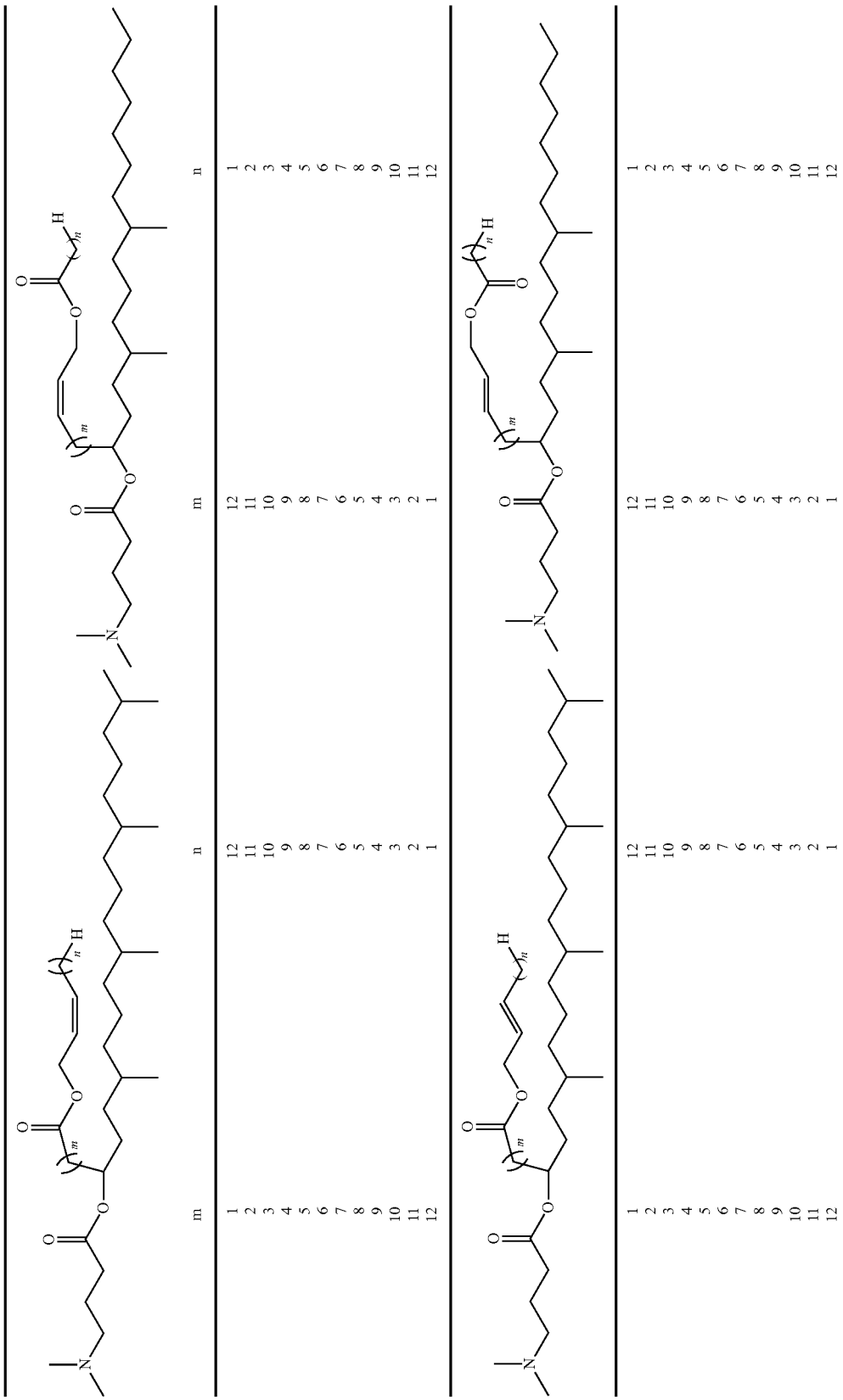

TABLE 13
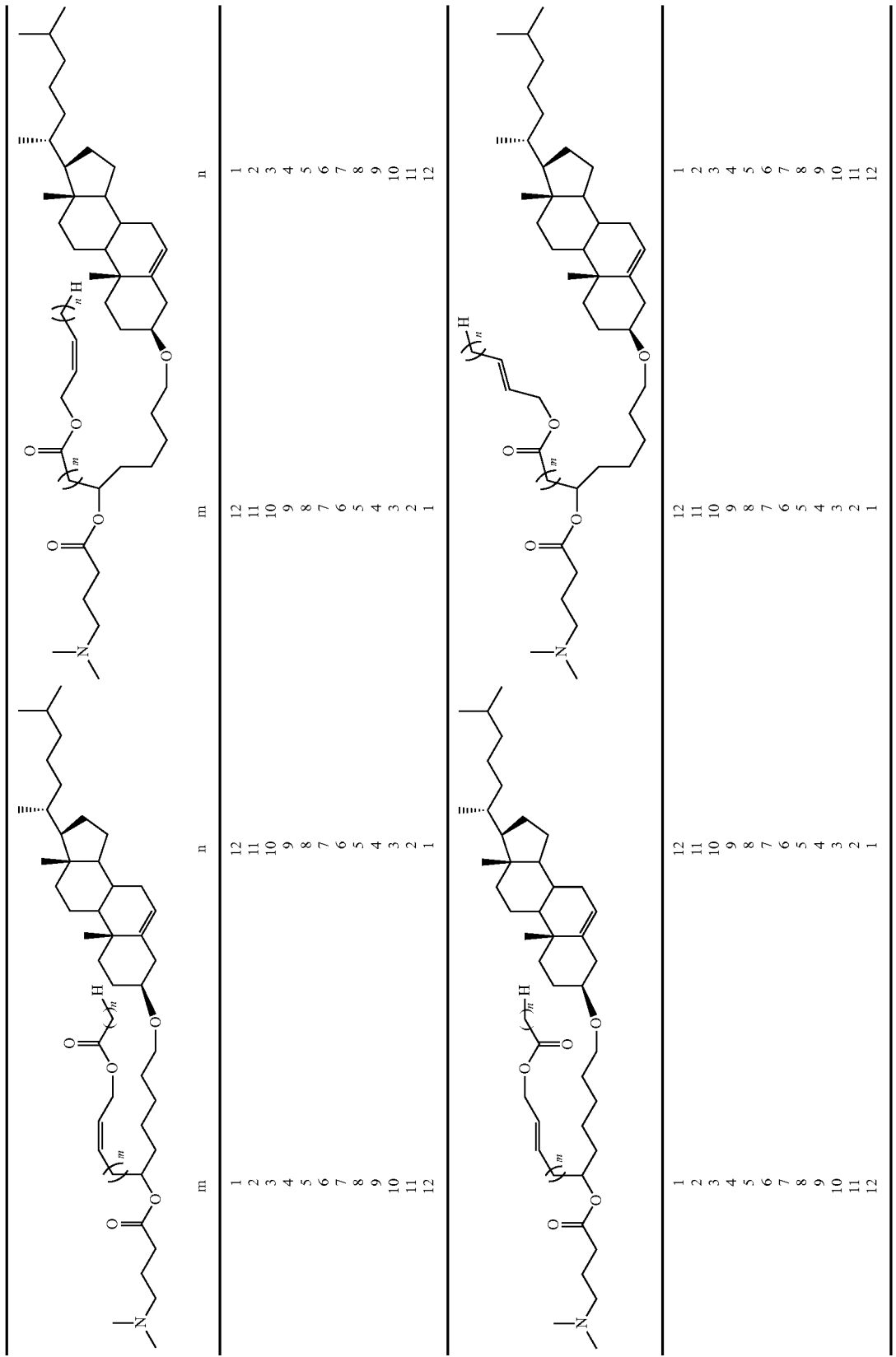

TABLE 14

The following compounds may be used as intermediates in the synthesis of cationic lipids according to the present invention.

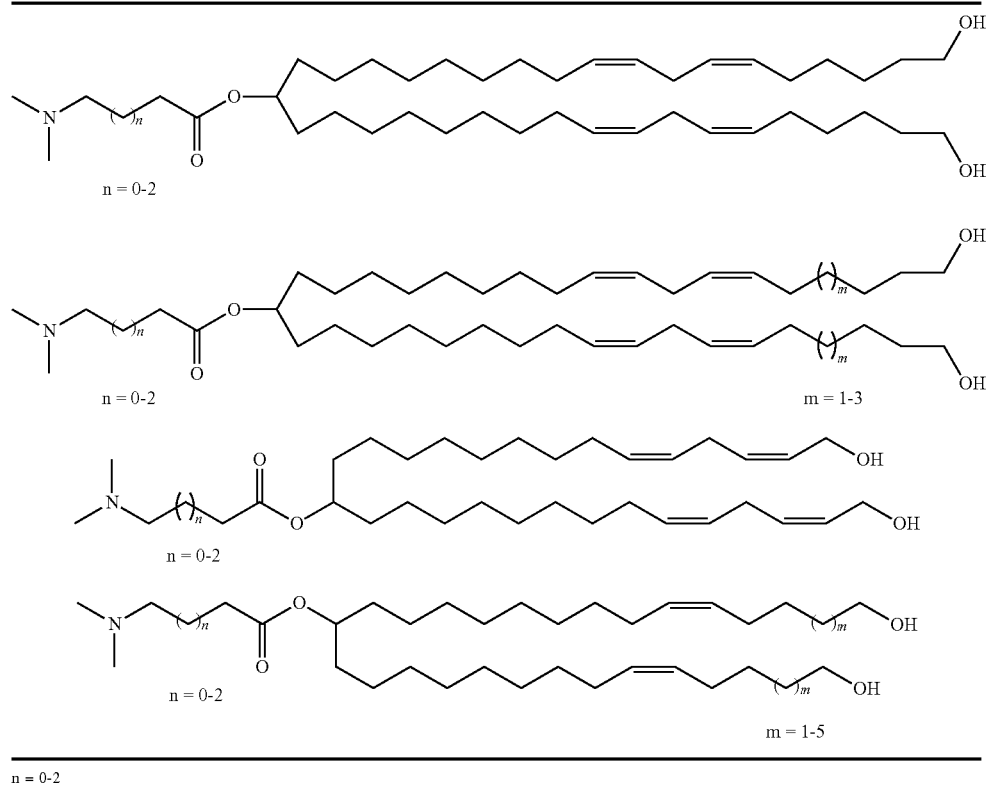

n = 0-2

In one embodiment, the cationic lipid of the present invention is selected from the following compounds, and salts thereof (including pharmaceutically acceptable salts thereof):

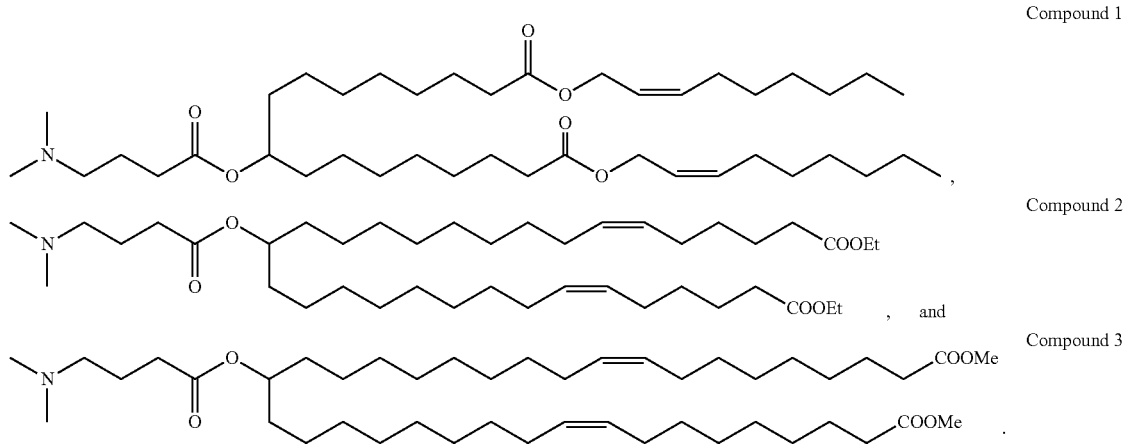

Cationic lipids include those having alternative fatty acid groups and other dialkylamino groups, including those in which the alkyl substituents are different (e.g., N-ethyl-N-methylamino-, N-propyl-N-ethylamino- and the like). For those embodiments in which $R^1$ and $R^2$ are both long chain alkyl, alkenyl, alkynyl, or cycloalkylalkyl groups, they can be the same or different. In general, lipids (e.g., a cationic lipid) having less-saturated acyl chains are more easily sized, particularly when the complexes are sized below about 0.3 microns, for purposes of filter sterilization. Cationic lipids containing unsaturated fatty acids with carbon chain lengths in the range of $C_{10}$ to $C_{20}$ are typical. Other scaffolds can also be used to separate the amino group (e.g., the amino group of the cationic lipid) and the fatty acid or fatty alkyl portion of the cationic lipid. Suitable scaffolds are known to those of skill in the art.

In certain embodiments, cationic lipids have at least one protonatable or deprotonatable group, such that the lipid is positively charged at a pH at or below physiological pH (e.g. pH 7.4), and neutral at a second pH, preferably at or above physiological pH. Such lipids are also referred to as cationic lipids. It will, of course, be understood that the addition or removal of protons as a function of pH is an equilibrium process, and that the reference to a charged or a neutral lipid refers to the nature of the predominant species and does not require that all of the lipid be present in the charged or neutral form. The lipids can have more than one protonatable or deprotonatable group, or can be zwiterrionic.

In certain embodiments, protonatable lipids (i.e., cationic lipids) have a p$K_a$ of the protonatable group in the range of about 4 to about 11. Typically, lipids will have a p$K_a$ of about 4 to about 7, e.g., between about 5 and 7, such as between about 5.5 and 6.8, when incorporated into lipid particles. Such lipids will be cationic at a lower pH formulation stage, while particles will be largely (though not completely) surface neutralized at physiological pH around pH 7.4. One of the benefits of a p$K_a$ in the range of between about 4 and 7 is that at least some nucleic acid associated with the outside surface of the particle will lose its electrostatic interaction at physiological pH and be removed by simple dialysis; thus greatly reducing the particle's susceptibility to clearance. p$K_a$ measurements of lipids within lipid particles can be performed, for example, by using the fluorescent probe 2-(p-toluidino)-6-napthalene sulfonic acid (TNS), using methods described in Cullis et al., (1986) *Chem Phys Lipids* 40, 127-144, which is incorporated by reference in its entirety.

In particular embodiments, the lipids are charged lipids. As used herein, the term "charged lipid" is meant to include those lipids having one or two fatty acyl or fatty alkyl chains and a quaternary amino head group. The quaternary amine carries a permanent positive charge. The head group can optionally include a ionizable group, such as a primary, secondary, or tertiary amine that may be protonated at physiological pH. The presence of the quaternary amine can alter the pKa of the ionizable group relative to the pKa of the group in a structurally similar compound that lacks the quaternary amine (e.g., the quaternary amine is replaced by a tertiary amine) In some embodiments, a charged lipid is referred to as an "amino lipid." See, for example, provisional U.S. patent application 61/267,419, filed Dec. 7, 2009, which is incorporated by reference in its entirety.

One or more additional cationic lipids, which carry a net positive charge at about physiological pH, in addition to those specifically described above, may also be included in lipid particles and compositions described herein. Such cationic lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoroacetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

The Neutral Lipid

The lipid particles and compositions described herein may also include one or more neutral lipids. Neutral lipids, when present, can be any of a number of lipid species which exist either in an uncharged or neutral zwitterionic form at physiological pH. Such lipids include, for example, diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{10}$ to $C_{20}$ are preferred. In another group of embodiments, lipids with mono or diunsaturated fatty acids with carbon chain lengths in the range of $C_{10}$ to $C_{20}$ are used. Additionally, lipids having mixtures of saturated and unsaturated fatty acid chains can be used. Preferably, the neutral lipids used are DOPE, DSPC, POPC, DPPC or any related phosphatidylcholine. The neutral lipids may also be composed of sphingomyelin, dihydrosphingomyelne, or phospholipids with other head groups, such as serine and inositol.

The Lipid Capable of Reducing Aggregation

The lipid particles and compositions described herein may also include one or more lipids capable of reducing aggregation. Examples of lipids that reduce aggregation of particles during formation include polyethylene glycol (PEG)-modified lipids, monosialoganglioside Gm1, and polyamide oligomers ("PAO") such as (described in U.S. Pat. No. 6,320,017, which is incorporated by reference in its entirety). Other compounds with uncharged, hydrophilic, steric-barrier moieties, which prevent aggregation during formulation, like PEG, Gm1 or ATTA, can also be coupled to lipids. ATTA-lipids are described, e.g., in U.S. Pat. No. 6,320,017, and PEG-lipid conjugates are described, e.g., in U.S. Pat. Nos. 5,820,873, 5,534,499 and 5,885,613, each of which is incorporated by reference in its entirety. Typically, the concentration of the lipid component selected to reduce aggregation is about 1 to 15% (by mole percent of lipids).

Specific examples of PEG-modified lipids (or lipid-polyoxyethylene conjugates) that can have a variety of "anchoring" lipid portions to secure the PEG portion to the surface of the lipid vesicle include PEG-modified phosphatidylethanolamine and phosphatidic acid, PEG-ceramide conjugates (e.g., PEG-CerC14 or PEG-CerC20) which are described in U.S. Pat. No. 5,820,873, incorporated herein by reference, PEG-modified dialkylamines and PEG-modified 1,2-diacyloxypropan-3-amines. Particularly preferred are PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mPEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 min in some assays. As illustrated in U.S. Pat. No. 5,820,873, at least three characteristics influence the rate of exchange: length of acyl chain, saturation of acyl chain, and size of the steric-barrier head group. Compounds having suitable variations of these features may be useful. For some therapeutic applications it may be preferable for the PEG-modified lipid to be rapidly lost from the nucleic acid-lipid particle in vivo and hence the PEG-modified lipid will possess relatively short lipid anchors. In other therapeutic applications it may be preferable for the nucleic acid-lipid particle to exhibit a longer plasma circulation lifetime and hence the PEG-modified lipid will possess relatively longer lipid anchors.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

Lipid Particles

In a further aspect, the present invent relates to lipid particles that include one or more of the cationic lipids described herein. In one embodiment, the lipid particle includes one or more compound of formula I-XXIII. In another embodiment, the lipid particle includes one or more compound of formula II-XXIII. In another embodiment, the lipid particle includes one or more compound of formula I. In another embodiment, the lipid particle includes a compound of formula IA-1, IA-2, IB, IC, ID or IE.

Lipid particles include, but are not limited to, liposomes. As used herein, a liposome is a structure having lipid-containing membranes enclosing an aqueous interior. Liposomes may have one or more lipid membranes. Liposomes can be single-layered, referred to as unilamellar, or multi-layered, referred to as multilamellar. When complexed with nucleic acids, lipid particles may also be lipoplexes, which are composed of cationic lipid bilayers sandwiched between DNA layers.

The lipid particles may further comprise one or more additional lipids and/or other components such as cholesterol. Other lipids may be included in the liposome compositions for a variety of purposes, such as to prevent lipid oxidation or to attach ligands onto the liposome surface. Any of a number of lipids may be present in liposomes, including amphipathic, neutral, cationic, and anionic lipids. Such lipids can be used alone or in combination.

Additional components that may be present in a lipid particle include bilayer stabilizing components such as polyamide oligomers (see, e.g., U.S. Pat. No. 6,320,017, which is incorporated by reference in its entirety), peptides, proteins, detergents, lipid-derivatives, such as PEG coupled to phosphatidylethanolamine and PEG conjugated to ceramides (see, U.S. Pat. No. 5,885,613, which is incorporated by reference in its entirety).

In one embodiment, the lipid particles include one or more of a second amino lipid or cationic lipid, a neutral lipid, a sterol, and a lipid selected to reduce aggregation of lipid particles during formation, which may result from steric stabilization of particles which prevents charge-induced aggregation during formation.

Lipid particles can include two or more cationic lipids. The lipids can be selected to contribute different advantageous properties. For example, cationic lipids that differ in properties such as amine $pK_a$, chemical stability, half-life in circulation, half-life in tissue, net accumulation in tissue, or toxicity can be used in a lipid particle. In particular, the cationic lipids can be chosen so that the properties of the mixed-lipid particle are more desirable than the properties of a single-lipid particle of individual lipids.

Net tissue accumulation and long term toxicity (if any) from the cationic lipids can be modulated in a favorable way by choosing mixtures of cationic lipids instead of selecting a single cationic lipid in a given formulation. Such mixtures can also provide better encapsulation and/or release of the drug. A combination of cationic lipids also can affect the systemic stability when compared to single entity in a formulation.

In one example, a series of structurally similar compounds can have varying $pK_a$ values that span a range, e.g. of less than 1 $pK_a$ unit, from 1 to 2 $pK_a$ units, or a range of more than 2 $pK_a$ units. Within the series, it may be found that a $pK_a$ in the middle of the range is associated with an enhancement of advantageous properties (greater effectiveness) or a decrease in disadvantageous properties (e.g., reduced toxicity), compared to compounds having $pK_a$ values toward the ends of the range. In such a case, two (or more) different compounds having $pK_a$ values toward opposing ends of the range can be selected for use together in a lipid particle. In this way, the net properties of the lipid particle (for instance, charge as a function of local pH) can be closer to that of a particle including a single lipid from the middle of the range. Cationic lipids that are structurally dissimilar (for example, not part of the series of structurally similar compounds mentioned above) can also be used in a mixed-lipid particle.

In some cases, two or more different cationic lipids may have widely differing $pK_a$ values, e.g., differing by 3 or more $pK_a$ units. In this case, the net behavior of a mixed lipid particle will not necessarily mimic that of a single-lipid particle having an intermediate $pK_a$. Rather, the net behavior may be that of a particle having two distinct protonatable (or deprotonatable, as the case may be) site with different $pK_a$ values. In the case of a single lipid, the fraction of protonatable sites that are in fact protonated varies sharply as the pH moves from below the $pK_a$ to above the $pK_a$ (when the pH is equal to the $pK_a$ value, 50% of the sites are protonated). When two or more different cationic lipids may have widely differing $pK_a$ values (e.g., differing by 3 or more $pK_a$ units) are combined in a lipid particle, the lipid particle can show a more gradual transition from non-protonated to protonated as the pH is varied.

In other examples, two or more lipids may be selected based on other considerations. For example, if one lipid by itself is highly effective but moderately toxic, it might be combined with a lipid that is less effective but non-toxic. In some cases, the combination can remain highly effective but have a greatly reduced toxicity, even where it might be predicted that the combination would be only moderately effective and only slightly less toxic.

The selection may be guided by a measured value of an experimentally determinable characteristic, e.g., a characteristic that can be assigned a numerical value from the results of an experiment. Experimentally determinable characteristics can include a measure of safety, a measure of efficacy, a measure of interaction with a predetermined biomolecule, or $pK_a$.

A measure of safety might include a survival rate, an $LD_{50}$, or a level of a biomarker (such as a serum biomarker) associated with tissue damage (e.g., liver enzymes for liver; CPK for muscle; ionic balance for kidney). A measure of efficacy can be any measurement that indicates whether a therapeutic agent is producing an effect; particularly, whether and/or to what degree it is producing a desired effect, such as treating, preventing, ameliorating, or otherwise improving a disease, disorder, or other clinical condition. The measure of efficacy can be an indirect measure; for example, if a therapeutic agent is intended to produce a particular effect at a cellular level, measurements of that effect on cell cultures can be a measure of efficacy. A measure of interaction with predetermined biomolecules can include a $K_d$ for binding to a particular protein or a measure of the character, degree or extent of interaction with other lipids, including cellular substructures such as cell membranes, endosomal membranes, nuclear membranes, and the like.

The cationic lipids can be selected on the basis of mechanism of action, e.g., whether, under what conditions, or to what extent the lipids interact with predetermined biomolecules. For example, a first cationic lipid can be chosen, in part, because it is associated with an ApoE-dependent mechanism; a second cationic lipid can be chosen, in part, because it is associated with an ApoE-independent mechanism.

For example, a lipid particle can also include a mixture of the cationic lipids described in, e.g., WO 2009/086558, and provisional U.S. Application No. 61/104,219, filed Oct. 9, 2008 (each of which is incorporated by reference in its entirety), and ester analogs thereof. In another example, a lipid particle can include a mixture of a lipid, for example, Lipid A, described in PCT/US10/22614, filed Jan. 29, 2010 and a lipid, for example, the lipid of formula V or formula VI, described in U.S. Provisional Application 61/175,770, filed May 5, 2009.

In certain embodiments, it is desirable to target the lipid particles using targeting moieties that are specific to a cell type or tissue. Targeting of lipid particles using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044, each of which is incorporated by reference in its entirety). The targeting moieties can comprise the entire protein or fragments thereof. Targeting mechanisms generally require that the targeting agents be positioned on the surface of the lipid particle in such a manner that the target moiety is available for interaction with the target, for example, a cell surface receptor. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002).

The use of lipid particles, i.e., liposomes, with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci.* (*USA*), 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes,* 149 *Methods in Enzymology* 111-119 (Academic Press, Inc. 1987)). Other targeting methods include the biotin-avidin system.

In some embodiments, the lipid particle includes a mixture of a cationic lipid and a fusion-promoting lipid. The lipid particle can further include a neutral lipid, a sterol, a PEG-modified lipid, or a combination of these. For example, the lipid particle can include a cationic lipid, a fusion-promoting lipid (e.g., DPPC), and a neutral lipid, but no sterol or PEG-modified lipid. The lipid particle can include a cationic lipid, a fusion-promoting lipid, and a neutral lipid, but no sterol or PEG-modified lipid. The lipid particle can include a cationic lipid, a fusion-promoting lipid, and a PEG-modified lipid, but no sterol or neutral lipid. The lipid particle can include a cationic lipid, a fusion-promoting lipid, a sterol, and a neutral lipid, but no PEG-modified lipid. The lipid particle can include a cationic lipid, a fusion-promoting lipid, a sterol, and a PEG-modified lipid, but no neutral lipid. The lipid particle can include a cationic lipid, a fusion-promoting lipid, a neutral lipid, and a PEG-modified lipid, but no sterol. The lipid particle can include a cationic lipid, a fusion-promoting lipid, a sterol, neutral lipid, and a PEG-modified lipid.

In one exemplary embodiment, the lipid particle comprises a mixture of a cationic lipid, a fusion-promoting lipid, neutral lipids (other than a cationic lipid), a sterol (e.g., cholesterol) and a PEG-modified lipid (e.g., a PEG-DMG or PEG-DMA). In certain embodiments, the lipid mixture consists of or consists essentially of a cationic lipid, a fusion-promoting lipid, a neutral lipid, cholesterol, and a PEG-modified lipid. In further preferred embodiments, the lipid particle includes the above lipid mixture in molar ratios of about 20-70% cationic lipid:0.1-50% fusion promoting lipid:5-45% neutral lipid:20-55% cholesterol:0.5-15% PEG-modified lipid. In some embodiments, the fusion-promoting lipid can be present in a molar ratio of 0.1-50%, 0.5-50%, 1-50%, 5%-45%, 10%-40%, or 15%-35%. In some embodiments, the fusion-promoting lipid can be present in a molar ratio of 0.1-50%, 0.5-50%, 1-50%, 5%-45%, 10%-40%, or 15%-35%. In some embodiments, the fusion-promoting lipid can be present in a molar ratio of 0.1-50%, 10-50%, 20-50%, or 30-50%. In some embodiments, the fusion-promoting lipid can be present in a molar ratio of 0.1-50%, 0.5-45%, 1-40%, 1%-35%, 1%-30%, or 1%-20%.

In further preferred embodiments, the lipid particle consists of or consists essentially of the above lipid mixture in molar ratios of about 20-70% cationic lipid:0.1-50% fusion promoting lipid:5-45% neutral lipid:20-55% cholesterol: 0.5-15% PEG-modified lipid.

In particular embodiments, the molar lipid ratio, with regard to mol % cationic lipid/DSPC/Chol/PEG-DMG or PEG-DMA) is approximately 40/10/40/10, 35/15/40/10 or 52/13/30/5; this mixture is further combined with a fusion-promoting lipid in a molar ratio of 0.1-50%, 0.1-50%, 0.5-50%, 1-50%, 5%-45%, 10%-40%, or 15%-35%; in other words, when a 40/10/40/10 mixture of lipid/DSPC/Chol/PEG-DMG or PEG-DMA is combined with a fusion-promoting peptide in a molar ratio of 50%, the resulting lipid particles can have a total molar ratio of (mol % cationic lipid/DSPC/Chol/PEG-DMG or PEG-DMA/fusion-promoting peptide) 20/5/20/5/50. In another group of embodiments, the neutral lipid, DSPC, in these compositions is replaced with POPC, DPPC, DOPE or SM.

The lipid particles described herein may further include one or more therapeutic agents. Thus, compositions that include a lipid particle and an active agent, where the active agent is associated with the lipid particle, are provided. In particular embodiments, the active agent is a therapeutic agent. In particular embodiments, the active agent is encapsulated within an aqueous interior of the lipid particle. In other embodiments, the active agent is present within one or more lipid layers of the lipid particle. In other embodiments, the active agent is bound to the exterior or interior lipid surface of a lipid particle.

"Fully encapsulated" as used herein indicates that the nucleic acid in the particles is not significantly degraded after exposure to serum or a nuclease assay that would significantly degrade free nucleic acids. In a fully encapsulated system, preferably less than 25% of particle nucleic acid is degraded in a treatment that would normally degrade 100% of free nucleic acid, more preferably less than 10% and most preferably less than 5% of the particle nucleic acid is degraded. Alternatively, full encapsulation may be determined by an Oligreen® assay. Oligreen® is an ultra-sensitive fluorescent nucleic acid stain for quantitating oligonucleotides and single-stranded DNA in solution (available from Invitrogen Corporation, Carlsbad, Calif.). Fully encapsulated also suggests that the particles are serum stable, that is, that they do not rapidly decompose into their component parts upon in vivo administration.

In one embodiment, the lipid particles comprise a cationic lipid of the present invention, a neutral lipid, a sterol and a PEG-modified lipid. In one embodiment, the lipid particles include from about 25% to about 75% on a molar basis of cationic lipid, e.g., from about 35 to about 65%, from about 45 to about 65%, about 60%, about 57.5%, about 57.1%, about 50% or about 40% on a molar basis. In one embodiment, the lipid particles include from about 0% to about 15% on a molar basis of the neutral lipid, e.g., from about 3 to about 12%, from about 5 to about 10%, about 15%, about 10%, about 7.5%, about 7.1% or about 0% on a molar basis. In one embodiment, the neutral lipid is DPPC. In one embodiment, the neutral lipid is DSPC.

In one embodiment, the formulation includes from about 5% to about 50% on a molar basis of the sterol, e.g., about 15 to about 45%, about 20 to about 40%, about 48%, about 40%, about 38.5%, about 35%, about 34.4%, about 31.5% or about 31% on a molar basis. In one embodiment, the sterol is cholesterol.

In one embodiment, the lipid particles include from about 0.1% to about 20% on a molar basis of the PEG-modified lipid, e.g., about 0.5 to about 10%, about 0.5 to about 5%, about 10%, about 5%, about 3.5%, about 1.5%, about 0.5%, or about 0.3% on a molar basis. In one embodiment, the PEG-modified lipid is PEG-DMG. In one embodiment, the PEG-modified lipid is PEG-c-DMA. In one embodiment, the lipid particles include 25-75% of cationic lipid, 0.5-15% of the neutral lipid, 5-50% of the sterol, and 0.5-20% of the PEG-modified lipid on a molar basis.

In one embodiment, the lipid particles include 35-65% of cationic lipid, 3-12% of the neutral lipid, 15-45% of the sterol, and 0.5-10% of the PEG-modified lipid on a molar basis. In one embodiment, the lipid particles include 45-65% of cationic lipid, 5-10% of the neutral lipid, 25-40% of the sterol, and 0.5-5% of the PEG-modified lipid on a molar basis. In one embodiment, the PEG modified lipid comprises a PEG molecule of an average molecular weight of 2,000 Da. In one embodiment, the PEG modified lipid is PEG-distyryl glycerol (PEG-DSG).

In one embodiment, the ratio of lipid:siRNA is at least about 0.5:1, at least about 1:1, at least about 2:1, at least about 3:1, at least about 4:1, at least about 5:1, at least about 6:1, at least about 7:1, at least about 11:1 or at least about 33:1. In one embodiment, the ratio of lipid:siRNA ratio is between about 1:1 to about 35:1, about 3:1 to about 15:1, about 4:1 to about 15:1, or about 5:1 to about 13:1. In one embodiment, the ratio of lipid:siRNA ratio is between about 0.5:1 to about 12:1.

In one embodiment, the lipid particles are nanoparticles. In additional embodiments, the lipid particles have a mean diameter size of from about 50 nm to about 300 nm, such as from about 50 nm to about 250 nm, for example, from about 50 nm to about 200 nm.

In one embodiment, a lipid particle containing a cationic lipid of any of the embodiments described herein has an in vivo half life ($t_{1/2}$) (e.g., in the liver, spleen or plasma) of less than about 3 hours, such as less than about 2.5 hours, less than about 2 hours, less than about 1.5 hours, less than about 1 hour, less than about 0.5 hour or less than about 0.25 hours.

In another embodiment, a lipid particle containing a cationic lipid of any of the embodiments described herein has an in vivo half life ($t_{1/2}$) (e.g., in the liver, spleen or plasma) of less than about 10% (e.g., less than about 7.5%, less than about 5%, less than about 2.5%) of that for the same cationic lipid without the biodegradable group or groups.

Additional Components

The lipid particles and compositions described herein can further include an apolipoprotein. As used herein, the term "apolipoprotein" or "lipoprotein" refers to apolipoproteins known to those of skill in the art and variants and fragments thereof and to apolipoprotein agonists, analogues or fragments thereof described below.

Suitable apolipoproteins include, but are not limited to, ApoA-I, ApoA-II, ApoA-IV, ApoA-V and ApoE, and active polymorphic forms, isoforms, variants and mutants as well as fragments or truncated forms thereof. In certain embodiments, the apolipoprotein is a thiol containing apolipoprotein. "Thiol containing apolipoprotein" refers to an apolipoprotein, variant, fragment or isoform that contains at least one cysteine residue. The most common thiol containing apolipoproteins are ApoA-I Milano (ApoA-$I_M$) and ApoA-I Paris (ApoA-$I_P$) which contain one cysteine residue (Jia et al., 2002, Biochem. Biophys. Res. Comm. 297: 206-13; Bielicki and Oda, 2002, Biochemistry 41: 2089-96). ApoA-II, ApoE2 and ApoE3 are also thiol containing apolipoproteins. Isolated ApoE and/or active fragments and polypeptide analogues thereof, including recombinantly produced forms thereof, are described in U.S. Pat. Nos. 5,672,685; 5,525,472; 5,473,039; 5,182,364; 5,177,189; 5,168,045; 5,116,739; the disclosures of which are herein incorporated by reference. ApoE3 is disclosed in Weisgraber, et al., "Human E apoprotein heterogeneity: cysteine-arginine interchanges in the amino acid sequence of the apo-E isoforms," J. Biol. Chem. (1981) 256: 9077-9083; and Rall, et al., "Structural basis for receptor binding heterogeneity of apolipoprotein E from type III hyperlipoproteinemic subjects," Proc. Nat. Acad. Sci. (1982) 79: 4696-4700. See also GenBank accession number K00396.

In certain embodiments, the apolipoprotein can be in its mature form, in its preproapolipoprotein form or in its proapolipoprotein form. Homo- and heterodimers (where feasible) of pro- and mature ApoA-I (Duverger et al., 1996, Arterioscler. Thromb. Vasc. Biol. 16(12):1424-29), ApoA-I Milano (Klon et al., 2000, Biophys. J. 79:(3)1679-87; Franceschini et al., 1985, J. Biol. Chem. 260: 1632-35), ApoA-I Paris (Daum et al., 1999, J. Mol. Med. 77:614-22), ApoA-II (Shelness et al., 1985, J. Biol. Chem. 260(14):8637-46; Shelness et al., 1984, J. Biol. Chem. 259(15):9929-35), ApoA-IV (Duverger et al., 1991, Euro. J. Biochem. 201(2): 373-83), and ApoE (McLean et al., 1983, J. Biol. Chem. 258(14):8993-9000) can also be utilized.

In certain embodiments, the apolipoprotein can be a fragment, variant or isoform of the apolipoprotein. The term "fragment" refers to any apolipoprotein having an amino acid sequence shorter than that of a native apolipoprotein and which fragment retains the activity of native apolipoprotein, including lipid binding properties. By "variant" is meant substitutions or alterations in the amino acid sequences of the apolipoprotein, which substitutions or alterations, e.g., additions and deletions of amino acid residues, do not abolish the activity of native apolipoprotein, including lipid binding properties. Thus, a variant can comprise a protein or peptide having a substantially identical amino acid sequence to a native apolipoprotein provided herein in which one or more amino acid residues have been conservatively substituted with chemically similar amino acids. Examples of conservative substitutions include the substitution of at least one hydrophobic residue such as isoleucine, valine, leucine or methionine for another. Likewise, for example, the substitution of at least one hydrophilic residue such as, for example, between arginine and lysine, between glutamine and asparagine, and between glycine and serine (see U.S. Pat. Nos. 6,004,925, 6,037,323 and 6,046,166) are conservative substitutions. The term "isoform" refers to a protein having the same, greater or partial function and similar, identical or partial sequence, and may or may not be the product of the same gene and usually tissue specific (see Weisgraber 1990, J. Lipid Res. 31(8):1503-11; Hixson and Powers 1991, J. Lipid Res. 32(9):1529-35; Lackner et al., 1985, J. Biol. Chem. 260(2): 703-6; Hoeg et al., 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vase. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sacre et al., 2003, FEBS Lett. 540(1-3): 181-7; Weers, et al., 2003, Biophys. Chem. 100(1-3):481-92; Gong et al., 2002, J. Biol. Chem. 277(33):29919-26; Ohta et al., 1984, J. Biol. Chem. 259(23):14888-93 and U.S. Pat. No. 6,372,886).

In certain embodiments, the lipid particles and compositions described herein include a chimeric construction of an apolipoprotein. For example, a chimeric construction of an apolipoprotein can be comprised of an apolipoprotein domain with high lipid binding capacity associated with an apolipoprotein domain containing ischemia reperfusion protective properties. A chimeric construction of an apolipoprotein can be a construction that includes separate regions within an apolipoprotein (i.e., homologous construction) or a chimeric construction can be a construction that includes separate regions between different apolipoproteins (i.e., heterologous constructions). Compositions comprising a chimeric construction can also include segments that are apolipoprotein variants or segments designed to have a specific character (e.g., lipid binding, receptor binding, enzymatic, enzyme activating, antioxidant or reduction-oxidation property) (see Weisgraber 1990, J. Lipid Res. 31(8):1503-11; Hixson and Powers 1991, J. Lipid Res. 32(9):1529-35; Lackner et al., 1985, J. Biol. Chem. 260(2):703-6; Hoeg et al, 1986, J. Biol. Chem. 261(9):3911-4; Gordon et al., 1984, J. Biol. Chem. 259(1):468-74; Powell et al., 1987, Cell 50(6):831-40; Aviram et al., 1998, Arterioscler. Thromb. Vasc. Biol. 18(10):1617-24; Aviram et al., 1998, J. Clin. Invest. 101(8):1581-90; Billecke et al., 2000, Drug Metab. Dispos. 28(11):1335-42; Draganov et al., 2000, J. Biol. Chem. 275(43):33435-42; Steinmetz and Utermann 1985, J. Biol. Chem. 260(4):2258-64; Widler et al., 1980, J. Biol. Chem. 255(21):10464-71; Dyer et al., 1995, J. Lipid Res. 36(1):80-8; Sorenson et al., 1999, Arterioscler. Thromb. Vasc. Biol. 19(9):2214-25; Palgunachari 1996, Arterioscler. Throb. Vasc. Biol. 16(2):328-38: Thurberg et al., J. Biol. Chem. 271(11):6062-70; Dyer 1991, J. Biol. Chem. 266(23): 150009-15; Hill 1998, J. Biol. Chem. 273(47):30979-84).

Apolipoproteins utilized also include recombinant, synthetic, semi-synthetic or purified apolipoproteins. Methods for obtaining apolipoproteins or equivalents thereof are well-known in the art. For example, apolipoproteins can be separated from plasma or natural products by, for example, density gradient centrifugation or immunoaffinity chromatography, or produced synthetically, semi-synthetically or using recombinant DNA techniques known to those of the art (see, e.g., Mulugeta et al., 1998, J. Chromatogr. 798(1-2): 83-90; Chung et al., 1980, J. Lipid Res. 21(3):284-91; Cheung et al., 1987, J. Lipid Res. 28(8):913-29; Persson, et al., 1998, J. Chromatogr. 711:97-109; U.S. Pat. Nos. 5,059, 528, 5,834,596, 5,876,968 and 5,721,114; and PCT Publications WO 86/04920 and WO 87/02062).

Apolipoproteins further include apolipoprotein agonists such as peptides and peptide analogues that mimic the activity of ApoA-I, ApoA-I Milano (ApoA-I$_M$), ApoA-I Paris (ApoA-I$_P$), ApoA-II, ApoA-IV, and ApoE. For example, the apolipoprotein can be any of those described in U.S. Pat. Nos. 6,004,925, 6,037,323, 6,046,166, and 5,840, 688, the contents of which are incorporated herein by reference in their entireties.

Apolipoprotein agonist peptides or peptide analogues can be synthesized or manufactured using any technique for peptide synthesis known in the art including, e.g., the techniques described in U.S. Pat. Nos. 6,004,925, 6,037,323 and 6,046,166. For example, the peptides may be prepared using the solid-phase synthetic technique initially described by Merrifield (1963, J. Am. Chem. Soc. 85:2149-2154). Other peptide synthesis techniques may be found in Bodanszky et al., Peptide Synthesis, John Wiley & Sons, 2d Ed., (1976) and other references readily available to those skilled in the art. A summary of polypeptide synthesis techniques can be found in Stuart and Young, Solid Phase Peptide. Synthesis, Pierce Chemical Company, Rockford, Ill., (1984). Peptides may also be synthesized by solution methods as described in The Proteins, Vol. II, 3d Ed., Neurath et. al., Eds., p. 105-237, Academic Press, New York, N.Y. (1976). Appropriate protective groups for use in different peptide syntheses are described in the above-mentioned texts as well as in McOmie, Protective Groups in Organic Chemistry, Plenum Press, New York, N.Y. (1973). The peptides might also be prepared by chemical or enzymatic cleavage from larger portions of, for example, apolipoprotein A-I.

In certain embodiments, the apolipoprotein can be a mixture of apolipoproteins. In one embodiment, the apolipoprotein can be a homogeneous mixture, that is, a single type of apolipoprotein. In another embodiment, the apolipoprotein can be a heterogeneous mixture of apolipoproteins, that is, a mixture of two or more different apolipoproteins. Embodiments of heterogenous mixtures of apolipoproteins can comprise, for example, a mixture of an apolipoprotein from an animal source and an apolipoprotein from a semi-synthetic source. In certain embodiments, a heterogenous mixture can comprise, for example, a mixture of ApoA-I and ApoA-I Milano. In certain embodiments, a heterogeneous mixture can comprise, for example, a mixture of ApoA-I Milano and ApoA-I Paris. Suitable mixtures for use in the methods and compositions described herein will be apparent to one of skill in the art.

If the apolipoprotein is obtained from natural sources, it can be obtained from a plant or animal source. If the apolipoprotein is obtained from an animal source, the apolipoprotein can be from any species. In certain embodiments, the apolipoprotien can be obtained from an animal source. In certain embodiments, the apolipoprotein can be obtained from a human source. In preferred embodiments, the apolipoprotein is derived from the same species as the individual to which the apolipoprotein is administered.

The lipid particles and compositions described herein may further contain a sterol component of the lipid mixture. When present, the sterol can be any of those sterols conventionally used in the field of liposome, lipid vesicle or lipid particle preparation. In one embodiment, the sterol is cholesterol.

The lipid particles and compositions described herein may further include an anionic lipid. Anionic lipids suitable for use in lipid particles include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In additional embodiments, amphipathic lipids are also included in the lipid particles and compositions described herein. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

Also suitable for inclusion in the lipid particles and compositions described herein are programmable fusion lipids or fusion-promoting lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. The fusion promoting-lipids can be, for example, compounds of formula (I) as described above. In some cases, the signal event can be a change in pH, for example, such as the difference in pH between an extracelluar environment and an intracellular environment, or between an intracellular environment and an endosomal environment.

When time is the signal event, a fusion delaying or "cloaking" component, such as an ATTA-lipid conjugate or a PEG-lipid conjugate, can simply exchange out of the lipid particle membrane over time. By the time the lipid particle is suitably distributed in the body, it has lost sufficient cloaking agent so as to be fusogenic. With other signal events, it can be desirable to choose a signal that is associated with the disease site or target cell, such as increased temperature at a site of inflammation.

Active (Therapeutic) Agents

The lipid particles and compositions described herein may further include one or more active agents (e.g., therapeutic agents). Active agents, as used herein, include any molecule or compound capable of exerting a desired effect on a cell, tissue, organ, or subject. Such effects may be biological, physiological, or cosmetic, for example. The lipid particles and compositions can be used to deliver any of a variety of active agents. The active agent can be a nucleic acid, peptide, polypeptide (e.g., an antibody), cytokines, growth factors, apoptotic factors, differentiation-inducing factors, cell surface receptors and their ligands, hormones, and small molecules. Suitable therapeutic agents also include anti-inflammatory compounds, anti-depressants, stimulants, analgesics, antibiotics, birth control medication, antipyretics, vasodilators, anti-angiogenics, cytovascular agents, signal transduction inhibitors, cardiovascular drugs, e.g., anti-arrhythmic agents, vasoconstrictors, hormones, and steroids. The lipid particles of the present invention can also deliver aptamers.

In certain embodiments, the therapeutic agent is an oncology drug, which may also be referred to as an anti-tumor drug, an anti-cancer drug, a tumor drug, an antineoplastic agent, or the like. Examples of oncology drugs that may be used include, but are not limited to, adriamycin, alkeran, allopurinol, altretamine, amifostine, anastrozole, araC, arsenic trioxide, azathioprine, bexarotene, biCNU, bleomycin, busulfan intravenous, busulfan oral, capecitabine (Xeloda), carboplatin, carmustine, CCNU, celecoxib, chlorambucil, cisplatin, cladribine, cyclosporin A, cytarabine, cytosine arabinoside, daunorubicin, cytoxan, daunorubicin, dexamethasone, dexrazoxane, dodetaxel, doxorubicin, doxorubicin, DTIC, epirubicin, estramustine, etoposide phosphate, etoposide and VP-16, exemestane, FK506, fludarabine, fluorouracil, 5-FU, gemcitabine (Gemzar), gemtuzumab-ozogamicin, goserelin acetate, hydrea, hydroxyurea, idarubicin, ifosfamide, imatinib mesylate, interferon, irinotecan (Camptostar, CPT-111), letrozole, leucovorin, leustatin, leuprolide, levamisole, litretinoin, megastrol, melphalan, L-PAM, mesna, methotrexate, methoxsalen, mithramycin, mitomycin, mitoxantrone, nitrogen mustard, paclitaxel, pamidronate, Pegademase, pentostatin, porfimer sodium, prednisone, rituxan, streptozocin, STI-571, tamoxifen, taxotere, temozolamide, teniposide, VM-26, topotecan (Hycamtin), toremifene, tretinoin, ATRA, valrubicin, velban, vinblastine, vincristine, VP16, and vinorelbine. Other examples of oncology drugs that may be used are ellipticin and ellipticin analogs or derivatives, epothilones, intracellular kinase inhibitors and camptothecins.

In a preferred embodiment, the active agent is a nucleic acid, such as a siRNA. For example, the active agent can be a nucleic acid encoded with a product of interest, including but not limited to, RNA, antisense oligonucleotide, an antagomir, a DNA, a plasmid, a ribosomal RNA (rRNA), a micro RNA (miRNA) (e.g., a miRNA which is single stranded and 17-25 nucleotides in length), transfer RNA (tRNA), a small interfering RNA (siRNA), small nuclear RNA (snRNA), antigens, fragments thereof, proteins, peptides, vaccines and small molecules or mixtures thereof. In one more preferred embodiment, the nucleic acid is an oligonucleotide (e.g., 15-50 nucleotides in length (or 15-30 or 20-30 nucleotides in length)). An siRNA can have, for instance, a duplex region that is 16-30 nucleotides long. In another embodiment, the nucleic acid is an immunostimulatory oligonucleotide, decoy oligonucleotide, supermir, miRNA mimic, or miRNA inhibitor. A supermir refers to a single stranded, double stranded or partially double stranded oligomer or polymer of ribonucleic acid (RNA) or deoxyribonucleic acid (DNA) or both or modifications thereof, which has a nucleotide sequence that is substantially identical to an miRNA and that is antisense with respect to its target. miRNA mimics represent a class of molecules that can be used to imitate the gene silencing ability of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression.

The nucleic acid that is present in a lipid-nucleic acid particle can be in any form. The nucleic acid can, for example, be single-stranded DNA or RNA, or double-stranded DNA or RNA, or DNA-RNA hybrids. Non-limiting examples of double-stranded RNA include siRNA. Single-stranded nucleic acids include, e.g., antisense oligonucleotides, ribozymes, microRNA, and triplex-forming oligonucleotides. The lipid particles of the present invention can also deliver nucleic acids which are conjugated to one or more ligands.

Pharmaceutical Compositions

The lipid particles, particularly when associated with a therapeutic agent, may be formulated as a pharmaceutical composition, e.g., which further comprises a pharmaceutically acceptable diluent, excipient, or carrier, such as physiological saline or phosphate buffer, selected in accordance with the route of administration and standard pharmaceutical practice.

In certain embodiments, compositions for the delivery of siRNA molecules are described. These compositions are effective in down-regulating the protein levels and/or mRNA levels of target proteins. The activity of these compositions can be influenced by the presence of cationic lipids and the molar ratio of cationic lipid in the formulation.

In particular embodiments, pharmaceutical compositions comprising the lipid-nucleic acid particles are prepared according to standard techniques and further comprise a pharmaceutically acceptable carrier. Generally, normal saline will be employed as the pharmaceutically acceptable carrier. Other suitable carriers include, e.g., water, buffered water, 0.9% saline, 0.3% glycine, and the like, including glycoproteins for enhanced stability, such as albumin, lipoprotein, globulin, etc. In compositions comprising saline or other salt containing carriers, the carrier is preferably added following lipid particle formation. Thus, after the lipid-nucleic acid compositions are formed, the compositions can be diluted into pharmaceutically acceptable carriers such as normal saline.

The resulting pharmaceutical preparations may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of lipid particle or lipid-nucleic acid particle in the pharmaceutical formulations can vary widely, i.e., from less than about 0.01%, usually at or at least about 0.05-5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, the lipid-therapeutic agent (e.g., nucleic acid) particles may include polyethylene glycol (PEG)-modified phospholipids, PEG-ceramide, or ganglioside $G_{M1}$-modified lipids or other lipids effective to prevent or limit aggregation. Addition of such components does not merely prevent complex aggregation. Rather, it may also provide a means for increasing circulation lifetime and increasing the delivery of the lipid-nucleic acid composition to the target tissues.

Lipid-therapeutic agent compositions can also be provided in kit form. The kit will typically be comprised of a container that is compartmentalized for holding the various elements of the kit. The kit will contain the particles or pharmaceutical compositions, preferably in dehydrated or concentrated form, with instructions for their rehydration or dilution and administration. In certain embodiments, the particles comprise the active agent, while in other embodiments, they do not.

Methods of Manufacture

Methods of making cationic lipids, lipid particles containing them, and pharmaceutical compositions containing the cationic lipids and/or lipid particles are described in, for example, International Publication Nos. WO 2010/054406, WO 2010/054401, WO 2010/054405, and WO 2010/054384, WO 2010/042877, WO 2010/129709, WO 2009/086558, and WO 2008/042973, each of which is incorporated by reference in its entirety.

Methods of making lipid particles and pharmaceutical compositions containing the lipid particles are also described in, for example, US Publication Nos. 2004/0142025, 2006/0051405 and 2007/0042031, each of which is incorporated by reference in its entirety. In addition, methods of preparing lipid particles, including those associated with a therapeutic agent, e.g., a nucleic acid are described. In the methods described herein, a mixture of lipids is combined with a buffered aqueous solution of nucleic acid to produce an intermediate mixture containing nucleic acid encapsulated in lipid particles. In one embodiment, the encapsulated nucleic acids are present in a nucleic acid/lipid ratio of about 3 wt % to about 25 wt %, preferably 5 to 15 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

For example, in one embodiment, a solution of one or more lipids (including a cationic lipid of any of the embodiments described herein) in an organic solution (e.g., ethanol) is prepared. Similarly, a solution of one or more active (therapeutic) agents (such as, for example an siRNA molecule or a 1:1 molar mixture of two siRNA molecules) in an aqueous buffered (e.g., citrate buffer) solution is prepared. The two solutions are mixed and diluted to form a colloidal suspension of siRNA lipid particles. In one embodiment, the siRNA lipid particles have an average particle size of about 80-90 nm. In further embodiments, the dispersion may be filtered through 0.45/2 micron filters, concentrated and diafiltered by tangential flow filtration. In a further embodiment, the concentration of the resulting product is adjusted to about 2 mg/mL. In a further embodiment, the product is sterile filtered, aseptically filtered and packaged. As described above, several of these cationic lipids are amino lipids that are charged at a pH below the $pK_a$ of the amino group and substantially neutral at a pH above the $pK_a$. These cationic lipids are termed titratable cationic lipids and can be used in the formulations using a two-step process. First, lipid vesicles can be formed at the lower pH with titratable cationic lipids and other vesicle components in the presence of nucleic acids. In this manner, the vesicles will encapsulate and entrap the nucleic acids. Second, the surface charge of the newly formed vesicles can be neutralized by increasing the pH of the medium to a level above the $pK_a$ of the titratable cationic lipids present, i.e., to physiological pH or higher. Particularly advantageous aspects of this process include both the facile removal of any surface adsorbed nucleic acid and a resultant nucleic acid delivery vehicle which has a neutral surface. Liposomes or lipid particles having a neutral surface are expected to avoid rapid clearance from circulation and to avoid certain toxicities which are associated with cationic liposome preparations. Additional details concerning these uses of such titratable cationic lipids in the formulation of nucleic acid-lipid particles are provided in U.S. Pat. No. 6,287,591 and U.S. Pat. No. 6,858,225, incorporated herein by reference.

It is further noted that the vesicles formed in this manner provide formulations of uniform vesicle size with high content of nucleic acids. Additionally, the vesicles have may have a size range of from about 30 to about 150 nm, more preferably about 30 to about 90 nm.

Without intending to be bound by any particular theory, it is believed that the very high efficiency of nucleic acid encapsulation is a result of electrostatic interaction at low pH. At acidic pH (e.g. pH 4.0) the vesicle surface is charged and binds a portion of the nucleic acids through electrostatic interactions. When the external acidic buffer is exchanged for a more neutral buffer (e.g., pH 7.5) the surface of the lipid particle or liposome is neutralized, allowing any external nucleic acid to be removed. More detailed information on the formulation process is provided in various publications (e.g., U.S. Pat. No. 6,287,591 and U.S. Pat. No. 6,858,225).

In view of the above, methods of preparing lipid/nucleic acid formulations are described. In the methods described herein, a mixture of lipids is combined with a buffered aqueous solution of nucleic acid to produce an intermediate mixture containing nucleic acid encapsulated in lipid particles, e.g., wherein the encapsulated nucleic acids are present in a nucleic acid/lipid ratio of about 10 wt % to about 20 wt %. The intermediate mixture may optionally be sized to obtain lipid-encapsulated nucleic acid particles wherein the lipid portions are unilamellar vesicles, preferably having a diameter of 30 to 150 nm, more preferably about 40 to 90 nm. The pH is then raised to neutralize at least a portion of the surface charges on the lipid-nucleic acid particles, thus providing an at least partially surface-neutralized lipid-encapsulated nucleic acid composition.

In certain embodiments, the mixture of lipids includes at least two lipid components: a first lipid component that is selected from among lipids which have a $pK_a$ such that the lipid is cationic at pH below the $pK_a$ and neutral at pH above the $pK_a$, and a second lipid component that is selected from among lipids that prevent particle aggregation during lipid-nucleic acid particle formation. In particular embodiments, the amino lipid is a cationic lipid.

In preparing the nucleic acid-lipid particles, the mixture of lipids is typically a solution of lipids in an organic solvent. This mixture of lipids can then be dried to form a thin film or lyophilized to form a powder before being hydrated with an aqueous buffer to form liposomes. Alternatively, in a preferred method, the lipid mixture can be solubilized in a water miscible alcohol, such as ethanol, and this ethanolic solution added to an aqueous buffer resulting in spontaneous liposome formation. In most embodiments, the alcohol is used in the form in which it is commercially available. For example, ethanol can be used as absolute ethanol (100%), or as 95% ethanol, the remainder being water. This method is described in more detail in U.S. Pat. No. 5,976,567).

In one exemplary embodiment, the mixture of lipids is a mixture of cationic lipids, neutral lipids (other than a cationic lipid), a sterol (e.g., cholesterol) and a PEG-modified lipid (e.g., a PEG-DMG or PEG-DMA) in an alcohol solvent. In preferred embodiments, the lipid mixture consists essentially of a cationic lipid, a neutral lipid, cholesterol and a PEG-modified lipid in alcohol, more preferably ethanol. In further preferred embodiments, the first solution consists of the above lipid mixture in molar ratios of about 20-70% cationic lipid:5-45% neutral lipid:20-55% cholesterol:0.5-15% PEG-modified lipid. In still further preferred embodiments, the first solution consists essentially of a mixture of cationic lipids chosen from lipids described in Tables 1-5, DSPC, Chol and PEG-DMG or PEG-DMA, more preferably in a molar ratio of about 20-60% cationic lipid:5-25% DSPC:25-55% Chol:0.5-15% PEG-DMG or PEG-DMA. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/Chol/PEG-DMG or PEG-DMA) or 52/13/30/5 (mol % cationic lipid/DSPC/Chol/PEG-DMG or PEG-DMA). In another group of preferred embodiments, the neutral lipid in these compositions is replaced with POPC, DPPC, DOPE or SM.

The lipid mixture is combined with a buffered aqueous solution that may contain the nucleic acids. The buffered aqueous solution of is typically a solution in which the buffer has a pH of less than the $pK_a$ of the protonatable lipid in the lipid mixture. Examples of suitable buffers include citrate, phosphate, acetate, and MES. A particularly preferred buffer is citrate buffer. Preferred buffers will be in the range of 1-1000 mM of the anion, depending on the chemistry of the nucleic acid being encapsulated, and optimization of buffer concentration may be significant to achieving high loading levels (see, e.g., U.S. Pat. No. 6,287,591 and U.S. Pat. No. 6,858,225, each of which is incorporated by reference in its entirety). Alternatively, pure water acidified to pH 5-6 with chloride, sulfate or the like may be useful. In this case, it may be suitable to add 5% glucose, or another non-ionic solute which will balance the osmotic potential across the particle membrane when the particles are dialyzed to remove ethanol, increase the pH, or mixed with a pharmaceutically acceptable carrier such as normal saline. The amount of nucleic acid in buffer can vary, but will typically be from about 0.01 mg/mL to about 200 mg/mL, more preferably from about 0.5 mg/mL to about 50 mg/mL.

The mixture of lipids and the buffered aqueous solution of therapeutic nucleic acids is combined to provide an intermediate mixture. The intermediate mixture is typically a mixture of lipid particles having encapsulated nucleic acids. Additionally, the intermediate mixture may also contain some portion of nucleic acids which are attached to the surface of the lipid particles (liposomes or lipid vesicles) due to the ionic attraction of the negatively-charged nucleic acids and positively-charged lipids on the lipid particle surface (the amino lipids or other lipid making up the protonatable first lipid component are positively charged in a buffer having a pH of less than the $pK_a$ of the protonatable group on the lipid). In one group of preferred embodiments, the mixture of lipids is an alcohol solution of lipids and the volumes of each of the solutions is adjusted so that upon combination, the resulting alcohol content is from about 20% by volume to about 45% by volume. The method of combining the mixtures can include any of a variety of processes, often depending upon the scale of formulation produced. For example, when the total volume is about 10-20 mL or less, the solutions can be combined in a test tube and stirred together using a vortex mixer. Large-scale processes can be carried out in suitable production scale glassware.

Optionally, the lipid-encapsulated therapeutic agent (e.g., nucleic acid) complexes which are produced by combining the lipid mixture and the buffered aqueous solution of therapeutic agents (nucleic acids) can be sized to achieve a desired size range and relatively narrow distribution of lipid particle sizes. Preferably, the compositions provided herein will be sized to a mean diameter of from about 70 to about 200 nm, more preferably about 90 to about 130 nm. Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the particle size distribution can be monitored by conventional laser-beam particle size determination. For certain methods herein, extrusion is used to obtain a uniform vesicle size.

Extrusion of liposome compositions through a small-pore polycarbonate membrane or an asymmetric ceramic membrane results in a relatively well-defined size distribution. Typically, the suspension is cycled through the membrane one or more times until the desired liposome complex size distribution is achieved. The liposomes may be extruded through successively smaller-pore membranes, to achieve a gradual reduction in liposome size. In some instances, the lipid-nucleic acid compositions which are formed can be used without any sizing.

In particular embodiments, methods further comprise a step of neutralizing at least some of the surface charges on the lipid portions of the lipid-nucleic acid compositions. By at least partially neutralizing the surface charges, unencapsulated nucleic acid is freed from the lipid particle surface and can be removed from the composition using conventional techniques. Preferably, unencapsulated and surface adsorbed nucleic acids are removed from the resulting compositions through exchange of buffer solutions. For example, replacement of a citrate buffer (pH about 4.0, used for forming the compositions) with a HEPES-buffered saline (HBS pH about 7.5) solution, results in the neutralization of liposome surface and nucleic acid release from the surface. The released nucleic acid can then be removed via chromatography using standard methods, and then switched into a buffer with a pH above the $pK_a$ of the lipid used.

Optionally the lipid vesicles (i.e., lipid particles) can be formed by hydration in an aqueous buffer and sized using any of the methods described above prior to addition of the nucleic acid. As described above, the aqueous buffer should be of a pH below the $pK_a$ of the amino lipid. A solution of the nucleic acids can then be added to these sized, preformed vesicles. To allow encapsulation of nucleic acids into such "pre-formed" vesicles the mixture should contain an alcohol, such as ethanol. In the case of ethanol, it should be present at a concentration of about 20% (w/w) to about 45% (w/w). In addition, it may be necessary to warm the mixture of pre-formed vesicles and nucleic acid in the aqueous buffer-ethanol mixture to a temperature of about 25° C. to about 50° C. depending on the composition of the lipid vesicles and the nature of the nucleic acid. It will be apparent to one of ordinary skill in the art that optimization of the encapsulation process to achieve a desired level of nucleic acid in the lipid vesicles will require manipulation of variable such as ethanol concentration and temperature. Examples of suitable conditions for nucleic acid encapsulation are provided in the Examples. Once the nucleic acids are encapsulated within the preformed vesicles, the external pH can be increased to at least partially neutralize the surface charge. Unencapsulated and surface adsorbed nucleic acids can then be removed as described above.

Methods of Treatment

The lipid particles and compositions described herein may be used for a variety of purposes, including the delivery of associated or encapsulated therapeutic agents to cells, both in vitro and in vivo. Accordingly, methods of treating diseases or disorders in a subject in need thereof can include contacting the subject with a lipid particle associated with a suitable therapeutic agent.

As described herein, the lipid particles are particularly useful for the delivery of nucleic acids, including, e.g., siRNA molecules and plasmids. Therefore, the lipid particles and compositions may be used to modulate the expression of target genes and proteins both in vitro and in vivo by contacting cells with a lipid particle associated with a nucleic acid that reduces target gene expression (e.g., an siRNA) or a nucleic acid that may be used to increase expression of a desired protein (e.g., a plasmid encoding the desired protein).

The lipid particles may be used to deliver a therapeutic agent to a cell, in vitro or in vivo. In particular embodiments, the therapeutic agent is a nucleic acid, which is delivered to a cell using nucleic acid-lipid particles. While the following description of various methods of using the lipid particles and related pharmaceutical compositions are exemplified by description related to nucleic acid-lipid particles, it is understood that these methods and compositions may be readily adapted for the delivery of any therapeutic agent for the treatment of any disease or disorder that would benefit from such treatment.

In certain embodiments, methods for introducing a nucleic acid into a cell are described. Preferred nucleic acids for introduction into cells are siRNA, immune-stimulating oligonucleotides, plasmids, antisense and ribozymes. These methods may be carried out by contacting the particles or compositions with the cells for a period of time sufficient for intracellular delivery to occur.

The compositions can be adsorbed to almost any cell type. Once adsorbed, the nucleic acid-lipid particles can either be endocytosed by a portion of the cells, exchange lipids with cell membranes, or fuse with the cells. Transfer or incorporation of the nucleic acid portion of the complex can take place via any one of these pathways. Without intending to be limited, it is believed that in the case of particles taken up into the cell by endocytosis the particles then interact with the endosomal membrane, resulting in destabilization of the endosomal membrane, possibly by the formation of non-bilayer phases, resulting in introduction of the encapsulated nucleic acid into the cell cytoplasm. Similarly in the case of direct fusion of the particles with the cell plasma membrane, when fusion takes place, the liposome membrane is integrated into the cell membrane and the contents of the liposome combine with the intracellular fluid. Contact between the cells and the lipid-nucleic acid compositions, when carried out in vitro, will take place in a biologically compatible medium. The concentration of compositions can vary widely depending on the particular application, but is generally between about 1 mol and about 10 mmol. In certain embodiments, treatment of the cells with the lipid-nucleic acid compositions will generally be carried out at physiological temperatures (about 37° C.) for periods of time from about 1 to 24 hours, preferably from about 2 to 8 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of embodiments, a lipid-nucleic acid particle suspension is added to 60-80% confluent plated cells having a cell density of from about $10^3$ to about $10^5$ cells/mL, more preferably about $2 \times 10^4$ cells/mL. The concentration of the suspension added to the cells is preferably of from about 0.01 to 20 μg/mL, more preferably about 1 μg/mL.

In another embodiment, the lipid particles can be may be used to deliver a nucleic acid to a cell or cell line (for example, a tumor cell line). Non-limiting examples of such cell lines include: HELA (ATCC Cat N: CCL-2), KB (ATCC Cat N: CCL-17), HEP3B (ATCC Cat N: HB-8064), SKOV-3 (ATCC Cat N: HTB-77), HCT-116 (ATCC Cat N: CCL-247), HT-29 (ATCC Cat N: HTB-38), PC-3 (ATCC Cat N: CRL-1435), A549 (ATCC Cat N: CCL-185), MDA-MB-231 (ATCC Cat N: HTB-26).

Typical applications include using well known procedures to provide intracellular delivery of siRNA to knock down or silence specific cellular targets. Alternatively applications include delivery of DNA or mRNA sequences that code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630-643 (1989), and for cystic fibrosis, see Goodfellow, *Nature* 341:102-103 (1989)). Other uses for the compositions include introduction of antisense oligonucleotides in cells (see, Bennett, et al., *Mol. Pharm.* 41:1023-1033 (1992)).

Alternatively, the compositions can also be used for deliver of nucleic acids to cells in vivo, using methods which are known to those of skill in the art. With respect to delivery of DNA or mRNA sequences, Zhu, et al., *Science* 261:209-211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250-256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278-281 (1989), incorporated herein by reference, describes the in vivo transfection of lungs of mice with a functioning prokaryotic gene encoding the intracellular enzyme, chloramphenicol acetyltransferase (CAT). Thus, the compositions can be used in the treatment of infectious diseases.

For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. For one example, see Stadler, et al., U.S. Pat. No. 5,286,634, which is incorporated herein by reference. Intracellular nucleic acid delivery has also been discussed in Straubringer, et al., Methods in Enzymology, Academic Press, New York. 101:512-527 (1983); Mannino, et al., *Biotechniques* 6:682-690 (1988); Nicolau, et al., *Crit. Rev. Ther. Drug Carrier Syst.* 6:239-271 (1989), and Behr, *Acc. Chem. Res.* 26:274-278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical," it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The lipid-nucleic acid compositions can also be administered in an aerosol inhaled into the lungs (see, Brigham, et al., *Am. J. Sci.* 298(4):278-281 (1989)) or by direct injection at the site of disease (Culver, Human Gene Therapy, Mary-Ann Liebert, Inc., Publishers, New York. pp. 70-71 (1994)).

Dosages for the lipid-therapeutic agent particles will depend on the ratio of therapeutic agent to lipid and the administrating physician's opinion based on age, weight, and condition of the patient.

In one embodiment, a method of modulating the expression of a target polynucleotide or polypeptide is described. These methods generally comprise contacting a cell with a lipid particle that is associated with a nucleic acid capable of modulating the expression of a target polynucleotide or polypeptide. As used herein, the term "modulating" refers to altering the expression of a target polynucleotide or polypeptide. In different embodiments, modulating can mean increasing or enhancing, or it can mean decreasing or reducing. Methods of measuring the level of expression of a target polynucleotide or polypeptide are known and available in the arts and include, e.g., methods employing reverse transcription-polymerase chain reaction (RT-PCR) and immunohistochemical techniques. In particular embodiments, the level of expression of a target polynucleotide or polypeptide is increased or reduced by at least 10%, 20%, 30%, 40%, 50%, or greater than 50% as compared to an appropriate control value.

For example, if increased expression of a polypeptide desired, the nucleic acid may be an expression vector that includes a polynucleotide that encodes the desired polypeptide. On the other hand, if reduced expression of a polynucleotide or polypeptide is desired, then the nucleic acid may be, e.g., an antisense oligonucleotide, siRNA, or microRNA that comprises a polynucleotide sequence that specifically hybridizes to a polnucleotide that encodes the target polypeptide, thereby disrupting expression of the target polynucleotide or polypeptide. Alternatively, the nucleic acid may be a plasmid that expresses such an antisense oligonucleotide, siRNA, or microRNA.

In particular embodiments, the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof, such that the expression of the polypeptide is reduced.

In other embodiments, the nucleic acid is a plasmid that encodes the polypeptide or a functional variant or fragment thereof, such that expression of the polypeptide or the functional variant or fragment thereof is increased.

In related embodiments, a method of treating a disease or disorder characterized by overexpression of a polypeptide in a subject, includes providing to the subject a pharmaceutical composition, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In one embodiment, the pharmaceutical composition comprises a lipid particle that consists of or consists essentially of a mixture of cationic lipids chosen from lipids described in Tables 1-5, DSPC, Chol and PEG-DMG or PEG-DMA, e.g., in a molar ratio of about 20-60% cationic lipid:5-25% DSPC:25-55% Chol:0.5-15% PEG-DMG or PEG-DMA, wherein the lipid particle is associated with the therapeutic nucleic acid. In particular embodiments, the molar lipid ratio is approximately 40/10/40/10 (mol % cationic lipid/DSPC/Chol/PEG-DMG or PEG-DMA), 35/15/40/10 (mol % cationic lipid/DSPC/Chol/PEG-DMG or PEG-DMA) or 52/13/30/5 (mol % cationic lipid/DSPC/Chol/PEG-DMG or PEG-DMA). In another group of embodiments, the neutral lipid in these compositions is replaced with POPC, DPPC, DOPE or SM.

In another related embodiment, a method of treating a disease or disorder characterized by underexpression of a polypeptide in a subject, includes providing to the subject a pharmaceutical composition, wherein the therapeutic agent is a plasmid that encodes the polypeptide or a functional variant or fragment thereof.

A method of inducing an immune response in a subject, can include providing to the subject the pharmaceutical composition, wherein the therapeutic agent is an immunostimulatory oligonucleotide. In certain embodiments, the immune response is a humoral or mucosal immune response.

In further embodiments, the pharmaceutical composition is provided to the subject in combination with a vaccine or antigen. Thus, vaccines can include a lipid particle, which comprises an immunostimulatory oligonucleotide, and is also associated with an antigen to which an immune response is desired. In particular embodiments, the antigen is a tumor antigen or is associated with an infective agent, such as, e.g., a virus, bacteria, or parasiste.

A variety of tumor antigens, infections agent antigens, and antigens associated with other disease are well known in the art and examples of these are described in references cited herein. Examples of suitable antigens include, but are not limited to, polypeptide antigens and DNA antigens. Specific examples of antigens are Hepatitis A, Hepatitis B, small pox, polio, anthrax, influenza, typhus, tetanus, measles, rotavirus, diphtheria, pertussis, tuberculosis, and rubella antigens. In a preferred embodiment, the antigen is a Hepatitis B recombinant antigen. In other aspects, the antigen is a Hepatitis A recombinant antigen. In another aspect, the antigen is a tumor antigen. Examples of such tumor-associated antigens are MUC-1, EBV antigen and antigens associated with Burkitt's lymphoma. In a further aspect, the antigen is a tyrosinase-related protein tumor antigen recombinant antigen. Those of skill in the art will know of other antigens suitable for use.

Tumor-associated antigens suitable for use include both mutated and non-mutated molecules that may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and BCR-abl oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Pathogens include, but are not limited to, infectious agents, e.g., viruses, that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Also, gram negative and gram positive bacteria serve as antigens in vertebrate animals. Such gram positive bacteria include, but are not limited to Pasteurella species, Staphylococci species, and Streptococcus species. Gram negative bacteria include, but are not limited to, Escherichia coli, Pseudomonas species, and Salmonella species. Specific examples of infectious bacteria include but are not limited to: Helicobacterpyloris, Borelia burgdorferi, Legionella pneumophilia, Mycobacteria sps (e.g., M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes (Group A Streptococcus), Streptococcus agalactiae (Group B Streptococcus), Streptococcus (viridans group), Streptococcus faecalis, Streptococcus bovis, Streptococcus (anaerobic sps.), Streptococcus pneumoniae, pathogenic Campylobacter sp., Enterococcus sp., Haemophilus infuenzae, Bacillus antracis, corynebacterium diphtheriae, corynebacterium sp., Erysipelothrix rhusiopathiae, Clostridium perfringers, Clostridium tetani, Enterobacter aerogenes, Klebsiella pneumoniae, Pasteurella multocida, Bacteroides sp., Fusobacterium nucleatum, Streptobacillus moniliformis, Treponema pallidium, Treponema pertenue, Leptospira, Rickettsia, and Actinomyces israelii.

Additional examples of pathogens include, but are not limited to, infectious fungi that infect mammals, and more particularly humans. Examples of infectious fingi include, but are not limited to: Cryptococcus neoformans, Histoplasma capsulatum, Coccidioides immitis, Blastomyces dermatitidis, Chlamydia trachomatis, Candida albicans. Examples of infectious parasites include Plasmodium such as Plasmodium falciparum, Plasmodium malariae, Plasmodium ovale, and Plasmodium vivax. Other infectious organisms (i.e., protists) include Toxoplasma gondii.

In one embodiment, the formulations can be used to silence or modulate a target gene such as but not limited to FVII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, SORT1 gene, XBP1 gene, topoisomerase I gene, topoisomerase II alpha gene, p73 gene, p21(WAF1/CIP1) gene, p27(KIP1) gene, PPM1D gene, RAS gene, caveolin I gene, MIB I gene, MTAI gene, M68 gene, tumor suppressor genes, p53 tumor suppressor gene, p53 family member DN-p63, pRb tumor suppressor gene, APC1 tumor suppressor gene, BRCA1 tumor suppressor gene, PTEN tumor suppressor gene, mLL fusion gene, BCR/ABL fusion gene, TEL/AML1 fusion gene, EWS/FLI1 fusion gene, TLS/FUS 1 fusion gene, PAX3/FKHR fusion gene, AML1/ETO fusion gene, alpha v-integrin gene, Flt-1 receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, *plasmodium* gene, a gene that is required for *plasmodium* gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene.

In another embodiment, the present invention relates to a method of delivering a nucleic acid molecule comprising administering a nucleic lipid particle comprising the nucleic acid molecule and a cationic lipid, the cationic lipid having
(i) a central carbon atom,
(ii) a head group directly bound to the central atom, and
(iii) two hydrophobic tails directly bound to the central carbon atom, each hydrophobic tail comprising a $C_{14}$ or greater aliphatic group attached to the central atom, where the aliphatic group is (a) interrupted by a biodegradable group such that there is a chain of at least four carbon atoms between the biodegradable group and the central carbon atom, or (b) includes a biodegradable group at the terminal end of the hydrophobic tail, such that the cationic lipid remains intact until delivery of the nucleic acid molecule after which cleavage of the hydrophobic tail occurs in vivo.

Definitions

As used herein, the term "cationic lipid" includes those lipids having one or two fatty acid or fatty aliphatic chains and an amino head group (including an alkylamino or dialkylamino group) that may be protonated to form a cationic lipid at physiological pH. In some embodiments, a cationic lipid is referred to as an "amino lipid."

A subject or patient in whom administration of the complex is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, and cats, avian species, such as chickens, turkeys, and songbirds, i.e., for veterinary medical use.

Many of the chemical groups recited in the generic formulas above are written in a particular order (for example, —OC(O)—). It is intended that the chemical group is to be incorporated into the generic formula in the order presented unless indicated otherwise. For example, a generic formula of the form —$(R)_i$-$(M^1)_k$-$(R)_m$— where $M^1$ is —C(O)O— and k is 1 refers to —$(R)_i$—C(O)O—$(R)_m$— unless specified otherwise. It is to be understood that when a chemical group is written in a particular order, the reverse order is also contemplated unless otherwise specified. For example, in a generic formula —$(R)_i$-$(M)_k$-$(R)_m$— where $M^1$ is defined as —C(O)NH— (i.e., —$(R)_i$—C(O)—NH—$(R)_m$—), the compound where $M^1$ is —NHC(O)—(i.e., —$(R)_i$—NHC(O)—$(R)_m$—) is also contemplated unless otherwise specified.

As used herein, the term "biodegradable group" refers to a group that include one or more bonds that may undergo bond breaking reactions in a biological environment, e.g., in an organism, organ, tissue, cell, or organelle. For example, the biodegradable group may be metabolizable by the body of a mammal, such as a human (e.g., by hydrolysis). Some groups that contain a biodegradable bond include, for example, but are not limited to esters, dithiols, and oximes. Non-limiting examples of biodegradable groups are —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, or —OC(O)(C$R^3R^4$)C(O)—.

As used herein, an "aliphatic" group is a non-aromatic group in which carbon atoms are linked into chains, and is either saturated or unsaturated.

The terms "alkyl" and "alkylene" refer to a straight or branched chain saturated hydrocarbon moiety. In one embodiment, the alkyl group is a straight chain saturated hydrocarbon. Unless otherwise specified, the "alkyl" or "alkylene" group contains from 1 to 24 carbon atoms. Representative saturated straight chain alkyl groups include methyl, ethyl, n-propyl, n-butyl, n-pentyl, and n-hexyl. Representative saturated branched alkyl groups include isopropyl, sec-butyl, isobutyl, tert-butyl, and isopentyl.

The term "alkenyl" refers to a straight or branched chain hydrocarbon moiety having one or more carbon-carbon double bonds. In one embodiment, the alkenyl group contains 1, 2, or 3 double bonds and is otherwise saturated. Unless otherwise specified, the "alkenyl" group contains from 2 to 24 carbon atoms. Alkenyl groups include both cis and trans isomers. Representative straight chain and branched alkenyl groups include ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl.

The term "alkynyl" refers to a straight or branched chain hydrocarbon moiety having one or more carbon-carbon triple bonds. Unless otherwise specified, the "alkynyl" group contains from 2 to 24 carbon atoms. Representative straight chain and branched alkynyl groups include acetylenyl, propynyl, 1-butynyl, 2-butynyl, 1-pentynyl, 2-pentynyl, and 3-methyl-1-butynyl.

The term "acyl" refers to a carbonyl group substituted with hydrogen, alkyl, partially saturated or fully saturated cycloalkyl, partially saturated or fully saturated heterocycle, aryl, or heteroaryl. For example, acyl groups include groups such as ($C_1$-$C_{20}$)alkanoyl (e.g., formyl, acetyl, propionyl, butyryl, valeryl, caproyl, and t-butylacetyl), ($C_3$-$C_{20}$)cycloalkylcarbonyl (e.g., cyclopropylcarbonyl, cyclobutylcarbonyl, cyclopentylcarbonyl, and cyclohexylcarbonyl), heterocyclic carbonyl (e.g., pyrrolidinylcarbonyl, pyrrolid-2-one-5-carbonyl, piperidinylcarbonyl, piperazinylcarbonyl, and tetrahydrofuranylcarbonyl), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, and benzo[b]thiophenyl-2-carbonyl).

The term "aryl" refers to an aromatic monocyclic, bicyclic, or tricyclic hydrocarbon ring system. Unless otherwise specified, the "aryl" group contains from 6 to 14 carbon atoms. Examples of aryl moieties include, but are not limited to, phenyl, naphthyl, anthracenyl, and pyrenyl.

The terms "cycloalkyl" and "cycloalkylene" refer to a saturated monocyclic or bicyclic hydrocarbon moiety such as cyclopropyl, cyclobutyl, cyclopentyl, and cyclohexyl. Unless otherwise specified, the "cycloalkyl" or "cycloalkylene" group contains from 3 to 10 carbon atoms.

The term "cycloalkylalkyl" refers to a cycloalkyl group bound to an alkyl group, where the alkyl group is bound to the rest of the molecule.

The term "heterocycle" (or "heterocyclyl") refers to a non-aromatic 5- to 8-membered monocyclic, or 7- to 12-membered bicyclic, or 11- to 14-membered tricyclic ring system which is either saturated or unsaturated, and which contains from 1 to 3 heteroatoms if monocyclic, 1-6 heteroatoms if bicyclic, or 1-9 heteroatoms if tricyclic, independently selected from nitrogen, oxygen and sulfur, and wherein the nitrogen and sulfur heteroatoms may be optionally oxidized, and the nitrogen heteroatom may be optionally quaternized. For instance, the heterocycle may be a cycloalkoxy group. The heterocycle may be attached to the rest of the molecule via any heteroatom or carbon atom in the heterocycle. Heterocycles include, but are not limited to, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

The term "heteroaryl" refers to an aromatic 5-8 membered monocyclic, 7-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively). The heteroaryl groups herein described may also contain fused rings that share a common carbon-carbon bond.

The term "substituted", unless otherwise indicated, refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and an aliphatic group. It is understood that the substituent may be further substituted. Exemplary substituents include amino, alkylamino, dialkylamino, and cyclic amino compounds.

The term "halogen" or "halo" refers to fluoro, chloro, bromo and iodo.

The terms "alkylamine" and "dialkylamine" refer to —NH(alkyl) and —N(alkyl)$_2$ radicals respectively.

The term "alkylphosphate" refers to —O—P(Q')(Q")—O—R, wherein Q' and Q" are each independently O, S, N(R)$_2$, optionally substituted alkyl or alkoxy; and R is optionally substituted alkyl, ω-aminoalkyl or ω-(substituted)aminoalkyl.

The term "alkylphosphorothioate" refers to an alkylphosphate wherein at least one of Q' or Q" is S.

The term "alkylphosphonate" refers to an alkylphosphate wherein at least one of Q' or Q" is alkyl.

The term "hydroxyalkyl" refers to —O— alkyl radical.

The term "alkylheterocycle" refers to an alkyl where at least one methylene has been replaced by a heterocycle.

The term "w-aminoalkyl" refers to -alkyl-NH$_2$ radical. And the term "ω-(substituted)aminoalkyl refers to an w-aminoalkyl wherein at least one of the H on N has been replaced with alkyl.

The term "ω-phosphoalkyl" refers to -alkyl-O—P(Q')(Q")—O—R, wherein Q' and Q" are each independently O or S and R optionally substituted alkyl.

The term "ω-thiophosphoalkyl refers to w-phosphoalkyl wherein at least one of Q' or Q" is S.

The following abbreviations are used in this application: DSPC: distearoylphosphatidylcholine; DPPC: 1,2-Dipalmitoyl-sn-glycero-3-phosphocholine; POPC: 1-palmitoyl-2-oleoyl-sn-phosphatidylcholine; DOPE: 1,2-dileoyl-sn-3-phosphoethanolamine; PEG-DMG generally refers to 1,2-dimyristoyl-sn-glycerol-methoxy polyethylene glycol (e.g., PEG 2000); TBDPSCl: tert-Butylchlorodiphenylsilane; DMAP: dimethylaminopyridine; NMO: N-methylmorpholin-N-oxide; LiHDMS: lithium bis(trimethylsilyl)amide;

HMPA: hexamethylphosphoramide; EDC: 1-ethyl-3-(3-dimethylaminopropyl) carbodiimide; DIPEA: diisopropylethylamine; DCM: dichloromethane; TEA: triethylamine; TBAF: tetrabutylammonium fluoride In some embodiments, the methods may require the use of protecting groups. Protecting group methodology is well known to those skilled in the art (see, for example, *Protective Groups in Organic Synthesis*, Green, T. W. et. al., Wiley-Interscience, New York City, 1999). Briefly, protecting groups are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

The compounds may be prepared by at least one of the techniques described herein or known organic synthesis techniques.

EXAMPLES

Example 1

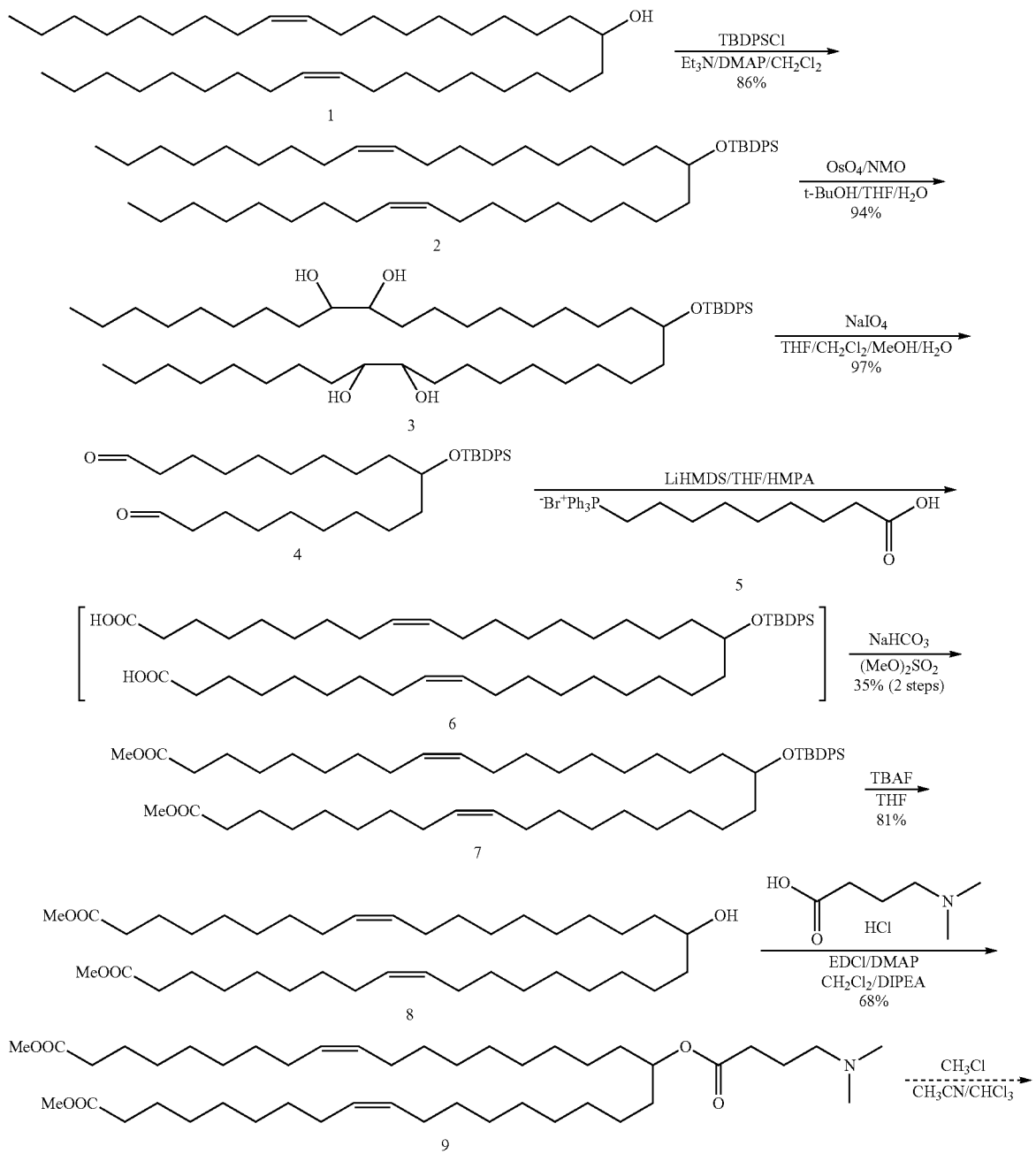

Scheme 1

-continued

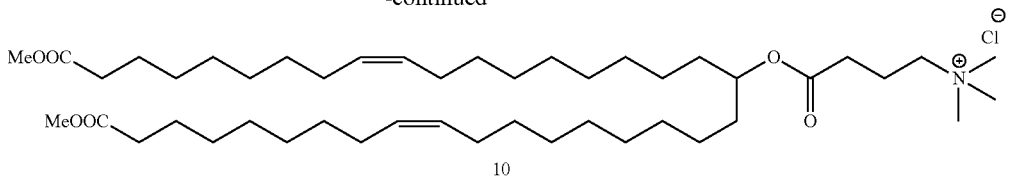

10

Compound 2:

To a solution of compound 1 (10.0 g, 18.8 mmol, see International Publication No. WO 2010/054406) in $CH_2Cl_2$ (80 mL) were added triethylamine (7.86 mL, 56.4 mmol), DMAP (459 mg, 3.76 mmol) and tert-butyl(chloro)diphenylsilane (9.62 mL, 37.6 mmol). The reaction mixture was stirred for 24 hours. The mixture was then diluted with $CH_2Cl_2$ and washed with aqueous saturated $NaHCO_3$ solution. The organic layer was separated and dried over anhydrous $Na_2SO_4$. After filtration and concentration, the crude product was purified by silica gel column chromatography (0-5% EtOAc in hexane) to afford 2 (12.4 g, 16.1 mmol, 86%, $R_f$=0.24 with hexane). $^1$H NMR (400 MHz, $CDCl_3$) δ 7.66-7.68 (m, 4H), 7.33-7.42 (m, 6H), 5.30-5.39 (m, 4H), 3.67-3.72 (m, 1H), 1.97-2.04 (m, 8H), 1.07-1.42 (m, 52H), 1.05 (s, 9H), 0.88 (t, J=6.8 Hz, 6H).

Compound 3:

To a solution of 2 (12.4 g, 16.1 mmol) in tert-butanol (100 mL), THF (30 mL) and $H_2O$ (10 mL) were added 4-methylmorpholine N-oxide (4.15 g, 35.4 mmol) and osmium tetroxide (41 mg, 0.161 mg). The reaction mixture was stirred for 16 hours, then quenched by adding sodium bisulfite. After removing the solvents by evaporation, the residue was extracted with $Et_2O$ (500 mL) and $H_2O$ (300 mL). The organic layer was separated and dried over anhydrous $Na_2SO_4$. After filtration and concentration, the crude was purified by silica gel column chromatography (hexane:EtOAc=1:1, $R_f$=0.49) to afford 3 (12.7 g, 15.1 mmol, 94%).

$^1$H NMR (400 MHz, $CDCl_3$) δ 7.66-7.68 (m, 4H), 7.33-7.43 (m, 6H), 3.67-3.73 (m, 1H), 3.57-3.62 (m, 4H), 1.82 (t, J=5.0 Hz, 4H), 1.10-1.51 (m, 60H), 1.04 (s, 9H), 0.88 (t, J=6.8 Hz, 6H).

Compound 4:

To a solution of 3 (12.6 g, 15.0 mmol) in 1,4-dioxane (220 mL), $CH_2Cl_2$ (70 mL), MeOH (55 mL), and $H_2O$ (55 mL) was added $NaIO_4$ (7.70 g, 36.0 mmol). The reaction mixture was stirred for 16 hours at room temperature. The mixture was extracted with $Et_2O$ (500 mL) and $H_2O$ (300 mL). The organic layer was separated and dried over anhydrous $Na_2SO_4$. After filtration and concentration, the crude product was purified by silica gel column chromatography (Hexane:EtOAc=9:1, $R_f$=0.30) to afford 4 (7.98 g, 14.5 mmol, 97%). Molecular weight for $C_{35}H_{54}NaO_3Si$ $(M+Na)^+$ Calc. 573.3740. Found 573.3.

Compound 7:

To a solution of 5 (see, Tetrahedron, 63, 1140-1145, 2006; 1.09 g, 2.18 mmol) in THF (20 mL) and HMPA (4 mL), LiHMDS (1 M THF solution, 4.36 mL, 4.36 mmol) was added at −20° C. The resulting mixture was stirred for 20 minutes at the same temperature, then cooled to −78° C. A solution of 4 (500 mg, 0.908 mmol) in THF (4 mL) was added. The mixture was stirred and allowed to warm to room temperature overnight. MS analysis showed the formation of the di-acid (6; $C_{53}H_{85}O_5Si$ $(M-H)^-$ calc. 829.6166, observed 829.5). To the mixture, $NaHCO_3$ (1.10 g, 13.1 mmol) and dimethyl sulfate (1.24 mL, 13.1 mmol) were added and stirred for 2 hours at room temperature. The reaction was quenched by adding saturated $NH_4Cl$ aqueous solution (50 mL) then extracted with $Et_2O$ (2×100 mL). The organic layer was separated and dried over anhydrous $Na_2SO_4$. After filtration and concentration, the crude product was purified by silica gel column chromatography (Hexane:EtOAc=9:1, $R_f$=0.35) to afford 7 (270 mg, 0.314 mmol, 35%). Molecular weight for $C_{55}H_{90}NaO_5Si$ $(M+Na)^+$ Calc. 881.6455. Found 881.6484.

Compound 8:

To a solution of 7 (265 mg, 0.308 mmol) in THF (2.5 mL), n-TBAF (1 M THF solution, 0.555 mL, 0.555 mmol) was added. The reaction mixture was stirred for 14 hours at 45° C. After concentration, the mixture was purified by silica gel column chromatography (Hexane:EtOAc=3:1, $R_f$=0.52) to afford 8 (155 mg, 0.250 mmol, 81%). Molecular weight for $C_{39}H_{72}NaO_5$ $(M+Na)^+$ Calc. 643.5277. Found 643.5273.

Compound 9:

To a solution of compound 8 (150 mg, 0.242 mmol) and 4-(dimethylamino)butyric acid hydrochloride (49 mg, 0.290 mmol) in $CH_2Cl_2$ (5 mL) were added diisopropylethylamine (0.126 mL, 0.726 mmol), N-(3-dimethylaminopropyl)-N'-ethylcarbodiimide hydrochloride (56 mg, 0.290 mmol) and DMAP (6 mg, 0.0484 mmol). The reaction mixture was stirred at room temperature for 14 hours. The reaction mixture was then diluted with $CH_2Cl_2$ (100 mL) and washed with saturated $NaHCO_3$ aq. (50 mL). The organic layer was dried over $MgSO_4$, filtered and concentrated. The crude product was purified by silica gel column chromatography (0-5% MeOH in $CH_2Cl_2$) to afford compound 9 (121 mg, 0.165 mmol, 68%, $R_f$=0.25 developed with 5% MeOH in $CH_2Cl_2$). Molecular weight for $C_{45}H_{84}NO_6$ $(M+H)^+$ Calc. 734.6299. Found 734.5.

Compound 10:

Treatment of compound 9 with $CH_3Cl$ in $CH_3CN$ and $CHCl_3$ can afford compound 10.

Example 2

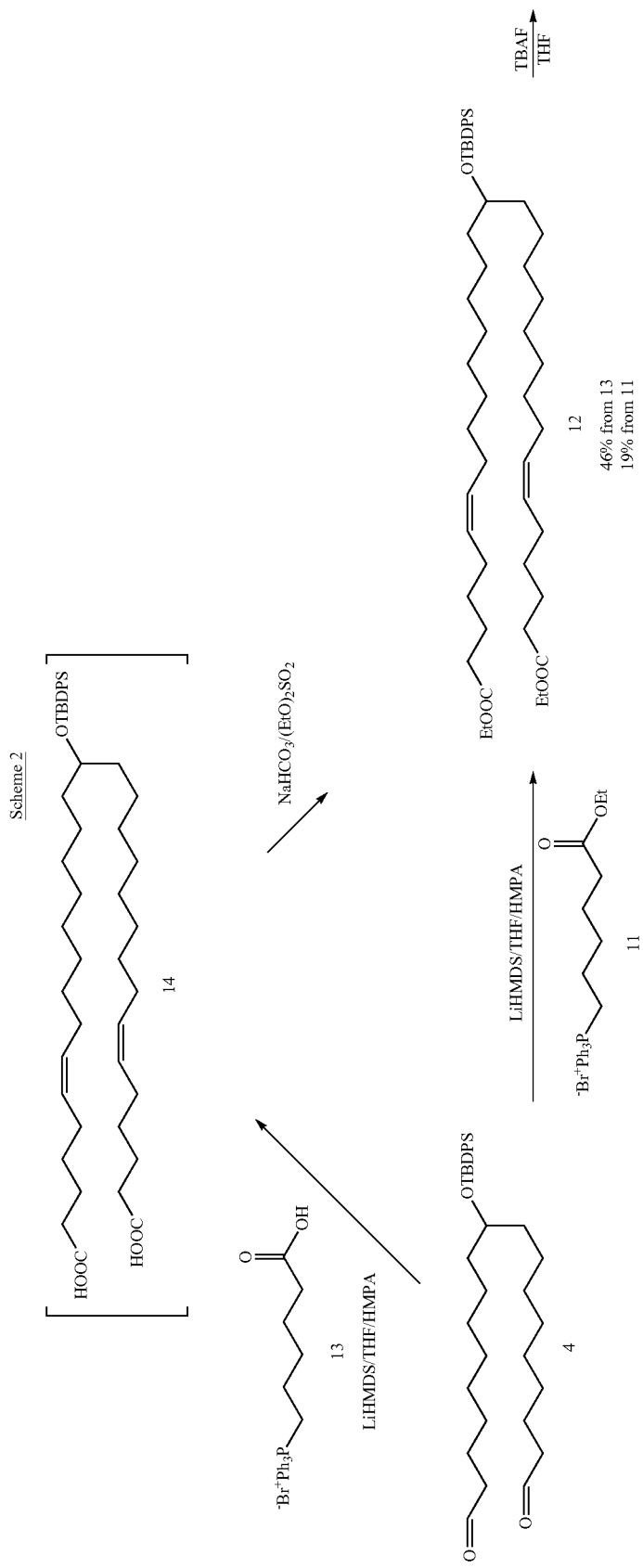

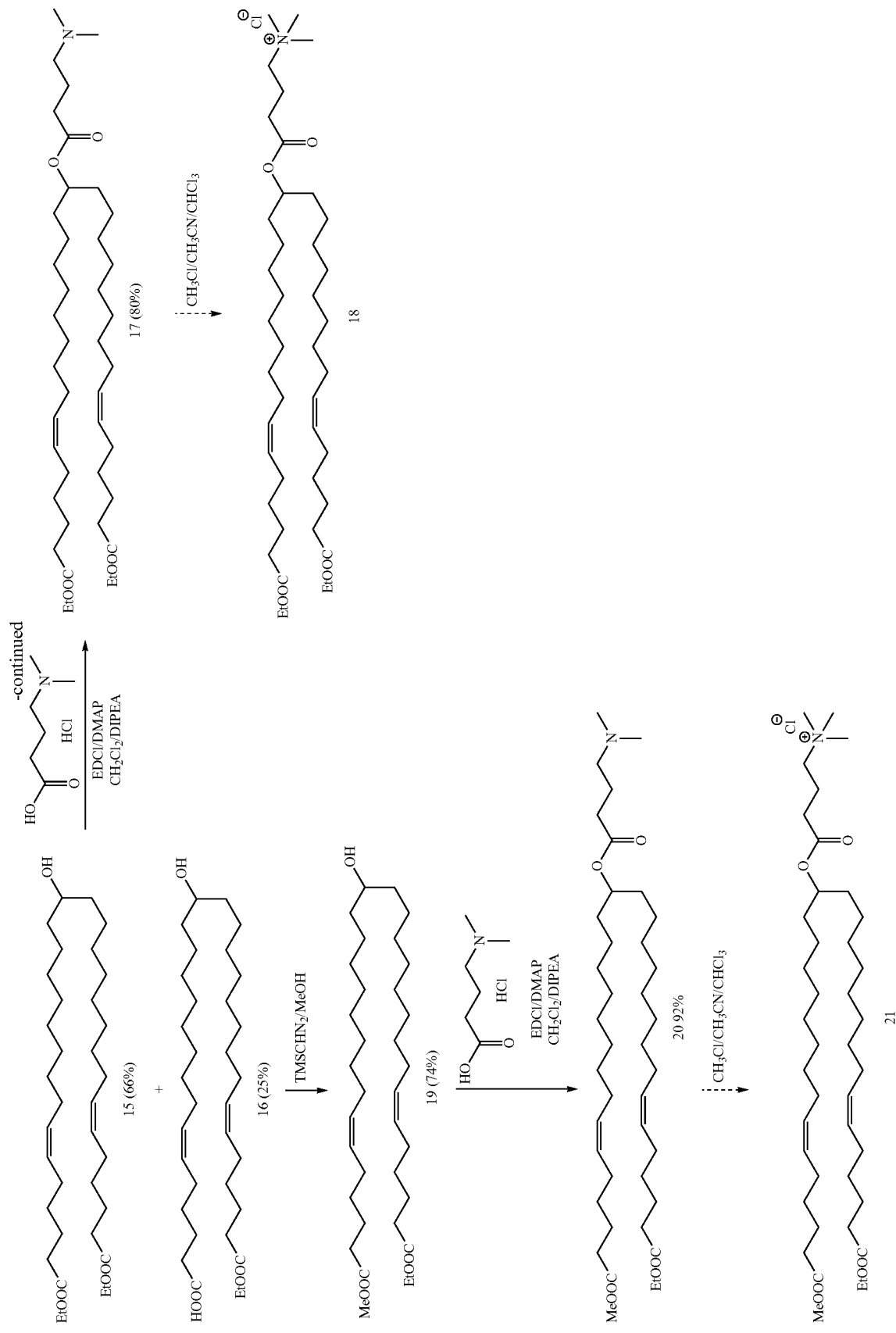

Compound 12:

To a solution of 11 (see, *J. Med. Chem.*, 38, 636-46, 1995; 1.25 g, 2.58 mmol) in THF (20 mL) and HMPA (4 mL), LiHMDS (1 M THF solution, 2.58 mL, 2.58 mmol) was added at −20° C. The mixture was stirred for 20 minutes at the same temperature, then cooled to −78° C. A solution of 4 (500 mg, 0.908 mmol) in THF (9 mL) and HMPA (0.9 mL) was added. The mixture was stirred and allowed to warm to room temperature overnight. The reaction was quenched by adding $H_2O$ (40 mL) then extracted with $Et_2O$ (150 mL×3). The organic layer was separated and dried over anhydrous $Na_2SO_4$. After filtration and concentration, the crude product was purified by silica gel column chromatography (Hexane: EtOAc=9:1, $R_f$=0.35) to afford 12 (136 mg, 0.169 mmol, 19%). Molecular weight for $C_{51}H_{82}NaO_5Si$ $(M+Na)^+$ Calc. 825.5829. Found 825.5.

Using 13 in place of 5, a procedure analogous to that described for compound 7 was followed to afford compound 12 (135 mg, 0.168 mmol, 46%).

Compound 15/Compound 16:

To a solution of 12 (800 mg, 0.996 mmol) in THF (5 mL), n-TBAF (1 M THF solution, 5 mL, 5.00 mmol) was added. The reaction mixture was stirred for 16 hours at 45° C. After concentration, the mixture was purified by silica gel column chromatography to afford 15 (hexane:EtOAc=3:1, $R_f$=0.46, 372 mg, 0.659 mmol, 66%) and 16 ($CH_2Cl_2$:MeOH=95:5, $R_f$=0.36, 135 mg, 0.251 mmol, 25%). Molecular weight for 15; $C_{35}H_{64}NaO_5$ $(M+Na)^+$ Calc. 587.4651. Found 587.4652. Molecular weight for 16; $C_{33}H_{61}O_5$ $(M+H)^+$ Calc. 537.4519. Found 537.5.

Compound 17:

To a solution of compound 15 (164 mg, 0.290 mmol) and 4-(dimethylamino)butyric acid hydrochloride (58 mg, 0.348 mmol) in $CH_2Cl_2$ (5 mL) were added diisopropylethylamine (0.152 mL, 0.870 mmol), N-(3-dimethylaminopropyl)-N'-ethylcarbodiimide hydrochloride (67 mg, 0.348 mmol) and DMAP (7 mg, 0.058 mmol). The reaction mixture was stirred at room temperature for 14 hours. The reaction mixture was diluted with $CH_2Cl_2$ (100 mL) and washed with saturated $NaHCO_3$ aq. (50 mL). The organic layer was dried over $MgSO_4$, filtered and concentrated. The crude product was purified by silica gel column chromatography (0-5% MeOH in $CH_2Cl_2$) to afford compound 17 (158 mg, 0.233 mmol, 80%, $R_f$=0.24 developed with 5% MeOH in $CH_2Cl_2$). Molecular weight for $C_{45}H_{84}NO_6$ $(M+H)^+$ Calc. 734.6299. Found 734.5.

Compound 18:

Treatment of compound 17 with $CH_3Cl$ in $CH_3CN$ and $CHCl_3$ can afford compound 18.

Compound 19:

To a solution of 16 (130 mg, 0.242 mmol) in THF (2 mL) and MeOH (2 mL), trimethylsilyldiazomethane (2 M solution in $Et_2O$, 0.158 mL, 0.315 mmol) was added. The reaction mixture was stirred for 14 hours. After evaporation, the residue was purified by silica gel column chromatography (hexane:EtOAc=3:1, $R_f$=0.50) to afford 19 (99 mg, 0.180 mmol, 74%). $^1$H NMR (400 MHz, $CDCl_3$) δ 5.29-5.40 (m, 4H), 4.12 (q, J=7.1 Hz, 2H), 3.66 (s, 3H), 3.55-3.59 (m, 1H), 2.30 (dd, J=14.7, 7.2 Hz, 4H), 1.98-2.07 (m, 8H), 1.60-1.68 (m, 4H), 1.23-1.43 (m, 37H).

Compound 20:

To a solution of compound 19 (95 mg, 0.168 mmol) and 4-(dimethylamino)butyric acid hydrochloride (42 mg, 0.252 mmol) in $CH_2Cl_2$ (3 mL) were added diisopropylethylamine (0.088 mL, 0.504 mmol), N-(3-dimethylaminopropyl)-N'-ethylcarbodiimide hydrochloride (48 mg, 0.504 mmol) and DMAP (4 mg, 0.034 mmol). The reaction mixture was stirred at room temperature for 14 hours. The reaction mixture was diluted with $CH_2Cl_2$ (100 mL) and washed with saturated $NaHCO_3$ aq. (50 mL). The organic layer was dried over $MgSO_4$, filtered and concentrated. The crude product was purified by silica gel column chromatography (0-5% MeOH in $CH_2Cl_2$) to afford compound 20 (103 mg, 0.155 mmol, 92%, $R_f$=0.19 developed with 5% MeOH in $CH_2Cl_2$). $^1$H NMR (400 MHz, $CDCl_3$) δ 5.29-5.40 (m, 4H), 4.83-4.89 (m, 1H), 4.12 (q, J=7.1 Hz, 2H), 3.67 (s, 3H), 2.28-2.34 (m, 8H), 2.23 (s, 6H), 1.98-2.07 (m, 8H), 1.76-1.83 (m, 2H), 1.60-1.68 (m, 4H), 1.23-1.51 (m, 35H).

Compound 21:

Treatment of compound 20 with $CH_3Cl$ in $CH_3CN$ and $CHCl_3$ can afford compound 21.

Example 3

Alternate Synthesis for Di-Aldehyde Intermediate 4

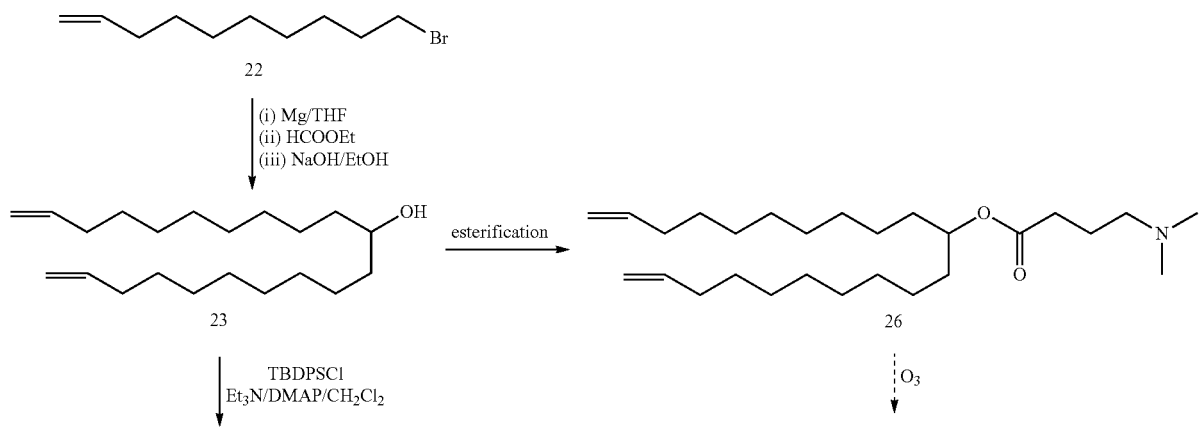

Scheme 3

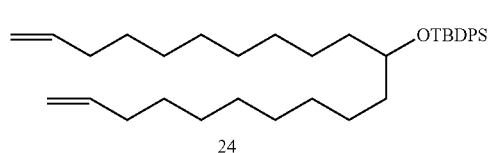
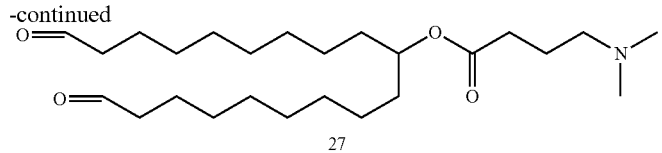
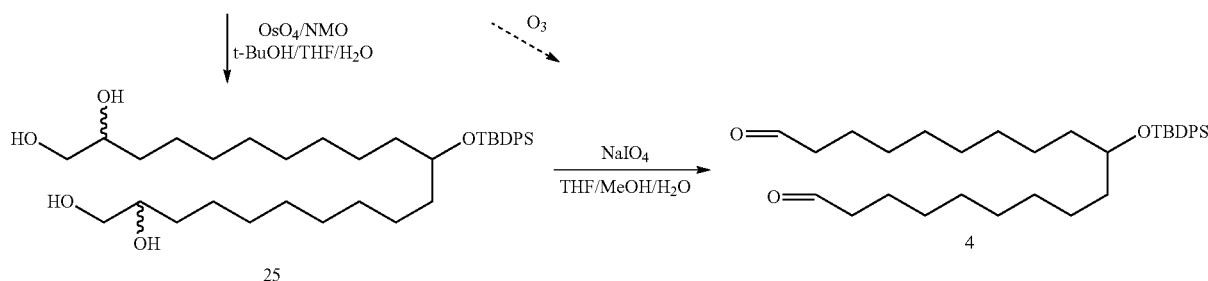
The di-aldehyde 4 can be synthesized as shown in Scheme 3, using 1-bromo-9-decene. Di-aldehyde containing a head group 27 can be useful for the synthesis of terminal ester-substituted lipids using, e.g., a Wittig reaction. Ozonolysis can afford di-aldehyde 4 and 27.
Example 4
Alternate Synthesis for Compound 8
Scheme 4
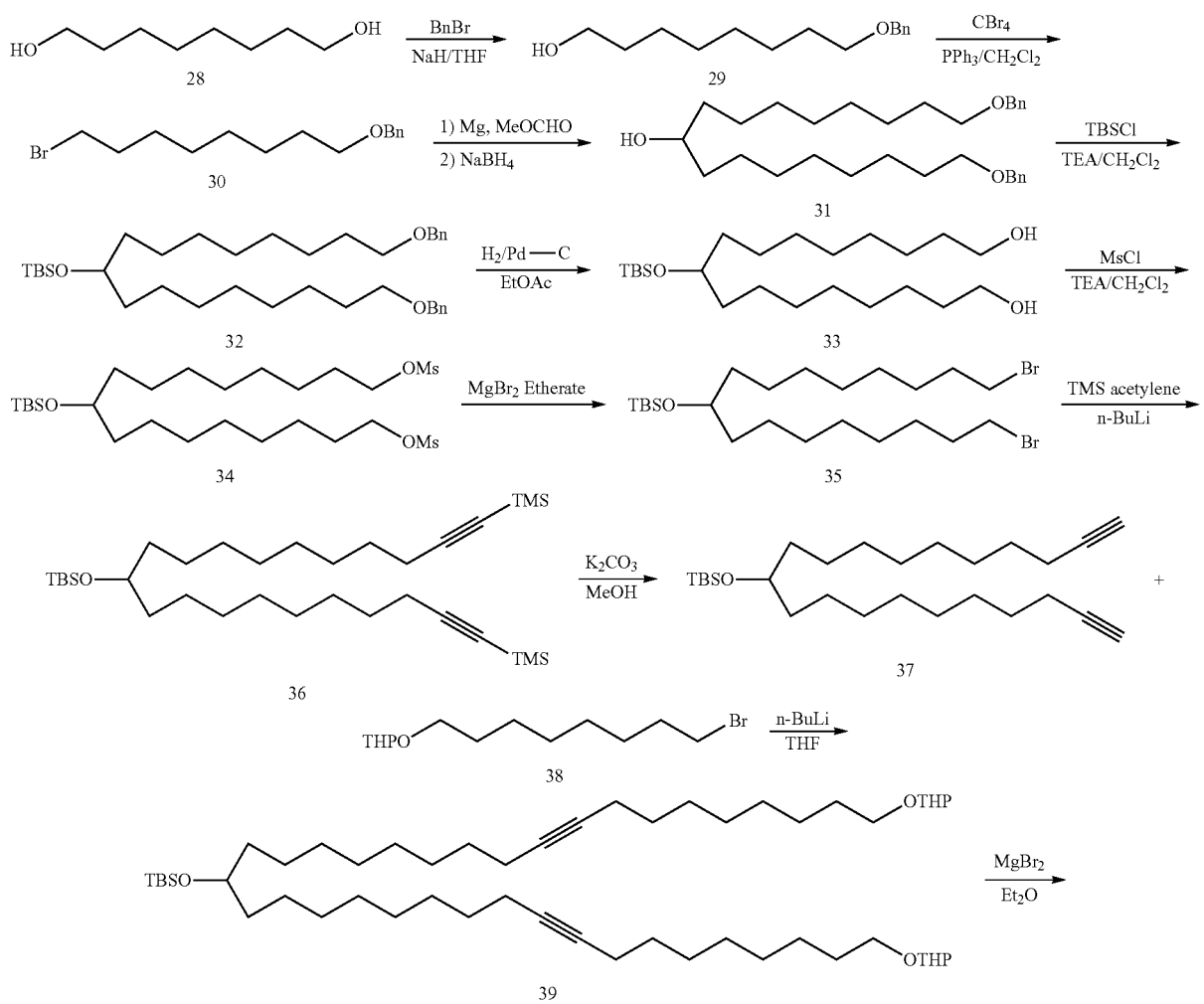

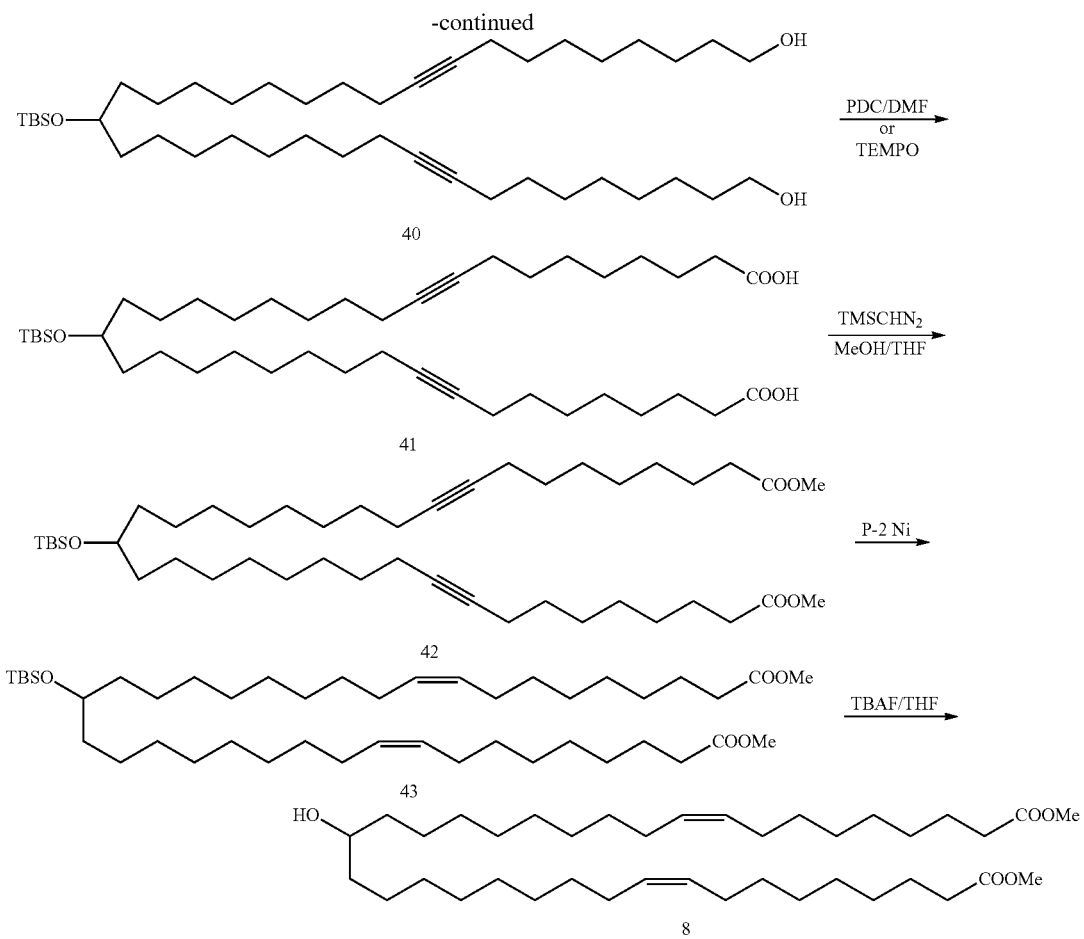

Compound 8 can be synthesized as shown in Scheme 4.

Compound 29: To a stirred suspension of NaH (60% in oil, 82 g, 1.7096 mol) in 500 mL anhydrous DMF, a solution of compound 28 (250 g, 1.7096 mol) in 1.5 L DMF was added slowly using a dropping funnel at 0° C. The reaction mixture was stirred for 30 minutes, then benzyl bromide (208.86 mL, 1.7096 mol) was added slowly under an atmosphere of nitrogen. The reaction was then warmed to ambient temperature and stirred for 10 hours. The mixture was then quenched with crushed ice (~2 kg) and extracted with ethyl acetate (2×1 L). The organic layer was washed with water (1L) to remove unwanted DMF, dried over $Na_2SO_4$ and evaporated to dryness in vacuo. The crude compound was purified on 60-120 silica gel, eluted with 0-5% MeOH in DCM to afford compound 29 (220 g, 54%) as a pale yellow liquid. $^1$H NMR (400 MHz, $CDCl_3$): δ=7.33-7.24 (m, 5H), 4.49 (s, 2H), 3.63-3.60 (m, 2H), 3.47-3.43 (m, 2H), 1.63-1.51 (m, 4H), 1.39-1.23 (m, 8H).

Compound 30:

Compound 29 (133 g, 0.5635 mol) was dissolved in 1.5 L of DCM, $CBr_4$ (280.35 g, 0.8456 mol) was added into this stirring solution and the reaction mixture was cooled to 0° C. under an inert atmosphere. $PPh_3$ (251.03 g, 0.9571 mol) was then added in portions keeping the temperature below 20° C. After complete addition, the reaction mixture was stirred for 3 hours at room temperature. After completion of the reaction, the solid ($PPh_3O$) that precipitated from the reaction mixture was removed by filtration, and the filtrate was diluted with crushed ice (~1.5 kg) and extracted with DCM (3×750 mL). The organic layer was separated, dried over anhydrous $Na_2SO_4$ and distilled under vacuum. The resulting crude compound was chromatographed on 60-120 mesh silica gel column using 0-5% ethyl acetate in hexanes as eluting system to afford compound 30 (150 g, 89%) as pale yellow liquid. $^1$H NMR (400 MHz, $CDCl_3$): δ=7.33-7.25 (m, 5H), 4.49 (s, 2H), 3.47-3.41 (m, 2H), 3.41-3.37 (m, 2H), 1.86-1.80 (m, 4H), 1.62-1.56 (m, 2H), 1.42-1.29 (m, 8H).

Compound 31:

To freshly activated Mg turnings (24.08 g, 1.003 mol) was added 200 mL anhydrous THF, followed by the addition of pinch of iodine into the mixture under an inert atmosphere. A solution of Compound 30 (150 g, 0.5016 mol) in 1 L of dry THF was added slowly, controlling the exothermic reaction. The reaction was then heated to reflux for 1 hour, then cooled to room temperature. Methyl formate (60.24 g, 1.0033 mol) was then added slowly and the reaction was continued for 2 hours. After completion, the reaction was quenched by slow addition of 10% HCl followed by water (1 L) and extracted with ethyl acetate (3×1 L). The organic layer was taken in 5 liter beaker, diluted with 500 mL of methanol and cooled to 0° C. To this solution, an excess of $NaBH_4$ (~5 eq) was added in portions to ensure hydrolysis of the formate ester which was not cleaved by addition of HCl. The resulting solution was stirred for an hour and then volatilites were removed under vacuum. The residue was taken in water (1 L) and acidified by 10% HCl solution (pH 4). The product was then extracted with ethyl acetate (3×1 L). the organic phase was then dried and concentrated on rotary evaporator to afford the desired compound 31 (57 g, 24%) as solid. $^1$H NMR (400 MHz, CDCl$_3$): δ=7.35-7.32 (m, 8H), 7.29-7.24 (m, 2H), 4.49 (s, 4H), 3.56 (m, 1H), 3.46-3.43 (m, 4H), 1.63-1.56 (m, 4H), 1.44-1.34 (m, 28H). $^{13}$C NMR (100 MHz, CDCl$_3$): δ=138.56, 128.21, 127.49, 127.34, 72.72, 71.76, 70.37, 37.37, 29.64, 29.56, 29.47, 29.33, 26.07, 25.54.

Compound 32:

Compound 31 (56 g, 0.1196 mol) was dissolved in 700 mL dry THF and cooled to 0° C. TBSCl (36.06 g, 0.2396 mol) was added slowly followed by the addition of imidazole (32.55 g, 0.4786 mol) under an inert atmosphere. The reaction was then stirred at room temperature for 18 hours. Upon completion, the reaction was quenched with ice (~1 kg) and extracted with ethyl acetate (3×500 mL). The organic layer was separated, washed with saturated NaHCO$_3$ solution to remove acidic impurities, dried over Na$_2$SO$_4$ and evaporated under reduce pressure to afford a crude compound that was purified by silica gel (60-120 mesh) and eluted with 0-10% ethyl acetate hexane to afford (60 g, 82%) of compound 32 as yellowish oil.

$^1$H NMR (400 MHz, CDCl$_3$): δ=7.33-7.24 (m, 10H), 4.49 (s, 4H), 3.60-3.57 (m, 1H), 3.46-3.43 (m, 4H), 1.61-1.54 (m, 4H), 1.41-1.26 (m, 28H), 0.87 (s, 9H), 0.02 (s, 6H).

Compound 33:

Compound 32 (60 g, 0.1030 mol) was dissolved in 500 mL ethyl acetate and degassed with N$_2$ for 20 minutes. (10 wt %) Pd on carbon (12 g) was added and the reaction was stirred under an atmosphere of hydrogen for 18 hours. After completion, the mixture was filtered through a bed of celite and washed with ethyl acetate. The filtrate was evaporated under vacuum to afford compound 33 (19 g, 46%) that was pure enough to use in the next synthetic sequence.

$^1$H NMR (400 MHz, CDCl$_3$): δ=3.64-3.58 (m, 5H), 1.59 (br, 2H), 1.57-1.51 (m, 4H), 1.38-1.22 (m, 28H), 0.87 (s, 9H), 0.02 (s, 6H).

Compound 34:

Compound 33 (8.2 g, 0.0199 mol) was dissolved in 100 mL dry DCM and cooled to 0° C. TEA (22.14 mL, 0.1592 mol) was added under an inert atmosphere. After stirring the mixture for 5 minutes, mesyl chloride (4.6 mL, 0.059 mol) was added drop wise and the reaction was stirred further for 3 hours. After completion of the reaction, the mixture was quenched with ice (~200 g) and extracted with DCM (3×75 mL). The organic layer was dried over anhydrous sodium sulfate and evaporated to afford a crude compound which was purified on a 60-120 mesh silica gel column using 0-30% ethyl acetate in hexane as eluting system to afford compound 34 (8.2 g, 73%) as a pale yellow liquid. $^1$H NMR (400 MHz, CDCl$_3$): δ=4.22-4.19 (m, 4H), 3.60-3.58 (m, 1H), 2.99 (s, 6H), 1.75-1.69 (m, 4H), 1.38-1.28 (m, 28H), 0.86 (s, 9H), 0.02 (s, 6H).

Compound 35:

To a solution of compound 34 (8.2 g, 0.0146 mol) in 400 mL dry ether was added MgBr$_2$.Et$_2$O (22.74 g, 0.08817 mol) in portions at 0° C. under a nitrogen atmosphere. After complete addition, the reaction mixture was heated to reflux for 28 hours. After completion of reaction, inorganic material formed in the reaction was removed by filtration. The filtrate was evaporated and the resulting crude compound was purified on 60-120 mesh silica gel column using 0-3% ethyl acetate in hexanes as eluting system to afford compound 35 (6.6 g, 85%) as a colorless liquid. $^1$H NMR (400 MHz, CDCl$_3$): δ=3.61-3.58 (m, 1H), 3.41-3.37 (t, 4H, J=6.8 Hz), 1.87-1.80 (m, 4H), 1.42-1.25 (m, 24H), 0.87 (s, 9H), 0.012 (s, 6H).

Compound 36:

A solution of ethynyl trimethyl silane (5.3 mL, 0.0378 mol) in 60 mL dry THF was cooled to −78° C. and 1.4 M n-BuLi (23 mL, 0.03405 mol) in hexane was added slowly under an inert atmosphere. The reaction was stirred for 10 minutes, then HMPA (2.3 g, 0.01324 mol) was added and the resulting mixture was then stirred for 2 hours at 0° C., then cooled to −78° C. To this a solution of compound 35 (5 g, 0.0094 mol) in 60 mL dry THF was added slowly and after complete addition, the reaction was warmed to room temperature and maintained for 18 hours. The reaction progress was monitored by $^1$H NMR. After completion, the reaction mixture was cooled to 0° C. and quenched by careful addition of saturated NH$_4$Cl solution (50 mL) followed by water (200 mL). The aqueous phase was extracted with hexane (3×250 mL). The organic layer was dried and solvent removed under vacuum to afford compound 36 (5 g, 94%), which was used without further purification. $^1$H NMR (400 MHz, CDCl$_3$): δ=3.62-3.56 (m, 1H), 2.21-2.17 (m, 4H), 1.49-1.47 (m, 4H), 1.37-1.26 (m, 24H), 0.87 (s, 9H), 0.13 (s, 18H), 0.021 (s, 6H).

Compound 37:

To a stirred solution of compound 36 (5 g, 0.0088 mol) in 50 mL methanol, was added K$_2$CO$_3$ (6.1 g, 0.044 mol) in one portion, and the resulting mixture was stirred for 18 hours at ambient temperature. Volatilities were then removed on a rotary evaporator and the crude mixture was diluted with 100 mL water and extracted with hexane (3×100 mL). The organic layer was dried over Na$_2$SO$_4$ and evaporated under vacuum to afford compound 37 (3.5 g, 97%) which was used which was used without further purification. $^1$H NMR (400 MHz, CDCl$_3$): δ=3.60-3.58 (m, 1H), 2.19-2.14 (m, 4H), 1.93-1.92 (m, 2H), 1.54-1.49 (m, 4H), 1.37-1.27 (m, 24H), 0.87 (s, 9H), 0.02 (s, 6H).

Compound 39:

Compound 37 (2.5 g, 0.00598 mol) was dissolved in 25 mL dry THF and cooled to −40° C. n-BuLi (1.4 M in hexane 12.9 mL, 0.01794 mol) was added slowly, followed, after a 10 minute interval, by slow addition of HMPA (25 mL). The resulting mixture was maintained for 30 minutes −40° C. under a nitrogen atmosphere. A solution of compound 38 (3.5 g, 1.01196 mol) in 25 mL dry THF was then added drop wise to the cooled reaction mixture. The resulting mixture was warmed to room temperature over 2 hours, then stirred at room temperature for 18 hours. The mixture was then quenched by adding saturated NH$_4$Cl solution (~50 mL) and the product was extracted with ethyl acetate (3×50 mL). The solvent was removed on a rotary evaporator and the resulting crude product was purified by (100-200 mesh) silica gel column using 0-3% ethyl acetate in dichloromethane as eluting system to afford compound 39 (0.9 g, 18%) as a yellow oil. $^1$H NMR (400 MHz, CDCl$_3$): δ=4.56-4.55 (m, 2H), 3.87-3.83 (m, 2H), 3.74-3.68 (m, 2H), 3.59-3.57 (m, 1H), 3.49-3.46 (m, 2H), 3.39-3.33 (m, 2H), 2.13-2.10 (m, 8H), 1.87-1.75 (m, 2H), 1.74-1.66 (m, 2H), 1.57-1.42 (m, 20H), 1.40-1.19 (m, 40H), 0.87 (s, 9H), 0.02 (s, 6H).

Compound 40:

To a solution of compound 39 (504 mg, 0.598 mmol) in 10 mL dry ether was added MgBr$_2$.Et$_2$O (926 mg, 3.59 mmol). The reaction mixture was stirred for 14 hours, then quenched by adding saturated NaHCO$_3$ aqueous solution. The product was extracted with CH$_2$Cl$_2$. The organic layer was dried over Na$_2$SO$_4$, filtered and concentrated. The crude product was purified by silica gel column chromatography to afford compound 40 (307 mg, 0.455 mmol, 76%, R$_f$=0.36 developed with hexane:EtOAc=2:1). $^1$H NMR (400 MHz, CDCl$_3$) δ 3.59-3.66 (m, 5H), 2.14 (t, J=6.6 Hz, 8H), 1.21-1.59 (m, 52H), 0.88 (s, 9H), 0.03 (s, 6H).

Compound 41:

To a stirred solution of 40 (180 mg, 0.267 mmol) in anhydrous DMF (5 mL) was added pyridinium dichromate (603 mg, 1.60 mmol). The reaction mixture was stirred for 48 hours. After dilution with water (20 mL), the mixture was extracted with Et$_2$O (3×40 mL). The organic layer was dried over Na$_2$SO$_4$, filtered and concentrated. The crude product was purified by silica gel column chromatography to afford compound 41 (53 mg, 0.075 mmol, 28%, R$_f$=0.25 developed with CH$_2$Cl$_2$:MeOH:AcOH=95:4.5:0.5). Molecular weight for C$_{43}$H$_{77}$O$_5$Si (M-H)$^-$ Calc. 701.5540. Found 701.5. This compound can be synthesized by TEMPO oxidation.

Compound 42:

A procedure analogous to that described for compound 19 afforded compound 42 (23 mg 0.032 mmol, 21% from compound 40). $^1$H NMR (400 MHz, CDCl$_3$) δ 3.67 (s, 6H), 3.59-3.62 (m, 1H), 2.30 (t, J=7.5 Hz, 4H), 2.13 (t, J=6.8 Hz, 8H), 1.27-1.64 (m, 48H), 0.88 (s, 9H), 0.03 (s, 6H).

Reduction using P-2 nickel conditions can give compound 43 and subsequent deprotection by TBAF can afford compound 8.

Example 5

Alternate Synthesis for Compound 8

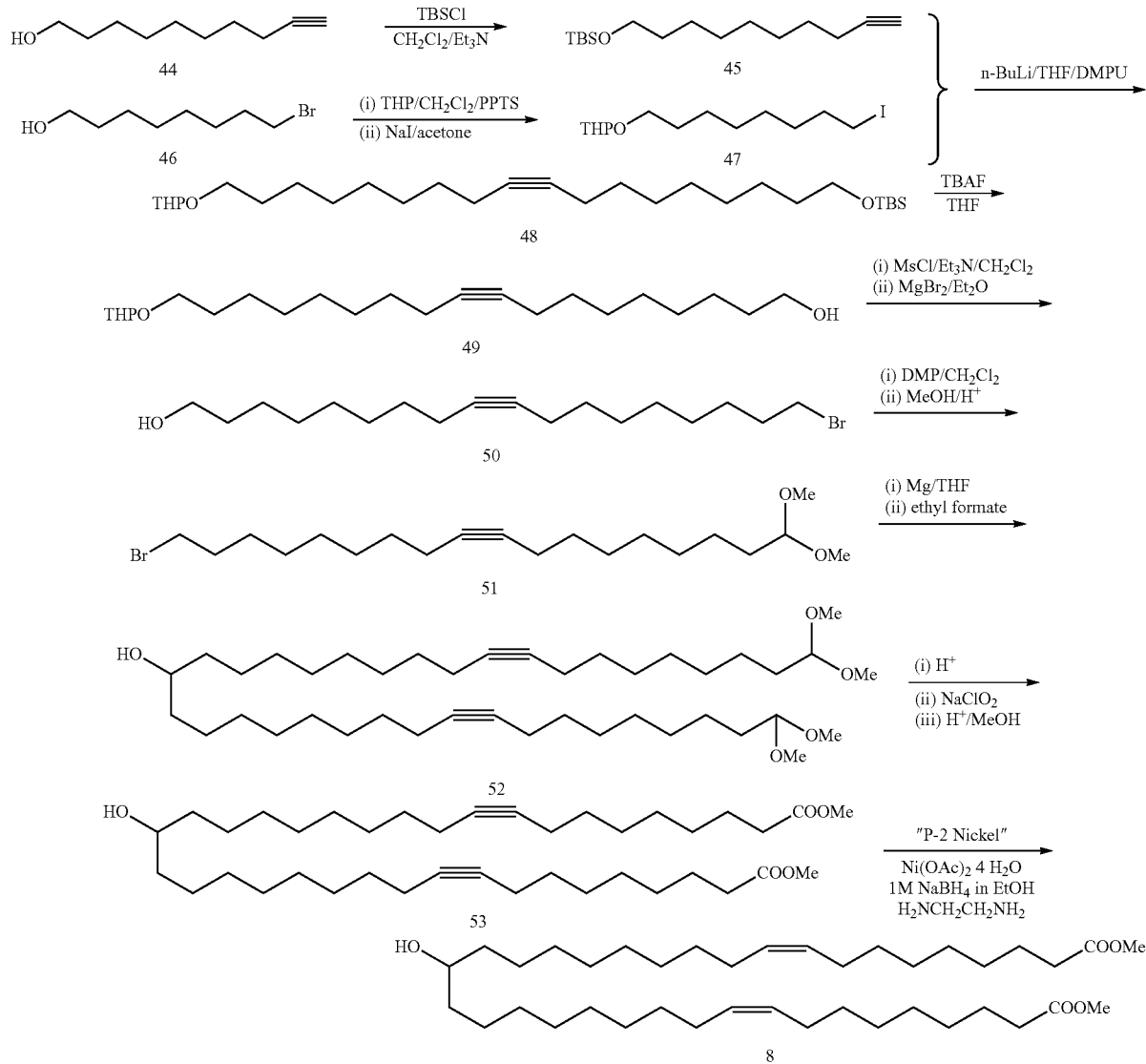

Compound 8 can be synthesized as shown in Scheme 5. The bromide 51 can be converted to its Grignard reagent then coupled with ethyl formate to afford compound 52. Subsequent acid treatment, oxidation, and reduction can give compound 8.

Example 6

Alternate Synthesis for Compound 8

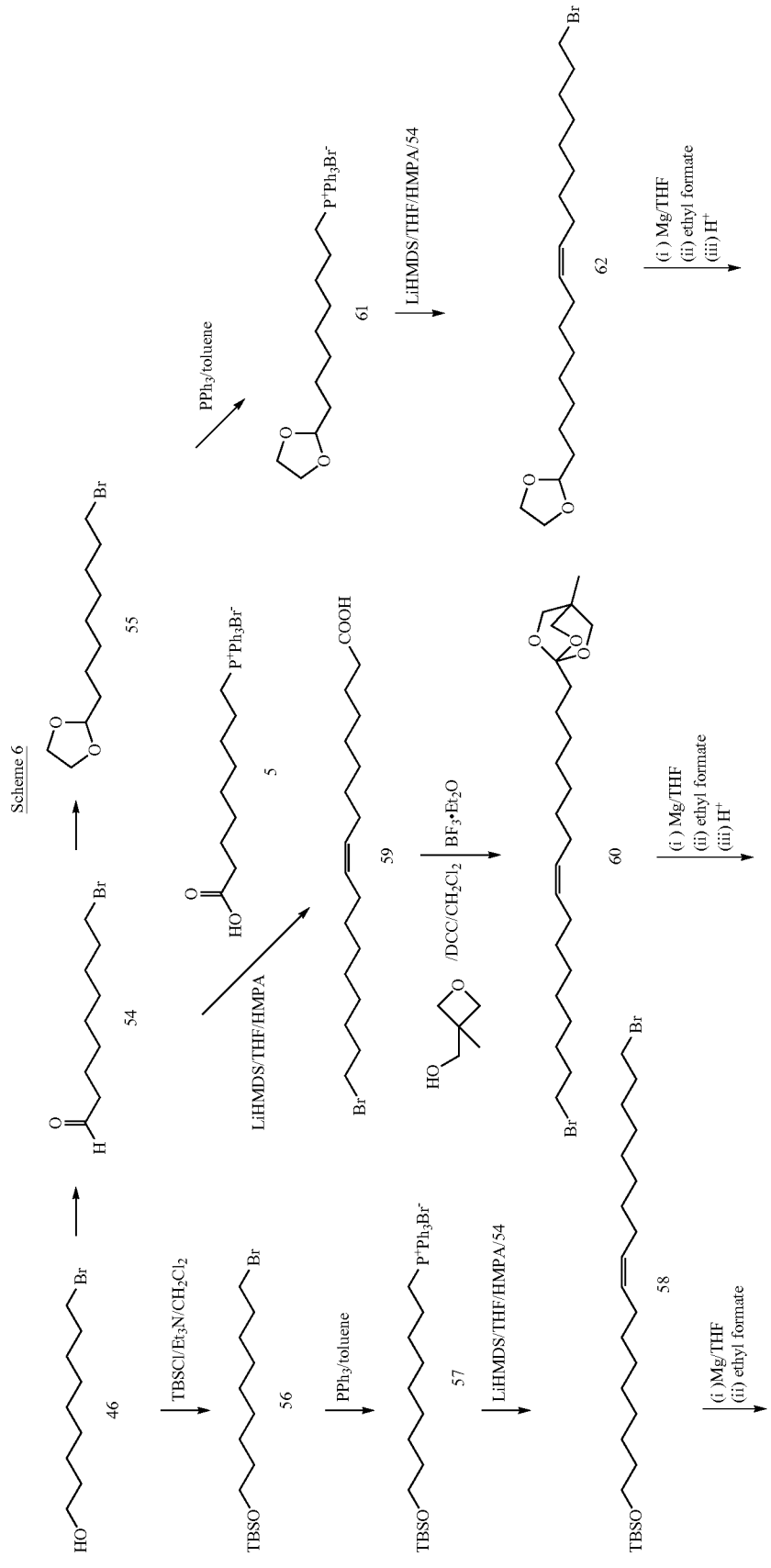

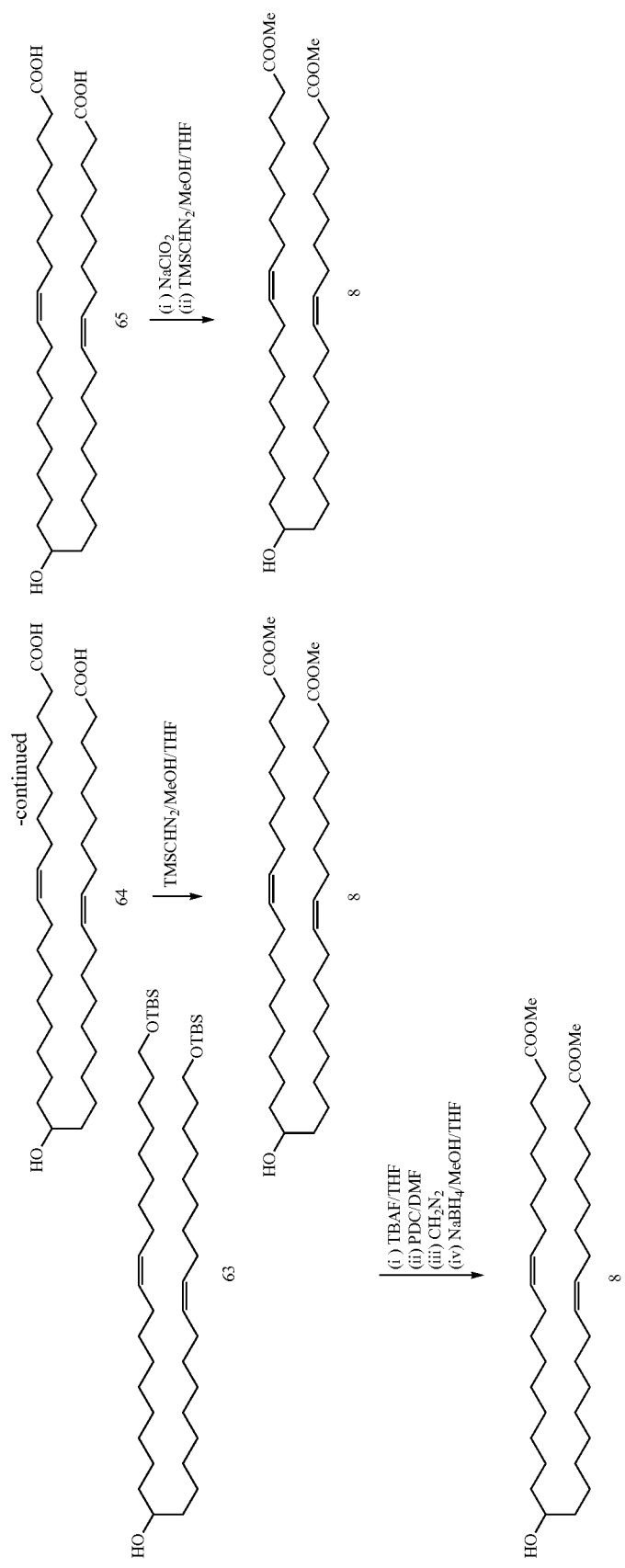

Compound 8 can be synthesized as shown in Scheme 6. Either bromides of compound 58, 60, or 62 can be reacted with ethyl formate to generate terminal-functionalized di-olefin chain. Compound 8 can then be prepared from the diolefin chain compounds using standard chemical reactions.

Example 7

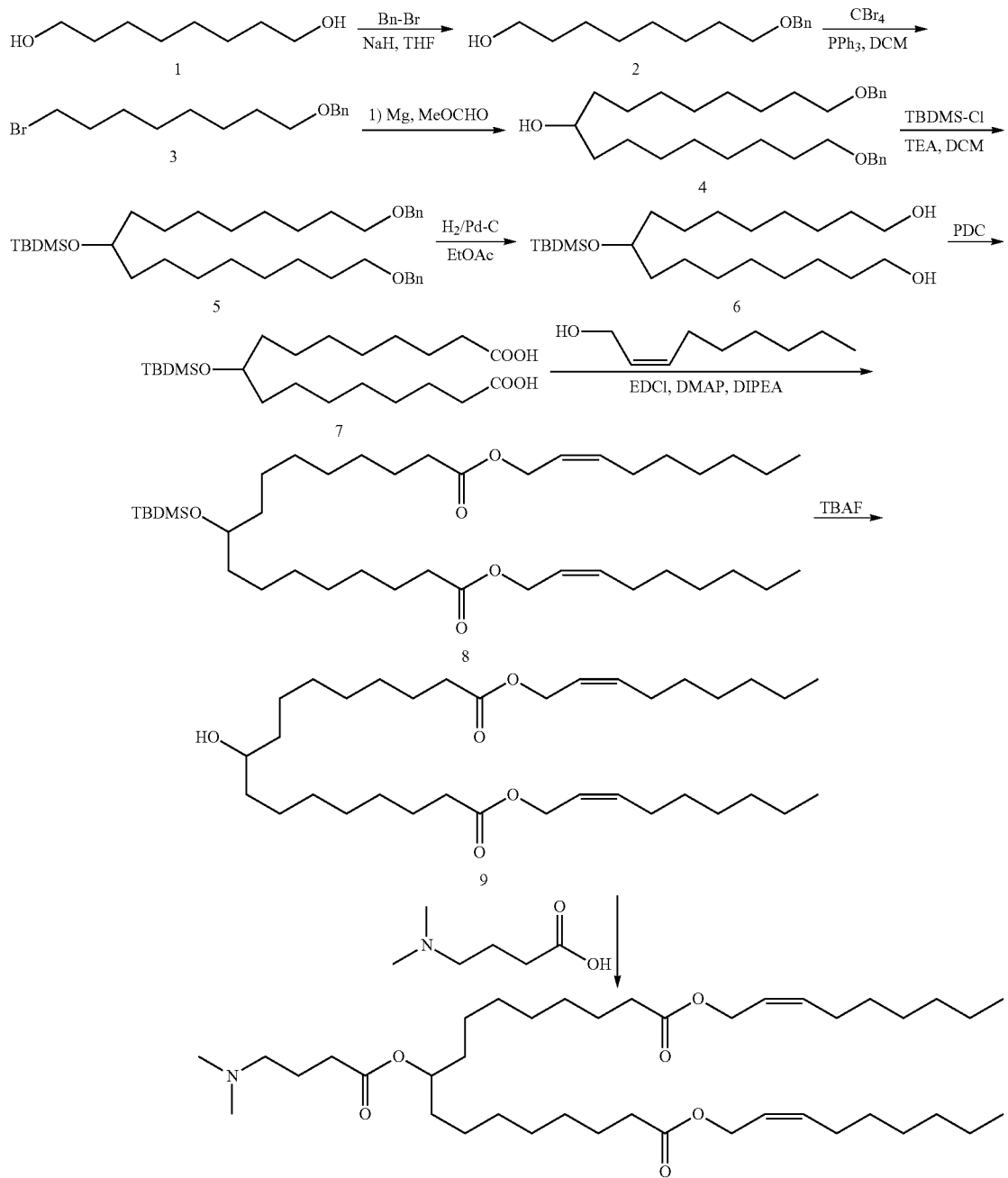

Synthesis of 8-benzyloxy-octan-1-ol (2)

To a stirred suspension of NaH (60% in oil, 82 g, 1.7096 mol) in 500 mL anhydrous DMF, a solution of compound 1 (250 g, 1.7096 mol) in 1.5 L DMF was added slowly using a dropping funnel at 0° C. The reaction mixture was stirred for 30 minutes, then benzyl bromide (208.86 mL, 1.7096 mol) was added slowly under a nitrogen atmosphere. The reaction was then warmed to ambient temperature and stirred for 10 hours. After completion of reaction, the mixture was quenched with crushed ice (~2 kg) and extracted with ethyl acetate (2×IL). The organic layer washed with water (IL) to remove unwanted DMF, dried over Na$_2$SO$_4$ and evaporated to dryness under vacuum. The crude compound was purified on 60-120 silica gel, eluted with 0-5% MeOH in DCM to afford compound 2 (220 g, 54%) as pale yellow liquid. H¹ NMR (400 MHz, CDCl₃): δ=7.33-7.24 (m, 5H), 4.49 (s, 2H), 3.63-3.60 (m, 2H), 3.47-3.43 (m, 2H), 1.63-1.51 (m, 4H), 1.39-1.23 (m, 8H).

Synthesis of (8-bromo-octyloxymethyl)-benzene (3)

Compound 2 (133 g, 0.5635 mol) was dissolved in 1.5 L of DCM, CBr₄ (280.35 g, 0.8456 mol) was added to this stirring solution and the reaction mixture was cooled to 0° C. under an inert atmosphere. PPh₃ (251.03 g, 0.9571 mol) was then added in portions maintaining the temperature below 20° C. and after complete addition, the reaction mixture was stirred for 3 hours at room temperature. After completion of reaction, solid (PPh₃O) precipitated out from the reaction mixture was isolated by filtration and the filtrate was diluted with crushed ice (~1.5 kg) and extracted with DCM (3×750 mL). The organic layer was separated, dried over anhydrous Na₂SO₄ and distilled under vacuum. The resulting crude compound was chromatographed on 60-120 mesh silica gel column using 0-5% ethyl acetate in hexanes as eluting system to afford compound 3 (150 g, 89%) as pale yellow liquid. ¹H NMR (400 MHz, CDCl₃): δ=7.33-7.25 (m, 5H), 4.49 (s, 2H), 3.47-3.41 (m, 2H), 3.41-3.37 (m, 2H), 1.86-1.80 (m, 4H), 1.62-1.56 (m, 2H), 1.42-1.29 (m, 8H).

Synthesis of 1, 17-bis-benzyloxy-heptadecan-9-ol (4)

To freshly activated Mg turnings (24.08 g, 1.003 mol) was added 200 mL anhydrous THF, followed by the addition of pinch of iodine into the mixture under inert atmosphere. After initiation of the Grignard formation a solution of Compound 3 (150 g, 0.5016 mol) in 1 L of dry THF was added slowly controlling the exothermic reaction. After complete addition, the reaction was heated to reflux for 1 hour, then cooled to room temperature. Methyl formate (60.24 g, 1.0033 mol) was then added slowly and reaction was continued for 2 hours. After completion, the reaction was quenched by slow addition of 10% HCl followed by water (1 L) and extracted with ethyl acetate (3×1 L). The organic layer was taken in 5 liter beaker, diluted with 500 mL of methanol and cooled to 0° C. To this solution excess of NaBH₄ (~5 eq) was added in portions to ensure the hydrolysis of formate ester which was not cleaved by addition of HCl. The resulting solution was stirred for an hour and then volatilites were removed under vacuum. The residue was taken in water (1 L) and acidified by 10% HCl solution (P^H 4). The product was then extracted with ethyl acetate (3×1 L). The organic phase was then dried and concentrated on rotary evaporator to afford compound 4 (57 g, 24%) as solid. ¹H NMR (400 MHz, CDCl₃): δ=7.35-7.32 (m, 8H), 7.29-7.24 (m, 2H), 4.49 (s, 4H), 3.56 (m, 1H), 3.46-3.43 (m, 4H), 1.63-1.56 (m, 4H), 1.44-1.34 (m, 28H). C¹³ NMR (100 MHz, CDCl₃): δ=138.56, 128.21, 127.49, 127.34, 72.72, 71.76, 70.37, 37.37, 29.64, 29.56, 29.47, 29.33, 26.07, 25.54.

Synthesis of [9-benzyloxy-1-(8-benzylozy-octyl)-nonyloxy]-tert-butyl-dimethyl-silane (5)

Compound 4 (56 g, 0.1196 mol) was dissolved in 700 mL of anhydrous THF and cooled to 0° C. TBMS-Cl (36.06 g, 0.2396 mol) was added slowly followed by addition of imidazole (32.55 g, 0.4786 mol) under an inert atmosphere. The reaction was then stirred at room temperature for 18 hours, then quenched with ice (~1 kg). The product was extracted with ethyl acetate (3×500 mL). The organic layer was separated, washed with saturated NaHCO₃ solution to remove the acidic impurity, dried over Na₂SO₄ and evaporated under reduce pressure to obtain crude compound which was purified by silica gel (60-120 mesh) and eluted with 0-10% ethyl acetate hexane to afford (60 g, 82%) of compound 5 as yellowish oil. H¹ NMR (400 MHz, CDCl₃): δ=7.33-7.24 (m, 10H), 4.49 (s, 4H), 3.60-3.57 (m, 1H), 3.46-3.43 (m, 4H), 1.61-1.54 (m, 4H), 1.41-1.26 (m, 28H), 0.87 (s, 9H), 0.02 (s, 6H)

Synthesis of 9-(tert-butyl-dimethyl-silanyloxy)-heptadecane-1, 17-diol (6)

Compound 5 (60 g, 0.1030 mol) was dissolved in 500 mL ethyl acetate and degassed with N₂ for 20 min. (10 wt %) Pd on carbon (12 g) was added and reaction was stirred under an atmosphere of hydrogen for 18 hours. After completion, the mixture was filtered through a bed of celite and washed with ethyl acetate. The filtrate was evaporated under vacuum. Compound 6 (19 g, 46%) thus obtained was pure enough to carry out the next reaction. ¹H NMR (400 MHz, CDCl₃): δ=3.64-3.58 (m, 5H), 1.59 (br, 2H), 1.57-1.51 (m, 4H), 1.38-1.22 (m, 28H), 0.87 (s, 9H), 0.02 (s, 6H).

Synthesis of 9-(tert-butyl-dimethyl-silanyloxy)-heptadecanedioic acid (7)

To a stirred solution of 6 (2 g, 0.0049 mol) in anhydrous DMF (40 mL) was added pyridinium dichromate (2.7 g, 0.0074 mol) at 0° C. under an inert atmosphere. The reaction mixture was then allowed to warm to room temperature over a period of 10-15 minutes and continued for 24 hours. Then, the reaction was diluted with water (100 mL). The aqueous phase was extracted using DCM (3×40 mL). The organic phase was washed with brine (1×25 mL) and concentrated under vacuum to afford crude acid which was then purified by (100-200 mesh) silica gel column using 0-30% ethyl acetate in hexanes system. Pure product (7) was obtained (0.7 g, 33%) as a pale yellow oil.

¹H NMR (400 MHz, CDCl₃): δ=3.61-3.56 (m, 1H), 2.35-2.32 (m, 4H), 1.64-1.59 (m, 4H), 1.40-1.19 (m, 24H), 0.86 (s, 9H), 0.017 (s, 6H); LC-MS [M+H]− 431.00; HPLC (ELSD) purity—96.94%

Synthesis of di((Z)-non-2-en-1-yl) 9-((tert-butyldimethylsilyl)oxy)heptadecanedioate (8)

The diacid 7 (0.42 g, 0.97 mmol) was dissolved in 20 mL of dichloromethane and to it cis-2-nonen-1-ol (0.35 g, 2.44 mmol) was added followed by Hunig's base (0.68 g, 4.9 mmol) and DMAP (12 mg). To this mixture EDCI (0.47 g, 2.44 mmol) was added and the reaction mixture was stirred at room temperature overnight. The reaction mixture was then diluted with CH₂Cl₂ (40 mL) and washed with saturated NaHCO₃ (50 mL), water (60 mL) and brine (60 mL). The combined organic layers were dried over anhydrous Na₂SO₄ and solvents were removed in vacuo. The crude product thus obtained was purified by Combiflash Rf purification system (40 g silicagel, 0-10% MeOH in CH₂Cl₂) to afford the pure product 8 (0.35 g, 53%) as a colorless oil.

¹H NMR (400 MHz, CDCl₃): δ ¹H NMR (400 MHz, CDCl₃) δ 5.64 (dt, J=10.9, 7.4 Hz, 2H), 5.58-5.43 (m, 2H), 4.61 (d, J=6.8 Hz, 4H), 3.71-3.48 (m, 1H), 2.30 (t, J=7.6 Hz, 4H), 2.20-1.98 (m, 4H), 1.71-1.53 (m, 4H), 1.31 (ddd, J=8.3, 7.0, 3.7 Hz, 34H), 1.07-0.68 (m, 14H), 0.02 (s, 5H). ¹³C NMR (101 MHz, CDCl₃) δ 178.18, 139.81, 127.78, 81.73, 81.42, 81.10, 76.72, 64.59, 41.52, 41.32, 38.76, 36.09, 34.10, 33.93, 33.80, 33.70, 33.59, 33.55, 33.26, 31.95, 30.34, 29.69, 29.58, 29.39, 27.01, 22.56, 18.48, 0.01.

Synthesis of di((Z)-non-2-en-1-yl) 9-hydroxyheptadecanedioate (9)

The silyl protected diester 8 (0.3 g, 0.44 mmol) was dissolved in 1 M solution of TBAF in THF (6 mL) and the solution was kept at 40° C. for two days. The reaction mixture was diluted with water (60 mL) and extracted with ether (2×50 mL). The combined organic layers were concentrated and the thus obtained crude product was purified by column to isolate the pure product (0.097 g, 39%). $^1$H NMR (400 MHz, CDCl$_3$) δ 5.64 (dt, J=10.9, 7.4 Hz, 2H), 5.52 (dt, J=11.0, 6.8 Hz, 2H), 4.61 (d, J=6.8 Hz, 4H), 3.57 (s, 1H), 2.30 (t, J=7.5 Hz, 4H), 2.09 (q, J=7.1 Hz, 4H), 1.75-1.53 (m, 4H), 1.53-1.06 (m, 36H), 0.88 (t, J=6.8 Hz, 6H). $^{13}$C NMR (101 MHz, CDCl$_3$) δ 173.98, 135.64, 123.57, 77.54, 77.22, 76.91, 72.14, 60.41, 37.69, 34.54, 31.89, 29.70, 29.60, 29.44, 29.29, 29.07, 27.76, 25.80, 25.15, 22.82, 14.29.

Synthesis of di((Z)-non-2-en-1-yl) 9-((4-(dimethylamino)butanoyl)oxy)heptadecanedioate The alcohol 9 (0.083 g, 0.147 mmol) was dissolved in 20 mL of dichloromethane and to it dimethylaminobutyric acid hydrochloride (0.030 g, 0.176 mmol) was added followed by Hunig's base (0.045 g, 0.44 mmol) and DMAP (2 mg). To this mixture EDCI (0.034 g, 0.176 mmol) was added and the reaction mixture was stirred at room temperature overnight and the TLC (silica gel, 10% MeOH in CH$_2$Cl$_2$) showed complete disappearance of the starting alcohol. The reaction mixture was diluted with CH$_2$Cl$_2$ (40 mL) and washed with saturated NaHCO$_3$ (50 mL), water (60 mL) and brine (60 mL). The combined organic layers were dried over anhyd. Na$_2$SO$_4$ and solvents were removed in vacuo. The crude product thus obtained was purified by Combiflash Rf purification system (40 g silicagel, 0-10% MeOH in CH$_2$Cl$_2$) to isolate the pure product (0.062 g, 62%) as a colorless oil. $^1$H NMR (400 MHz, CDCl$_3$) δ 5.74-5.58 (m, 2H), 5.51 (dtt, J=9.7, 6.8, 1.3 Hz, 2H), 4.95-4.75 (m, 1H), 4.61 (d, J=6.8 Hz, 4H), 2.35-2.24 (m, 8H), 2.22 (d, J=7.9 Hz, 6H), 2.09 (q, J=6.9 Hz, 4H), 1.83-1.72 (m, 2H), 1.60 (dd, J=14.4, 7.2 Hz, 4H), 1.49 (d, J=5.7 Hz, 4H), 1.41-1.13 (m, 30H), 0.88 (t, J=6.9 Hz, 6H). $^{13}$C NMR (101 MHz, CDCl$_3$) δ 173.72, 173.36, 135.40, 123.35, 74.12, 60.18, 58.95, 45.46, 34.30, 34.11, 32.45, 31.67, 29.38, 29.35, 29.17, 29.07, 28.84, 27.53, 25.28, 24.93, 23.16, 22.59, 14.06. MW calc. for C$_{41}$H$_{75}$NO$_6$ (MH$^+$): 678.04. found: 678.5.

Example 8

The following shorter route may be used for the synthesis of Compound 1 of the present invention The commercial 9-bromonon-1-ene 10 was treated with magnesium to form the corresponding Grignard reagent which was reacted with ethylformate to give the corresponding adduct 11 which on treatment with bromobutyryl chloride to provide the bromoester 12. The bromoester 12 on treatment with RuO$_4$ provided the diacid 13. The bromodiacid 13 on treatment with dimethylamine provided the amino diacid 14. The aminodiacid 14 on coupling with the alcohol 15 provided the product in good yields.

Scheme 8

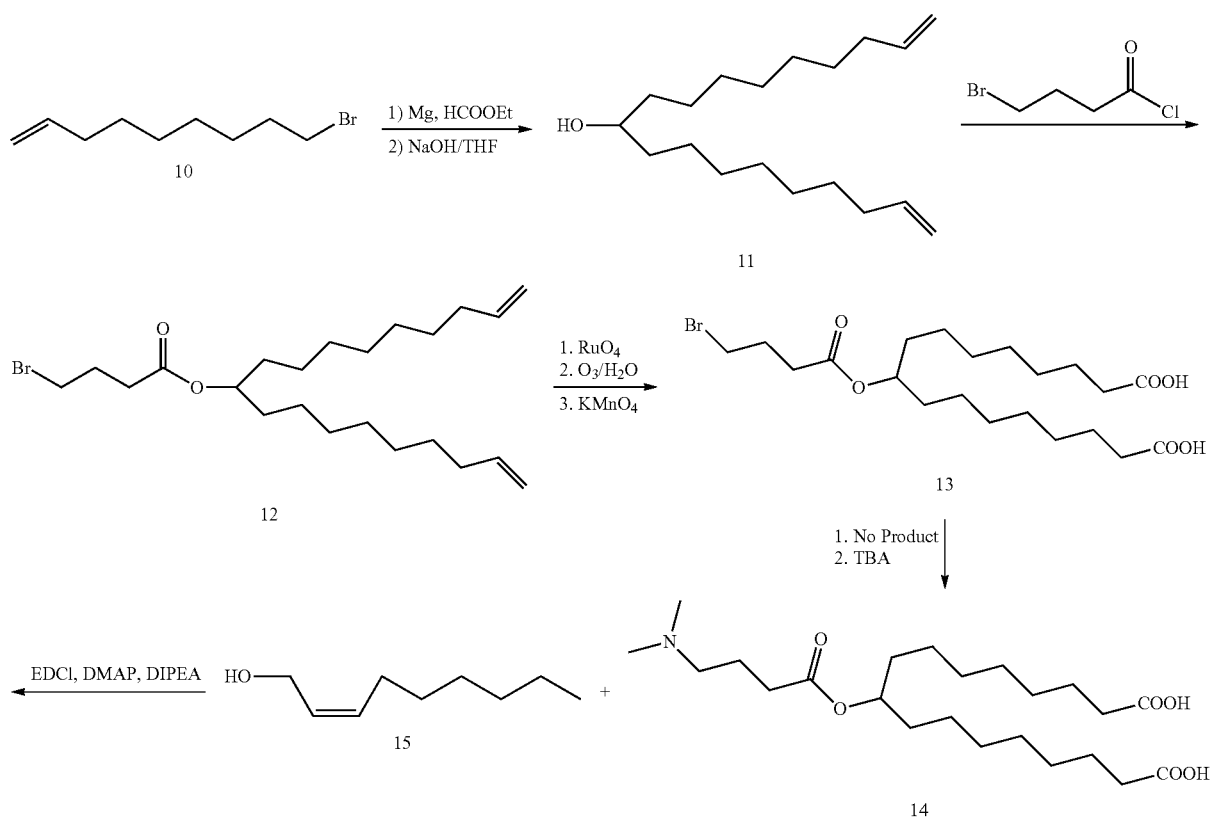

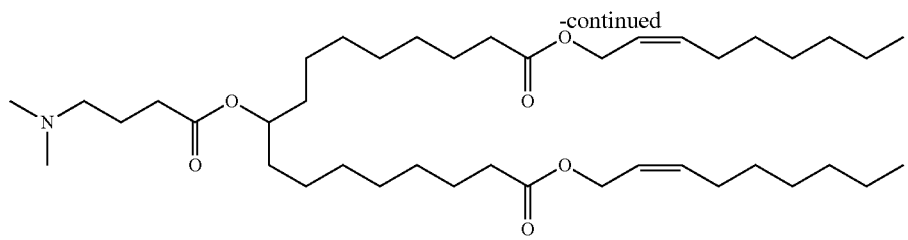

Synthesis of nonadeca-1,18-dien-10-ol (11)

To a flame dried 500 mL RB flask, freshly activated Mg turnings (9 g) were added and the flask was equipped with a magnetic stir bar, an addition funnel and a reflux condenser. This set-up was degassed and flushed with argon and 100 mL of anhydrous ether was added to the flask via syringe. The bromide 3 (51.3 g, 250 mmol) was dissolved in anhydrous ether (100 mL) and added to the addition funnel. About 5 mL of this ether solution was added to the Mg turnings while stirring vigorously. An exothermic reaction was noticed (to confirm/accelerate the Grignard reagent formation, 5 mg of iodine was added and immediate decolorization was observed confirming the formation of the Grignard reagent) and the ether started refluxing. The rest of the solution of the bromide was added dropwise while keeping the reaction under gentle reflux by cooling the flask in water. After the completion of the addition the reaction mixture was kept at 35° C. for 1 hour and then cooled in ice bath. Ethyl formate (9 g, 121 mmol) was dissolved in anhydrous ether (100 mL) and transferred to the addition funnel and added dropwise to the reaction mixture with stirring. An exothermic reaction was observed and the reaction mixture started refluxing. After the initiation of the reaction the rest of the ethereal solution of formate was quickly added as a stream and the reaction mixture was stirred for a further period of 1 h at ambient temperature. The reaction was quenched by adding 10 mL of acetone dropwise followed by ice cold water (60 mL). The reaction mixture was treated with aq. $H_2SO_4$ (10% by volume, 300 mL) until the solution became homogeneous and the layers were separated. The aq. phase was extracted with ether (2×200 mL). The combined ether layers were dried ($Na_2SO_4$) and concentrated to afford the crude product which was purified by column (silica gel, 0-10% ether in hexanes) chromatography. The product fractions were evaporated to provide the pure product 11 as a white solid (30.6 g, 90%). $^1$H NMR (400 MHz, $CDCl_3$) δ 7.26 (s, 1H), 5.81 (ddt, J=16.9, 10.2, 6.7 Hz, 8H), 5.04-4.88 (m, 16H), 3.57 (dd, J=7.6, 3.3 Hz, 4H), 2.04 (q, J=6.9 Hz, 16H), 1.59 (s, 1H), 1.45 (d, J=7.5 Hz, 8H), 1.43-1.12 (m, 94H), 0.88 (t, J=6.8 Hz, 2H). $^{13}$C NMR (101 MHz, $cdcl_3$) δ 139.40, 114.33, 77.54, 77.22, 76.90, 72.21, 37.70, 34.00, 29.86, 29.67, 29.29, 29.12, 25.85.

Synthesis of nonadeca-1,18-dien-10-yl 4-bromobutanoate (12)

To a solution of the alcohol 11 (5.6 g, 20 mol) in anhydrous DCM (300 mL) was added slowly and carefully Bromobutryl chloride (20 mmol) at 0° C. under inert atmosphere. The reaction mixture was warmed to room temperature, stirred for 20 h and monitored by TLC (silica gel, 10% ethyl acetate in hexanes). Upon completion of the reaction, mixture was diluted with water (400 mL) and organic layer was separated out. Organic phase was then washed with sat. solution of $NaHCO_3$ (1×400 mL) followed by brine (1×100 mL) and concentrated under vacuum. Crude product was then purified by silica gel (100-200 mesh) column, eluted with 2-3% ethyl acetate in hexane solution to give 6 g (90%) of desired product 12 as colorless liquid. $^1$H NMR (400 MHz, $CDCl_3$) δ 5.80 (ddt, J=16.9, 10.2, 6.7 Hz, 2H), 5.05-4.81 (m, 5H), 3.46 (t, J=6.5 Hz, 2H), 2.48 (t, J=7.2 Hz, 2H), 2.17 (p, J=6.8 Hz, 2H), 2.11-1.93 (m, 4H), 1.65-1.44 (m, 4H), 1.43-1.17 (m, 19H). $^{13}$C NMR (101 MHz, $cdcl_3$) δ 172.51, 139.37, 114.35, 77.54, 77.23, 76.91, 74.86, 34.31, 33.99, 33.01, 32.96, 29.65, 29.56, 29.24, 29.09, 28.11, 25.52.

Synthesis of 9-((4-bromobutanoyl)oxy)heptadecanedioic acid (13)

To a solution of the bromoester 12 (12.1 g, 28.2 mmol) in dichloromethane (300 mL) and acetonitrile (300 mL), $RuCl_3$ (1.16 g, 5 mol %) was added and the mixture was cooled to 10° C. and sodium metaperiodate (60 g) in water (400 mL) was added dropwise. It was stirred at 10° C. for 20 hr. The reaction mixture was diluted with water, The layers were separated and to the organic layer, was added saturated brine solution with stirring followed by 3% sodium sulfide solution drop wise for the decolourisation (dark green to pale yellow). The layers were separated, the organic layer was dried over sodium sulfate and evaporated at reduced pressure to afford pure product. MW calcd for $C_{20}H_{35}BrO_7$ 467.39. Found 465.4 (M−2H).

Synthesis of 9-((4-(dimethylamino)butanoyl)oxy)heptadecanedioic acid (14)

The Bromoacid 13 (2 mmol) is dissolved in 2M solution of dimethylamine in THF (20 mL) and to it 1 g of anhudrous $K_2CO_3$ was added and the mixture was heated in a pressure bottle at 50° C. overnight. The TLC showed the completion of the reaction. The reaction mixture was acidified with acetic acid and diluted with water (100 mL) and extracted with dichloromethane (2×60 mL). The combined organic layers were concentrated dried and used as such in the next reaction. MW calcd for $C_{23}H_{43}NO_6$ 429.59. Found 430.6 $(MH)^+$.

Synthesis of di((Z)-non-2-en-1-yl) 9-((4-(dimethylamino)butanoyl)oxy)heptadecanedioate The diacid 14 is converted to the corresponding diester as described for the synthesis of 8 and the analytical and spectral data were consistent with that of the product.

Example 9

In another approach the following synthetic approach is used for the synthesis of Compound 1 of the present invention.

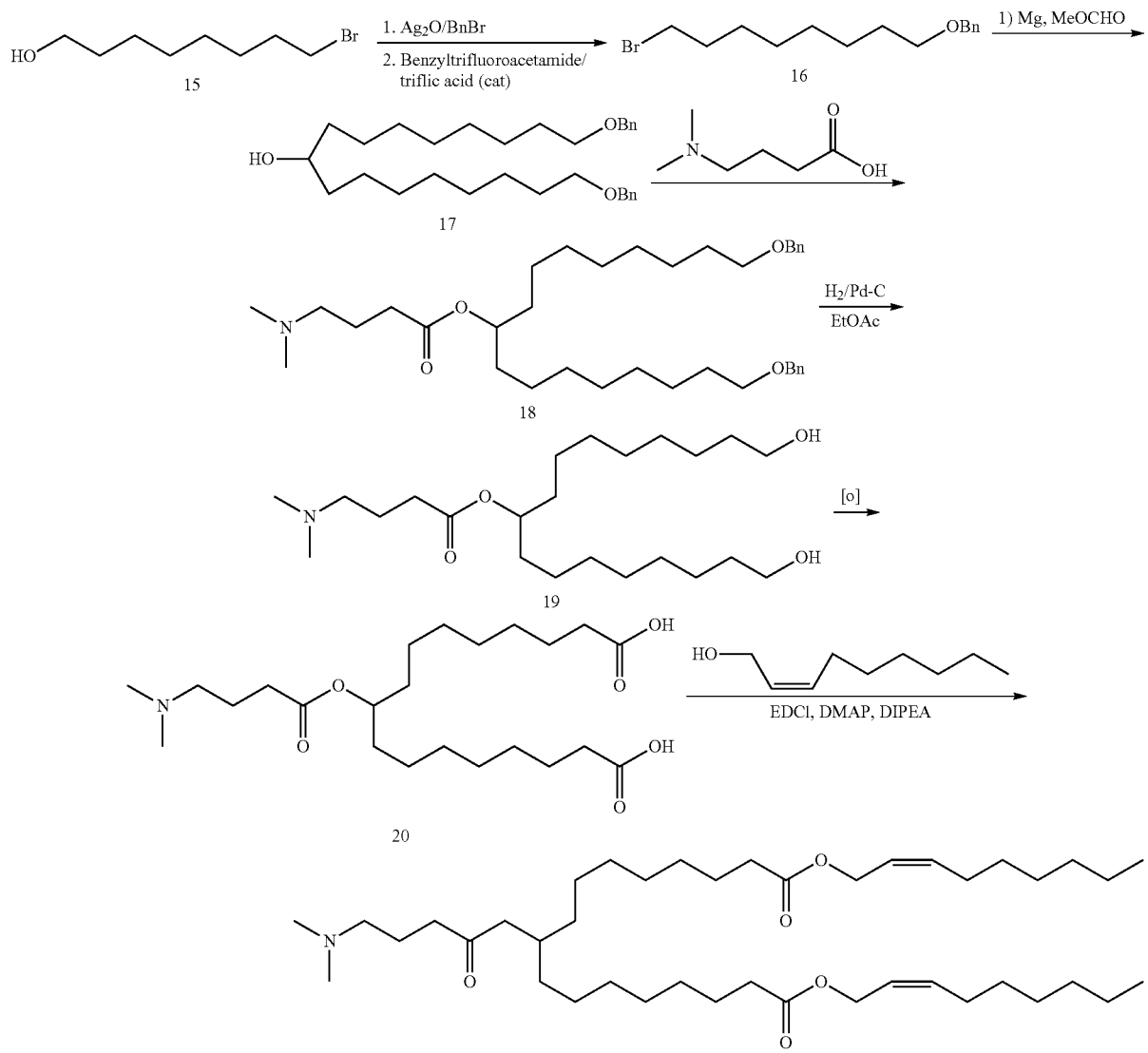

Scheme 9

Example 10

FVII In Vivo Evaluation Using the Cationic Lipid Derived Liposomes

C57BL/6 mice (Charles River Labs, MA) receive either saline or siRNA in desired formulations via tail vein injection at a volume of 0.01 mL/g. At various time points post-administration, animals are anesthesized by isofluorane inhalation and blood is collected into serum separator tubes by retro orbital bleed. Serum levels of Factor VII protein are determined in samples using a chromogenic assay (Coaset Factor VII, DiaPharma Group, OH or Biophen FVII, Aniara Corporation, OH) according to manufacturer protocols. A standard curve is generated using serum collected from saline treated animals. In experiments where liver mRNA levels are assessed, at various time points post-administration, animals are sacrificed and livers are harvested and snap frozen in liquid nitrogen. Frozen liver tissue is ground into powder. Tissue lysates are prepared and liver mRNA levels of Factor VII and apoB are determined using a branched DNA assay (QuantiGene Assay, Panomics, Calif.).

Example 11

Determination of Efficacy of Lipid Particle Formulations Containing Various Cationic Lipids Using an In Vivo Rodent Factor VII Silencing Model Factor VII (FVII), a prominent protein in the coagulation cascade, is synthesized in the liver (hepatocytes) and secreted into the plasma. FVII levels in plasma can be determined by a simple, plate-based colorimetric assay. As such, FVII represents a convenient model for determining siRNA-mediated downregulation of hepatocyte-derived proteins, as well as monitoring plasma concentrations and tissue distribution of the nucleic acid lipid particles and siRNA, such as the siRNA shown in Table 19.

TABLE 19

| Duplex | Sequence 5'-3' | SEQ ID NO: | Target |
|---|---|---|---|
| AD-1661 | GGAfUfCAfUfCfUfCAAGfUfC fUfUAfCdTsdTGfUAAGAfCfU fUGAGAfUGAfUfCfCdTsdT | 5 | FVII |

Lower case is 2' OMe modification and
Nf is a 2'F modified nucleobase,
dT is deoxythymidine,
s is phosphothioate The cationic lipids described herein are used to formulate liposomes containing the AD-1661 duplex using an in-line mixing method, as described in International Publication No. WO 2010/088537, which is incorporated by reference in its entirety. Lipid particles are formulated using the following molar ratio: 50% Cationic lipid/10% distearoylphosphatidylcholine (DSPC)/38.5% Cholesterol/1.5% PEG-DMG (1-(monomethoxy-polyethyleneglycol)-2,3-dimyristoylglycerol, with an average PEG molecular weight of 2000).

C57BL/6 mice (Charles River Labs, MA) receive either saline or formulated siRNA via tail vein injection. At various time points after administration, serum samples are collected by retroorbital bleed. Serum levels of Factor VII protein are determined in samples using a chromogenic assay (Biophen FVII, Aniara Corporation, OH). To determine liver mRNA levels of Factor VII, animals are sacrificed and livers are harvested and snap frozen in liquid nitrogen. Tissue lysates are prepared from the frozen tissues and liver mRNA levels of Factor VII are quantified using a branched DNA assay (QuantiGene Assay, Panomics, Calif.).

FVII activity is evaluated in FVII siRNA-treated animals at 48 hours after intravenous (bolus) injection in C57BL/6 mice. FVII is measured using a commercially available kit for determining protein levels in serum or tissue, following the manufacturer's instructions at a microplate scale. FVII reduction is determined against untreated control mice, and the results are expressed as % Residual FVII. Two dose levels (0.05 and 0.005 mg/kg FVII siRNA) are used in the screen of each novel liposome composition.

Example 12 siRNA Formulation Using Preformed Vesicles

Cationic lipid containing particles are made using the preformed vesicle method. Cationic lipid, DSPC, cholesterol and PEG-lipid are solubilized in ethanol at a molar ratio of 40/10/40/10, respectively. The lipid mixture is added to an aqueous buffer (50 mM citrate, pH 4) with mixing to a final ethanol and lipid concentration of 30% (vol/vol) and 6.1 mg/mL respectively and allowed to equilibrate at room temperature for 2 min before extrusion. The hydrated lipids are extruded through two stacked 80 nm pore-sized filters (Nuclepore) at 22° C. using a Lipex Extruder (Northern Lipids, Vancouver, BC) until a vesicle diameter of 70-90 nm, as determined by Nicomp analysis, is obtained. This generally requires 1-3 passes. For some cationic lipid mixtures which do not form small vesicles hydrating the lipid mixture with a lower pH buffer (50 mM citrate, pH 3) to protonate the phosphate group on the DSPC headgroup helps form stable 70-90 nm vesicles.

The FVII siRNA (solubilised in a 50 mM citrate, pH 4 aqueous solution containing 30% ethanol) is added to the vesicles, pre-equilibrated to 35° C., at a rate of ~5 mL/min with mixing. After a final target siRNA/lipid ratio of 0.06 (wt/wt) is achieved, the mixture is incubated for a further 30 minutes at 35° C. to allow vesicle re-organization and encapsulation of the FVII siRNA. The ethanol is then removed and the external buffer replaced with PBS (155 mM NaCl, 3 mM Na2HPO4, 1 mM KH2PO4, pH 7.5) by either dialysis or tangential flow diafiltration. The final encapsulated siRNA-to-lipid ratio is determined after removal of unencapsulated siRNA using size-exclusion spin columns or ion exchange spin columns.

Example 13

In Vivo Determination of Efficacy of Lipid Formulations

Test formulations are initially assessed for their FVII knockdown in female 7-9 week old, 15-25 g, female C57Bl/6 mice at 0.1, 0.3, 1.0 and 5.0 mg/kg with 3 mice per treatment group. All studies include animals receiving either phosphate-buffered saline (PBS, Control group) or a benchmark formulation. Formulations are diluted to the appropriate concentration in PBS immediately prior to testing. Mice are weighed and the appropriate dosing volumes calculated (10 μl/g body weight). Test and benchmark formulations as well as PBS (for Control animals) are administered intravenously via the lateral tail vein. Animals are anesthetised 24 hours later with an intraperitoneal injection of Ketamine/Xylazine and 500-700 μl of blood is collected by cardiac puncture into serum separator tubes (BD Microtainer). Blood is centrifuged at 2,000×g for 10 minutes at 15° C. and serum is collected and stored at −70° C. until analysis. Serum samples are thawed at 37° C. for 30 minutes, diluted in PBS and aliquoted into 96-well assay plates. Factor VII levels are assessed using a chromogenic assay (Biophen FVII kit, Hyphen BioMed) according to manufacturer's instructions and absorbance is measured in a microplate reader equipped with a 405 nm wavelength filter. Plasma FVII levels are quantified and $ED_{50}$s (dose resulting in a 50% reduction in plasma FVII levels compared to control animals) calculated using a standard curve generated from a pooled sample of serum from Control animals. Those formulations of interest showing high levels of FVII knockdown ($ED_{50} \ll 0.1$ mg/kg) are re-tested in independent studies at a lower dose range to confirm potency and establish $ED_{50}$ levels.

Example 14

Study to Determine Lipid Profiles and Tissue Clearance in Mice

A study was conducted to determine the lipid profile and tissue clearance in mice for cationic lipids according to the present invention.

Male mice (C57BL, 20-30 g) were separated into four groups and administered (intravenously) either Compound 1, 2 or 3 of the present invention, or a Reference Lipid, as shown below in Table 20.

TABLE 20

| Group | Lipid | Lipid Dose (mg/kg) | Lipid Concentration (mg/mL) | No. of Male Mice |
|---|---|---|---|---|
| I | Reference Lipid | 0.3 | 0.03 | 12 |
| II | Compound 1 | 0.3 | 0.03 | 12 |
| III | Compound 2 | 0.3 | 0.03 | 12 |
| IV | Compound 3 | 0.3 | 0.03 | 12 |

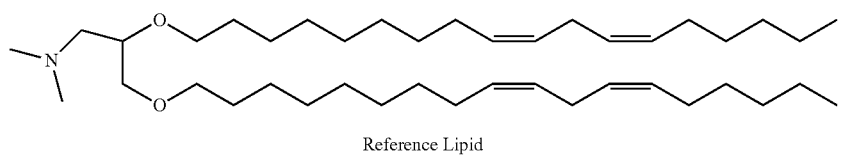

Reference Lipid

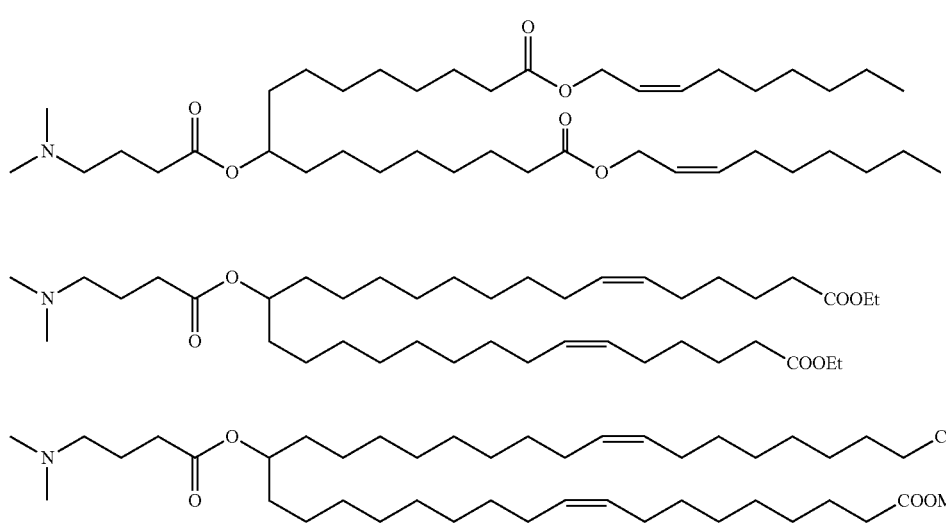

Compound 1

Compound 2

Compound 3

The mice were not fasted. Blood, liver and spleen samples were collected (two samples per time point per group) at 0.17, 8, 24, 72, 168, 336 and 672 hours post dose.

FIG. 1 shows the liver lipid concentration over time for the mice in each of Groups I-IV. The liver pharmacokinetic data is presented in Table 21 below.

TABLE 21

| Lipid | $C_{max}$ (ng/mL) | AUC (h · ng/mL) | $MRT_{0-t}$ (hours) |
|---|---|---|---|
| Reference Lipid | 22,400 | 6,954,787 | 221 |
| Compound 1 | 1,136 | 4,594 | NC |
| Compound 2 | 118 | 436 | NC |
| Compound 3 | 208 | NC | NC |

MRT stands for mean residence time.
NC stands for not calculatable.

Figure 2:
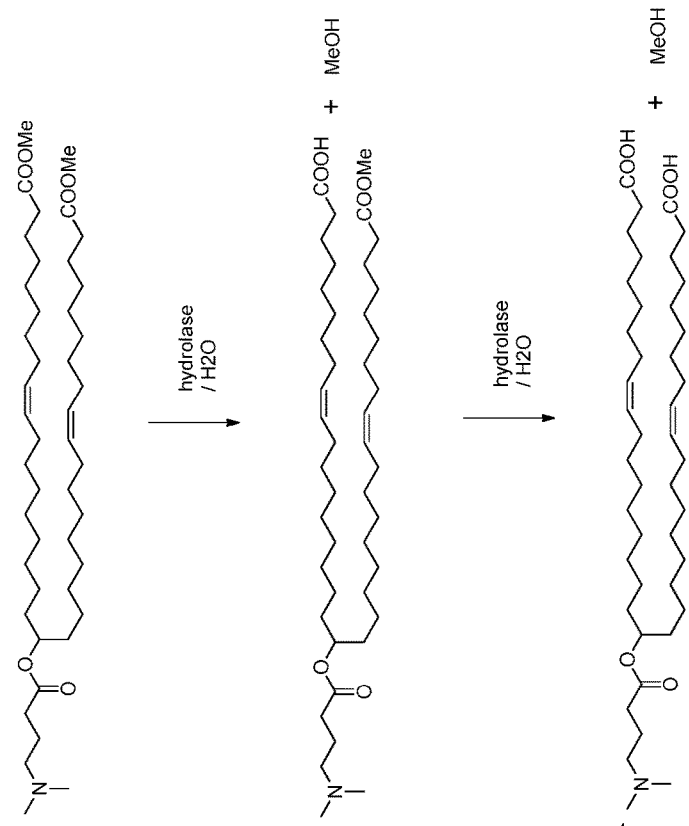
FIG. 2 shows the anticipated metabolic pathway for compounds 1 and 3 of Example 14.
Figure 2:
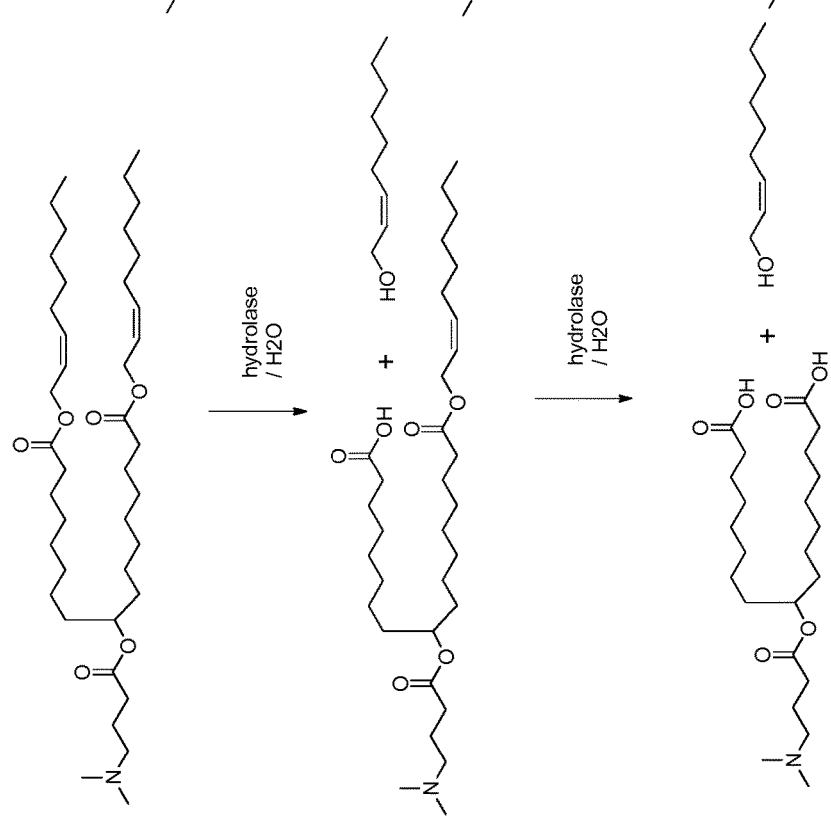

The anticipated metabolic pathway for compounds 1 and 3 is shown in FIG. 2. The concentration of these metabolites was measured in the liver. The results are shown in table 22 below. All measurements after 24 hours (including those taken at 72, 168, 336, and 672 hours post-administration) were below the level of quantification (BLQ).

TABLE 22

| Time (hr) | Compound 1 | | Compound 2 | | Compound 3 | |
|---|---|---|---|---|---|---|
| | Mono-acid | Di-acid | Mono-acid | Di-acid | Mono-acid | Di-acid |
| 0.17 | 126.00 | 125.50 | 10.62 | 14.75 | 20.15 | 23.95 |
| 8 | 1.25 | 1.31 | 0.40 | 0.56 | BLQ | BLQ |
| 24 | BLQ | BLQ | BLQ | BLQ | BLQ | BLQ |

Figure 3:
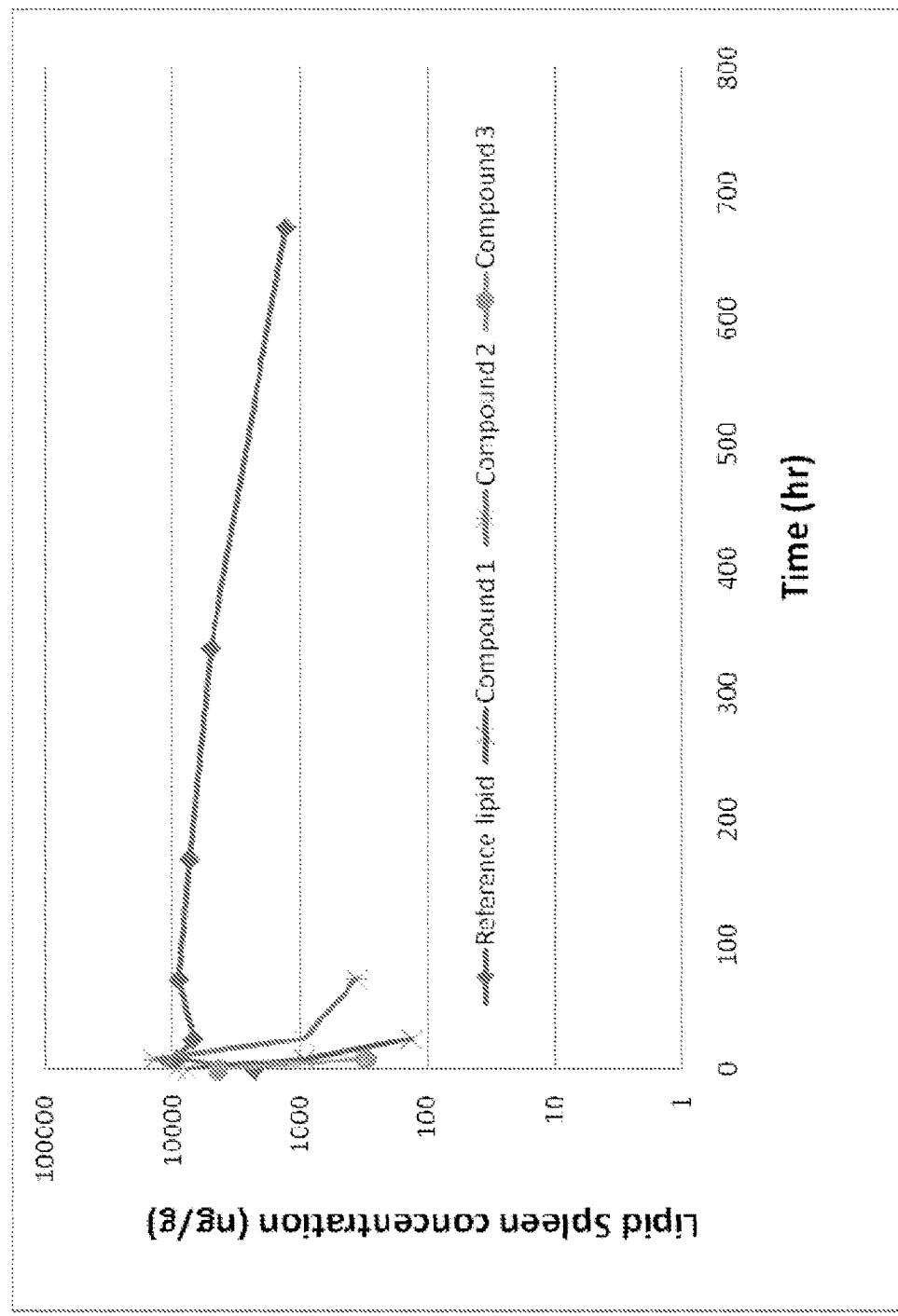
FIG. 3 is a graph of the concentration of a cationic lipid (Compounds 1-3 and reference lipid) in the spleen of mice over time, after administration of the cationic lipid in a lipid particle as described in Example 14.

FIG. 3 shows the spleen lipid concentration over time for the mice in each of Groups I-IV. The spleen pharmacokinetic data is presented in Table 23 below.

TABLE 23

| Lipid | $C_{max}$ (ng/mL) | AUC (h · ng/mL) | $MRT_{0-t}$ (hours) |
|---|---|---|---|
| Reference Lipid | 9,152 | 3,426,038 | 229.7 |
| Compound 1 | 7,460 | 41,967 | 2.8 |
| Compound 2 | 13,640 | 238,044 | 11.1 |
| Compound 3 | 4368 | 18,686 | 0.7 |

The concentration of the metabolites of compounds 1-3 in the spleen was measured and the results are shown in table 24 below.

185

TABLE 24

| Time (hr) | Compound 1 | | Compound 2 | | Compound 3 | |
|---|---|---|---|---|---|---|
| | Mono-acid | Di-acid | Mono-acid | Di-acid | Mono-acid | Di-acid |
| 0.17 | 208.1 | 37.5 | 624.8 | 95.1 | 1591.5 | 687.3 |
| 8 | 36.2 | BLQ | 792.0 | 127.2 | 182.6 | 121.9 |
| 24 | BLQ | BLQ | 62.1 | BLQ | BLQ | No sample |
| 72 | BLQ | BLQ | BLQ | BLQ | BLQ | 99.7 |
| 168 | BLQ | BLQ | BLQ | BLQ | BLQ | 33.6 |
| 336 | BLQ | BLQ | BLQ | BLQ | BLQ | 52.0 |
| 672 | BLQ | BLQ | BLQ | BLQ | BLQ | BLQ |

Figure 4:
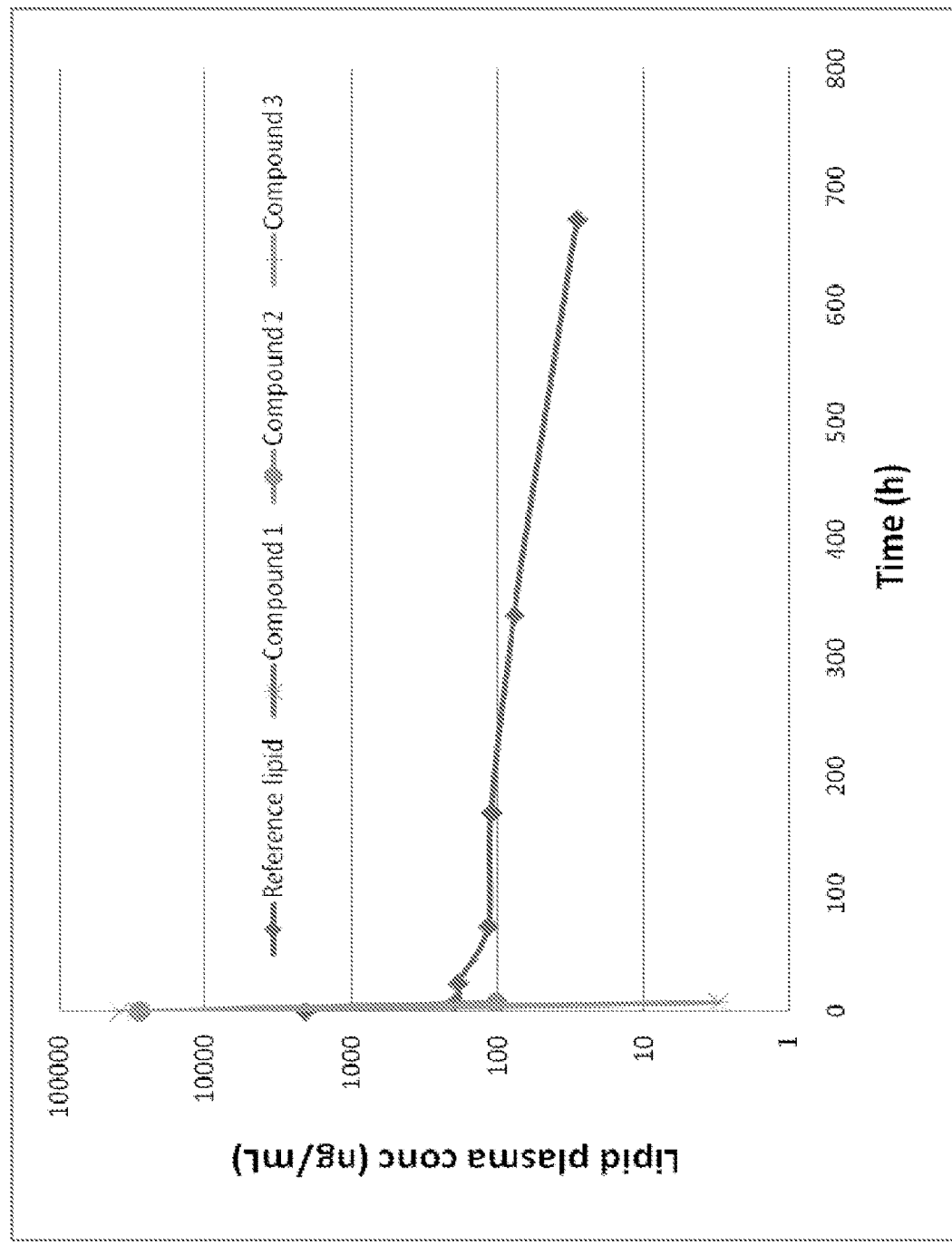
FIG. 4 is a graph of the concentration of a cationic lipid (Compounds 1-3 and reference lipid) in the plasma of mice over time, after administration of the cationic lipid in a lipid particle as described in Example 14.

FIG. 4 shows the plasma lipid concentration over time for the mice in each of Groups I-IV. The plasma pharmacokinetic data is presented in Table 25 below.

TABLE 25

| Lipid | $C_{max}$ (ng/mL) | AUC (h·ng/mL) | $MRT_{0-t}$ (hours) |
|---|---|---|---|
| Reference Lipid | 2,110 | 63,775 | 201 |
| Compound 1 | 38,750 | 155,012 | 0.0006 |
| Compound 2 | 28,800 | 115,612 | 0.0285 |
| Compound 3 | 30,600 | 122,412 | 0.0008 |

The concentration of the metabolites of compounds 1-3 in the plasma was measured and the results are shown in table 26 below. All measurements after 24 hours (including those taken at 72, 168, 336, and 672 hours post-administration) were below the level of quantification (BLQ).

TABLE 26

| Time (hr) | Compound 1 | | Compound 2 | | Compound 3 | |
|---|---|---|---|---|---|---|
| | Mono-acid | Di-acid | Mono-acid | Di-acid | Mono-acid | Di-acid |
| 0.17 | 181.43 | 1186.40 | 1355.56 | 605.56 | 1037.63 | 871.64 |
| 8 | BLQ | BLQ | 2.66 | 3.53 | BLQ | 21.18 |
| 24 | BLQ | BLQ | BLQ | BLQ | BLQ | 2.45 |

As can be seen from FIGS. 1, 3, and 4 and Tables 22, 24 and 26, Compounds 1, 2 and 3 of the present invention exhibit dramatically improved tissue clearance and activity when compared to the Reference Lipid.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:
1. A compound of Formula (I)

Formula (I)

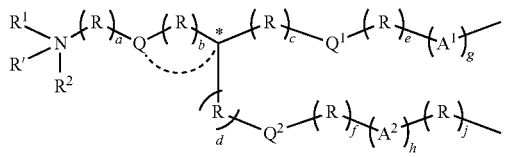

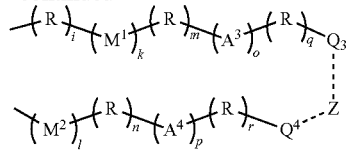

or a salt thereof;
wherein
R' is absent, hydrogen, or alkyl;
with respect to $R^1$ and $R^2$,
(i) $R^1$ and $R^2$ are each, independently, optionally substituted alkyl, alkenyl, alkynyl, cycloalkyl, cycloalkylalkyl, or heterocycle;
(ii) $R^1$ and $R^2$, together with the nitrogen atom to which they are attached, form an optionally substituted heterocylic ring; or
(iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl with (a) the adjacent nitrogen atom and (b) the $(R)_a$ group adjacent to the nitrogen atom;
each occurrence of R is, independently, —$(CR^3R^4)$—;
each occurrence of $R^3$ and $R^4$ are, independently, H, OH, alkyl, alkoxy, —$NH_2$, alkylamino, or dialkylamino;
or $R^3$ and $R^4$, together with the carbon atom to which they are directly attached, form a cycloalkyl group, wherein no more than three R groups in each chain attached to the carbon C* are cycloalkyl;
the dashed line to Q is absent or a bond;
when the dashed line to Q is absent then Q is absent or is —O—, —NH—, —S—, —C(O)O—, —OC(O)—, —C(O)N($R^4$)—, —N($R^5$)C(O)—, —S—S—, —OC(O)O—, —O—N=C($R^5$)—, —C($R^5$)=N—O—, —OC(O)N($R^5$)—, —N($R^5$)C(O)N($R^5$)—, —N($R^5$)C(O)O—, —C(O)S—, —C(S)O— or —C($R^5$)=N—O—C(O)—; or
when the dashed line to Q is a bond then (i) b is 0 and (ii) Q and the tertiary carbon adjacent to it (C*) form a substituted or unsubstituted, mono- or bi-cyclic heterocyclic group having from 5 to 10 ring atoms;
$Q^1$ and $Q^2$ are each, independently, absent, —O—, —S—, —OC(O)—, —C(O)O—, —SC(O)—, —C(O)S—, —OC(S)—, —C(S)O—, —S—S—, —C(O)(N$R^5$)—, —N($R^5$)C(O)—, —C(S)(NR$^5$)—, —N($R^5$)C(O)—, —N($R^5$)C(O)N($R^5$)—, or —OC(O)O—;
$Q^3$ and $Q^4$ are each, independently, H, —$(CR^3R^4)$—, aryl, or a cholesterol moiety;
each occurrence of $A^1$, $A^2$, $A^3$ and $A^4$ is, independently, —$(CR^5R^5—CR^5=CR^5)$—;
each occurrence of $R^5$ is, independently, H or alkyl;
$M^1$ and $M^2$ are each, independently, a biodegradable group;

Z is absent, alkylene or —O—P(O)(OH)—O—;
each ------ attached to Z is an optional bond, such that when Z is absent, $Q^3$ and $Q^4$ are not directly covalently bound together;
a is 1, 2, 3, 4, 5 or 6;
b is 0, 1, 2, or 3;
c, d, e, f, i, j, m, n, q and r are each, independently, 0, 1, 2, 3, 4, 5, 6, 7, 8, 9, or 10;
g and h are each, independently, 0, 1 or 2;
k and l are each, independently, 0 or 1, where at least one of k and 1 is 1; and
o and p are each, independently, 0, 1 or 2,
wherein
(i) the compound does not contain the following moiety:

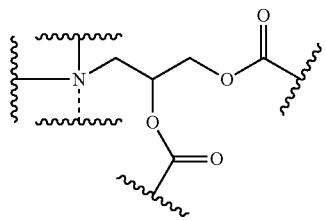

wherein ---- is an optional bond; and
$Q^3$ and $Q^4$ are each, independently, separated from the tertiary carbon atom marked with an asterisk (*) by a chain of 8 or more atoms.

2. The compound of claim 1, wherein the biodegradable group is selected from —OC(O)—, —C(O)O—, —SC(O)—, —C(O)S—, —OC(S)—, —C(S)O—, —S—S—, —C($R^5$)=N—, —N=C($R^5$)—, —C($R^5$)=N—O—, —O—N=C($R^5$)—, —C(O)(N$R^5$)—, —N($R^5$)C(O)—, —C(S)(N$R^5$)—, —N($R^5$)C(O)—, —N($R^5$)C(O)N($R^5$)—, —OC(O)O—, —OSi($R^5$)$_2$O—, —C(O)(C$R^3R^4$)C(O)O—, and —OC(O)(C$R^3R^4$)C(O)—.

3. The compound of claim 1, wherein the compound is in the form of a pharmaceutically acceptable salt.

4. The compound of claim 1, wherein the compound is in the form of a cationic lipid.

5. A lipid particle comprising a neutral lipid selected from DSPC, DPPC, POPC, DOPE, or SM, a lipid capable of reducing aggregation, wherein the lipid capable of reducing aggregation is a PEG lipid, and a cationic lipid of claim 4.

6. The lipid particle of claim 5, wherein the lipid particle further comprises a sterol.

7. The lipid particle of claim 6, wherein the cationic lipid is present in a mole percentage of about 20% and about 60%; the neutral lipid is present in a mole percentage of about 5% to about 25%; the sterol is present in a mole percentage of about 25% to about 55%; and the PEG lipid is PEG-DMA, PEG-DMG, or a combination thereof, and is present in a mole percentage of about 0.5% to about 15%.

8. The lipid particle of claim 5, further comprising an active agent.

9. The lipid particle of claim 8, wherein the active agent is a nucleic acid selected from a plasmid, an immunostimulatory oligonucleotide, an siRNA, an antisense oligonucleotide, a microRNA, an antagomir, an aptamer, and a ribozyme.

10. The lipid particle of claim 5, wherein the lipid particle has an in vivo half life ($t_{1/2}$) of less than about 3 hours.

11. The lipid particle of claim 5, wherein the lipid particle has an in vivo half life ($t_{1/2}$) of less than about 10% of that for a lipid particle containing the same cationic lipid without a biodegrable group.

12. A pharmaceutical composition comprising a lipid particle of claim 5 and a pharmaceutically acceptable carrier.

13. A method of modulating the expression of a target gene in a cell, comprising providing to the cell a lipid particle of claim 5.

14. The method of claim 13, wherein the active agent is a nucleic acid selected from a plasmid, an immunostimulatory oligonucleotide, an siRNA, an antisense oligonucleotide, a microRNA, an antagomir, an aptamer, and a ribozyme.

15. The compound of claim 1, wherein (i) $R^1$ and $R^2$ are each, independently, optionally substituted alkyl, alkenyl, alkynyl, cycloalkyl, cycloalkylalkyl, or heterocycle; or (ii) $R^1$ and $R^2$, together with the nitrogen atom to which they are attached, form an optionally substituted heterocylic ring.

16. The compound of claim 1, wherein
(a) when $Q^1$ is a biodegradable group (e.g., —C(O)O—), then c is at least 4;
(b) when $Q^2$ is a biodegradable group, then d is at least 4; and
(c) $Q^3$ and $Q^4$ are each, independently, separated from the tertiary carbon atom marked with an asterisk (*) by a chain of 10 or more atoms.

17. The compound of claim 1, wherein a carbon atom alpha or beta to a biodegradable group in formula (I) is substituted with one or two alkyl groups.

18. The compound of claim 1, wherein the $M^1$ or $M^2$ group and neighboring variable(s) form the group:

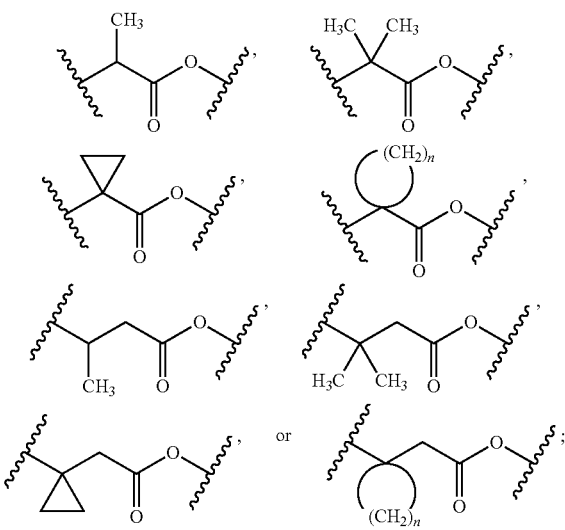

wherein n is 4-6.

* * * * *